US009422314B2

(12) United States Patent
Burns et al.

(10) Patent No.: US 9,422,314 B2
(45) Date of Patent: *Aug. 23, 2016

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Denis Daigle, Havre de Grace, MD (US); Bin Liu, Dayton, NJ (US); Daniel McGarry, Exton, PA (US); Daniel C. Pevear, Downingtown, PA (US); Robert E. Lee Trout, Collegeville, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/649,527

(22) PCT Filed: Dec. 5, 2013

(86) PCT No.: PCT/US2013/073428
§ 371 (c)(1),
(2) Date: Jun. 3, 2015

(87) PCT Pub. No.: WO2014/089365
PCT Pub. Date: Jun. 12, 2014

(65) Prior Publication Data
US 2015/0291630 A1 Oct. 15, 2015

Related U.S. Application Data

(60) Provisional application No. 61/734,900, filed on Dec. 7, 2012, provisional application No. 61/783,238, filed on Mar. 14, 2013.

(51) Int. Cl.
*A61K 31/69* (2006.01)
*A61K 45/06* (2006.01)
*C07F 5/04* (2006.01)
*C07F 5/02* (2006.01)

(52) U.S. Cl.
CPC ............... *C07F 5/04* (2013.01); *A61K 31/69* (2013.01); *A61K 45/06* (2013.01); *C07F 5/025* (2013.01); *C07F 5/027* (2013.01)

(58) Field of Classification Search
CPC .......... A61K 31/69; A61K 45/06; C07F 5/04
See application file for complete search history.

(56) References Cited

U.S. PATENT DOCUMENTS

| 7,271,186 | B1 | 9/2007 | Shoichet et al. |
| 8,680,136 | B2 | 3/2014 | Hirst et al. |
| 8,912,169 | B2* | 12/2014 | Burns ............ A61K 45/06 514/64 |
| 9,040,504 | B2* | 5/2015 | Burns et al. ............ 514/64 |
| 9,101,638 | B2 | 8/2015 | Reddy et al. |
| 2010/0056478 | A1 | 3/2010 | Desarbre et al. |
| 2010/0120715 | A1 | 5/2010 | Burns et al. |
| 2010/0286092 | A1 | 11/2010 | Burns et al. |
| 2010/0292185 | A1 | 11/2010 | Burns et al. |
| 2010/0317621 | A1 | 12/2010 | Burns et al. |
| 2011/0294777 | A1 | 12/2011 | Blizzard et al. |
| 2012/0040932 | A1 | 2/2012 | Hirst et al. |
| 2016/0016978 | A1 | 1/2016 | Burns et al. |
| 2016/0024121 | A1 | 1/2016 | Burns et al. |

FOREIGN PATENT DOCUMENTS

| WO | WO-2005004799 A2 | 1/2005 |
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2013053372 A1 | 4/2013 |
| WO | WO-2013122888 A2 | 8/2013 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |

OTHER PUBLICATIONS

Burns et al., caplus an 2014:1130723, 2014.*
Isomer, 2015, https://en.wikipedia.org/wiki/Isomer.*
Reddy et al., 2014, caplus an 2014:1118372.*
Co-pending U.S. Appl. No. 14/693,318, filed Apr. 22, 2015.
Co-pending U.S. Appl. No. 14/736,921, filed Jun. 11, 2015.
Co-pending U.S. Appl. No. 14/737,156, filed Jun. 11, 2015.
Co-pending U.S. Appl. No. 14/737,323, filed Jun. 11, 2015.
Eidam et al. Design, synthesis, crystal structures, and antimicrobial activity of sulfonamide boronic acids as β-lactamase inhibitors. J. Med. Chem. 53(21):7852-7863 (2010).
Ettmayer et al. Lessons Learned from Marketed and Investigational Prodrugs. J Medicinal Chem. 47(10):2393-2404. 2004.
Han. Targeted Prodrug Design to Optimize Drug Delivery. AAPS Pharmsci. 2(1)Article 6:1-11 (2000).
Morandi et al. Structure-based optimization of cephalothin-analogue boronic acids as β-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
PCT/US2013/073428 International Preliminary Report on Patentability dated Jun. 18, 2015.
PCT/US2013/073428 International Search Report dated Apr. 25, 2014.

(Continued)

*Primary Examiner* — Sun Jae Yoo
(74) *Attorney, Agent, or Firm* — Wilson, Sonsini, Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

21 Claims, No Drawings

(56) References Cited

OTHER PUBLICATIONS

PCT/US2014/011144 International Search Report dated May 12, 2014.
PCT/US2014/026727 International Search Report dated Jul. 25, 2014.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry. 40(31):9207-9214 (2001).
Testa. Prodrug research: futile or fertile? Biochem. Pharm. 68:2097-2106 (2004).
U.S. Appl. No. 14/152,916 Office Action dated Aug. 29, 2014.
Weston et al. Structure-based enhancement of boronic acid-based inhibitors of AmpC β-lactamase. J. Med. Chem. 41(23):4577-4586 (1998).
Bodner Research Web. The Chemistry of the Halogens. Available from <a href="http://web.archive.org/web/20090414155348/http://chemechem/topicreview/bp/ch10/group3.php">http://web.archive.org/web/20090414155348/http://chemechem/topicreview/bp/ch10/group3.php</a>.
Lima et al. Bioisosterism: A Useful Strategy for Molecular Modification and Drug Design. Current Medicinal Chemistry 12:23-49 (2005).
PCT/US2014/011144 International Preliminary Report on Patentability dated Jul. 23, 2015.
PCT/US2015/035407 International Search Report and Written Opinion dated Oct. 20, 2015.
U.S. Appl. No. 14/693,318 Office Action dated Sep. 1, 2015.
U.S. Appl. No. 14/759,853 Office Action dated Dec. 11, 2015.

* cited by examiner

BETA-LACTAMASE INHIBITORS

CROSS-REFERENCE TO RELATED APPLICATIONS

This application is a U.S. National Stage entry of International Application No. PCT/US13/73428, filed Dec. 5, 2013, which claims the benefit of priority from U.S. Provisional Application Ser. No. 61/734,900, filed Dec. 7, 2012, and U.S. Provisional Application Ser. No. 61/783,238, filed Mar. 14, 2013, each of which are hereby incorporated by reference in their entirety.

STATEMENT AS TO FEDERALLY SPONSORED RESEARCH

This invention was made with the support of the United States government under Contract numbers AI096679-01 by National Institutes of Health (NIH), AI096613-01 by National Institutes of Health (NIH), and AI089512-01 by National Institutes of Health (NIH). The government has certain rights in the invention.

FIELD OF INVENTION

The present invention relates to boron-containing compounds, compositions, preparations and their use as inhibitors of beta-lactamase enzymes and as antibacterial agents.

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) are widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections.

In one aspect, provided herein are compounds of Formula I or Formula Ia, or pharmaceutically acceptable salts, solvates, polymorphs, stereoisomers, tautomers, prodrugs, metabolites, N-oxides, or isomers thereof:

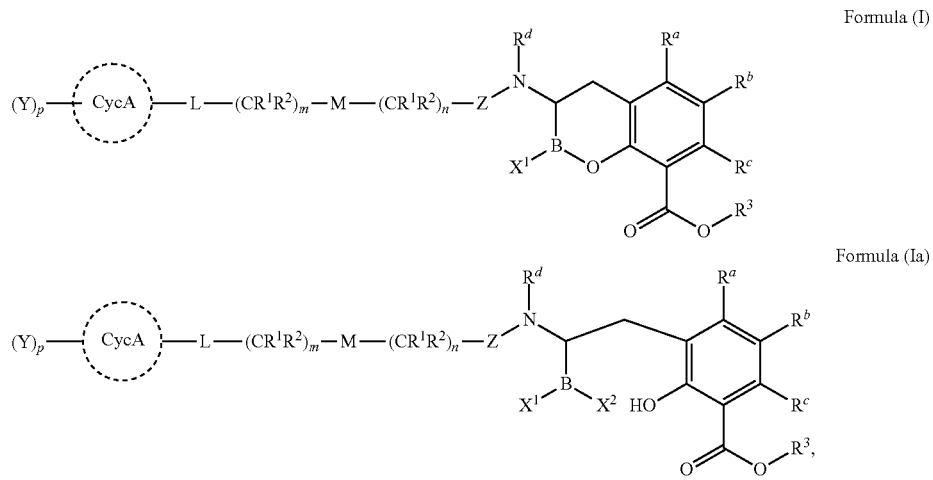

wherein:
L is a bond, —$CR^1R^2$—, >C=O, or =$CR^1$—;
M is a bond, —O—, —S—, —S(O)—, $SO_2$—, or —N($R^4$)—;
m is 0, 1, or 2;
n is 0, 1, 2, or 3;
  provided that
    when n is 0, then M is a bond;
p is 0, 1, 2, 3, or 4;
  provided that
    when p is 0, then L is —$CR^1R^2$— or =$CR^1$—;
$X^1$ and $X^2$ are independently selected from —OH, —$OR^8$, or F;
Z is >C=O, >C=S, or >$SO_2$;
CycA is an optionally substituted 3-10 membered non-aromatic carbocycle, wherein an optional olefin functionality of the non-aromatic carbocycle is not directly attached to an oxygen, sulfur, or nitrogen substituent;
$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —$OR^{10}$, —$NR^4R^5$, and —$SR^{10}$;

each $R^1$ and $R^2$ is independently selected from the group consisting of hydrogen, fluoro, chloro, bromo, optionally substituted $C_1$-$C_6$ alkyl, optionally substituted $C_3$-$C_6$ cycloalkyl, —OH, —$OR^{10}$, —$SR^{10}$, and —$NR^4R^5$, or $R^1$ and $R^2$ taken together form an oxo, oxime, or an optionally substituted carbocycle or optionally substituted heterocycle with the carbon to which they are attached;

$R^3$ is hydrogen, optionally substituted $C_1$-$C_6$ alkyl, or a pharmaceutically acceptable prodrug;

each $R^d$, $R^4$ and $R^5$ is independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^4$ and $R^5$ taken together form an optionally substituted heterocycle with the nitrogen to which they are attached;

$R^8$ is optionally substituted $C_1$-$C_6$ alkyl, optionally substituted $C_3$-$C_6$ cycloalkyl, or a pharmaceutically acceptable boronate ester group;

$R^{10}$ is optionally substituted $C_1$-$C_6$ alkyl or optionally substituted $C_3$-$C_6$ cycloalkyl and each Y is independently a group comprising 1-50 non-hydrogen atoms selected from the group consisting of C, N, O, S, and P.

In some embodiments of a compound of Formula I or Formula Ia, $R^a$, $R^b$, and $R^c$ are independently selected from the group consisting of hydrogen, fluoro, chloro, optionally substituted $C_1$-$C_6$ alkyl, optionally substituted $C_3$-$C_6$ cycloalkyl, —OH, —$OR^{10}$, —$NR^4R^5$, and —$SR^{10}$. In certain embodiments, $R^a$, $R^b$, and $R^c$ are independently hydrogen, fluoro, or chloro. In preferred embodiments, $R^a$, $R^b$, and $R^c$ are hydrogen.

In some embodiments of a compound of Formula I or Formula Ia, $R^3$ is hydrogen, methyl, ethyl, propyl, butyl, or isopropyl. In preferred embodiments, $R^3$ is hydrogen.

In some embodiments of a compound of Formula I or Formula Ia, $X^1$ and $X^2$ are —OH.

In some embodiments of a compound of Formula I or Formula Ia, $R^d$ is hydrogen or $C_1$-$C_4$-alkyl. In preferred embodiments, $R^d$ is hydrogen.

In some embodiments of a compound of Formula I or Formula Ia, Z is Z is >C═O or >$SO_2$. In preferred embodiments, Z is >C═O.

In some embodiments of a compound of Formula I or Formula Ia, L is —$CR^1R^2$— or ═$CR^1$—; M is —O—, —S—, —$SO_2$—, or —$N(R^4)$—; m is 0 or 1; and n is 1 or 2. In certain embodiments, L is a bond, —$CR^1R^2$—, or ═$CR^1$—; M is a bond or —O—; m is 0; and n is 1 or 2. In further embodiments, L is a bond or >C═O; M is a bond or —$N(R^4)$—; and m and n are 0. In other embodiments, L is a bond; M is a bond; and m or n are 1. In some embodiments, L is —$CR^1R^2$— or ═$CR^1$—; M is a bond; and m and n are 0. In certain embodiments, L is —$CR^1R^2$— or ═$CR^1$—; M is a bond; and m or n are 1.

In some embodiments of a compound of Formula I or Formula Ia, CycA is selected from the group consisting of cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent. In certain embodiments, CycA is cyclobutane, cyclopentane, cyclohexane, or cyclohexene, wherein the olefin functionality of the cyclohexene is not directly attached to an oxygen, sulfur, or nitrogen substituent. In other embodiments, CycA is selected from the group consisting of bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane. In preferred embodiments, CycA is cyclobutane, cyclopentane, and cyclohexane. In some embodiments of a compound of Formula I or Formula Ia, at least one Y is selected from the group fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, ═O, —OH, —$OR^{10}$, —$SR^{10}$, —$NR^4R^5$, —$(CR^6R^7)_vNR^4R^5$, —$NR^4(CR^6R^7)_vR_6$, —$NR^4(CR^6R^7)_vNR^4R^5$, —$NR^4(CR^6R^7)_vNR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(═NR^7)NR^4(CR^6R^7)_vNR^4R^5$, —$N(R^4)C(═NR^5)R^6$, —$(CR^6R^7)_vN(R^4)C(═NR^5)R^6$, —$NR^4(CR^6R^7)_vN(R^4)C(═NR^5)R^6$, —$O(CR^6R^7)_vN(R^4)C(═NR^5)R^6$, —$S(O)_{0,1,2}(CR^6R^7)_vN(R^4)C(═NR^5)R^6$, —$(CR^6R^7)_vC(═NR^5)NR^4R^5$, —$NR^4(CR^6R^7)_vC(═NR^5)NR^4R^5$, —$O(CR^6R^7)_vC(═NR^5)NR^4R^5$, —$S(O)_{0,1,2}(CR^6R^7)_vC(═NR^5)NR^4R^5$, —$(CR^6R^7)_vN(R^4)C(═NR^5)NR^4R^5$, —$NR^4(CR^6R^7)_vN(R^4)C(═NR^5)NR^4R^5$, —$O(CR^6R^7)_vN(R^4)C(═NR^5)NR^4R^5$, —$S(O)_{0,1,2}(CR^6R^7)_vN(R^4)C(═NR^5)NR^4R^5$, —$NR^4C(═NR^5)NR^4C(═NR^5)NR^4R^5$, —$(CR^6R^7)_vC(═NR^4)NR^5C(═NR^4)NR^4R^5$, —$NR^4(CR^6R^7)_vC(═NR^4)NR^5C(═NR^4)NR^4R^5$, —$NR^4(CR^6R^7)_vNR^4C(═NR^4)NR^4R^5$, —$O(CR^6R^7)_vC(═NR^4)NR^5C(═NR^5)NR^4R^5$, —$S(O)_{0,1,2}(CR^6R^7)_vC(═NR^5)NR^5C(═NR^4)NR^4R^5$, —$NR^4C(═NR^4)NR^4NR^4R^5$, —$C(═NR^4)NR^4R^5$, —$C(═NR^4)NR^4C(O)R^6$, —$NR^4SO_2R^6$, —$NR^4C(O)R^6$, —$NR^4C(═O)OR^5$, —$C(O)NR^4R^5$, —$(CR^6R^7)_vC(O)NR^4R^5$, —$SO_2NR^4R^5$, -Heteroaryl-$NR^4R^5$, -Heterocyclyl-$NR^4R^5$, -Heteroaryl-$N(R^4)C(═NR^5)NR^4R^5$, -Heterocyclyl-$N(R^4)C(═NR^5)NR^4R^5$, —$N(R^4)$-Heteroaryl-$NR^4R^5$, —$N(R^4)$-Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(═NR^5)NR^4R^5$, —$(CR^6R^7)_v$Heterocyclyl-$N(R^4)C(═NR^5)NR^4R^5$, —$NR^4(CR^6R^7)_v$Heterocyclyl-$C(═NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, —$NR^4(CR^6R^7)_vNR^5$-Heteroaryl, —$NR^4(CR^6R^7)_vNR^5$-Heterocyclyl, —$O(CR^6R^7)_vNR^5$-Heteroaryl, —$O(CR^6R^7)_vNR^5$-Heterocyclyl, —$O(CR^6R^7)_v$O-Heterocyclyl, —$NR^4R^5R^{9+}Q^-$, —$(CR^6R^7)_vNR^4R^5R^{9+}Q^-$, —$NR^4(CR^6R^7)_vNR^4R^5R^{9+}Q^-$, —$NR^4R^{9+}(CR^6R^7)_vNR^4R^5R^{9+}Q^-_2$, —$(CR^6R^7)_v(T)^+Q^-$, and —$O(CR^6R^7)_vNR^4R^5R^{9+}Q^-$;

wherein:
each T is independently selected from the group consisting of pyridine-1-yl, pyrimidin-1-yl, and thiazol-3-yl;

each Q is independently a pharmaceutically acceptable counterion; and each v is independently 1, 2, 3, or 4;

or Y taken together with the carbon atom to which it is attached forms an optionally substituted spiro-carbocycle or optionally substituted spiro-heterocycle;

or two Ys taken together with the carbon atoms to which they are attached form an optionally substituted carbocycle or an optionally substituted heterocycle;

each $R^6$ and $R^7$ is independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{10}$, —$SR^{10}$, —$NR^4R^5$, —$NR^4C(O)R^5$, —$NR^4C(O)OR^5$, —$NR^4C(O)NR^5$, —$C(O)OR^5$, —$C(O)NR^4R^5$, —$C(N$=$NR^5)NR^4R^5$, —$NR^4SO_2R^5$, optionally substituted heterocyclyl, optionally substituted aryl, and optionally substituted heteroaryl;

or $R^6$ and $R^7$ taken together form an oxo, oxime, or an optionally substituted carbocycle or an optionally substituted heterocycle with the carbon to which they are attached;

each $R^9$ is independently optionally substituted $C_1$-$C_6$ alkyl. In some embodiments, at least one Y comprises 1-6 basic nitrogen atoms. In some embodiments, at least one Y comprises 1, 2 or 3 basic nitrogen atoms. In some embodiments, at least one Y comprises 2 basic nitrogen atoms.

In some embodiments of a compound of Formula I or Formula Ia, at least one Y is selected from the group consisting fluoro, chloro, optionally substituted $C_1$-$C_6$ alkyl, =O, —OH, —$OR^{10}$, —$NR^4R^5$, —$(CR^6R^7)_vNR^4R^5$, —$NR^4(CR^6R^7)_vNR^4R^5$, —$(CR^6R^7)_vNR^4(CR^6R^7)_vNR^4R^5$, —$NR^4(CR^6R^7)_vR_6$, —$NR^4(CR^6R^7)_v$Heterocyclyl-C(=$NR^5$)$NR^4R^5$, —$NR^4(CR^6R^7)_vNR^4C$(=$NR^4$)$NR^4R^5$, —$NR^4(CR^6R^7)_vNR^4(CR^6R^7)_vNR^4R^5$, —$O(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C$(=$NR^7$)$NR^4(CR^6R^7)_vNR^4R^5$, —$N(R^4)C$(=$NR^5$)$R^6$, —$(CR^6R^7)_vN(R^4)C$(=$NR^5$)$R^6$, —$NR^4(CR^6R^7)_vN(R^4)C$(=$NR^5$)$R^6$, —$O(CR^6R^7)_vN(R^4)C$(=$NR^5$)$R^6$, —$(CR^6R^7)_vC$(=$NR^5$)$NR^4R^5$, —$NR^4(CR^6R^7)_vC$(=$NR^5$)$NR^4R^5$, —$O(CR^6R^7)_vC$(=$NR^5$)$NR^4R^5$, —$(CR^6R^7)_vN(R^4)C$(=$NR^5$)$NR^4R^5$, —$NR^4(CR^6R^7)_vN(R^4)C$(=$NR^5$)$NR^4R^5$, —$O(CR^6R^7)_vN(R^4)C$(=$NR^5$)$NR^4R^5$, —$NR^4C$(=$NR^5$)$NR^4C$(=$NR^5$)$NR^4R^5$, —$(CR^6R^7)_vC$(=$NR^4$)$NR^5C$(=$NR^4$)$NR^4R^5$, —$NR^4(CR^6R^7)_vC$(=$NR^4$)$NR^5C$(=$NR^4$)$NR^4R^5$, —$O(CR^6R^7)_vC$(=$NR^4$)$NR^5C$(=$NR^4$)$NR^4R^5$, —$NR^4C$(=$NR^5$)$NR^4R^5$, —$C$(=$NR^4$)$NR^4R^5$, —$C$(=$NR^4$)$NR^4C(O)R^6$, —$NR^4SO_2R^6$, —$NR^4C(O)R^6$, —$NR^4C$(=$O$)$OR^6$, —$C(O)NR^4R^5$, —$(CR^6R^7)_vC(O)NR^4R^5$, -Heteroaryl-$NR^4R^5$, -Heterocyclyl-$NR^4R^5$, -Heteroaryl-$N(R^4)C$(=$NR^5$)$NR^4R^5$, -Heterocyclyl-$N(R^4)C$(=$NR^5$)$NR^4R^5$, —$N(R^4)$-Heteroaryl-$NR^4R^5$, —$N(R^4)$-Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C$(=$NR^5$)$NR^4R^5$, —$(CR^6R^7)_v$Heterocyclyl-$N(R^4)C$(=$NR^5$)$NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, and —$O(CR^6R^7)_v$O-Heterocyclyl. In certain embodiments, at least one Y is selected from the group consisting fluoro, optionally substituted $C_1$-$C_6$ alkyl, —OH, —$NR^4R^5$, —$(CR^6R^7)_vNR^4R^5$, —$(CR^6R^7)_vNR^4(CR^6R^7)_vNR^4R^5$, —$NR^4(CR^6R^7)_vR_6$, —$NR^4(CR^6R^7)_v$Heterocyclyl-C(=$NR^5$)$NR^4R^5$, —$NR^4(CR^6R^7)_vNR^4C$(=$NR^4$)$NR^4R^5$, —$NR^4(CR^6R^7)_vNR^4R^5$, —$(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C$(=$NR^7$)$NR^4(CR^6R^7)_vNR^4R^5$, —$N(R^4)C$(=$NR^5$)$R^6$, —$(CR^6R^7)_vN(R^4)C$(=$NR^5$)$R^6$, —$NR^4(CR^6R^7)_vN(R^4)C$(=$NR^5$)$R^6$, —$(CR^6R^7)_vC$(=$NR^5$)$NR^4R^5$, —$NR^4(CR^6R^7)_vC$(=$NR^5$)$NR^4R^5$, —$(CR^6R^7)_vN(R^4)C$(=$NR^5$)$NR^4R^5$, —$NR^4(CR^6R^7)_vN(R^4)C$(=$NR^5$)$NR^4R^5$, —$NR^4C$(=$NR^5$)$NR^4C$(=$NR^5$)$NR^4R^5$, —$(CR^6R^7)_vC$(=$NR^4$)$NR^5C$(=$NR^4$)$NR^4R^5$, —$NR^4(CR^6R^7)_vC$(=$NR^4$)$NR^5C$(=$NR^4$)$NR^4R^5$, —$NR^4C$(=$NR^5$)$NR^4R^5$, —$C$(=$NR^4$)$NR^4R^5$, —$C$(=$NR^4$)$NR^4C(O)R^6$, —$NR^4C(O)R^6$, —$(CR^6R^7)_vC(O)NR^4R^5$, -Heterocyclyl-$NR^4R^5$, -Heterocyclyl-$N(R^4)C$(=$NR^5$)$NR^4R^5$, —$N(R^4)$-Heterocyclyl-$NR^4R^5$, —$(CR^6R^7)_v$Heterocyclyl-$NR^4R^5$, —$(CR^6R^7)_v$Heterocyclyl-$N(R^4)C$(=$NR^5$)$NR^4R^5$, —$(CR^6R^7)_v$Heterocyclyl, and —$NR^4(CR^6R^7)_v$Heterocyclyl. In further embodiments, at least one Y is selected from the group consisting of -Heteroaryl-$NR^4R^5$, -Heterocyclyl-$NR^4R^5$, -Heteroaryl-$N(R^4)C$(=$NR^5$)$NR^4R^5$, -Heterocyclyl-$N(R^4)C$(=$NR^5$)$NR^4R^5$, —$N(R^4)$-Heteroaryl-$NR^4R^5$, —$N(R^4)$-Heterocyclyl-$NR^4R^5$, -Heteroaryl-C(=$NR^5$)$NR^4R^5$, -Heterocyclyl-C(=$NR^5$)$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C$(=$NR^5$)$NR^4R^5$, and —$(CR^6R^7)_v$Heterocyclyl-$N(R^4)C$(=$NR^5$)$NR^4R^5$. In preferred embodiments, at least one Y is selected from the group consisting of —$NR^4R^5$, —$NR^4C$(=$NR^5$)$NR^4R^5$, —$C$(=$NR^4$)$NR^4R^5$, —$N(R^4)C$(=$NR^5$)$R^6$, —$(CR^6R^7)_vNR^4R^5$, —$(CR^6R^7)_vN(R^4)C$(=$NR^5$)$NR^4R^5$, —$NR^4(CR^6R^7)_vNR^4R^5$, —$NR^4(CR^6R^7)_vOR^{10}$, —$(CR^6R^7)_vNR^4(CR^6R^7)_vNR^4R^5$, $NR^5C$(=$NR^5$)$NR^4(CR^6R^7)_vNR^4R^5$, —$NR^4(CR^6R^7)_vN(R^4)C$(=$NR^5$)$NR^4R^5$, —$NR^5C(O)CR^6(NR^4R^5)(CR^6R^7)_vNR^4R^5$, —$(CR^6R^7)_vC$(=$NR^5$)$NR^4R^5$, —$(CR^6R^7)_vN(R^4)C(O)(CR^6R^7)_vNR^4R^5$, —$C$(=$NR^4$)$NR^4C(O)R^6$, —$NR^4(CR^6R^7)_v$Heteroaryl, and —$O(CR^6R^7)_vNR^4R^5$.

In some embodiments, p is 0, 1, 2, 3, or 4. In certain embodiments, p is 1 or 2. In some embodiments, p is 1.

In some embodiments of a compound of Formula I or Formula Ia, $R^4$ and $R^5$ are independently selected from the group consisting of hydrogen, —OH, optionally substituted $C_1$-$C_6$ alkyl, optionally substituted alkoxyalkyl, optionally substituted hydroxyalkyl, and optionally substituted heterocyclyl. In preferred embodiments, $R^4$ and $R^5$ are independently hydrogen or optionally substituted $C_1$-$C_6$ alkyl.

In some embodiments of a compound of Formula I or Formula Ia, $R^6$ and $R^7$ are independently selected from the group consisting of hydrogen, optionally substituted $C_1$-$C_6$ alkyl, —OH, —$NR^4R^5$, and optionally substituted heterocyclyl, or $R^6$ and $R^7$ taken together form an optionally substituted heterocycle with the carbon to which they are attached. In preferred embodiments, $R^6$ and $R^7$ are independently hydrogen, fluoro, or optionally substituted $C_1$-$C_6$ alkyl. In some embodiments,

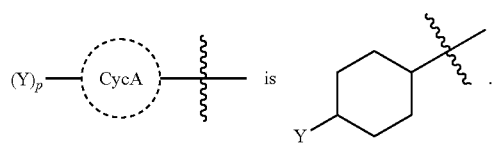

In some embodiments,

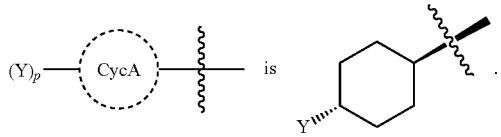

In some embodiments, Y is —NR$^4$(CR$^6$R$^7$)$_v$NR$^4$R$^5$. In some embodiments, Y is —NR$^4$(CR$^6$R$^7$)$_v$NR$^4$C(=NR$^4$)NR$^4$R$^5$. In some embodiments, Y is —NR$^4$R$^5$. In other embodiments, Y is —NR$^4$C(=NR$^4$)NR$^4$R$^5$. In some embodiments, Y is —(CR$^6$R$^7$)$_v$NR$^4$R$^5$. In some embodiments, Y is (CR$^6$R$^7$)$_v$NR$^4$C(=NR$^4$)NR$^4$R$^5$. In some embodiments, v is 2. In some embodiments, v is 1. In some embodiments, each R$^4$ and R$^5$ is selected from H, optionally substituted C$_1$-C$_6$ alkyl or optionally substituted C$_3$-C$_6$ cycloalkyl. In some embodiments, each R$^4$, R$^6$, and R$^7$ is H.

In certain embodiments of a compound of Formula I or Formula Ia, the compound is selected from the group represented by the following structures:

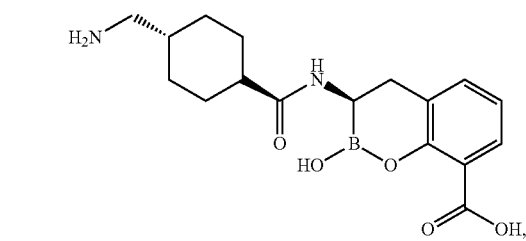

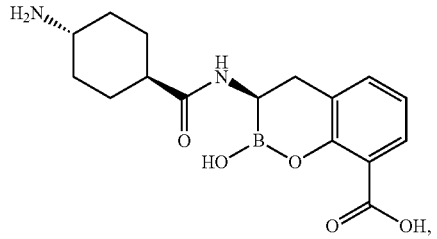

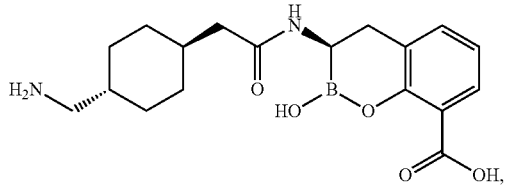

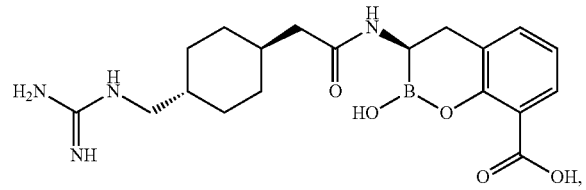

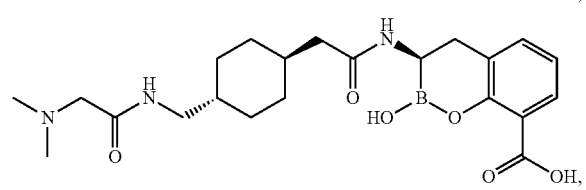

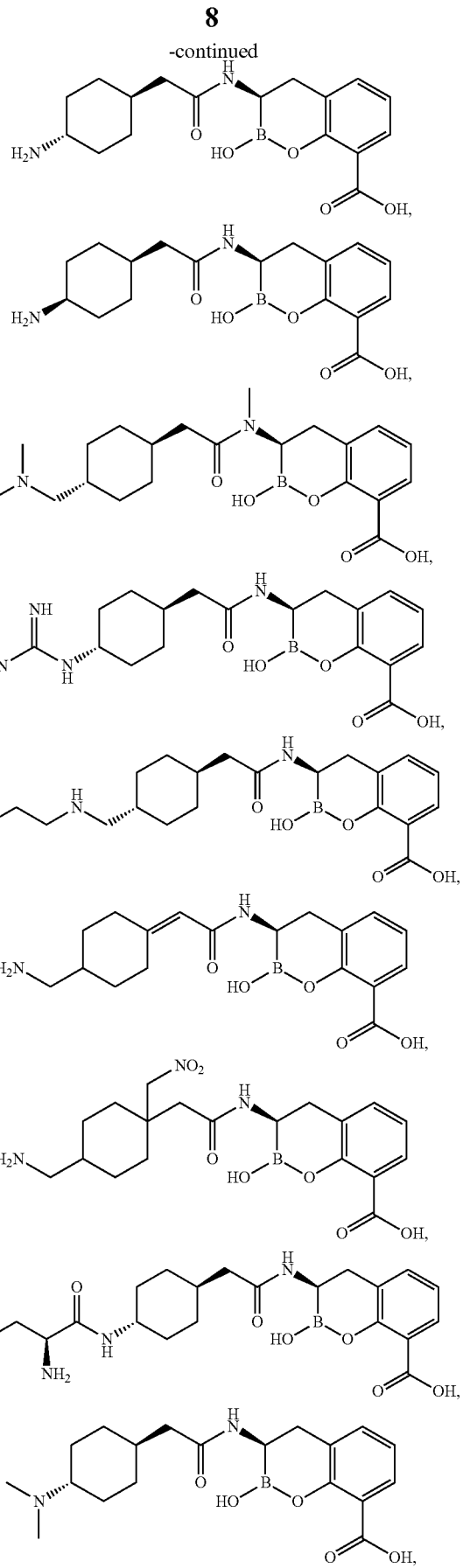

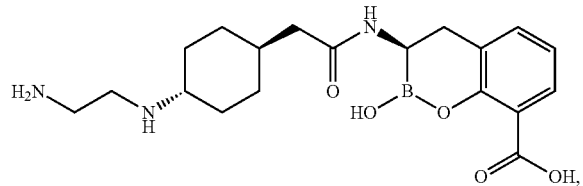
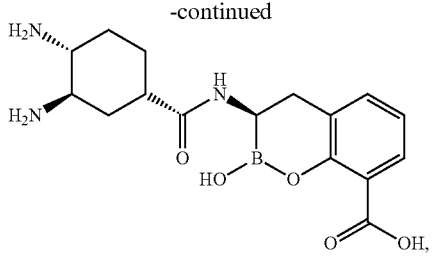
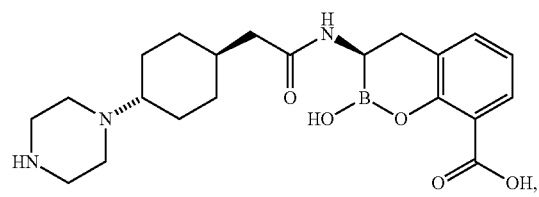
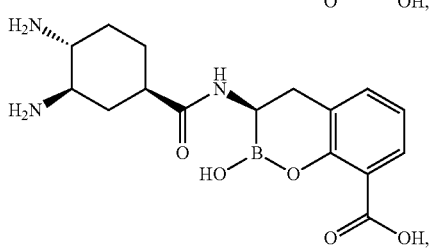
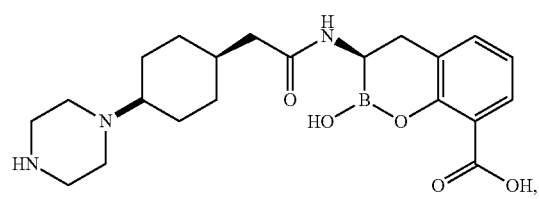
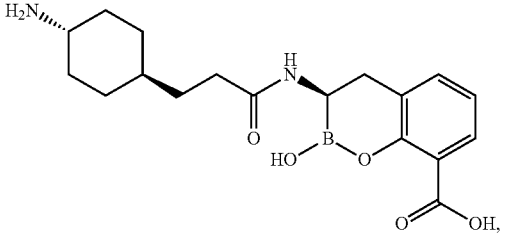
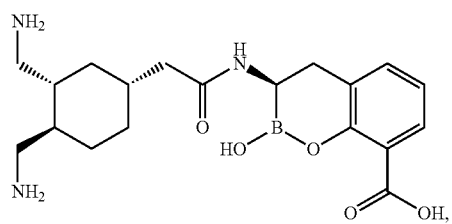
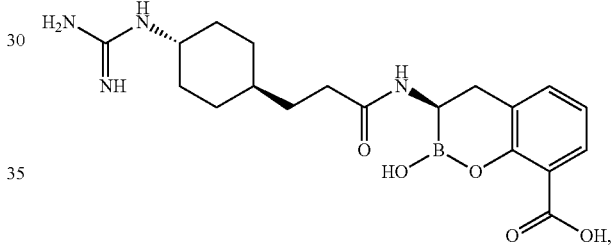
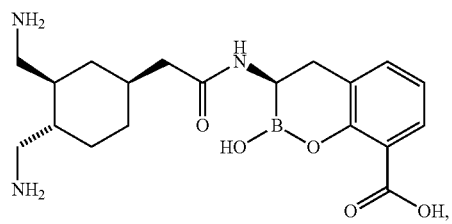
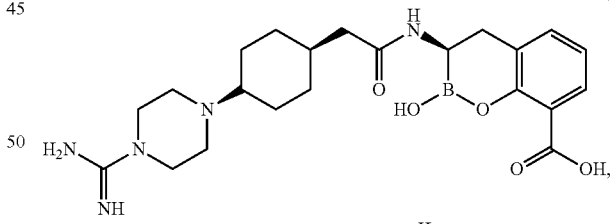
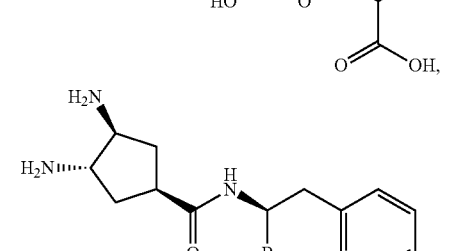
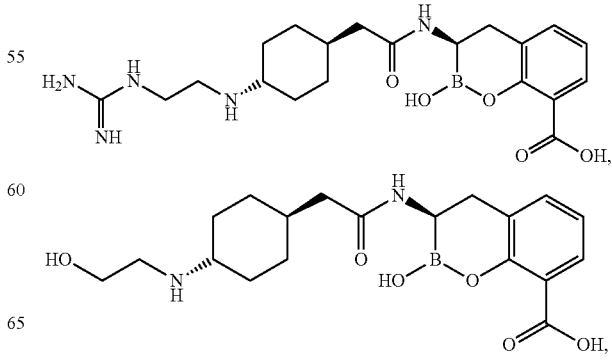

-continued
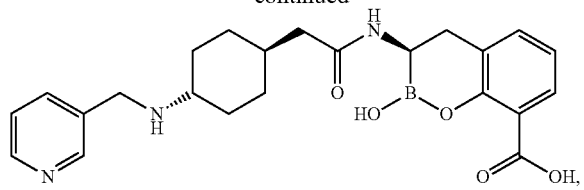
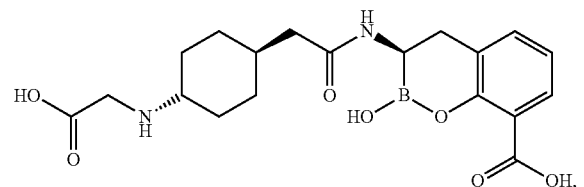
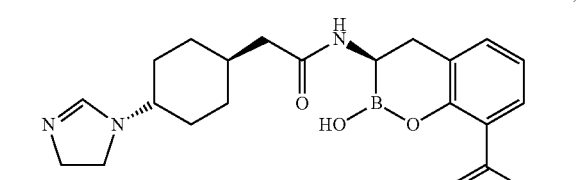
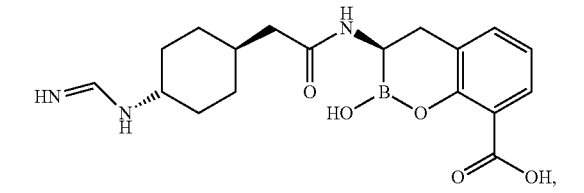
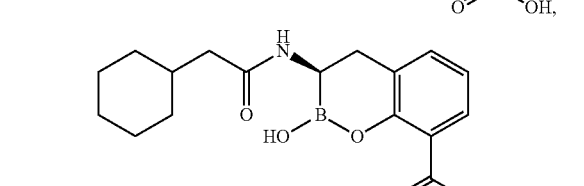
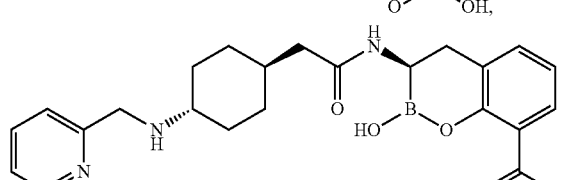
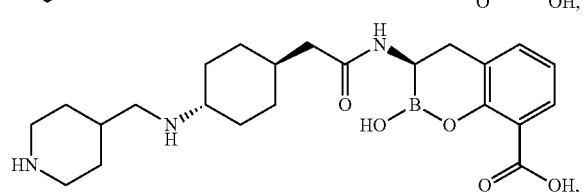
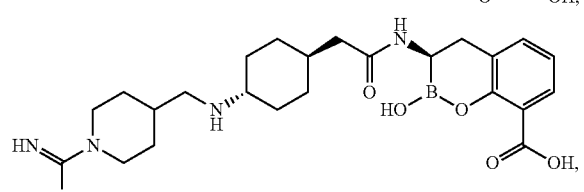
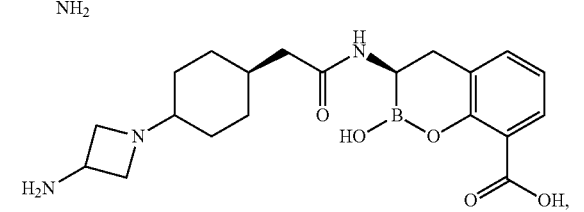
-continued
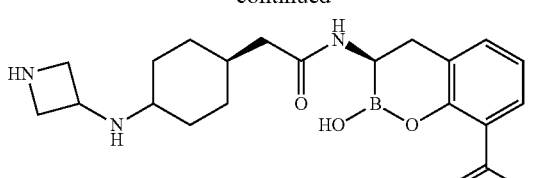
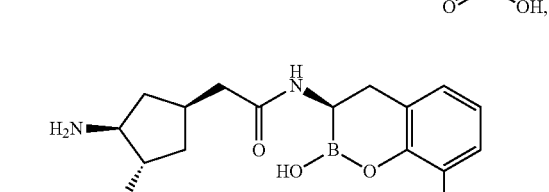
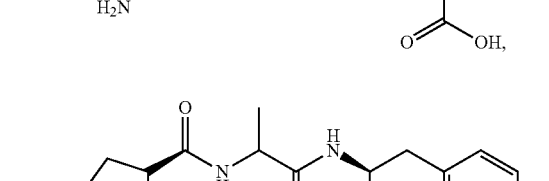
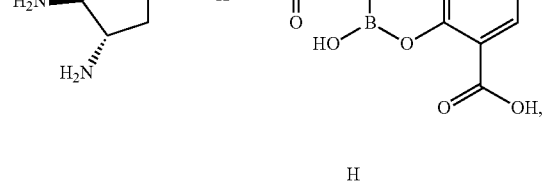
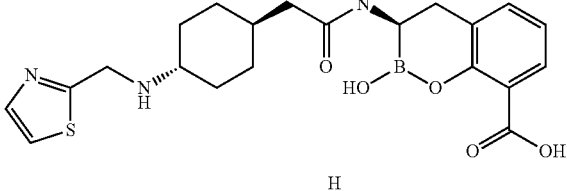
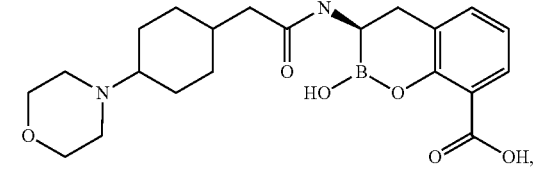
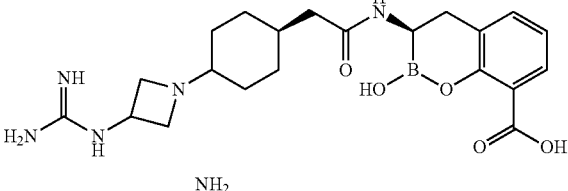
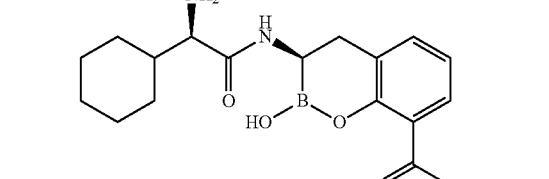
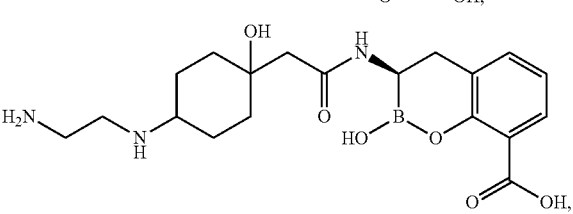

13
-continued
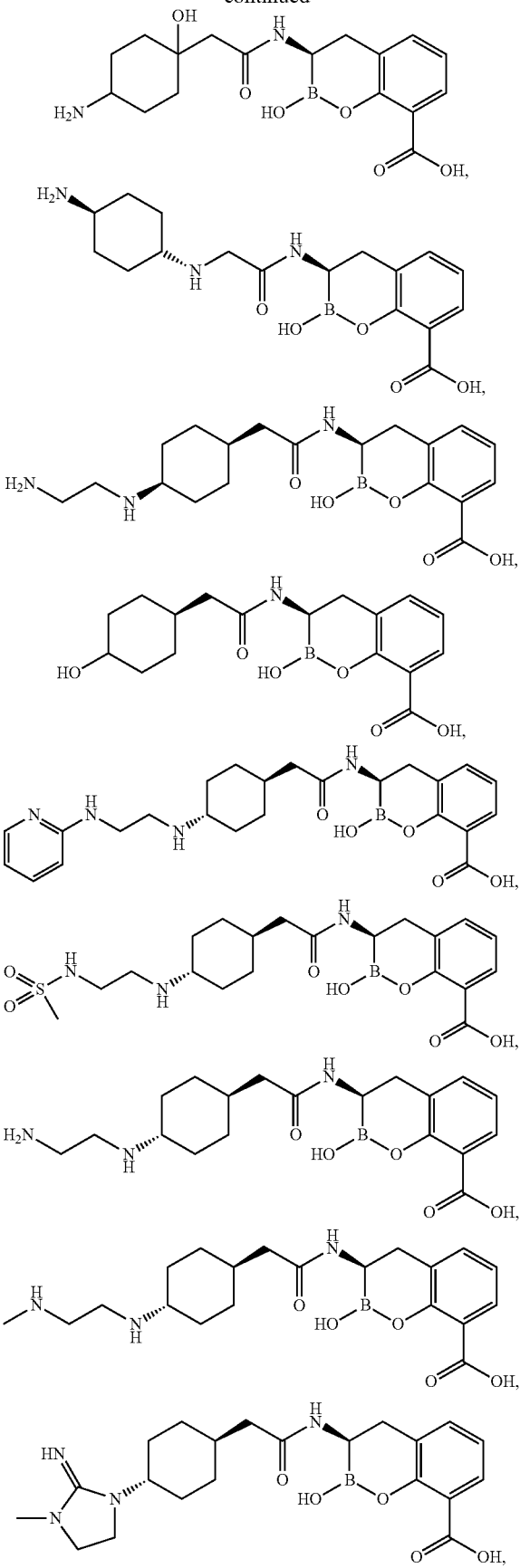
14
-continued
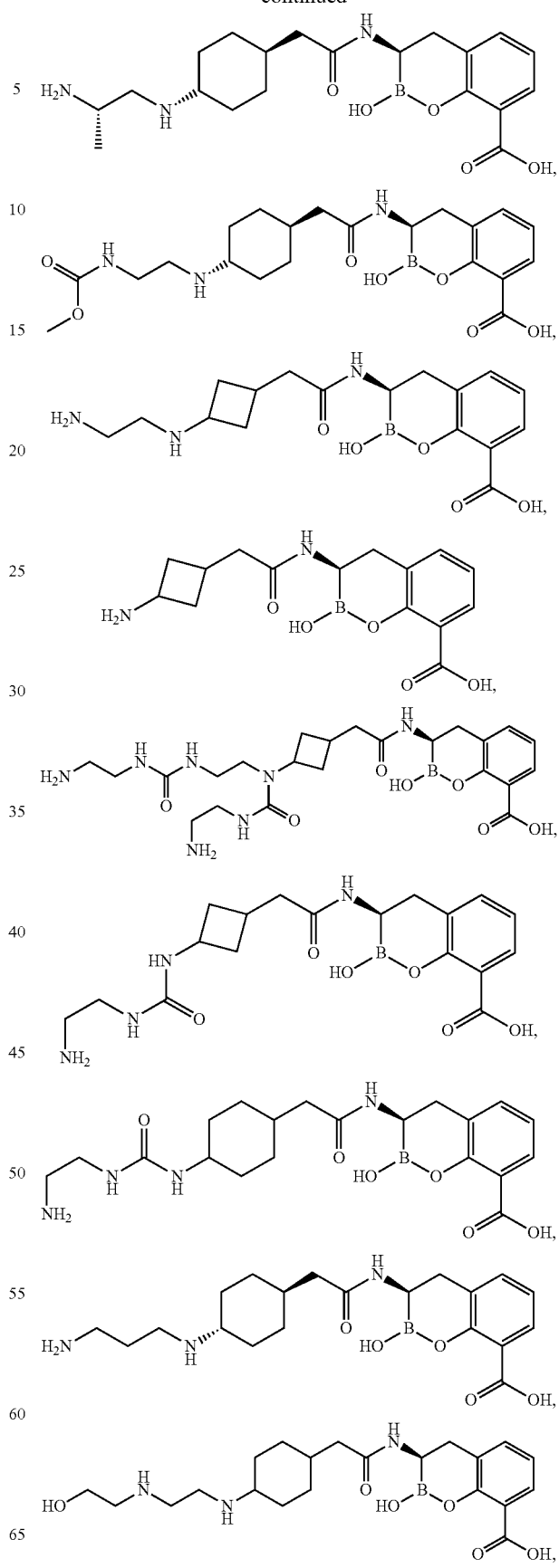

15
-continued
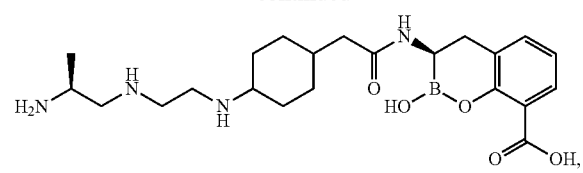
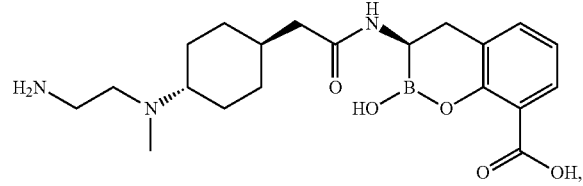
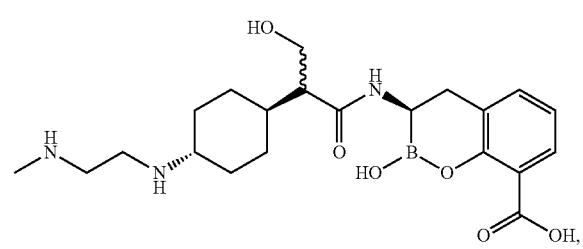
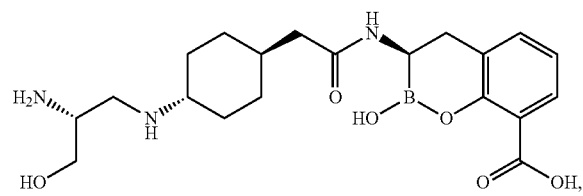
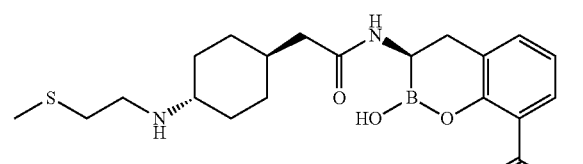
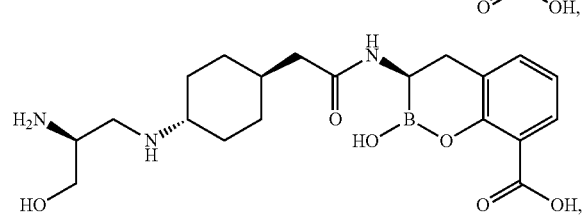
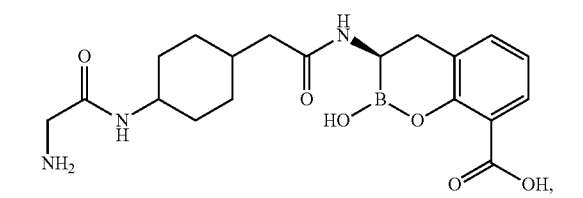
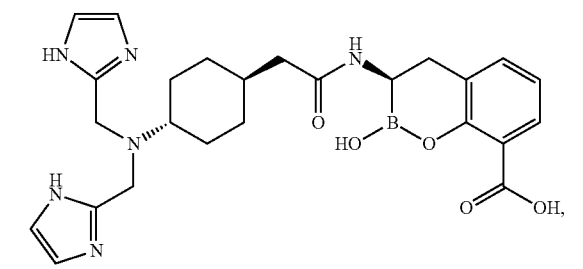
16
-continued
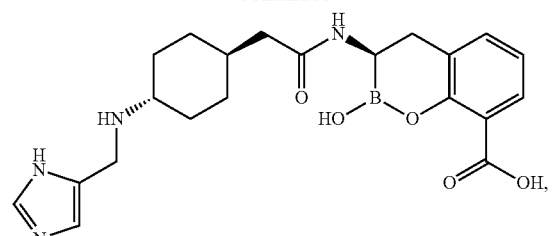
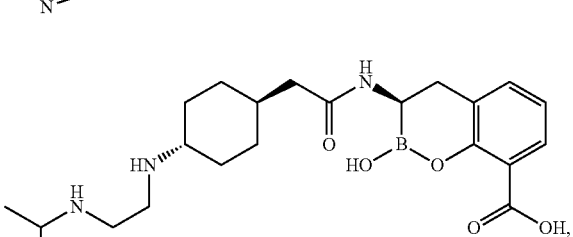
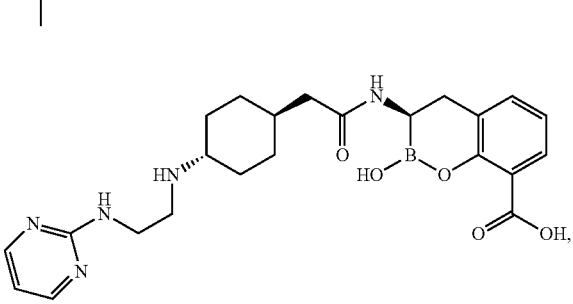
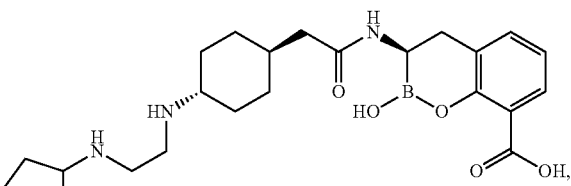
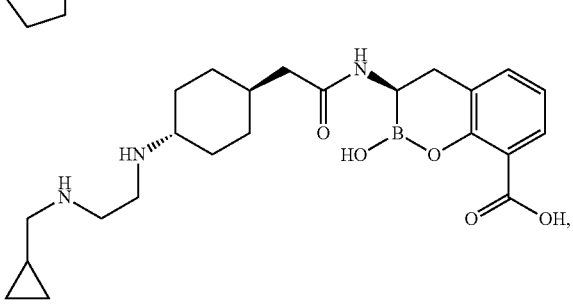
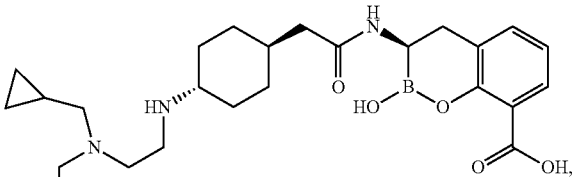
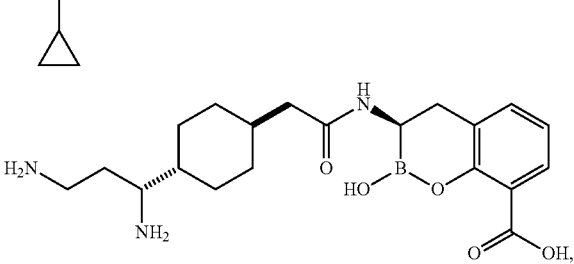

-continued
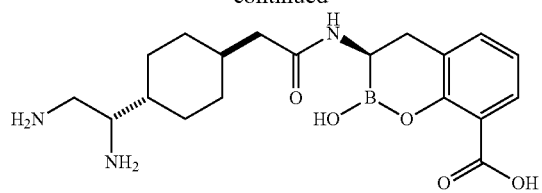
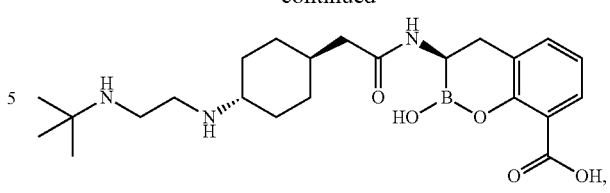
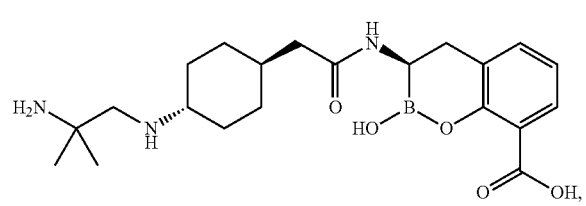
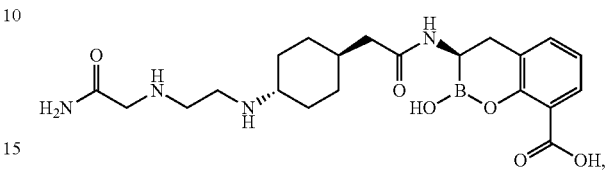
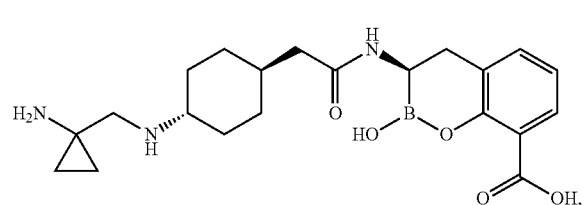
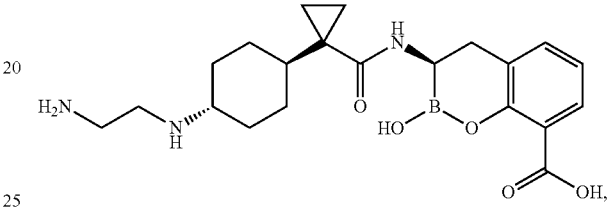
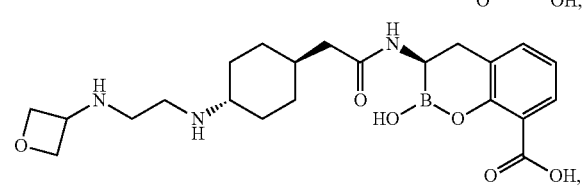
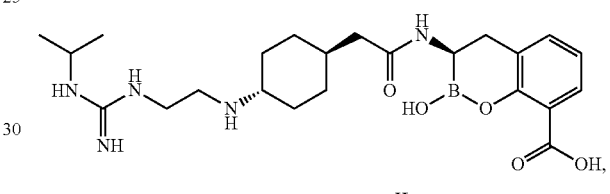
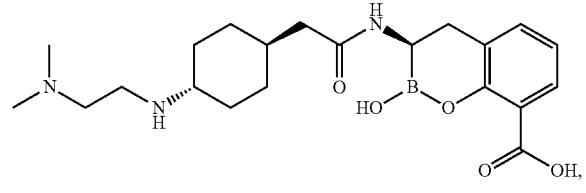
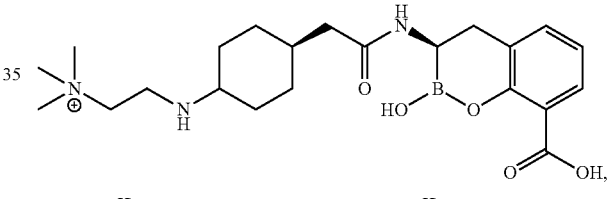
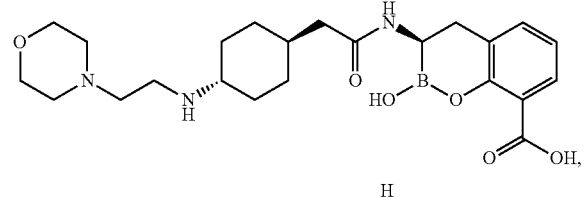
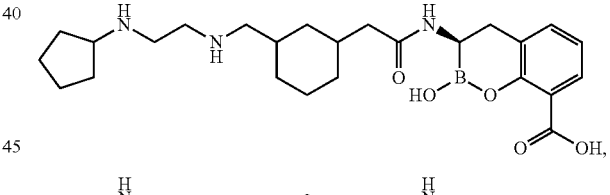
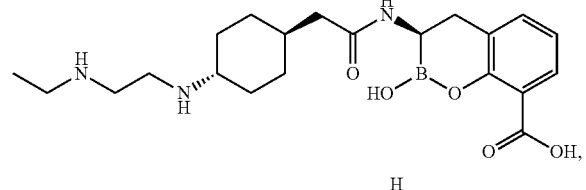
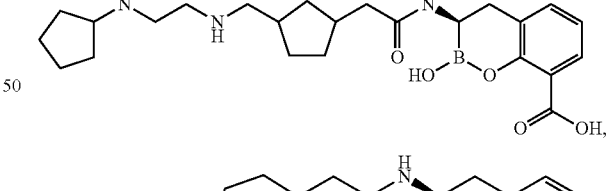
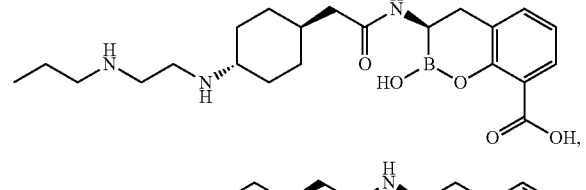
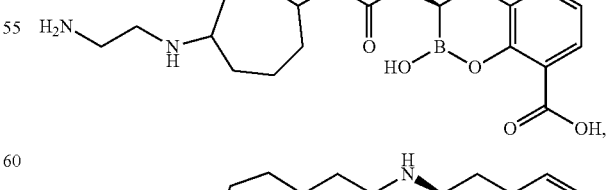
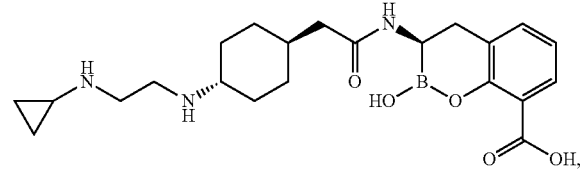
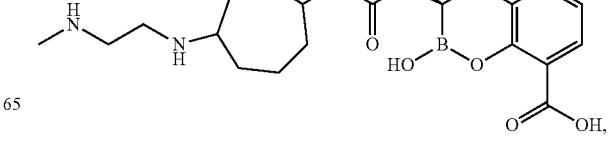

-continued

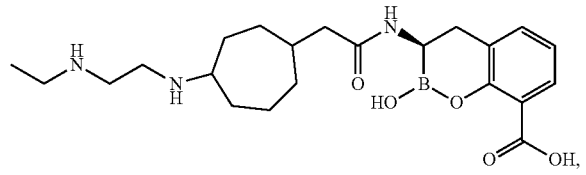

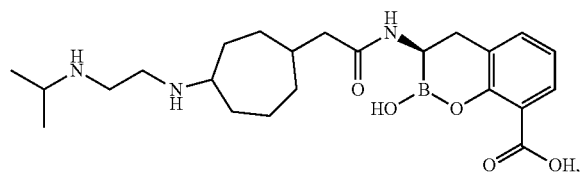

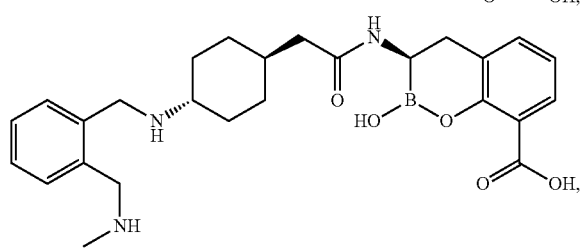

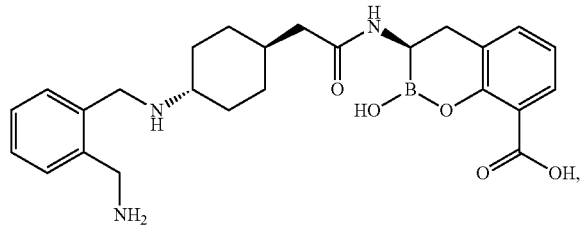

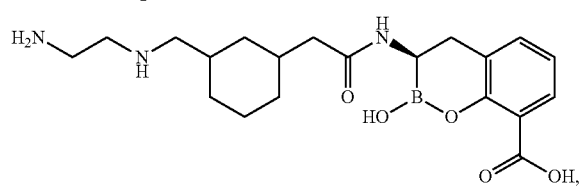

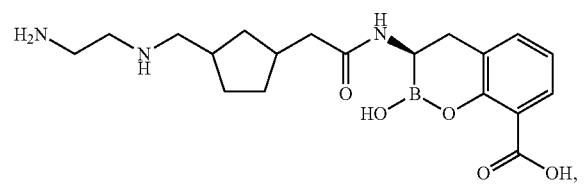

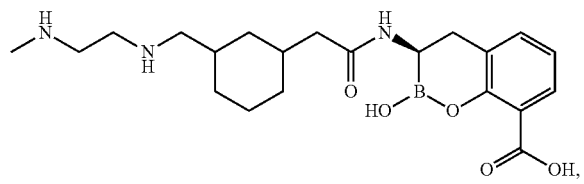

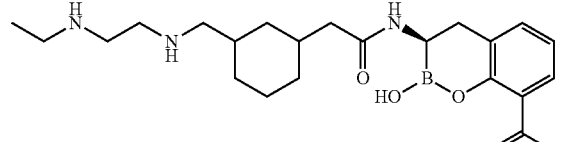

-continued

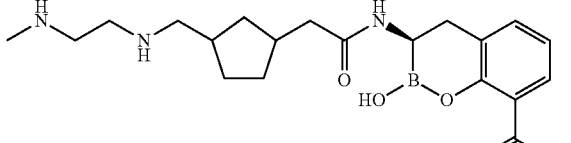

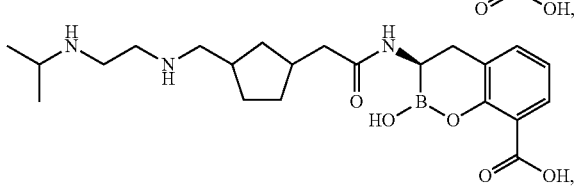

or a pharmaceutically acceptable salt, solvate, polymorph, stereoisomer, tautomer, prodrug, metabolite, N-oxide, or isomer thereof, wherein the compound is present in a closed, cyclic form according to Formula I and as shown in the structures above, an open, acyclic form according to Formula Ia, or mixtures thereof. In some embodiments, the compound of Formula I or Formula Ia is the stereoisomer represented by any of the structures above. In some embodiments, the compound of Formula I or Formula Ia is an enantiomer of the stereoisomer represented by any of the structures above. In certain embodiments, the compound of Formula I or Formula Ia is a diastereomer of the stereoisomer represented by any of the structures above. In some embodiments, the compound of Formula I or Formula Ia is a mixture of enantiomers and/or diastereomers of the stereoisomer represented by any of the structures above. In certain embodiments, the compound of Formula I or Formula Ia is a racemate of the stereoisomer represented by any of the structures above.

In another aspect, provided herein are pharmaceutical compositions comprising a compound Formula I or Formula Ia as described herein, or a pharmaceutically acceptable salt, solvate, polymorph, stereoisomer, tautomer, prodrug, metabolite, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In a further aspect, provided herein are methods of treating a bacterial infection in a subject, comprising administering to the subject a pharmaceutical composition as described herein, optionally in combination with a beta-lactam antibiotic. In certain embodiments, the methods of treating a bacterial infection in a subject comprise administering to the subject a pharmaceutical composition as described herein in combination with a betalactam antibiotic

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases—for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases—as well as Class B metallo-beta-lactamases (e.g. VIM, NDM) has begun to diminish the utility of the beta-lactam antibiotic family, including the more recent generation beta-lactam drugs, leading to a serious medical problem. Indeed the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These beta-lactamase inhibitors are poorly active against the diversity of beta-lactamase enzymes (both serine- and metallo-based) now emerging clinically. In addition, these enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta-lactamase inhibitors are largely ineffective against the new Class A and Class B carbapenemases, against the chromosomal and plasmid-mediated Class C cephalosporinases and against many of the Class D oxacillinases.

To address this growing therapeutic vulnerability, and because there are three major molecular classes of serine-based beta-lactamases, and one major class of metallo-beta-lactamases, and each of these classes contain significant numbers of beta-lactamase variants, we have identified an approach for developing novel beta-lactamase inhibitors with broad spectrum functionality. In particular, we have identified an approach for developing compounds that are active against both serine- and metallo-based beta-lactamase enzymes. Compounds of the current invention demonstrate potent activity across all four major classes of beta-lactamases.

The present invention is directed to certain boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

DEFINITIONS

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase. β-Lactamases of interest include those disclosed in an ongoing website that monitors beta-lactamase nomenclature (www.lahey.org) and in Bush, K. and G. A. Jacoby. 2010. An updated functional classification of β-lactamases. Antimicrob. Agents Chemother. 54:969-976. β-Lactamases of particular interest herein include β-lactamases found in bacteria such as class A β-lactamases including the SHV, CTX-M and KPC subclasses, class B β-lactamases such as VIM, class C β-lactamases (both chromosomal and plasmid-mediated), and class D β-lactamases. The term "β-lactamase inhibitor" refers to a compound which is capable of inhibiting β-lactamase activity Inhibiting β-lactamase activity means inhibiting the activity of a class A, B, C, or β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in Bush, K. and G. A. Jacoby. 2010. An updated functional classification of β-lactamases. Antimicrob. Agents Chemother. 54:969-976.

The terms below, as used herein, have the following meanings, unless indicated otherwise:

"Amino" refers to the —NH$_2$ radical.

"Cyano" or "nitrile" refers to the —CN radical.

"Hydroxy" or "hydroxyl" refers to the —OH radical.

"Nitro" refers to the —NO$_2$ radical.

"Oxo" refers to the =O substituent.

"Oxime" refers to the =N—OH substituent.

"Thioxo" refers to the =S substituent.

"Alkyl" refers to an optionally substituted straight-chain, or optionally substituted branched-chain saturated hydrocarbon monoradical having from one to about ten carbon atoms, more preferably one to six carbon atoms, wherein an sp3-hybridized carbon of the alkyl residue is attached to the rest of the molecule by a a single bond. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. Unless stated otherwise specifically in the specification, an alkyl group may be optionally substituted as described below, for example, with oxo, amino, nitrile, nitro, hydroxyl, alkyl, alkylene, alkynyl, alkoxy, aryl, cycloalkyl, heterocyclyl, heteroaryl, and the like.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a a single bond. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butyryl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

"Alkylene" or "alkylene chain" refers to a straight or branched divalent hydrocarbon chain. Unless stated otherwise specifically in the specification, an alkylene group may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cyclohexenyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

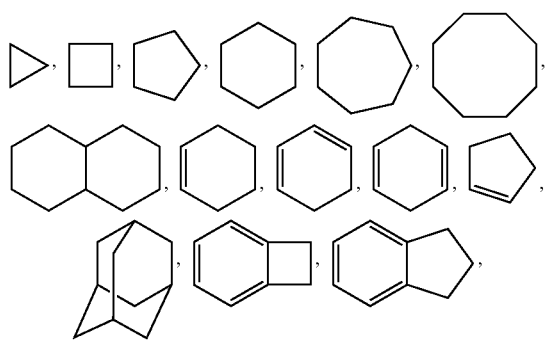

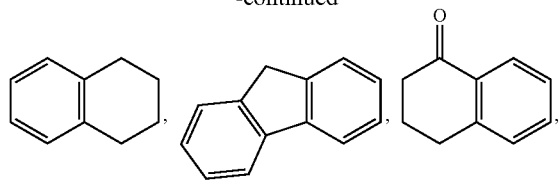

and the like.

"Aralkyl" means an (alkylene)-R radical where R is aryl as defined above.

"Cycloalkylalkyl" means a (alkylene)-R radical where R is cycloalkyl as defined above; e.g., cyclopropylmethyl, cyclobutylmethyl, cyclopentylethyl, or cyclohexylmethyl, and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo

[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarity, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

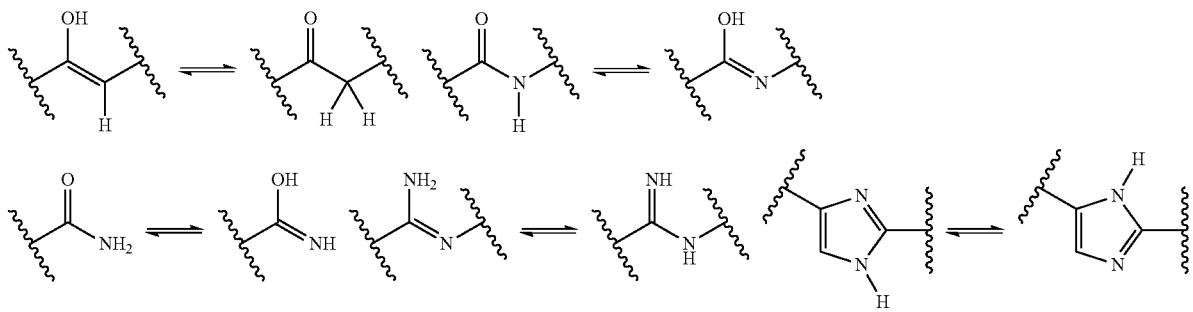

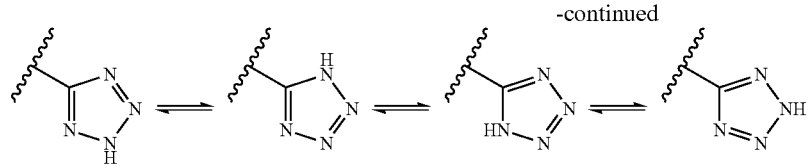

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

Described herein are compounds that modulate the activity of beta-lactamase. In some embodiments, the compounds described herein inhibit beta-lactamase. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula I or Formula Ia, or pharmaceutically acceptable salts, solvates, polymorphs, stereoisomers, tautomers, prodrugs, metabolites, N-oxides, or isomers thereof:

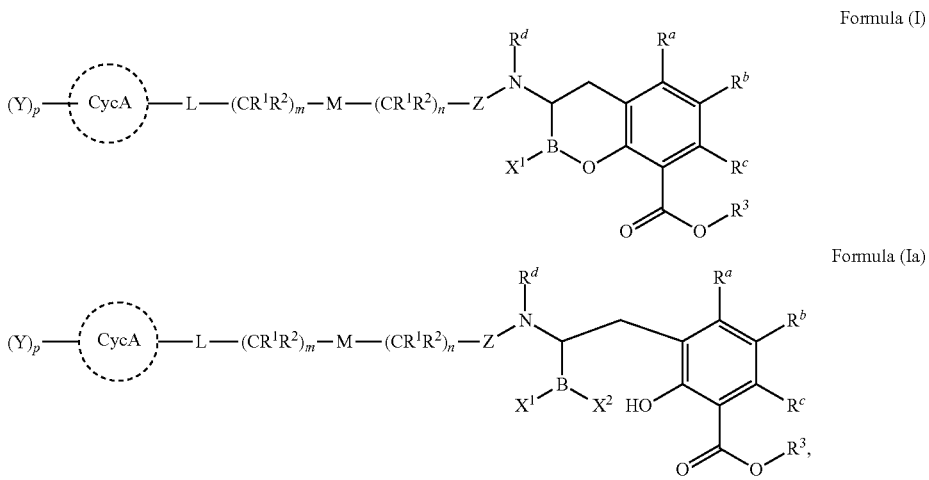

Formula (I)

Formula (Ia)

wherein:
L is a bond, $CR^1R^2$, >C=O, or =$CR^1$—;
M is a bond, —O—, —S—, —S(O)—, $SO_2$, or —N($R^4$)—;
m is 0, 1, or 2;
n is 0, 1, 2, or 3;
  provided that
    when n is 0, then M is a bond;
p is 0, 1, 2, 3, or 4;
  provided that
    when p is 0, then L is —$CR^1R^2$— or =$CR^1$—;
$X^1$ and $X^2$ are independently selected from —OH, —$OR^8$, or F;
Z is >C=O, >C=S, or >$SO_2$;
CycA is an optionally substituted 3-10 membered non-aromatic carbocycle, wherein an optional olefin functionality of the nonaromatic carbocycle is not directly attached to an oxygen, sulfur, or nitrogen substituent;
$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —$OR^{10}$, —$NR^4R^5$, and —$SR^{10}$;
each $R^1$ and $R^2$ is independently selected from the group consisting of hydrogen, fluoro, chloro, bromo, optionally substituted $C_1$-$C_6$ alkyl, optionally substituted $C_3$-$C_6$ cycloalkyl, —OH, —$OR^{10}$, —$SR^{10}$, and —$NR^4R^5$, or $R^1$ and $R^2$ taken together form an oxo, oxime, or an optionally substituted carbocycle or optionally substituted heterocycle with the carbon to which they are attached;

$R^3$ is hydrogen, optionally substituted $C_1$-$C_6$ alkyl, or a pharmaceutically acceptable prodrug; each $R^d$, $R^4$, and $R^5$ is independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^4$ and $R^5$ taken together form an optionally substituted heterocycle with the nitrogen to which they are attached;

$R^8$ is optionally substituted $C_1$-$C_6$ alkyl, optionally substituted $C_3$-$C_6$ cycloalkyl, or a pharmaceutically acceptable boronate ester group;

$R^{10}$ is optionally substituted $C_1$-$C_6$ alkyl or optionally substituted $C_3$-$C_6$ cycloalkyl;

and each Y is independently a group comprising 1-50 non-hydrogen atoms selected from the group consisting of C, N, O, S, and P.

In some embodiments of a compound of Formula I or Formula Ia, $R^a$, $R^b$, and $R^c$ are independently selected from the group consisting of hydrogen, fluoro, chloro, optionally substituted $C_1$-$C_6$ alkyl, optionally substituted $C_3$-$C_6$ cycloalkyl, —OH, —$OR^{10}$, —$NR^4R^5$, and —$SR^{10}$. In certain embodiments, $R^a$, $R^b$, and $R^c$ are independently hydrogen, fluoro, or chloro. In preferred embodiments, $R^a$, $R^b$, and $R^c$ are hydrogen.

In some embodiments of a compound of Formula I or Formula Ia, $R^3$ is hydrogen, methyl, ethyl, propyl, butyl, or isopropyl. In preferred embodiments, $R^3$ is hydrogen.

In some embodiments of a compound of Formula I or Formula Ia, $X^1$ and $X^2$ are OH.

In some embodiments of a compound of Formula I or Formula Ia, $R^d$ is hydrogen or $C_1$-$C_4$-alkyl. In some embodiments, $R^d$ is methyl. In preferred embodiments, $R^d$ is hydrogen.

In some embodiments of a compound of Formula I or Formula Ia, Z is Z is >C=O or >$SO_2$. In preferred embodiments, Z is >C=O.

In some embodiments of a compound of Formula I or Formula Ia, L is —$CR^1R^2$— or =$CR^1$—. In certain embodiments, L is a bond. In some embodiments of a compound of Formula I or Formula Ia, M is —O—, —S—, —$SO_2$—, or —$N(R^4)$—. In certain embodiments, M is a bond or —O—. In further embodiments, M is a bond. In some embodiments of a compound of Formula I or Formula Ia, m is 0 or 1. In certain embodiments, m is 0. In other embodiments, m is 1. In some embodiments of a compound of Formula I or Formula Ia, n is 1 or 2. In certain embodiments, n is 1. In further embodiments, n is 0. In other embodiments, n is 2. In some embodiments, m and n are 0. In certain embodiments, and m or n are 1.

In some embodiments of a compound of Formula I or Formula Ia, L is —$CR^1R^2$— or =$CR^1$—; M is —O—, —S—, —$SO_2$—, or —$N(R^4)$—; m is 0 or 1; and n is 1 or 2. In certain embodiments, L is a bond, —$CR^1R^2$—, or =$CR^1$—; M is a bond or —O—; m is 0; and n is 1 or 2. In further embodiments, L is a bond or >C=O; M is a bond or —$N(R^4)$—; and m and n are 0. In some embodiments, L is >C=O; M is —$N(R^4)$—; and m and n are 0. In certain embodiments, L is a bond; M is a bond; and m and n are 0. In other embodiments, L is a bond; M is a bond; and m or n are 1. In some embodiments, L is —$CR^1R^2$— or =$CR^1$—; M is a bond; and m and n are 0. In certain embodiments, L is —$CR^1R^2$— or =$CR^1$—; M is a bond; and m or n are 1.

In some embodiments of a compound of Formula I or Formula Ia, CycA is selected from the group consisting of cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent. In certain embodiments, CycA is cyclobutane, cyclopentane, cyclohexane, or cyclohexene, wherein the olefin functionality of the cyclohexene is not directly attached to an oxygen, sulfur, or nitrogen substituent. In other embodiments, CycA is selected from the group consisting of bicyclo[3.3.0]octane, bicyclo[4.3.0]nonane, cisdecalin, transdecalin, bicyclo[2.1.1]hexane, bicyclo[2.2.1]heptane, bicyclo[2.2.2]octane, bicyclo[3.2.2]nonane, and bicyclo[3.3.2]decane. In some embodiments, CycA is cyclopentane. In preferred embodiments, CycA is cyclohexane. In some embodiments, CycA is cyclohexane covalently bonded to one Y and L; said covalent bonds in 1,4-trans arrangement.

In some embodiments of a compound of Formula I or Formula Ia, each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, =O, —OH, —$OR^{10}$, —$SR^{10}$, —$NR^4R^5$, —$(CR^6R^7)_vNR^4R^5$, —$NR^4(CR^6R^7)_vR^6$, —$NR^4(CR^6R^7)_v$Heterocyclyl-C(=$NR^5$)$NR^4R^5$, —$NR^4(CR^6R^7)_vNR^4C(=NR^4)NR^4R^5$, —$NR^4(CR^6R^7)_vNR^4(CR^6R^7)_vNR^4R^5$, —$NR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$S(O)_{0,1,2}(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$S(O)_{0,1,2}(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$S(O)_{0,1,2}(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$S(O)_{0,1,2}(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, —$SO_2NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$-Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —NR⁴(CR⁶R⁷)ᵥHeterocyclyl, —O(CR⁶R⁷)ᵥHeteroaryl, —O(CR⁶R⁷)ᵥHeterocyclyl, —NR⁴(CR⁶R⁷)ᵥNR⁵-Heteroaryl, —NR⁴(CR⁶R⁷)ᵥNR⁵-Heterocyclyl, —O(CR⁶R⁷)ᵥNR⁵-Heteroaryl, —O(CR⁶R⁷)ᵥNR⁵-Heterocyclyl, —O(CR⁶R⁷)ᵥO-Heterocyclyl, —NR⁴R⁵R⁹⁺Q⁻, —(CR⁶R⁷)ᵥNR⁴R⁵R⁹⁺Q⁻, —NR⁴(CR⁶R⁷)ᵥNR⁴R⁵R⁹⁺Q⁻, —NR⁴R⁹⁺(CR⁶R⁷)ᵥNR⁴R⁵R⁹⁺Q⁻₂, —(CR⁶R⁷)ᵥ(T)⁺Q⁻, and —O(CR⁶R⁷)ᵥNR⁴R⁵R⁹⁺Q⁻;

wherein:
each T is independently pyridine-1-yl, pyrimidin-1-yl, or thiazol-3-yl;
Q is a pharmaceutically acceptable counterion; and
each v is independently 1, 2, 3, or 4;
or Y taken together with the carbon atom to which it is attached forms an optionally substituted spiro-carbocycle or optionally substituted spiro-heterocycle;
or two Ys taken together with the carbon atoms to which they are attached form an optionally substituted carbocycle or an optionally substituted heterocycle;
each R⁶ and R⁷ is independently selected from the group consisting of hydrogen, fluoro, chloro, bromo, optionally substituted C₁-C₆ alkyl, optionally substituted alkoxyalkyl, optionally substituted hydroxyalkyl, optionally substituted C₃-C₆ cycloalkyl, —NR⁴C(O)OR⁵, —NR⁴C(O)NR⁵, —C(O)OR⁵, —C(N=R⁵)NR⁴R⁵, —OH, —OR¹⁰, —SR¹⁰, —NR⁴R⁵, —NR⁴C(O)R⁵, —C(O)NR⁴R⁵, —NR⁴SO₂R⁵, optionally substituted heterocyclyl, optionally substituted aryl, and optionally substituted heteroaryl;
or R⁶ and R⁷ taken together form an oxo, oxime, or an optionally substituted carbocycle or an optionally substituted heterocycle with the carbon to which they are attached;
and each R⁹ is independently an optionally substituted C₁-C₆ alkyl.

In some embodiments of a compound of Formula I or Formula Ia, at least one Y is selected from the group consisting fluoro, chloro, optionally substituted C₁-C₆ alkyl, =O, —OH, —OR¹⁰, —NR⁴R⁵, —(CR⁶R⁷)ᵥNR⁴R⁵, —(CR⁶R⁷)ᵥNR⁴(CR⁶R⁷)ᵥNR⁴R⁵, —NR⁴(CR⁶R⁷)ᵥR₆, —NR⁴(CR⁶R⁷)ᵥHeterocyclyl-C(=NR⁵)NR⁴R⁵, —NR⁴(CR⁶R⁷)ᵥNR⁴C(=NR⁴)NR⁴R⁵, —NR⁴(CR⁶R⁷)ᵥNR⁴(CR⁶R⁷)ᵥNR⁴R⁵, —NR⁴(CR⁶R⁷)ᵥNR⁴R⁵, —O(CR⁶R⁷)ᵥNR⁴R⁵, —N(R⁴)C(O)(CR⁶R⁷)ᵥNR⁴R⁵, —N(R⁴)C(O)(CR⁶R⁷)ᵥNR⁴R⁵, —C(O)NR⁴(CR⁶R⁷)ᵥNR⁴R⁵, —S(O)₀,₁,₂NR⁴(CR⁶R⁷)ᵥNR⁴R⁵, —NR⁵C(O)NR⁴(CR⁶R⁷)ᵥNR⁴R⁵, —OC(O)NR⁴(CR⁶R⁷)ᵥNR⁴R⁵, —NR⁵C(=NR⁷)NR⁴(CR⁶R⁷)ᵥNR⁴R⁵, —N(R⁴)C(=NR⁵)R⁶, —(CR⁶R⁷)ᵥN(R⁴)C(=NR⁵)R⁶, —NR⁴(CR⁶R⁷)ᵥN(R⁴)C(=NR⁵)R⁶, —O(CR⁶R⁷)ᵥN(R⁴)C(=NR⁵)R⁶, —(CR⁶R⁷)ᵥC(=NR⁵)NR⁴R⁵, —NR⁴(CR⁶R⁷)ᵥC(=NR⁵)NR⁴R⁵, —O(CR⁶R⁷)ᵥC(=NR⁵)NR⁴R⁵, —(CR⁶R⁷)ᵥN(R⁴)C(=NR⁵)NR⁴R⁵, —NR⁴(CR⁶R⁷)ᵥN(R⁴)C(=NR⁵)NR⁴R⁵, —O(CR⁶R⁷)ᵥN(R⁴)C(=NR⁵)NR⁴R⁵, —NR⁴C(=NR⁵)NR⁴C(=NR⁵)NR⁴R⁵, —(CR⁶R⁷)ᵥC(=NR⁴)NR⁵C(=NR⁴)NR⁴R⁵, —NR⁴(CR⁶R⁷)ᵥC(=NR⁴)NR⁵C(=NR⁴)NR⁴R⁵, —O(CR⁶R⁷)ᵥC(=NR⁴)NR⁵C(=NR⁴)NR⁴R⁵, —NR⁴C(=NR⁵)NR⁴R⁵, —C(=NR⁴)NR⁴R⁵, —C(=NR⁴)NR⁴C(O)R⁶, —NR⁴SO₂R⁶, —NR⁴C(O)R⁶, —NR⁴C(=O)OR⁶, —C(O)NR⁴R⁵, —(CR⁶R⁷)ᵥC(O)NR⁴R⁵, -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, —N(R⁴)-Heteroaryl-NR⁴R⁵, —N(R⁴)-Heterocyclyl-NR⁴R⁵, —(CR⁶R⁷)ᵥHeterocyclyl-NR⁴R⁵, —(CR⁶R⁷)ᵥHeteroaryl-NR⁴R⁵, —(CR⁶R⁷)ᵥHeterocyclyl-N(R⁴)C(=NR⁵)NR⁴R⁵, —(CR⁶R⁷)ᵥHeterocyclyl-N(R⁴)C(=NR⁵)NR⁴R⁵, —(CR⁶R⁷)ᵥHeteroaryl, —(CR⁶R⁷)ᵥHeterocyclyl, —O-Heteroaryl, —O-Heterocyclyl, —NR⁴(CR⁶R⁷)ᵥHeteroaryl, —NR⁴(CR⁶R⁷)ᵥHeterocyclyl, —O(CR⁶R⁷)ᵥHeteroaryl, —O(CR⁶R⁷)ᵥHeterocyclyl, and —O(CR⁶R⁷)ᵥO-Heterocyclyl. In certain embodiments, at least one Y is selected from the group consisting fluoro, optionally substituted C₁-C₆ alkyl, —OH, —NR⁴R⁵, —(CR⁶R⁷)ᵥNR⁴R⁵, —(CR⁶R⁷)ᵥNR⁴(CR⁶R⁷)ᵥNR⁴R⁵, —NR⁴(CR⁶R⁷)ᵥR₆, —NR⁴(CR⁶R⁷)ᵥHeterocyclyl-C(=NR⁵)NR⁴R⁵, —NR⁴(CR⁶R⁷)ᵥNR⁴C(=NR⁴)NR⁴R⁵, —NR⁴(CR⁶R⁷)ᵥNR⁴(CR⁶R⁷)ᵥNR⁴R⁵, —NR⁴(CR⁶R⁷)ᵥNR⁴R⁵, —O(CR⁶R⁷)ᵥNR⁴R⁵, —C(O)NR⁴(CR⁶R⁷)ᵥNR⁴R⁵, —NR⁵C(O)NR⁴(CR⁶R⁷)ᵥNR⁴R⁵, —NR⁵C(=NR⁷)NR⁴(CR⁶R⁷)ᵥNR⁴R⁵, —N(R⁴)C(=NR⁵)R⁶, —(CR⁶R⁷)ᵥN(R⁴)C(=NR⁵)R⁶, —NR⁴(CR⁶R⁷)ᵥN(R⁴)C(=NR⁵)R⁶, —(CR⁶R⁷)ᵥC(=NR⁵)NR⁴R⁵, —NR⁴(CR⁶R⁷)ᵥC(=NR⁵)NR⁴R⁵, —(CR⁶R⁷)ᵥN(R⁴)C(=NR⁵)NR⁴R⁵, —NR⁴(CR⁶R⁷)ᵥN(R⁴)C(=NR⁵)NR⁴R⁵, —NR⁴C(=NR⁵)NR⁴C(=NR⁵)NR⁴R⁵, —(CR⁶R⁷)ᵥC(=NR⁴)NR⁵C(=NR⁴)NR⁴R⁵, —NR⁴(CR⁶R⁷)ᵥC(=NR⁴)NR⁵C(=NR⁴)NR⁴R⁵, —NR⁴C(=NR⁵)NR⁴R⁵, —C(=NR⁴)NR⁴R⁵, —C(=NR⁴)NR⁴C(O)R⁶, —NR⁴C(O)R⁶, —(CR⁶R⁷)ᵥC(O)NR⁴R⁵, -Heterocyclyl-NR⁴R⁵, -Heterocyclyl-N(R⁴)C(=NR⁵)NR⁴R⁵, —N(R⁴)-Heterocyclyl-NR⁴R⁵, —(CR⁶R⁷)ᵥHeterocyclyl-NR⁴R⁵, —(CR⁶R⁷)ᵥHeterocyclyl-N(R⁴)C(=NR⁵)NR⁴R⁵, —(CR⁶R⁷)ᵥHeterocyclyl, and —NR⁴(CR⁶R⁷)ᵥHeterocyclyl. In further embodiments, at least one Y is selected from the group consisting of -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, —N(R⁴)-Heteroaryl-NR⁴R⁵, —N(R⁴)-Heterocyclyl-NR⁴R⁵, -Heteroaryl-C(=NR⁵)NR⁴R⁵, -Heterocyclyl-C(=NR⁵)NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, and —(CR⁶R⁷)ᵥHeterocyclyl-N(R⁴)C(=NR⁵)NR⁴R⁵. In specific embodiments, at least one Y is 2-(NR₄R₅)-pyridyl, 2-(NR₄R₅)-pyrimidinyl, 2-(NR₄R₅)-thiazolyl, 2-(NR₄R₅)-imidazolyl, 3-(NR₄R₅)-pyrazolyl, 3-(R₄R₅N)-isothiazolyl, 2-(R₄R₅N)-oxazolyl, piperidine, pyrrolidine, 4-amino-piperidinyl, 3-amino-pyrrolidinyl, piperazine, or 4-carboximidoyl-piperazinyl. In preferred embodiments, at least one Y is selected from the group consisting of —NR⁴R⁵, —NR⁴C(=NR⁵)NR⁴R⁵, —C(=NR⁴)NR⁴R⁵, —N(R⁴)C(=NR⁵)R⁶, —(CR⁶R⁷)ᵥNR⁴R⁵, —(CR⁶R⁷)ᵥN(R⁴)C(=NR⁵)NR⁴R⁵, —NR⁴(CR⁶R⁷)ᵥNR⁴R⁵, —NR⁴(CR⁶R⁷)ᵥOR¹⁰, —(CR⁶R⁷)ᵥNR⁴(CR⁶R⁷)ᵥNR⁴R⁵, NR⁵C(=NR⁵)NR⁴(CR⁶R⁷)ᵥNR⁴R⁵, —NR⁴(CR⁶R⁷)ᵥN(R⁴)C(=NR⁵)NR⁴R⁵, —NR⁵C(O)CR⁶(NR⁴R⁵)(CR⁶R⁷)ᵥNR⁴R⁵, —(CR⁶R⁷)ᵥC(=NR⁵)NR⁴R⁵, —(CR⁶R⁷)ᵥN(R⁴)C(O)(CR⁶R⁷)ᵥNR⁴R⁵, —C(=NR⁴)NR⁴C(O)R⁶, —NR⁴(CR⁶R⁷)ᵥHeteroaryl, and —O(CR⁶R⁷)ᵥNR⁴R⁵.

In some embodiments, p is 0, 1, 2, 3, or 4. In certain embodiments, p is 1 or 2. In some embodiments, p is 2. In other embodiments, p is 1.

In some embodiments of a compound of Formula I or Formula Ia, each R⁴ and R⁵ is independently selected from the group consisting of hydrogen, —OH, optionally substituted C₁-C₆ alkyl, optionally substituted alkoxyalkyl, optionally substituted hydroxyalkyl, and optionally substituted heterocyclyl. In preferred embodiments, each R⁴ and R⁵ is independently hydrogen or optionally substituted C₁-C₆ alkyl.

In some embodiments of a compound of Formula I or Formula Ia, each R⁶ and R⁷ is independently selected from the group consisting of hydrogen, optionally substituted C₁-C₆ alkyl, —OH, —NR⁴R⁵, and optionally substituted heterocyclyl, or R⁶ and R⁷ taken together form an optionally substituted heterocycle with the carbon to which they are attached. In preferred embodiments, each $R^6$ and $R^7$ is independently hydrogen, fluoro, or optionally substituted $C_1$-$C_6$ alkyl.

In some embodiments of a compound of Formula I or Formula Ia, $R^6$ and $R^7$ are independently selected from the group consisting of hydrogen, optionally substituted $C_1$-$C_6$ alkyl, —OH, —$NR^4R^5$, and optionally substituted heterocyclyl, or $R^6$ and $R^7$ taken together form an optionally substituted heterocycle with the carbon to which they are attached. In preferred embodiments, $R^6$ and $R^7$ are independently hydrogen, fluoro, or optionally substituted $C_1$-$C_6$alkyl. In some embodiments,

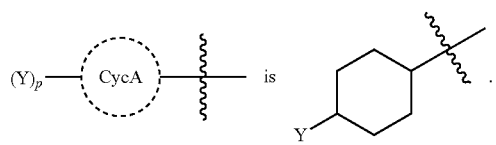

In some embodiments,

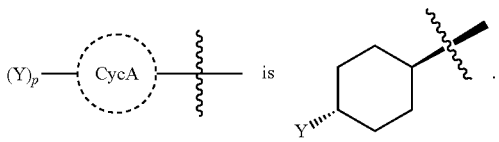

In some embodiments, Y is —$NR^4(CR^6R^7)_vNR^4R^5$. In some embodiments, Y is —$NR^4(CR^6R^7)_vNR^4C(=NR^4)NR^4R^5$. In some embodiments, Y is —$NR^4R^5$. In other embodiments, Y is —$NR^4C(=NR^4)NR^4R^5$. In some embodiments, Y is —$(CR^6R^7)_vNR^4R^5$. In some embodiments, Y is —$(CR^6R^7)_vNR^4C(=NR^4)NR^4R^5$. In some embodiments, v is 2. In some embodiments, v is 1. In some embodiments, each $R^4$ and $R^5$ is selected from H, optionally substituted $C_1$-$C_6$ alkyl or optionally substituted $C_3$-$C_6$ cycloalkyl. In some embodiments, each $R^4$, $R^6$, and $R^7$ is H.

In some embodiments of a compound of Formula I or Formula Ia, each Y is defined the inclusion of non-hydrogen atoms. For example, in some embodiments, each Y comprises at least 1, 2, 3, 4, 5, 6, 7, 8, 9, 10, 12, 14, 16, 18, 20, 24, 28, 32, 36, 40, 50, or 60 non-hydrogen atoms. In some embodiments each Y comprises fewer than 50, 40, 36, 32, 28, 24, 20, 18, 16, 14, 12, 10, 9, 8, 7, 6, 5, 4, 3 or 2 non-hydrogen atoms. In some embodiments, each Y is independently a group comprising 1-50 non-hydrogen atoms. In some embodiments, non-hydrogen atoms are any atom that is not a hydrogen atom. In some embodiments, non-hydrogen atoms are atoms generally found in organic molecules. In some embodiments, non-hydrogen atoms are atoms selected from the group consisting of C, N, O, S and P. In some embodiments, each Y is independently a group comprising 1-50 non-hydrogen atoms selected from the group consisting of C, N, O, S, and P.

In some embodiments of a compound of Formula I or Formula Ia, each Y is defined by its molecular formula. For example, in some embodiments, each Y has the formula $C_wH_xN_yO_z$; wherein each w is independently 0-30; each x is independently 1-69; each y is independently 1-8; and each z is independently 0-10. In some embodiments, each Y has the formula $C_wH_xN_yO_z$; wherein each w is independently 0-10; each x is independently 1-25; each y is independently 1-4; and each z is independently 0-3. In some embodiments, each y is 2.

In some embodiments of a compound of Formula I or Formula Ia, each Y is defined by its molecular weight. In some embodiments, each Y has a molecular weight of less than 500, 450, 400, 350, 300, 250, 200, 190, 180, 170, 160, 150, 140, 130, 120, 110, 100, 90, 80, 75, 70 or 50 daltons, for example. In some embodiments, each Y has a molecular weight of less than 200 daltons. In some embodiments, each Y has a molecular weight of less than 150 daltons. In some embodiments, each Y has a molecular weight between 30 and 280 daltons.

In some embodiments of a compound of Formula I or Formula Ia, each Y is defined by the number of basic nitrogen atoms it comprises. For example, each Y can comprise 10, 9, 8, 7, 6, 5, 4, 3, 2, 1, or 0 basic nitrogen atoms. In some embodiments, each Y comprises 1-6 basic nitrogen atoms. In some embodiments, each Y comprises 1, 2, or 3 basic nitrogen atoms. In some embodiments, each Y comprises 2 basic nitrogen atoms. In some embodiments, at least one Y comprises 1-6 basic nitrogen atoms. In some embodiments, at least one Y comprises 1, 2, or 3 basic nitrogen atoms. In some embodiments, at least one Y comprises 2 basic nitrogen atoms. A basic nitrogen atom is a nitrogen atom that can be at least partially protonated in a substantially neutral aqueous buffer. For example, a basic nitrogen atom can be a nitrogen atom of an amine group or a nitrogen atom in a functional group such as an alkyl amine, a cycloalkyl amine, a heterocycloalkyl group, a heteroaryl group comprising a nitrogen, an amidine, or a guanidine.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is a group comprising 2 basic nitrogen atoms. In some embodiments, the basic nitrogen atoms are each an atom within an amine group, and amidine group, a guanidine group, a heterocyclo alkyl group, and heteroaryl group, or an alkyl amino group. In some embodiments, Y comprises two amine groups. In some embodiments, Y comprises two guanidine groups. In some embodiments, Y comprises an amine group and guanidine group.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y has the formula $C_wH_xN_yO_z$; wherein w is 0-10; x is 1-25; y is 1-4; and z is 0-3. In some embodiments, y is 2. In some embodiments, y is 4.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y has a molecular weight between 30 and 280 daltons and Y comprises at least 1 basic nitrogen atom. In some embodiments, Y has a molecular weight between 30 and 280 daltons and Y comprises at least 2 basic nitrogen atoms. In some embodiments, Y is an alkyl group comprising 2 amino groups, and Y has a molecular weight between 30 and 280 daltons.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is —$NR^4(CR^6R^7)_vNR^4R^5$; and v is 2. In some embodiments, each $R^6$ and $R^7$ is independently selected from the group consisting of H, methyl, or OH. In some embodiments, each $R^6$ and $R^7$ is independently H or methyl. In some embodiments, each $R^6$ and $R^7$ is H. In some embodiments, each $R^4$ is H. In some embodiments, $R^5$ is selected from H, optionally substituted $C_1$-$C_6$ alkyl, and optionally substituted $C_3$-$C_6$ cycloalkyl. In some embodiments, $R^5$ is selected from H, optionally substituted $C_1$-$C_6$ alkyl, and optionally substituted $C_3$-$C_6$ cycloalkyl. In some embodiments, $R^5$ is selected from group consisting of methyl, ethyl, propyl, isopropyl and H. In some embodiments, each $R^4$, $R^6$, and $R^7$ is H, and $R^5$ is selected from H, optionally substituted $C_1$-$C_6$ alkyl, and optionally substituted $C_3$-$C_6$ cycloalkyl. In some embodiments, each $R^4$ is independently H or optionally substituted $C_1$-$C_3$ alkyl; each $R^6$ and $R^7$ are H; and $R^5$ is selected from H, optionally substituted $C_1$-$C_6$ alkyl, and optionally substituted $C_3$-$C_6$ cycloalkyl. In some embodiments, $R^5$ is a guanidine group. In some embodiments, $R^5$ is an amidine group. In some embodiments CycA is trans-1,4-cyclohexyl.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is —$NR^4R^5$. In some embodiments, $R^4$ and $R^5$ are each selected from the group consisting of H, guanidine, amidine, optionally substituted alkyl, and heterocycloalkyl. In some embodiments, $R^4$ and $R^5$ are each H. In some embodiments, $R^5$ is an amidine group. In some embodiments, $R^5$ is a guanidine group.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is $(CR^6R^7)_vNR^4R^5$; and v is 1 or 2. In some embodiments, $R^4$ and $R^5$ are each selected from the group consisting of H, guanidine, amidine, optionally substituted alkyl, and heterocycloalkyl. In some embodiments, v is 1; $R^6$ and $R^7$ are each H or methyl; and $R^4$ and $R^5$ are each independently H, optionally substituted $C_1$-$C_6$ alkyl, or optionally substituted $C_3$-$C_6$ cycloalkyl. In some embodiments, v is 1; $R^6$ and $R^7$ are each H; and $R^4$ and $R^5$ are each independently H, optionally substituted $C_1$-$C_6$ alkyl, or optionally substituted $C_3$-$C_6$ cycloalkyl. In some embodiments, v is 1; $R^6$ and $R^7$ are each H; and $R^4$ and $R^5$ are each H, $C_1$-$C_6$ alkyl, or $C_3$-$C_6$ cycloalkyl. In some embodiments, v is 1; $R^6$ and $R^7$ are each H or methyl; and $R^4$ and $R^5$ are each H.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is $(CR^6R^7)_vNR^4C(=NR^4)NR^4R^5$; and v is 1 or 2. In some embodiments, $R^4$ and $R^5$ are each selected from the group consisting of H, optionally substituted $C_1$-$C_6$ alkyl, or optionally substituted $C_3$-$C_6$ cycloalkyl. In some embodiments, v is 1; $R^6$ and $R^7$ are each H or methyl; and $R^4$ and $R^5$ are each independently H, optionally substituted $C_1$-$C_6$ alkyl, or optionally substituted $C_3$-$C_6$ cycloalkyl. In some embodiments, v is 1; $R^6$ and $R^7$ are each H; and $R^4$ and $R^5$ are each independently H, optionally substituted $C_1$-$C_6$ alkyl, or optionally substituted $C_3$-$C_6$ cycloalkyl. In some embodiments, v is 1; $R^6$ and $R^7$ are each H; and $R^4$ and $R^5$ are each H, $C_1$-$C_6$ alkyl, or $C_3$-$C_6$ cycloalkyl. In some embodiments, v is 1; $R^6$ and $R^7$ are each H or methyl; and $R^4$ and $R^5$ are each H.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is —$NR^4(CR^6R^7)_vNR^4C(=NR^4)NR^4R^5$; and v is 2. In some embodiments, $R^4$ and $R^5$ are each selected from the group consisting of H, optionally substituted alkyl, and heterocycloalkyl. In some embodiments, $R^6$ and $R^7$ are each H or methyl; and $R^4$ and $R^5$ are each independently H, optionally substituted $C_1$-$C_6$ alkyl, or optionally substituted $C_3$-$C_6$ cycloalkyl. In some embodiments; $R^6$ and $R^7$ are each H; and $R^4$ and $R^5$ are each independently H, optionally substituted $C_1$-$C_6$ alkyl, or optionally substituted $C_3$-$C_6$ cycloalkyl. In some embodiments, $R^6$ and $R^7$ are each H; and $R^4$ and $R^5$ are each H, $C_1$-$C_6$ alkyl, or $C_3$-$C_6$ cycloalkyl. In some embodiments, $R^6$ and $R^7$ are each H or methyl; and $R^4$ and $R^5$ are each H.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; CycA is 1,4-cyclohexyl; and Y is $(CR^6R^7)_v$; v is 1 or 2; each $R^7$ is H or methyl; and at least one $R^6$ is —$C(N=R^5)NR^4R^5$. In some embodiments, each $R^4$ and $R^5$ is selected from H, optionally substituted $C_1$-$C_6$ alkyl, and optionally substituted $C_3$-$C_6$ cycloalkyl. In some embodiments, each $R^4$ and $R^5$ is selected from H, $C_1$-$C_6$ alkyl, and $C_3$-$C_6$ cycloalkyl. In some embodiments, each $R^4$ and $R^5$ is selected from H and methyl. In some embodiments, each $R^4$ and $R^5$ is H.

In some embodiments of a compound of Formula I or Formula Ia, $R^a$, $R^b$, $R^c$, $R^d$, and $R^3$ are H; $X^1$ is OH; $X^2$ when present is OH, Z is >C=O; n is 0; m is 1; p is 1; M and L are each a bond; $R^1$ and $R^2$ are each H; Y is —$NR^4(CR^6R^7)_vNR^4R^5$; and v is 2; each $R^6$ and $R^7$ is independently selected from the group consisting of H, methyl, or OH; each $R^4$ is H; $R^5$ is selected from H, optionally substituted $C_1$-$C_6$ alkyl, and optionally substituted $C_3$-$C_6$ cycloalkyl; and CycA is an optionally substituted 3-10 membered nonaromatic carbocycle, wherein an optional olefin functionality of the non-aromatic carbocycle is not directly attached to an oxygen, sulfur, or nitrogen substituent. In some embodiments, CycA is selected from the group consisting of cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent. In certain embodiments, CycA is cyclobutane, cyclopentane, cyclohexane, or cyclohexene, wherein the olefin functionality of the cyclohexene is not directly attached to an oxygen, sulfur, or nitrogen substituent. In other embodiments, CycA is selected from the group consisting of bicyclo[3.3.0]octane, bicyclo[4.3.0]nonane, cis decalin, transdecalin, bicyclo[2.1.1]hexane, bicyclo[2.2.1]heptane, bicyclo[2.2.2]octane, bicyclo[3.2.2]nonane, and bicyclo[3.3.2]decane. In some embodiments, CycA is cyclopentane. In preferred embodiments, CycA is cyclohexane. In some embodiments, CycA is cyclohexane covalently bonded to one Y and L; said covalent bonds in 1,4-trans arrangement.

In some embodiments of a compound of Formula I or Formula Ia, $R^a$, $R^b$, $R^c$, $R^d$, and $R^3$ are H; $X^1$ is OH; $X^2$ when present is OH; n is 0; m is 1; p is 1; M and L are each a bond; $R^1$ and $R^2$ are each H; CycA is cyclohexane, cyclopentane, or cyclobutane; Y is —$NR^4(CR^6R^7)_vNR^4R^5$; and v is 2; each $R^6$ and $R^7$ is independently selected from the group consisting of H, methyl, or OH; each $R^4$ is H; $R^5$ is selected from H, optionally substituted $C_1$-$C_6$ alkyl, and optionally substituted $C_3$-$C_6$ cycloalkyl; and Z is selected from the group consisting of >C=O, >C=S, or >$SO_2$.

Preparation of Compounds

Described herein are compounds of Formula I or Formula Ia that inhibit the activity of beta-lactamases, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula I or Formula Ia may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein
Isomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may exist in an equilibrium between the "closed" cyclic form shown in Formula I and the "open" acyclic form shown in FIG. Ia. In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. It should be understood that the compounds described herein also include the quaternization of any boron-containing groups they contain. Such a quaternization could result from the treatment of the Lewis acidic boron with a Lewis base to form a complex or a salt. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

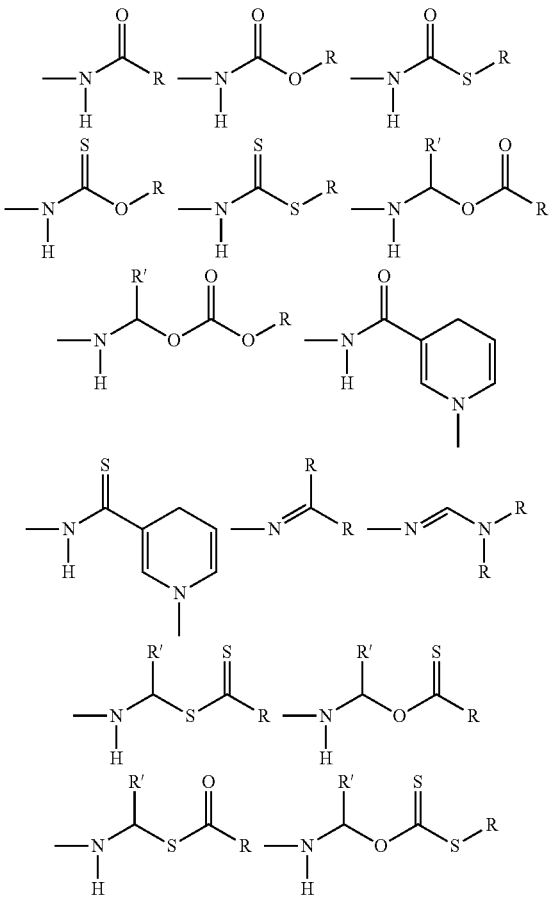

45
-continued

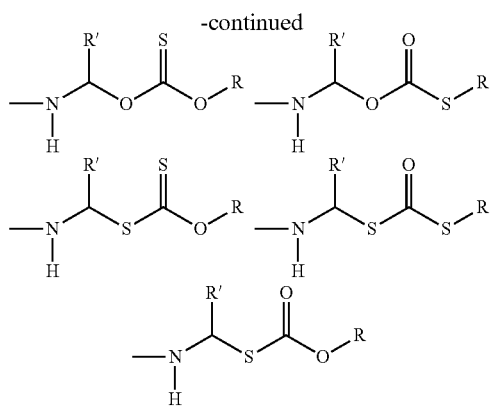

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds of Formula I or Formula Ia are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula I or Formula Ia described herein are metabolized upon administration to an organism in need to produce a metabolite that is then used to produce a desired effect, including a desired therapeutic effect.

Pharmaceutical Compositions/Formulations

In another aspect, provided herein are pharmaceutical composition comprising a compound of Formula I or Formula Ia as described herein, or a pharmaceutically acceptable salt, polymorph, solvate, prodrug, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula I or Formula Ia and at least one pharmaceutically acceptable inactive ingredient. In some embodiments, the compounds described herein are administered as pharmaceutical compositions in which a compound of Formula I or Formula Ia is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula I or Formula Ia with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula I or Formula Ia are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula I or Formula Ia as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds according to Formula I or Formula Ia may be used in combination with one or more antibiotics in the treatment of bacterial infections. Such antibiotics may be administered, by a route and in an amount commonly used therefore, contemporaneously or sequentially with a compound of Formula I or Ia. When a compound of Formula I or Ia is used contemporaneously with one or more antibiotic, a pharmaceutical composition in unit dosage form containing such other drugs and the compound of the present invention is preferred. However, the combination therapy may also include therapies in which the compound of Formula I or IA and one or more antibiotic are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound according to Formula I or Formula Ia. In some embodiments, a pharmaceutical composition comprising a compound of Formula I or Ia further comprises a beta-lactam antibiotic. In certain embodiments, the beta-lactam antibiotic is a penicillin, cephalosporin, carbapenem, monobactam, bridged monobactam, or a combination thereof.

The above combinations include combinations of a compound of Formula I or Ia not only with one antibiotic, but also with two or more antibiotics. Likewise, compounds of formula I or Ia, either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound of Formula I or Ia. When a compound of Formula I or Ia is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of Formula I or Ia. The weight ratio of the compound of Formula I or Ia to the second active ingredient may be varied and will depend upon the effective dose of each ingredient. Generally, an effective dose of each will be used.

In some embodiments, the compounds according to Formula I or Formula Ia are used in combination with one or more antibiotics in the treatment of bacterial infections. In certain embodiments, the bacterial infection is a upper or lower respiratory tract infection, a urinary tract infection, a intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin. Penems include, but are not limited to, faropenem. Carbapenems include, but are not limited to, biapenem, ertapenem, doripenem, imipenem, meropenem, panipenem. Cephalosprins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef. Monobactams include, but are not limited to, aztreonam, carumonam, nocardicin A, tigemonam.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula I or Formula Ia and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e g, Page, *Biochem J*, 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221:505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g, Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art. Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor of Formula I or Ia are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound of Formula I or Ia is administered to an experimental cell culture in vitro to prevent the growth of beta-lactam resistant bacteria. In certain other embodiments, a compound of Formula I or Ia is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound of Formula I or Formula Ia, or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a betalactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, or Staphylococcus saccharolyticus.*

In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmo-* nella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii, or Bacteroides splanchnicus.

EXAMPLES

List of Abbreviations

As used above, and throughout the description of the invention, the following abbreviations, unless otherwise indicated, shall be understood to have the following meanings ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium Hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl

General Examples for the Preparation of Compounds of the Invention

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com).

Certain compounds of the invention (I) (SCHEME 1) are prepared from the corresponding functional-group-protected boronic acid esters (II) by treatment with a Lewis acid such as $BCl_3$, in a solvent such as dichloromethane, at a temperature between −78° C. and 0° C. followed by an aqueous quench.

SCHEME 1

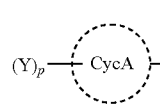
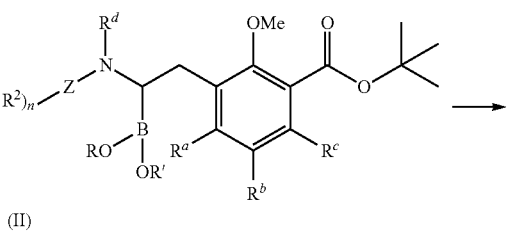

(II)

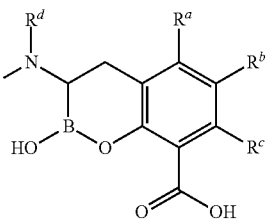

(I)

Alternatively, (I) is obtained from (II) by treatment of (II) with aqueous hydrochloric acid (around 3-5 Molar) in dioxane at a temperature between room temperature and 100° C.

The requisite boronic acid esters (II) are obtained (SCHEME 2) by coupling of amine (III) with (carboxylic or sulphonic) acid (IV). This transformation is effected by first activating the acid functionality as an acid chloride, anhydride or reactive ester (Va, Vb or Vc), followed by treatment of the activated substrate with (III) in a solvent such as DMF, DMA, NMP, THF or dichloromethane (or a mixture thereof) at about room temperature, usually in the presence of a non-nucleophilic base such as 4-methyl-morpholine, triethylamine or diisopropylethylamine.

is also used as a co-solvent. Formation of the anhydride (Vb) (Z is C=O) involves treatment of (IV) with a sterically hindered acid chloride or chloroformate, such as trimethylacetyl chloride or isopropylchloroformate, in an inert solvent such as dichloromethane, in the presence of a non-nucleophilic base, such as triethyl amine or diisopropylamine at room temperature or below. Formation of the activated ester (Vc) involves treatment of (IV) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

SCHEME 2

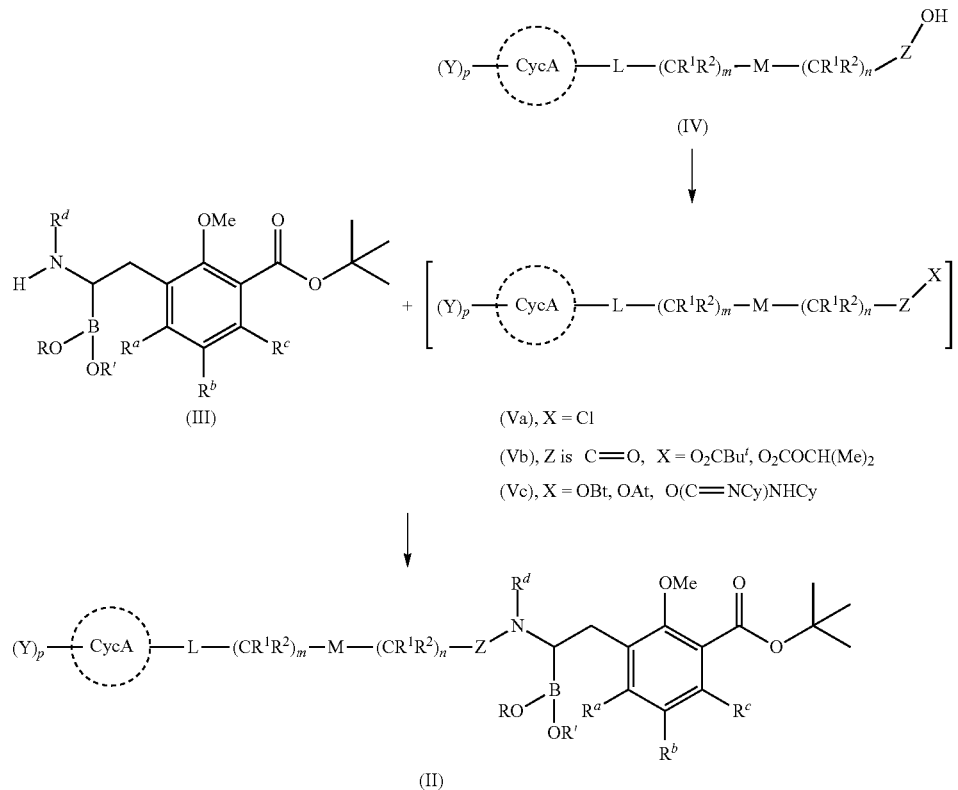

Formation of the acid chloride (Va) involves treatment of (IV) with a chlorinating agent such as thionyl chloride, phosphorous pentachloride or oxalyl chloride, in a solvent such as dichloromethane, in the presence of a catalyst such as DMF, at around room temperature. In certain cases, DMF The requisite acids (IV) are prepared by a number of different reaction sequences. While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

In the case where $Y_1$ is linked to CycA through an amine functionality, the requisite acids (IV) (SCHEME 3) are conveniently prepared from an appropriately substituted-carbocyclic ketone (VI). For example, treatment of (VI) with a suitable amine (VII) in the presence of a reducing agent such as sodium tri-acetoxyborohydride, sodium cyanoborohydride or sodium borohydride in a solvent such as dichloromethane, 1,2-dichloro-ethane, THF, methanol, acetic acid or a mixture thereof, at a temperature around room temperature gives ester (VIII). In the case where the use of a primary amine (VII, $R^5$=H) is called for, (VIII) can also be prepared by treatment of an equimolar mixture of (VI) and (VII, $R^5$=H) with a Lewis acid/dessicant, such as $Ti(OEt)_4$, in a solvent such as dichloromethane or 1,2-dichloroethane, at room temperature or above to provide the intermediate imine. This is followed by reduction of the imine with sodium borohydride, in a solvent such as methanol, at a temperature between −78° C. and room temperature.

Acid (IV) is obtained from the ester (VIII) by formal hydrolysis of the ester functionality. The reaction conditions employed depend on the type of ester used. In the case of a methyl, ethyl or other simple alkyl, hydrolysis is usually achieved by brief treatment with an aqueous base, such as sodium hydroxide or lithium hydroxide, in a solvent mixture of THF, water and methanol. However, other acid protecting groups can also be used, such as benzyl, allyl, 2-trimethyl-silyl-ethyl or 2,2,2-trichloroethyl. In these cases, conversion of the ester to the corresponding acid is achieved using the standard de-protection procedures in the literature (*Greene's Protective Groups in Organic Synthesis*. Fourth Edition. John Wiley & Sons, Inc. 2006).

In certain cases, it is convenient to perform the reductive amination sequence using a keto-acid derivative (VI, R=H). In this case, treatment of an equimolar mixture of keto-acid (VI, R=H) and amine (VII) with hydrogen gas in a solvent such as methanol, in the presence of a catalyst such as palladium on carbon provides acid (IV) directly.

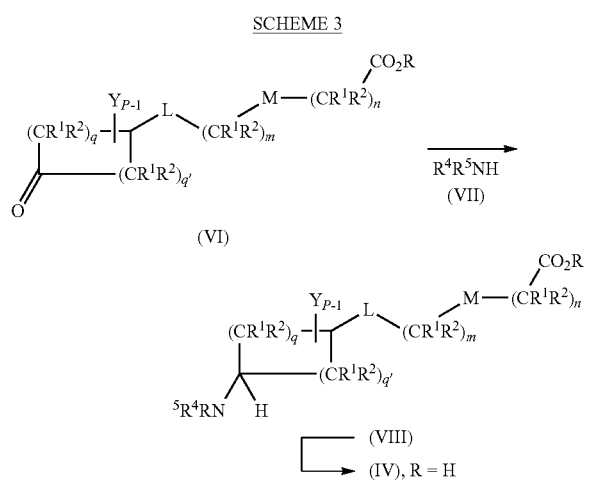

In another approach to amino linked systems (SCHEME 4), treatment of ketone (VI) with a reducing agent, such as sodium borohydride in methanol at around 0° C. or L-selectride in THF, at a temperature between −78° C. and room temperature gives alcohol (IX). Treatment of the alcohol (IX) with methanesulphonyl chloride or p-toluene-sulphonyl chloride, in the presence of a non nucleophilic base, such as triethylamine or DIEA, in a solvent such as dichloromethane or pyridine, at around 0° C. provides the corresponding sulphonate ester (X). Displacement of the sulphonate group with azide by treatment of (X) with sodium azide or a tetra-alkylammonium azide in a solvent such as DMA, DMF, NMP, acetonitrile or DMSO, at a temperature between room temperature and 120° C., yields the azide (XI). Reduction of the azide with triphenylphosphine and water in THF at around room temperature (Staudinger reaction) yields the primary amine (XII). Further derivatization of (XII), where appropriate, can be accomplished by reductive amination with an appropriate aldehyde or ketone, using conditions already described to give (XV).

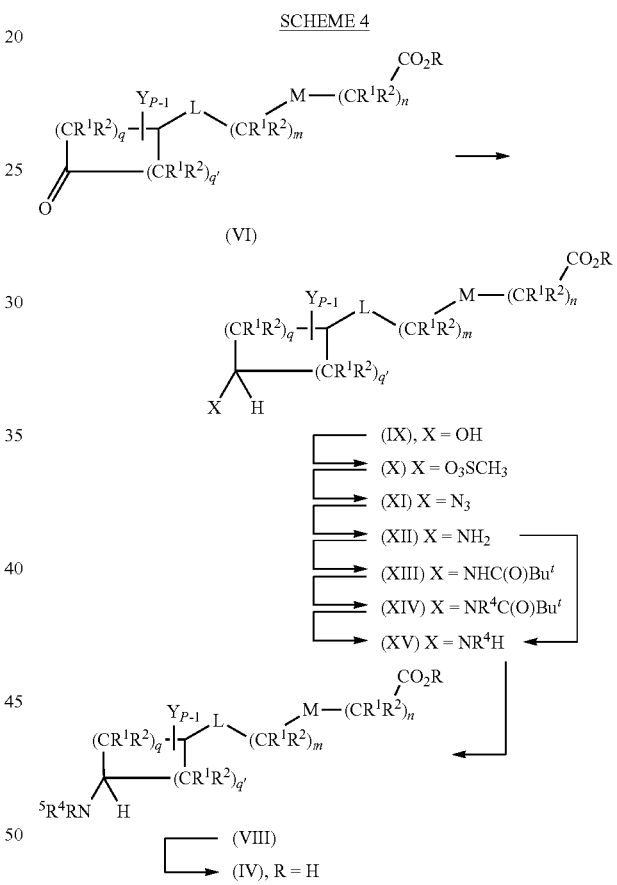

Alternatively, formation of the N—BOC derivative of (XII) by treatment with $BOC_2O$, in the presence of a non nucleophilic base such as triethylamine or DIEA, in a solvent such as dichloromethane, at around room temperature gives carbamate (XIII). Treatment of (XIII) with an alkyl halide or sulphonate in the presence of a base, such as sodium hydride, potassium carbonate or tetramethylguanidine, in a solvent such as DMF, DMA, NMP, THF, DMPU or ethanol (or a mixture thereof), at room temperature or below, provides (XIV). Cleavage of the BOC group with an acid, such as TFA in dichloromethane or HCl in dioxane, ethyl acetate or ether, at around room temperature, provides the secondary amine (XV). Further derivatization of (XV), where appropriate, can be accomplished by reductive amination with an appropriate aldehyde or ketone, using conditions already described to give (VIII). Hydrolysis of (VIII) as already outlined yields (IV).

In the case where $Y_1$ is a guanidine, the guanidino group is derived from the appropriate carbocyclic primary (XII) or secondary amine (XV) (SCHEME 5) by treatment with a reagent such as 1,3-Di-tert-butyloxycarbonyl-S-methylisothiourea, in a solvent such as DMF, (*Synthesis*, (2004), 37-42) or pyridine at room temperature or above, or by treatment with N,N' Bis-(BOC)-1H-pyrazole-1-carboxamidine in the presence of a base such as diisopropylethylamine, in a solvent such as DMF or DMA at around room temperature. Selective cleavage of the ester functionality, as already described, provides the corresponding acid (IV).

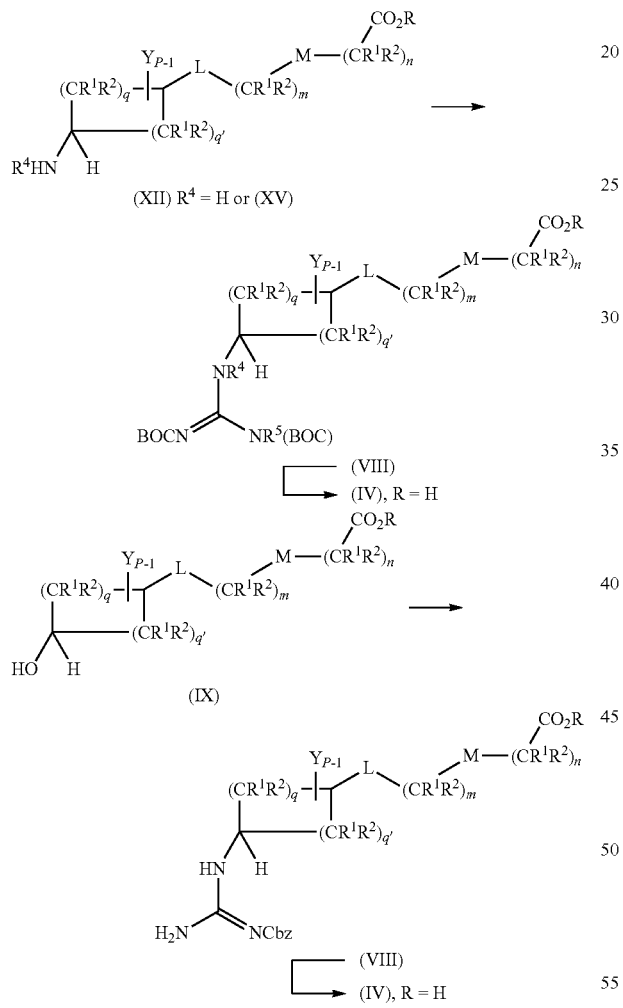

Alternatively, the guanidinyl group can be introduced by treatment of an appropriate carbocyclic alcohol (IX) with a reagent such as Cbz-guanidine, in the presence of triphenylphosphine and diethyl-azo-dicarboxylate, in a solvent such as THF (Mitsunobu conditions: *Chemical Reviews*, (2009), 109, 2551-2651) to give (VIII) directly.

In the case where $Y_1$ is an amidine linked to Cyc A through nitrogen, the requisite acids (SCHEME 6) are prepared from the appropriate primary (XII) or secondary amine (XV) by treatment with a suitable alkyl thioimidate, such as the 2-napthylmethylthioimidate derivative (XVI), in a solvent such as ethanol at a temperature between 0° C. and room temperature (*Tetrahedron Letters*, (1997), 38(2), 179-182) to give (XVII). Protection of the amidine (XVII) as a carbamate derivative, such as BOC or Cbz under standard conditions, followed by selective ester hydrolysis provides acid (IV).

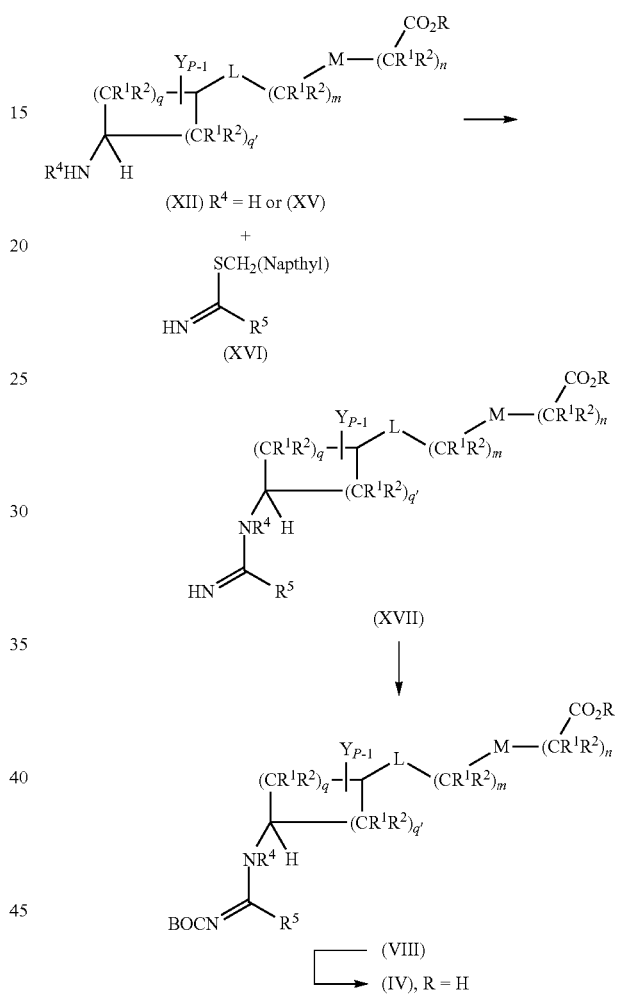

In the case where $Y_1$ is an amidine linked to CycA through carbon, the amidine functionality (SCHEME 7) is introduced by conversion of an appropriate carbocyclic ketone (XVIII) to the corresponding exocyclic nitrile (XIX) by treatment (XVIII) with toluenesulphonyl-methylisocyanide (*Journal of Organic Chemistry* (1977), 42(19), 3114-18) in the presence of a base such as KOBu$^t$ in a solvent such as DMSO or DME containing about 2% of t-butanol or ethanol at a temperature between 0° C. and 50° C. Treatment of (XIX) with HCl in methanol to form the corresponding imidate ester (XX) is followed by reaction of this intermediate with an appropriate amine ($R^4R^5NH$), in a solvent such as methanol or THF at around room temperature to give the amidine (XXI). In certain cases, it is convenient to effect direct amidine formation from the nitrile (XIX) using a suitable methyl-chloroaluminum amide, in a solvent such as toluene at around 80° C. (*Tetrahedron Letters*, (1990), 31(14), 1969-1972). Furthermore, in the case where $R^5$=H, the amidine functionality can also be introduced by treatment of the appropriate carbocyclic nitrile (XIX) with hydroxylamine or an O-alkyl-hydroxylamine to give the N-hydroxyl-(or alkoxy)-amidine (XXII, $R^5$=OH, OR). This is followed by removal of the protecting groups by catalytic hydrogenolysis to provide the amidine (XXIII). Selective acylation of the amidine functionality in (XXIII) by treatment with BOC anhydride or Cbz chloride, as previously described yields primary alcohol (XXIV). Conversion of the primary-alcohol (XXIV) to the corresponding acid (IV) is accomplished using one of a number of oxidation protocols such as $NaIO_4$ with catalytic $RuCl_3$ in a solvent mixture of water/$CCl_4$/$CH_3CN$ in the ratio 3/2/2, at around room temperature (*Journal of Organic Chemistry*, (1981), 46(19), 3936-8) or with pyridinium dichromate in DMF (*Tetrahedron Letters*, (1979). 20 (52), 399).

In the case where $Y_1$ is a nitrogen substituted methylene group, the requisite acids (SCHEME 8) are prepared from the appropriate carbocyclic-ketones (XVIII) by conversion of the ketone functionality into, first, the corresponding hydroxyl-methyl derivative by treatment with an olefination reagent such as methyltriphenylphosphonium bromide in the presence of sodium hexamethyldisilazide, in a solvent such as THF at around 0° C. (Wittig reaction) or by treatment with lithium trimethylsilylmethane/$CeCl_3$ at around 0° C. to room temperature, in a solvent such as THF or ether (Peterson reaction) (*Journal of Organic Chemistry*, (1987) 52(2), 281-3) or by reaction with the Petasis modified Tebbe reagent (dicyclpentadienyl-dimethyltitanium) in THF/toluene at around 60° C. (*Journal of the American Chemical Society*, (1990), 112 (17) 6392-6394 to give (XXV). This is followed by hydroboration oxidation of the exocyclic alkene in (XXV) with a reagent such as borane THF or an alkyl

SCHEME 7

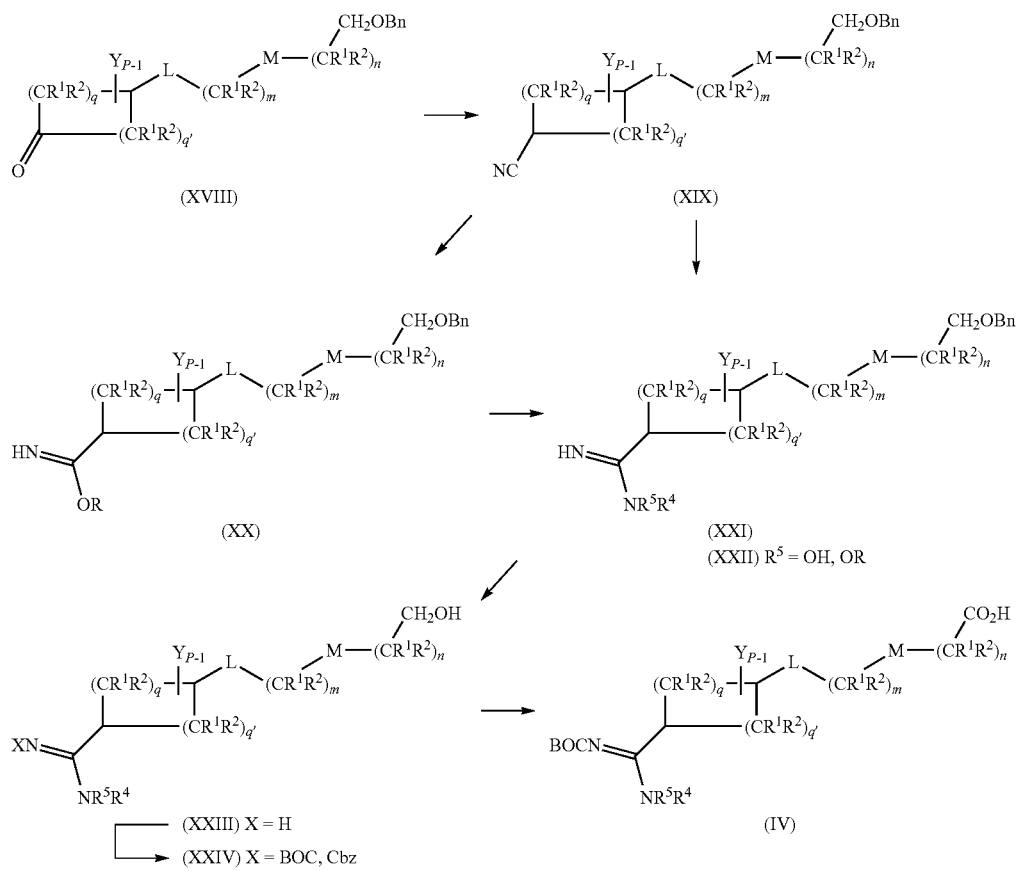

In certain cases, the primary alcohol (XXIV) is oxidized to the corresponding carboxylic acid using a two-step procedure, involving initial oxidation to the aldehyde using a DMSO based oxidant system, such as Swern oxidation (*Organic Reactions*. (1990), 39, 297-572.) or by treatment with excess Dess Martin periodinane in a solvent such as dichloromethane at around room temperature. Subsequent oxidation of the aldehyde is accomplished by treatment with sodium chlorite/sodium dihydrogenphosphate in the presence of tetramethylethylene, in a solvent such as t-butanol/water at around room temperature (*Journal of Organic Chemistry*, (1980), 45, 4825).

derivative, at around 0° C., in a solvent such as THF, followed by oxidative workup with hydrogen peroxide NaOH aq. to provide (XXVI). Conversion of the hydroxymethyl (XXVI) into the functionalized amino-methyl derivative (XXVII) is accomplished by conversion to the corresponding tosylate, azide and primary amine as described above. Alternatively, oxidation of (XXVI) to the aldehyde (XXVIII) followed by reductive amination of (XXVIII) with an amine ($R^4R^5NH$), as already described, also provides amine (XXVII). Conversion of (XXVII) to the requisite acid (IV) is accomplished by side chain modification as previously described.

SCHEME 8

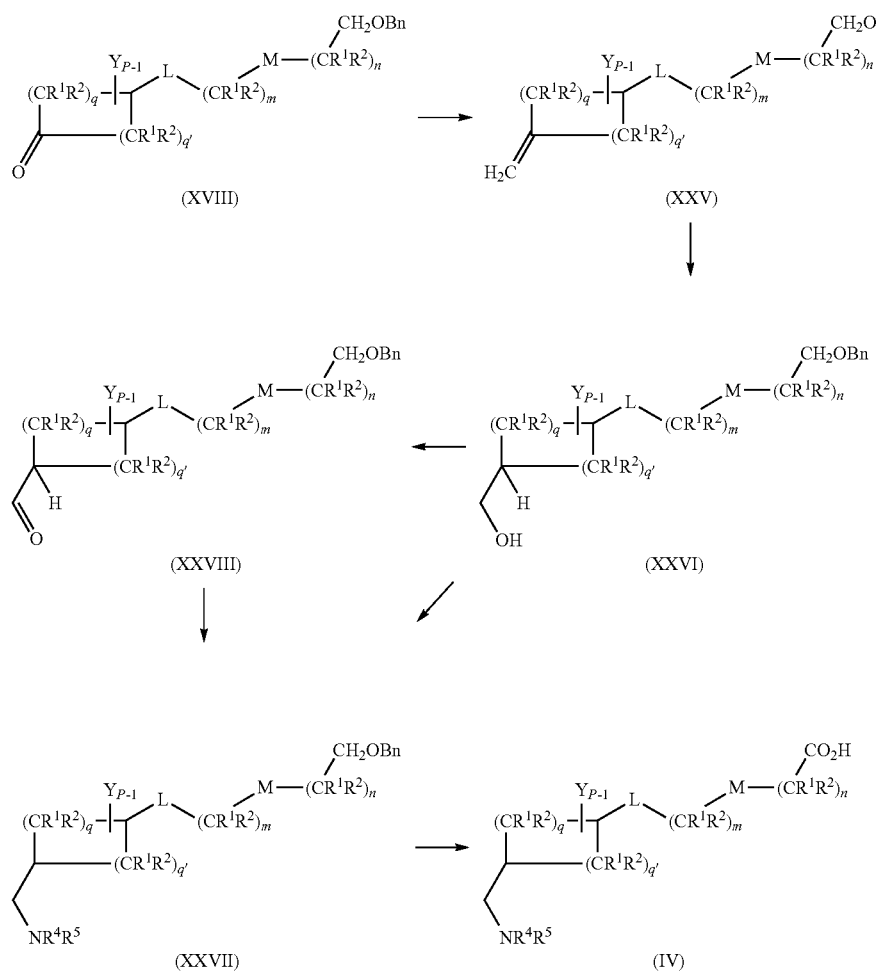

In an alternative approach to systems wherein $Y_1$ is a nitrogen substituted methylene group, CycA is a 5-7 membered carbocycle and Z is a carbonyl group, the requisite carboxylic acids (IV) are prepared from an acrylamide derivative (XXIX) (SCHEME 9). (XXIX) is condensed, in a Diels Alder reaction, with an appropriately substituted diene, such as siloxy-diene (XXX), in an inert solvent such as toluene, xylene or DMA at a temperature between 70° and 190° C. to give the carbocylic-silyl-enol-ether (XXXI).

SCHEME 9

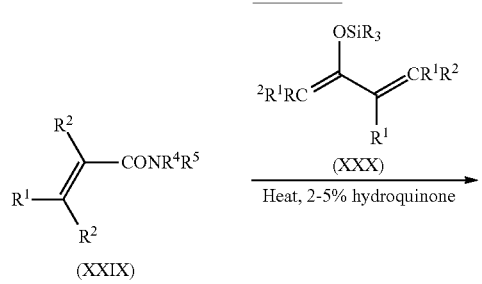

-continued

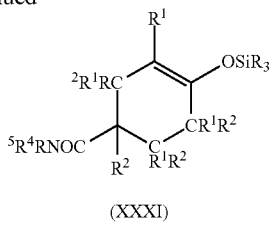

(XXXI)

Carbocylic-silyl-enol-ether (XXXI) is then elaborated to provide several of the requisite carboxylic acids (IV) by the application of known functional group transformations. For example (SCHEME 10), treatment of (XXXI) with N-phenyl-triflimide and CsF in a sealed system, using a solvent such as DME, at around room temperature or below, furnishes the corresponding enol triflate (XXXII) (*Journal of the American Chemical Society*, (2002) 124, 11290-11291). Methoxy-carbonylation of (XXXII) with carbon monoxide/methanol in the presence of a non nucleophilic base, such as triethylamine and a catalyst, such as $Pd(OAc)_2$, in conjunction with 1,3-(bis-diphenylphosphino)-propane, in a solvent such as DMSO, at a temperature between 50 and 100° C. provides unsaturated ester (XXXIII). Unsaturated ester (XXXIII) is reduced using a heterogeneous Pd, Rh or Pt catalyst, such as 10% Pd on carbon, under an atmosphere of hydrogen gas (1-4 atm), in a solvent such as ethyl acetate, methanol or THF (or a mixture thereof) at room temperature to 70° C. to give the saturated ester (XXXIV). Alternatively, in certain cases, unsaturated-ester (XXXIII) may be reduced by treatment with excess Magnesium, in a solvent such as methanol, at around room temperature (*Tetrahedron Letters*, (1986); 27(21), 2409-2410) to provide (XXXIV).

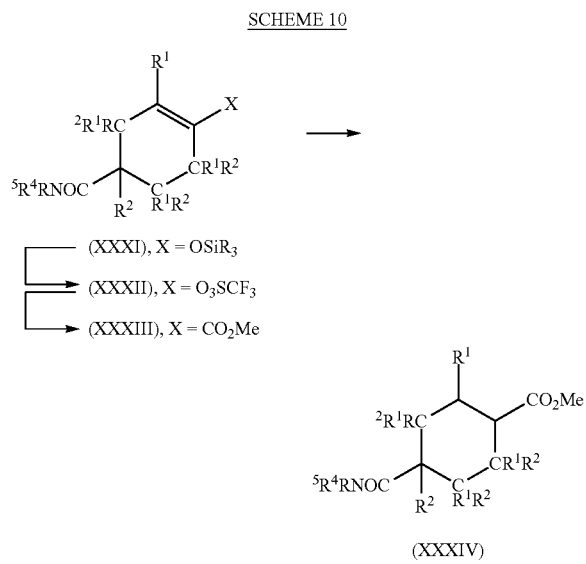

SCHEME 10

(XXXI), X = OSiR$_3$
(XXXII), X = O$_3$SCF$_3$
(XXXIII), X = CO$_2$Me (XXXIV)

In suitable cases, selective reduction of the amide functionality of intermediate (XXXIV) to provide the corresponding amine (XXXV) (SCHEME 11) is accomplished by treatment of (XXXIV) with a silane reducing agent, such as diphenylsilane and a rhodium catalyst such as rhodiumhydrocarbonyltriphenylphosphine, in a solvent such as THF, at around room temperature (*Tetrahedron Letters*, (1998); 39(9), 1017) or by treatment with 1,1,3,3-tetramethyldisiloxane and a catalytic amount of chloroplatinic acid hydrate, in a solvent such as toluene, at a temperature between room temperature and 90° C. (*Journal of the American Chemical Society*, (2009); 131(41), 15032-15040).

The ester functionality in (XXXV) is hydrolyzed to give the requisite acid (IV) by brief treatment with a base such as sodium hydroxide or lithium hydroxide, in a solvent such as THF/methanol/water, at around room temperature.

Alternatively, Reduction of the amide functionality in (XXXIV), with concomitant reduction of the ester group, to give (XXXVI) is accomplished by treatment of (XXXIV) with a hydride reducing agent, such as lithium aluminum hydride, in an ethereal solvent such as THF, diethyl-ether, dimethoxy-ethane or methyl-t-butyl-ether, at a temperature between 0° C. and 65° C. Conversion of the resulting amino-alcohol (XXXVI; R$^4$,R$^5$=H) to the corresponding acid (IV) is accomplished by amine derivitization and oxidation of the primary alcohol as already described.

The corresponding one carbon homologated carboxylic acid (IV) where Cyc A is a six membered ring, L,M=bond, m=0, n=1, Y$_1$=(R$^4$R$^5$NCH$_2$) (SCHEME 12) is also prepared from carbocyclic silyl enol ether (XXXI). Treatment of (XXXI) with potassium carbonate in methanol at around room temperature or with tetra-n-butylammonium fluoride hydrate in a solvent such as THF (and where appropriate, buffered with an equimolar amount of acetic acid) provides ketone (XXXVII). Treatment of (XXXVII) with a trialkylphosphonoacetate, such as triethylphosphonoacetate, in a solvent such as THF, in the presence of a base such sodium hydride, at a temperature between about −5° C. and room temperature gives the corresponding α,β-unsaturated ester (XXXVIII) (*Liebigs Annalen/Recueil*, (1997), 7, 1283-1301.). Reduction of the alkene and amide functionality in (XXXVIII) and subsequent processing (ester hydrolysis or alcohol oxidation), analogous to that described above furnishes the requisite acid (IV).

SCHEME 12

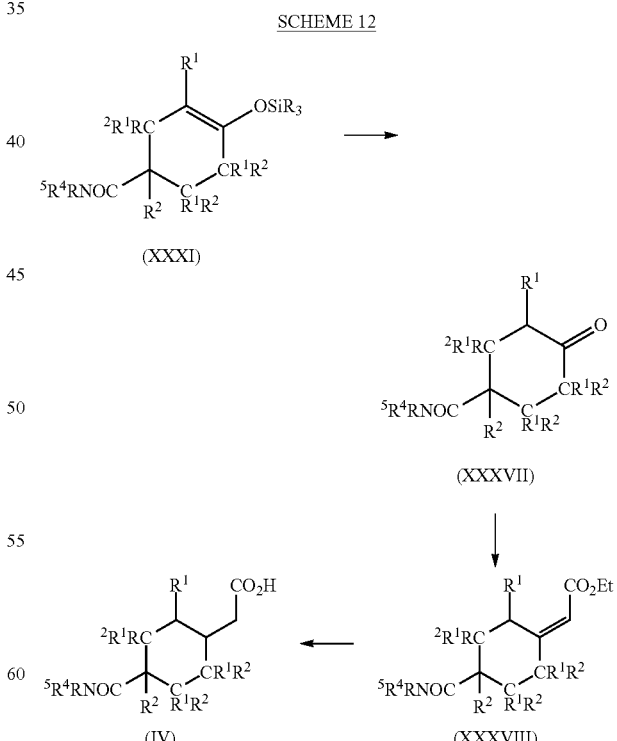

SCHEME 11

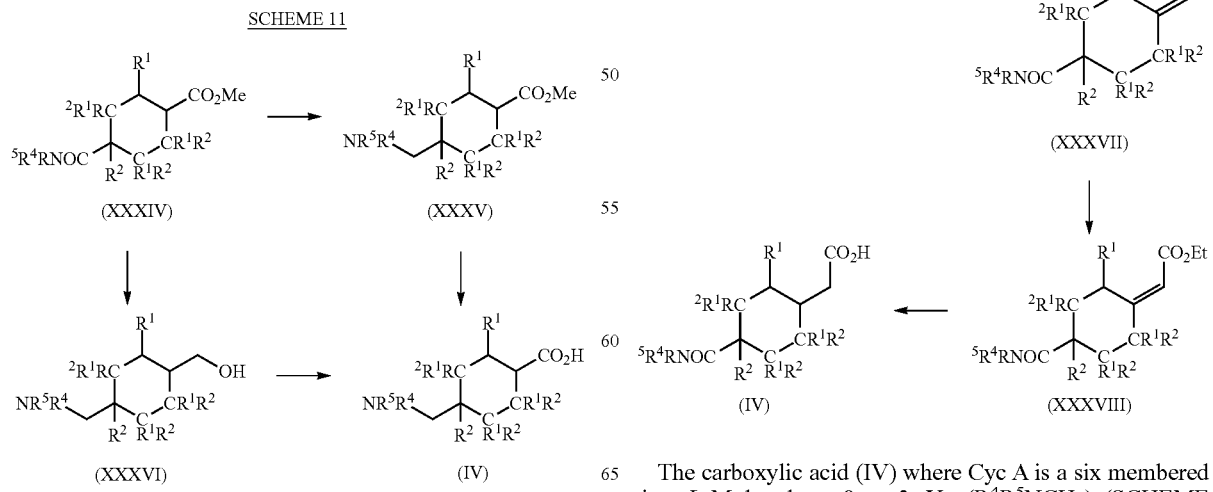

The carboxylic acid (IV) where Cyc A is a six membered ring, L,M=bond, m=0, n=2, Y$_1$=(R$^4$R$^5$NCH$_2$) (SCHEME 13) is prepared from alcohol (XXXVI) by oxidation to the corresponding aldehyde (XXXIX) under standard conditions followed by a Horner-Wadsworth-Emmons reaction, as described above, to provide α,β-unsaturated ester (XL). Reduction of the alkene in (XL) and ester hydrolysis analogous to that described above furnishes the requisite acid (IV).

The carboxylic acid (IV) where Cyc A is a six membered ring, L=O, M=bond, m=0, n=1, $Y_1=R^4R^5NCH_2$) (SCHEME 14) is prepared from ketone (XXXVII) by treatment with a reagent such as sodium borohydride in methanol at around 0° C. or L-selectride in THF, at a temperature between −78° C. and room temperature to give alcohol (XLI). Condensation of (XLI) with ethyl diazoacetate in the presence of a catalyst such as Rh(acac) dimer in a solvent such as dichloromethane provides the alkoxyacetate derivative (XLII). Selective amide reduction and ester hydrolysis of (XLII) as already described yields (IV).

The carboxylic acid (IV) where Cyc A is a six membered ring, L=NR$_4$, M=bond, m=0, $Y_1=(R^4R^5NCH_2)$ (SCHEME 15) is prepared from ketone (XXXVII) by treatment with an appropriate amino ester (XLIII) under the reductive amination conditions already described to yield (XLIV). Selective amide reduction and ester hydrolysis of (XLIV), as already described, provides the requisite acid (IV).

The seven membered carbocyclic systems (IV) (SCHEME 16) are accessed by ring expansion of carbocyclic-silyl-enol ether (XXXI).

For example, treatment of (XXXI) with a carbene-synthetic-equivalent, such as Simmons Smith reagent, followed by mild oxidation of the resulting cyclopropane, using a reagent such as $FeCl_3$ (*Journal of Organic Chemistry*, (1985), 50(4), 531-534) or CAN/NaOAc (Organic Letters, (2007), 9(7), 1323-1326) provides the seven membered enone (XLV). Treatment of (XLV) with a silane, such as $PhMe_2SiH$, in the presence of a catalyst, such as Wilkinson's

SCHEME 13

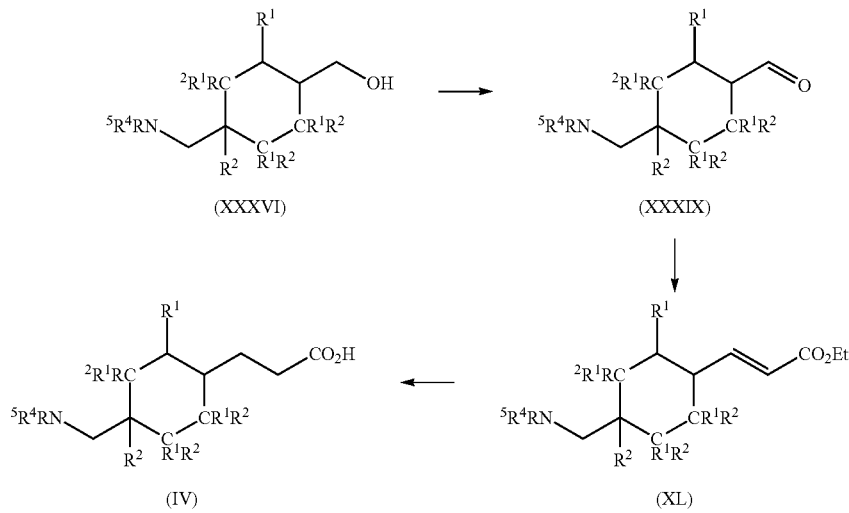

SCHEME 14

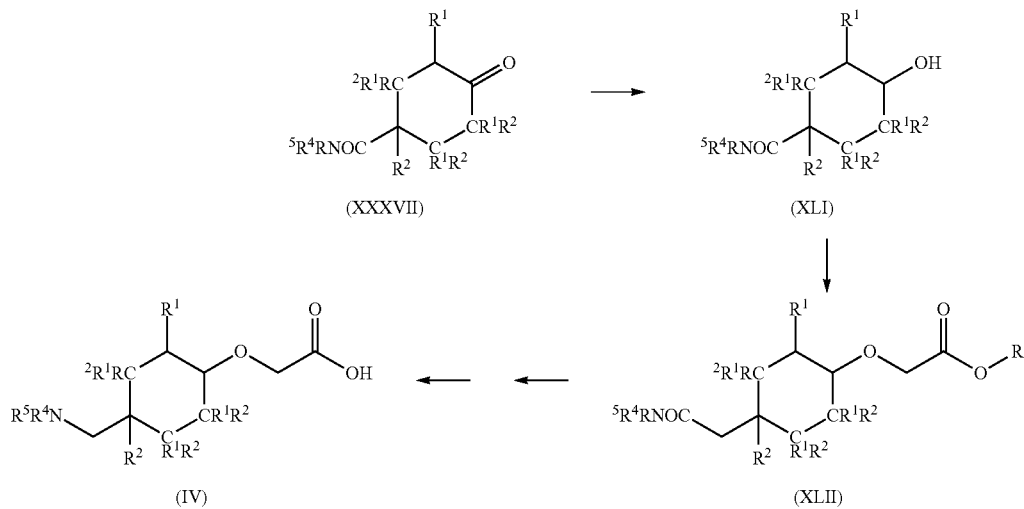

catalyst $(Ph_3P)_3RhCl$, either neat or in a solvent such as benzene or toluene, provides the ring expanded silyl-enol ether (XLVI). This seven membered carbocycle is processed in a manner directly analogous to its six membered ring congener (XXXI) described above, to furnish the requisite acids (IV, CycA=heptane).
SCHEME 15
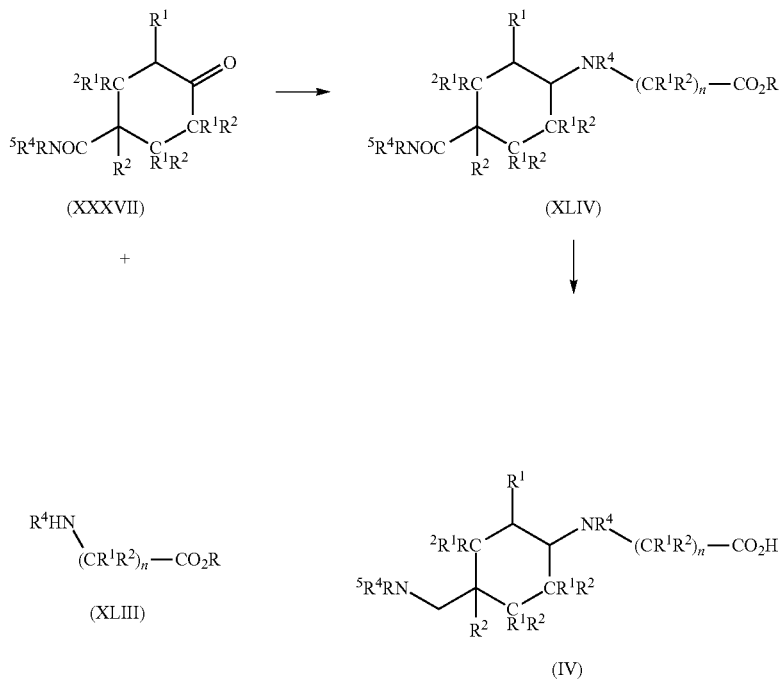
SCHEME 16
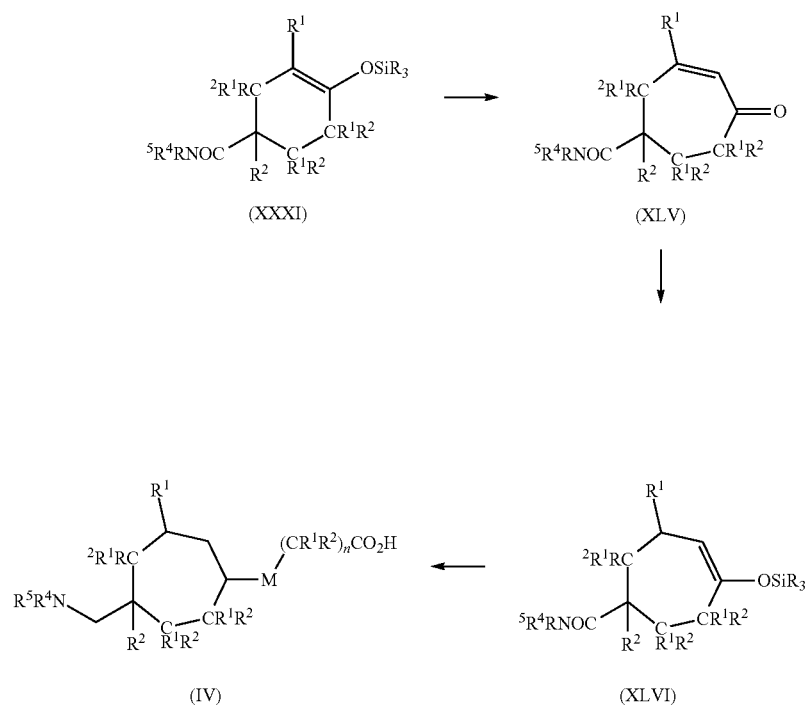

In certain cases, it is convenient to prepare the carbocyclic systems (IV, CycA=cyclopentane) (SCHEME 17) from ketone (XXXI) by Favorskii rearrangement of the corresponding α-halo-ketone (XLVII) (*Current Organic Chemistry* (2005), 9(17), 1713-1735). For example, treatment of (XXXI) with a halogenating reagent, such as bromine, NCS, or pyridinium tribromide in an inert solvent such as dichloromethane or hexane, at a temperature between −78° C. and room temperature furnishes the α-halo-ketone (XLVII). Application of the Favorskii rearrangement conditions to (XLVII) (slow addition to a suspension of sodium methoxide in ether, at around room temperature) then provides the ring contracted ester-substituted-carbocycle (XLVIII).

SCHEME 18

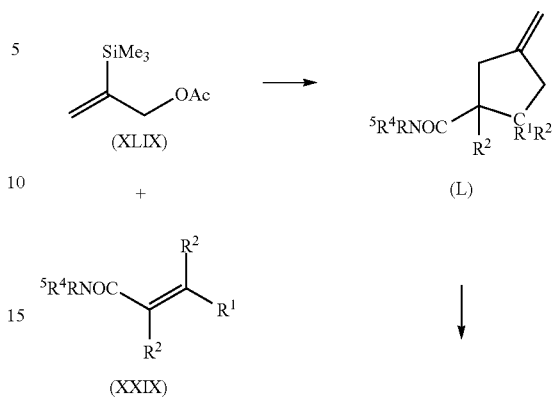

SCHEME 17

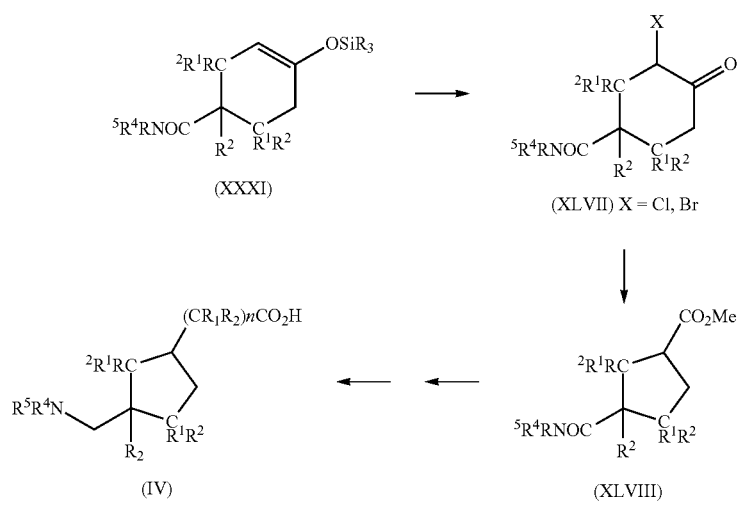

This intermediate is processed in a manner directly analogous to its six membered ring congener (XXXIV) described above, to furnish the requisite acids (IV).

In certain cases the carbocyclic systems (IV, CycA=cyclopentane) are prepared by a cycloaddition reaction between an acrylamide derivative (XXIX) and 2-((trimethylsilyl)methyl)allyl acetate (XLIX), in a solvent such as THF, toluene or xylene, in the presence of a catalyst such as bis (diphenylphosphinopropane)/palladium acetate, at a temperature between 70° and 160° C. (*Journal of the American Chemical Society*. (1979), 101(21), 6429-6431) to give (L). The exocyclic olefin in (L) is oxidatively cleaved by treatment with catalytic amounts of osmium tetroxide (*Org. Synth. Oxid. Met. Compd.* (1986), 633-93. Publisher: Plenum, N.Y.) in the presence of a co-oxidant such as N-methyl morpholine N-oxide, in a solvent such as tert-butanol/water to yield the corresponding di-hydroxy-derivative (LI). This diol is then oxidatively cleaved using sodium periodate, in a solvent such as THF/water, at around room temperature, to give (LII).

-continued

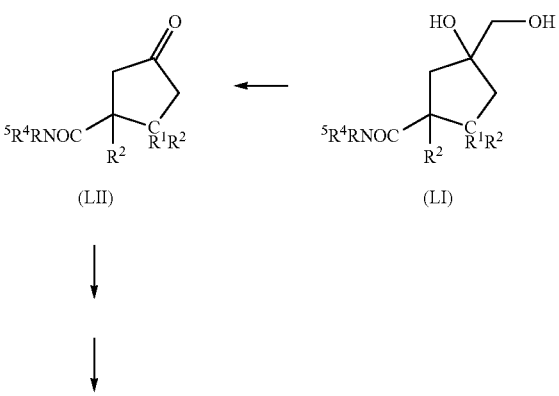

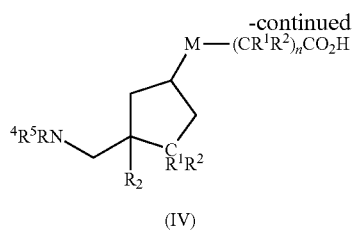

(IV)

Carbocyclic ketone (LII) is then processed in a manner directly analogous to its six membered ring congener (XXXVII) to provide the corresponding acids (IV).

In the case where $Y_1$ and $Y_2$ are both nitrogen substituted methylene groups such that $Y_1$ and $Y_2$ are positioned vicinally on the carbocycle, the requisite acids (IV) are prepared as illustrated above (SCHEMES 9-18) except starting with a fumaric or maleic acid diamide in place of an acrylamide.

In the case where CycA is a 5, 6, or 7 membered carbocycle wherein $Y_3$ and $Y_4$ taken together form a ring, the requisite carboxylic acids (IV) (SCHEME 19) are prepared by the methods described above, except a cyclic siloxy-diene such as (LIII) is employed in the Diels Alder reaction to provide the bicyclic silyl-enol ether (LIV). The starting diene structures are prepared from the corresponding α,β-unsaturated ketone (LV) by treatment of the appropriate enone with trialkylsilyltriflate in the presence of a base such as triethylamine, proton sponge or DBU in a solvent such as ether at 0° C. or above.

azide, in the presence of a mild oxidant, such as Mn(OAc)$_3$(H$_2$O)$_2$ and an acid such as acetic acid or trifluoroacetic acid, in a solvent such as acetonitrile, at a temperature between −30° C. and 0° C. provides the diazide (LVII) in predominantly the trans isomer configuration (*Synthetic Communications*, 28(10), 1913-1922; 1998). Subsequent reduction of the bis-azide by treatment with a reducing agent, such as triphenylphosphine, in a solvent such as THF, followed by in situ hydrolysis of the intermediate azaphosphorane by the addition of excess water yields the bis-amine (LVIII). In certain instances, reduction of the bis azide is also achieved by treatment with hydrogen gas in the presence of a catalyst such as palladium on carbon in a solvent such as THF or methanol.

This bis-primary-amine (LVIII) is protected as a BOC, Cbz or other suitable N-protected derivative (Greene's Protective Groups in Organic Synthesis; 4th Edition: John Wiley & Sons, Inc., 2006). For example, treatment of (LVIII) with an appropriate anhydride or chloroformate, in the presence of a base such as triethylamine, in a solvent such as THF or dichloromethane, at around room temperature provides the carbamate intermediate (LIX). Where appropriate, the carbamate is further derivatized by treatment with a suitable alkylating agent, in the presence of a base, such as K$_2$CO$_3$, in a solvent such as DMF, DMA, or acetonitrile to give (LX). Removal of the carbamate protecting group, followed by treatment of the resulting sec-

SCHEME 19

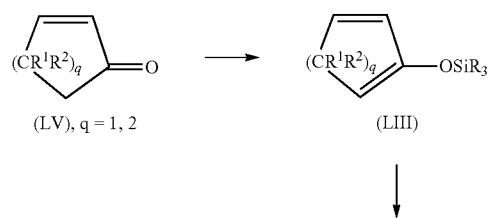

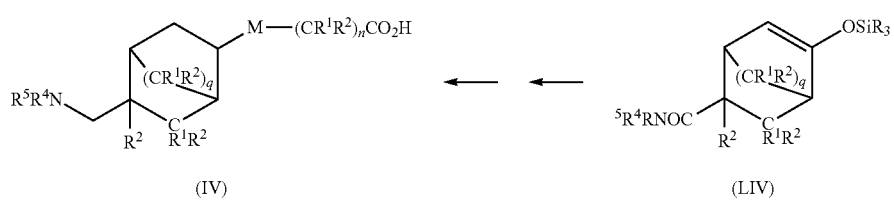

In the case where CycA is a 5, 6 or 7 membered carbocycle, M=bond, O, NR$^4$, $Y_1$ and $Y_2$ are each linked to CycA through a nitrogen atom and $Y_1$ and $Y_2$ are positioned vicinally to each other on the carbocycle, the requisite acids (IV) (SCHEME 20) are prepared from the appropriate cyclic olefins (LVI). For example, treatment of (LVI) with sodium ondary amine with an aldehyde or ketone in the presence of a reducing agent such as sodium borohydride, sodium cyanoborohydride or sodium triacetoxyborohydride in a solvent such as dichloromethane, 1,2-dichloroethane, methanol or THF at around room temperature provides (LXI). Ester hydrolysis of (LXI), as described above, yields the desired acid (IV).

SCHEME 20

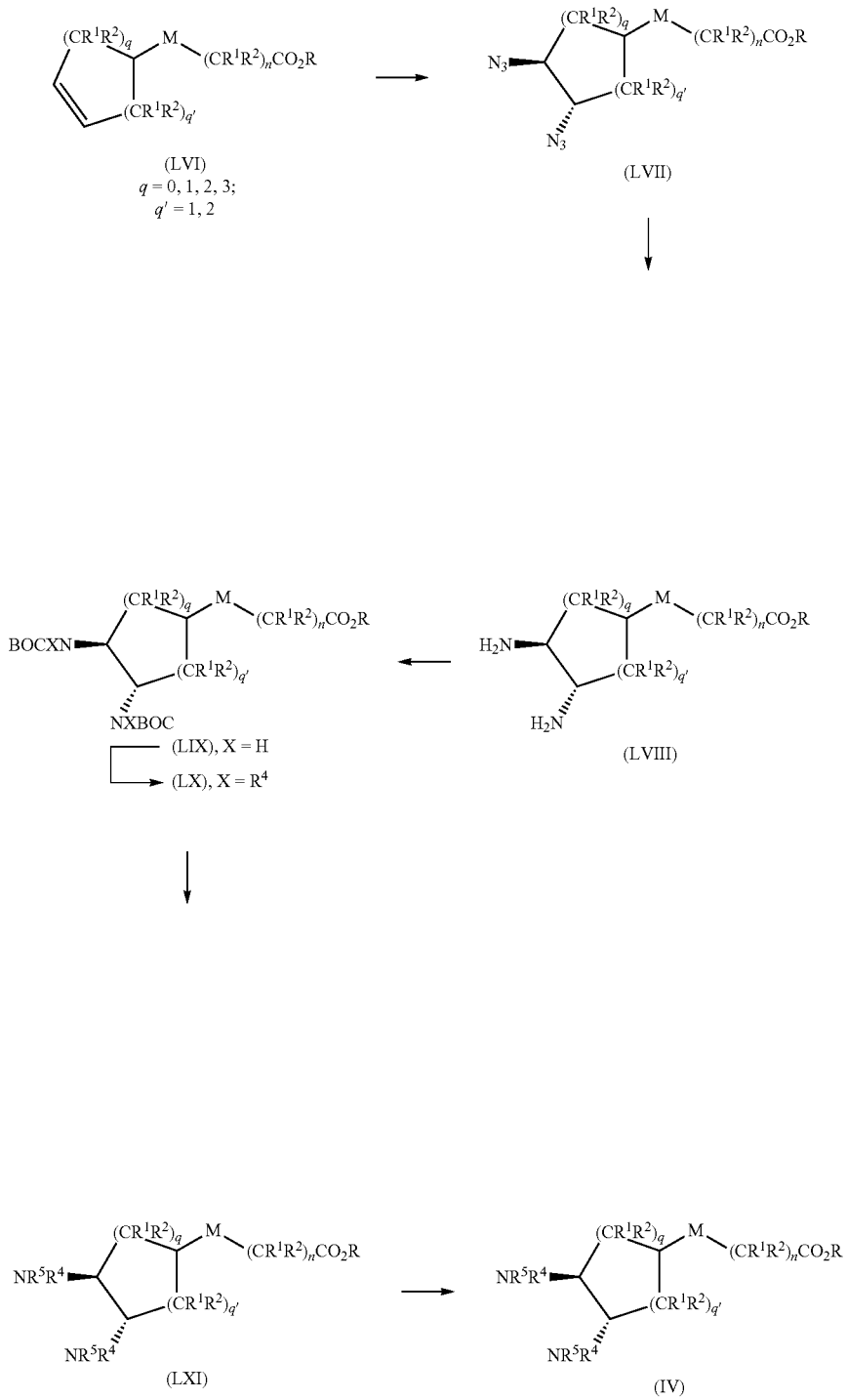

Alternatively, treatment of the appropriate cyclic olefin (LVI) (SCHEME 21) with an oxidant such as meta-chloroperbenzoic acid in a solvent such as dichloromethane at around 0° C. provides the corresponding cyclic epoxide (LXII). Ring opening of the epoxide by treatment with sodium azide and ammonium chloride in a solvent such as ethanol, poly-ethylene-glycol, or DMF/water at a temperature between room temperature and 80° C., provides the trans hydroxyl azide (LXIII). Reaction of (LIII) with methanesulphonyl chloride in pyridine at around 0° C. yields the mesylate (LXIV). Treatment of (LXIV) with tetrabutylammonium azide in a solvent such as toluene provides the cis-oriented bis azide (LXV). Processing of intermediate (LXV) is carried out as previously described to provide acids (IV).

SCHEME 21

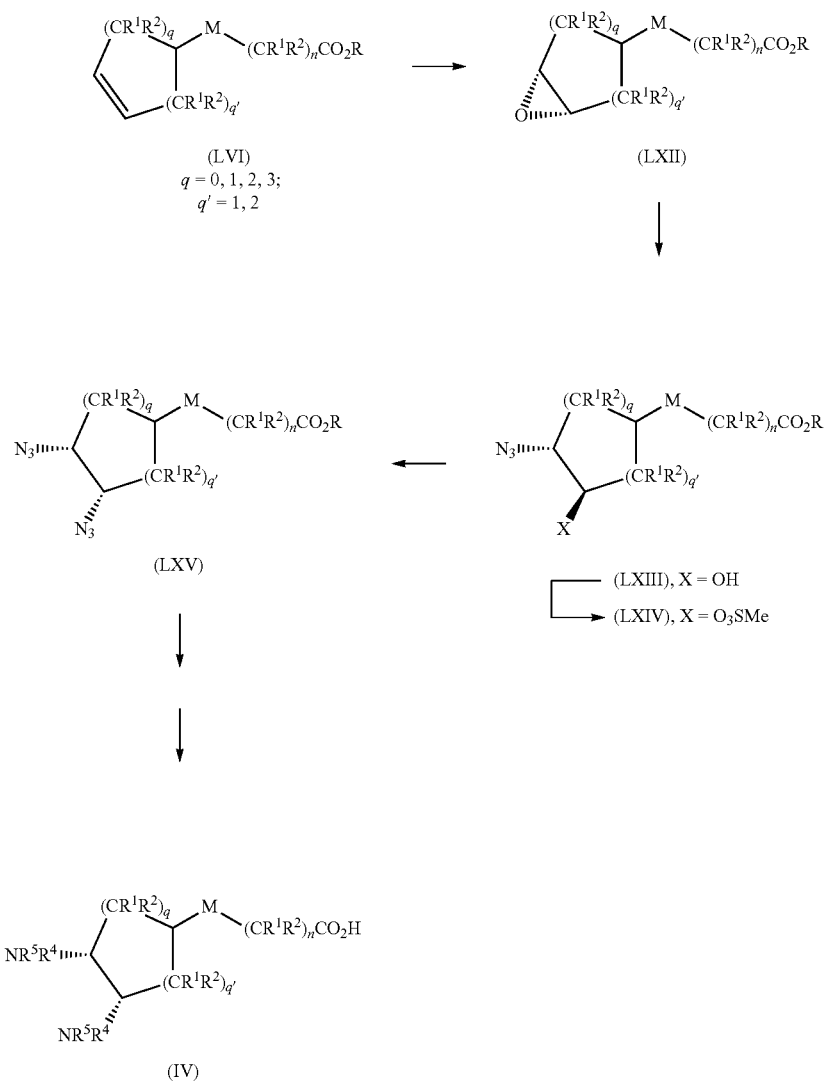

Where appropriate, the cyclic olefins (LVI) (SCHEME 22) are prepared from acyclic starting materials by olefin metathesis. For example, treatment of ester (LXVI) with a strong base, such as LDA in a solvent such as THF, THF/DMPU or DME at a temperature between −78° C. and 0° C. forms the corresponding lithium enolate. This lithium enolate is treated with a suitable halo-alkyl olefin to yield the bis-olefin (LXVII). Treatment of (LXVII) with one of a range of Grubb's or Schrock metathesis catalysts (*Tetrahedron*, (2012), 68(2) 397-421*; Organic Letters*, (2007), 9(23), 4885-4888*; Tetrahedron*, (2004), 60, 7117-7139) in a solvent such as dichloromethane, at room temperature or above or, in an aqueous $PEG_{500}$ dimethyl ether solution, provides the cyclic olefin (LVI, M=bond, n=0).

It should be noted that the cyclic silyl-enol ethers or alkyl enol ethers corresponding to (LVI) which are precursors of cyclic ketones are also conveniently prepared by this approach by employing a suitable acyclic silyl or alkyl enol ether in the ring closure metathesis reaction (*Tetrahedron Letters*, (2001), 42 (45), 8023).

SCHEME 22

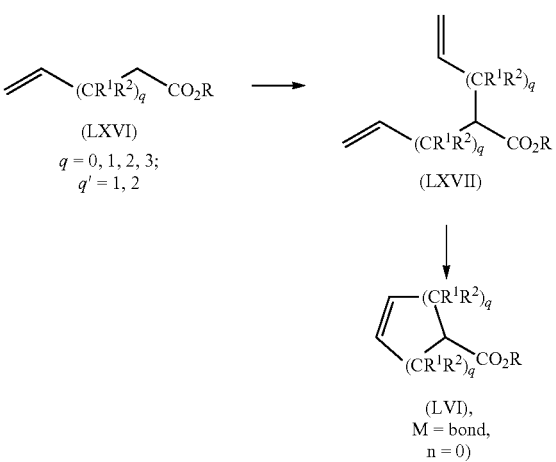

SCHEME 23

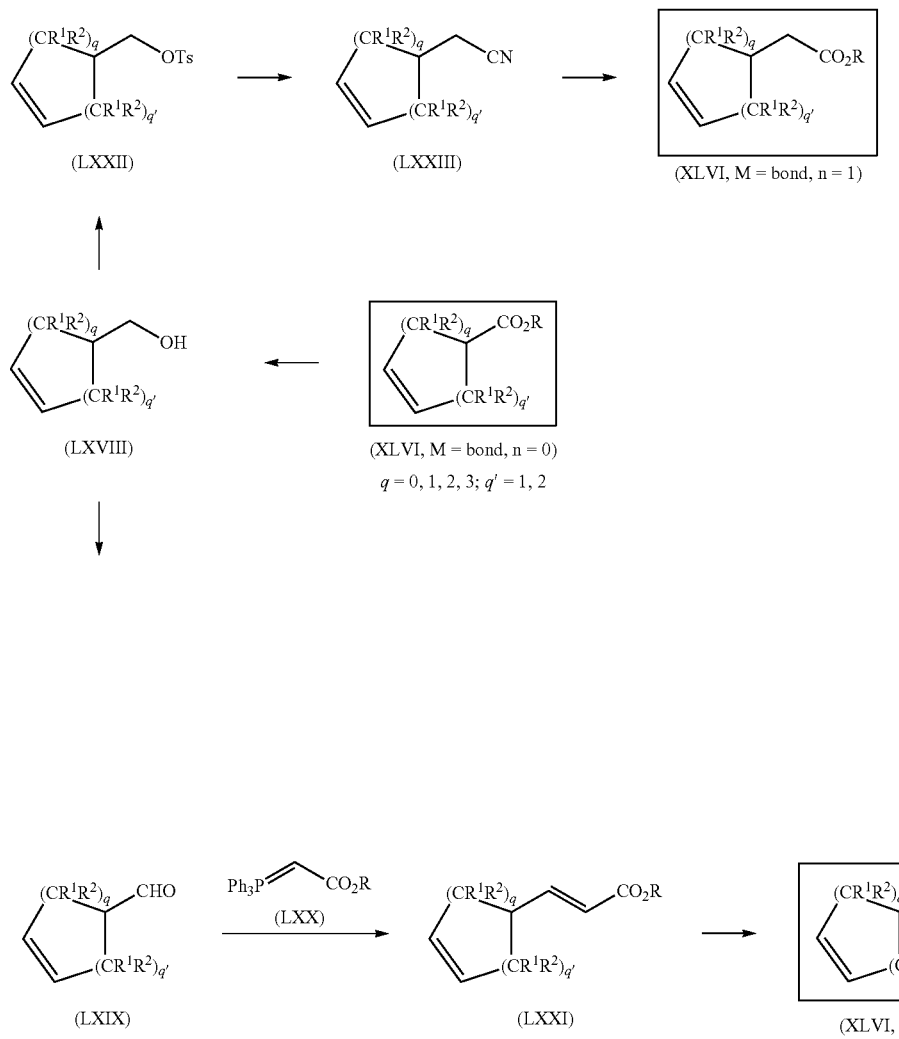

Subsequent standard functional group transformations on the exocyclic alkoxycarbonyl group of (LVI, M=bond, n=0) provides a range of homologous alkoxycarbonyl-alkyl substituted cyclic olefins (SCHEME 23). For example, reduction of the ester functionality by treatment with a reducing agent such as DIBALH, in a solvent such as toluene, THF or dichloromethane at a temperature between −78° and 0° C. provides the primary alcohol (LXVIII). Oxidation of (LXVIII) with one of a range of oxidants described above, (such as Dess-Martin periodinane), in a solvent such as dichloromethane yields the corresponding aldehyde (LXIX). Wittig olefination of (LXIX) using a triphenylphosphoranylidine-acetate ester (LXX), in a solvent such as toluene or THF, at a temperature between room temperature and 80° C. provides the unsaturated ester (LXXI). Selective reduction of the conjugated double bond in (LXXI) to the corresponding saturated ester (LVI, n=2) is accomplished by treatment with magnesium ribbon, in a solvent such as methanol, at around room temperature.

Alternatively, treatment of alcohol (LXVIII) with p-toluenesulphonyl chloride, in a solvent such as pyridine or dichloromethane, in the presence of a base such as triethylamine or DMAP, at a temperature between −20° C. and room temperature provides the tosylate derivative (LXXII). Displacement of the tosyl group in (LXXII) by treatment with sodium cyanide in DMF, DMA or DMSO, at a temperature between room temperature and 160° C. provides the nitrile (LXXIII). Solvolysis of this nitrile by treatment with HCl in an appropriate alcohol (such as methanol or ethanol) yields (LVI, M=bond, n=1).

Ring closure metathesis can be used to provide access to (LVI, M=O or NR4) by use of the appropriate alkoxy or amino substituted bis alkene substrate (SCHEME 24). For example, coupling of an appropriately substituted aldehyde or imine (LXXIV) with a suitable Grignard provides the secondary alcohol (sulphinamine) (LXXV). Alkylation or reductive amination of (LXXV) under standard conditions provides (LXXVI). Exposure of (LXXVI) to ring closure metathesis conditions, as described above provides the carbocyclic alkene (LVI, M=O, NR$_4$).

SCHEME 24

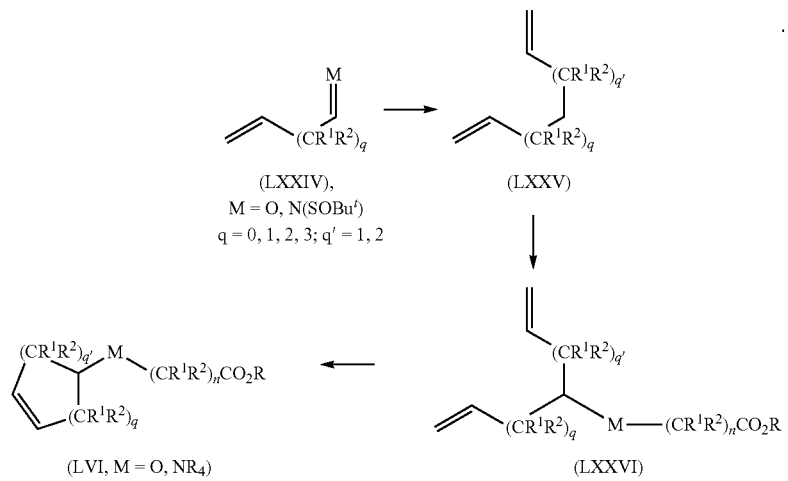

In the case where CycA is a 4-7 membered carbocycle. $Y_1$ is a 1-amino-t-amino-alkyl group (t=2, 3, 4) the requisite acids (IV) (SCHEME 25) are generally prepared by sequential installation of the amino functionality into the corresponding hydroxyl-substituted or carboxy-substituted carbon scaffold. For example, Selective reduction of the ester functionality in (LXXVIII) to the corresponding alcohol (LXXIX) is accomplished by treatment with a reducing agent, such as borane:THF, in a solvent such as THF, at around room temperature. Oxidation of the primary alcohol to the corresponding aldehyde (LXXX) is achieved by one of a wide range of standard oxidation protocols such as Swern oxidation or Dess-Martin periodane oxidation. The aldehyde is then treated with an olefin substituted-alkyl Grignard reagent, in a solvent such as THF, diethyl ether or DME at a temperature between about −50° C. and room temperature to give secondary alcohol (LXXXI). In certain cases, where the requisite olefin substituted-alkyl is an allyl (t=1), condensation with the aldehyde (LXXX) can also be effected using an allyl boronate or allyl silane in the presence of a Lewis acid such as $TiCl_4$ or $BF_3$ etherate in a solvent such as dichloromethane at a temperature between −78° C. and room temperature. The olefin substituted secondary alcohol (LXXXI) is then converted to the corresponding amine by treatment with p-toluenesulphonylchloride in the presence of a base such as triethylamine or DMAP, in a solvent such as dichloromethane or pyridine, at a temperature between −20° C. and room temperature to afford the corresponding tosylate (DOOM). The tosylate is then treated with azide salt such as sodium azide, tetrabutylammonium azide in a solvent such as DMF, DMA or DMSO at a temperature between room temperature and 160° C. to yield the corresponding azide (LXXXIII). This intermediate is reduced to the primary amine (LXXXIV) and subsequently derivatized as described above to give (LXXXV). Alternatively, Introduction of the primary amino functionality is effected by conversion of the secondary alcohol (LXXXI) to the corresponding pthalimide (LXXXVI) under Mitsunobu conditions (*Chemical Reviews*, (2009) 2551-2651) followed by deprotection of the pthalimide by treatment with excess hydrazine in a solvent such as ethanol at room temperature or above to provide the primary amine (LXXXIV).

Installation of a second amino functionality into (LXXXV) is accomplished by oxidative cleavage of the olefin as previously described, to furnish aldehyde (LXXXVII). This intermediate is converted to the requisite amine (LXXXVIII) by direct reductive alkylation or by reduction to the primary alcohol using a reducing agent such as sodium borohydride in a solvent such as THF/methanol at a temperature between −78° C. and 0° C., followed by derivatization of the resulting primary alcohol (via the corresponding tosylate, azide and primary amine) as described above. Side chain processing of (LXXXVIII) as previously described gives (IV).

SCHEME 25

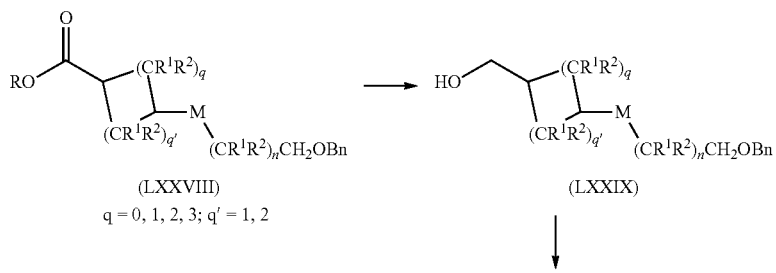

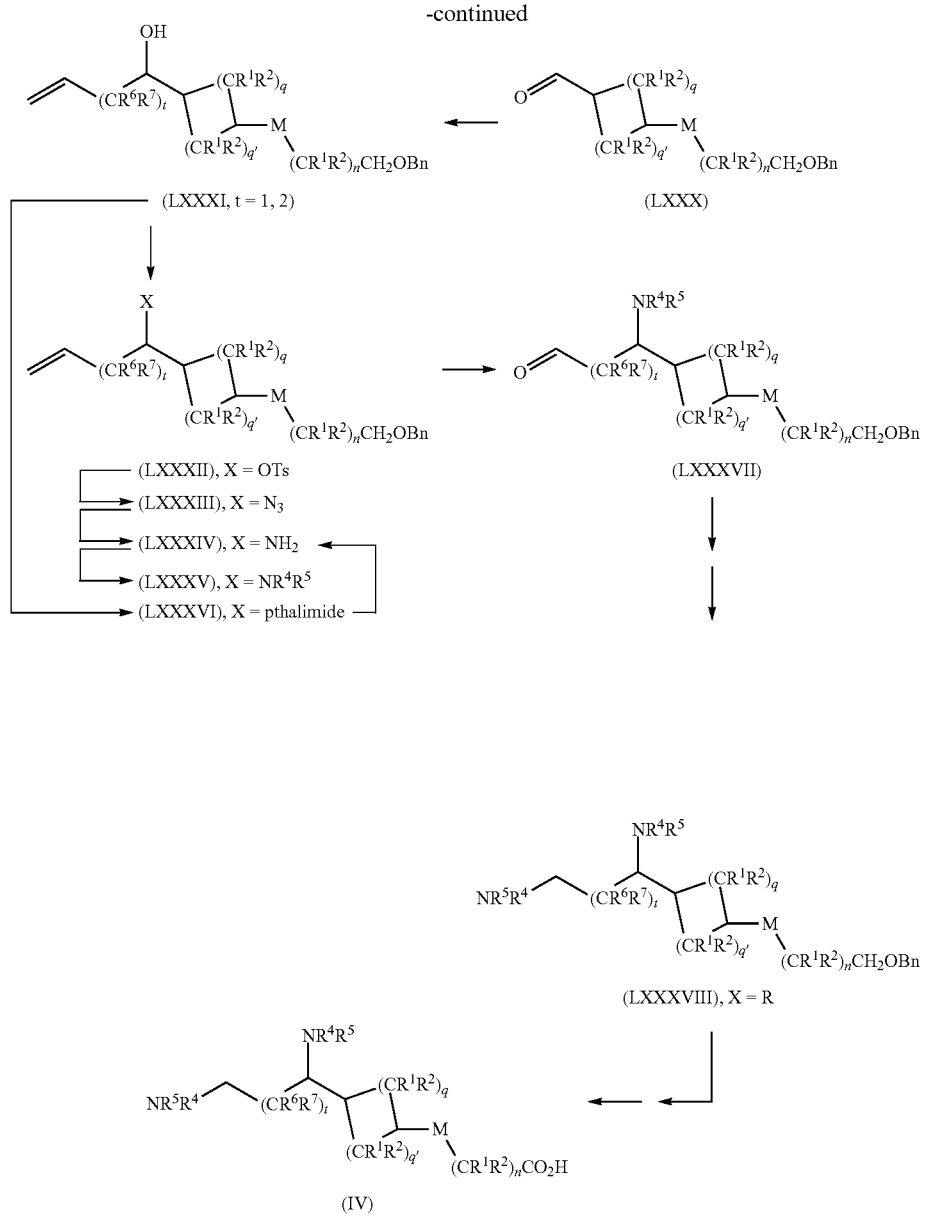

In the particular case where $Y_1$ is an optionally substituted 1-amino-2-amino-ethyl group installation of the diamine functionality can be accomplished by direct amination of the appropriate exocyclic alkene ($Mn(OAc)_3/NaN_3/TFA$ then reduction). The requisite exocyclic olefin is prepared by Wittig, Peterson or Tebbe type olefination of (LXXX) as already described.

In the case where CycA is an optionally substituted 4-7 membered carbocycle, $Y_1$ is an optionally substituted t-amino-alkyl group (t=1, 2, 3, 4), $Y_2$ is an optionally substituted amine, and $Y_1$ and $Y_2$ are both attached to the same ring carbon of CycA, the requisite acids (IV) (SCHEME 26) are prepared from the appropriate carbocyclic ketone precursor (LXXXIX) by treatment with t-butyl-sulphinamine (*Chemical Reviews*, (2010), 110(6), 3600-3740), typically in a solvent such as THF or methanol, in the presence of $Ti(OEt)_4$, at a temperature between room temperature and 60° C. The resulting t-butylsulphinimine is then condensed with an appropriate organometallic, such as an olefin substituted alkyl Grignard (or where appropriate, a $CeCl_3$ modified Grignard reagent) in a solvent such as THF, ether, dichloromethane or toluene at a temperature between −60° and 0° C. to provide the sulfinamine substituted carbocycle (XC). Removal of the sulfinyl group is effected by treatment with an acid such as trifluoroacetic acid in a solvent such as dichloromethane at around room temperature to yield the corresponding primary amine (XCI, $R^4$, $R^5$=H). The primary amine is derivitized or protected, as appropriate, by methods described above. Processing of the alkene functionality to provide the appropriate amine is effected by oxidative cleavage ($Osa_4/NMO$ then $NaIO_4$) then reductive amination of the resulting aldehyde to give (XCII). Alternatively, hydride reduction of the aldehyde and derivitization of the alcohol, as described above, also provides (XCII). Conversion of (XCII) to the requisite acid is accomplished by processing of the acid side chain precursor group Y as already described.

SCHEME 26

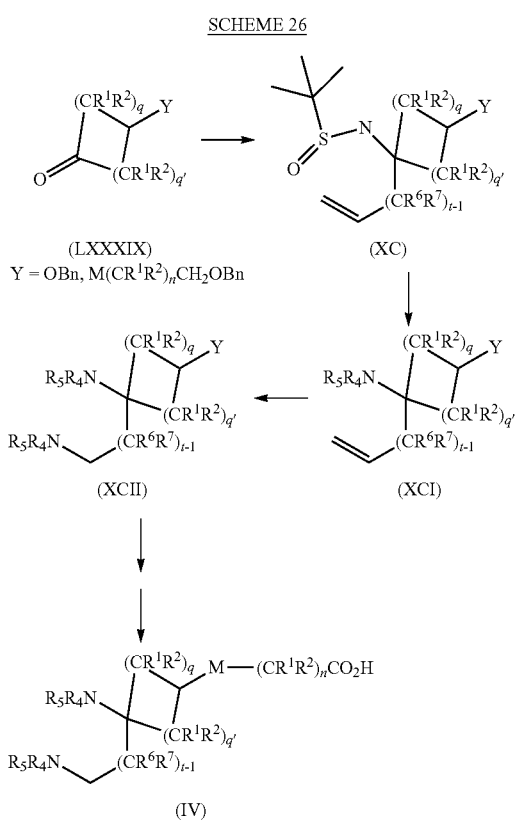

In the specific case where t=1, (IV) is prepared from ketone (LXXXIX) by a Strecker reaction (*Synthesis*, (2007), 1230-1234. *Organic Letters*, (2008), 10, 1509-1512) followed by reduction of the resulting nitrile group. Subsequent processing of this intermediate to provide (IV) is carried out as already described.

In a variation of the above system wherein CycA is an optionally substituted 4-7 membered carbocycle, $Y_1$ is an t-amino-alkyl group (t=2, 3, 4), $Y_2$ is an amine, $Y_1$ and $Y_2$ are both attached to the same ring carbon of CycA and $Y_1$ and $Y_2$ are connected to each other through their substituents (by a $CH_2$ group), the requisite acids (IV) (SCHEME 27) are prepared from the intermediate (XCI) by treatment with $OsO_4$ in a solvent such as acetone/water in the presence of an oxidant such as N-methyl-morpholine N-oxide to yield the corresponding diol. This intermediate is treated with sodium periodate in THF/water to form the truncated aldehyde (XCIII). (XCIII) is then condensed with an α-phosphonoglycine ester derivative, such as the BOC-protected α-phosphono-glycine trimethyl ester, in the presence of a base such as potassium t-butoxide in a solvent such as dichloromethane at a temperature between −78° C. and −50° C. to give the unsaturated ester (XCIV) (*Tetrahedron*, (2001), 57, 6463). (XCIV) is selectively hydrogenated using a cationic rhodium phosphine-phosphite catalyst to give the corresponding saturated-BOC-TCEOC-protected amino ester. This intermediate is de-protected under standard conditions (Zinc/acetic acid in THF) to yield the BOC protected amino ester (XCV).

Cyclization of the amino ester, in the presence of a base such as DBU, in a solvent such as toluene, at a temperature between room temperature and 110° C. provides lactam (XCVI). Selective reduction of the tertiary amide in (XCVI) using a silane reducing agent in the presence of rhodium-hydrocarbonyltriphenylphosphine, or chloroplatinic acid, as described above, followed by amine derivatization provides (XCVII). Subsequent processing of the side chain Y, as previously described, provides the requisite acids (IV).

SCHEME 27

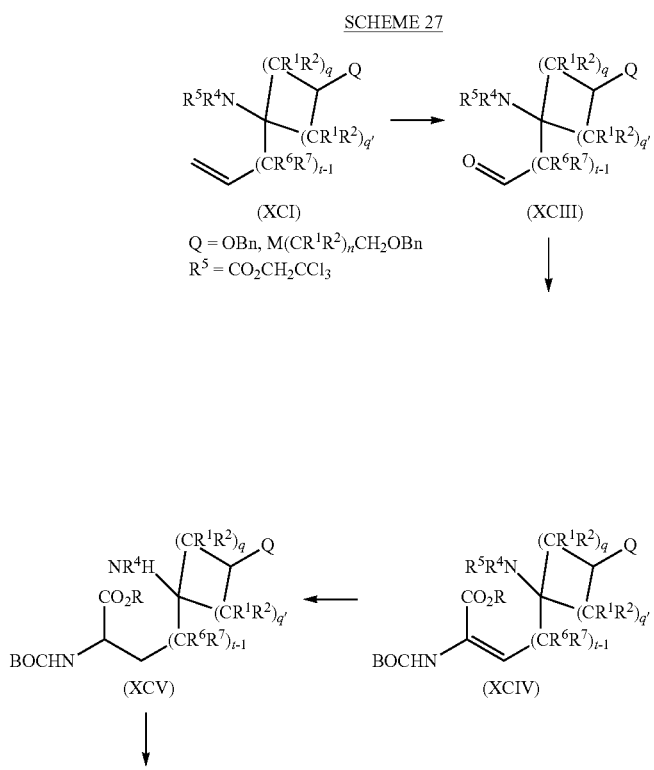

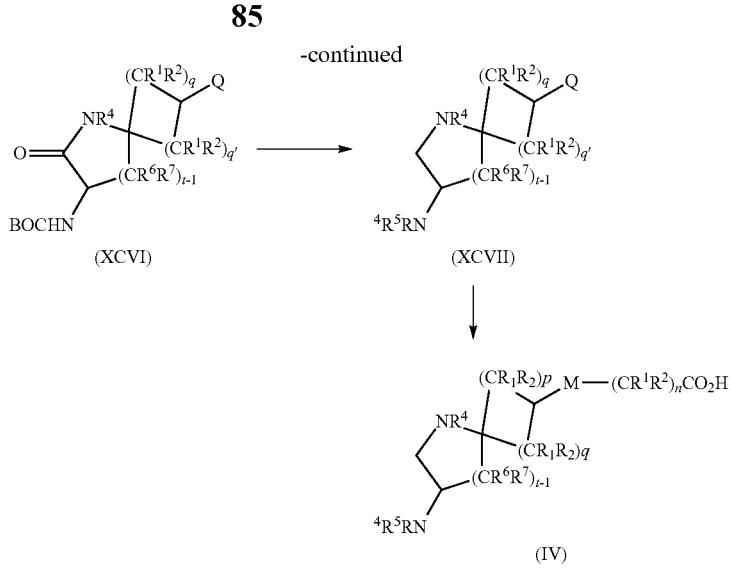

In the case where CycA is an optionally substituted 4-7 membered carbocycle, $Y_1$ is an optionally substituted t-amino-alkyl group (t=2, 3, 4), $Y_2$ is an optionally substituted amine, and the ring carbon of CycA attached to $Y_1$ and the ring carbon of CycA attached to $Y_2$ are positioned vicinal to each other, the requisite acids (IV) (SCHEME 28) can be prepared from the appropriate cyclic ketone (XCVIII). For example, in the case where t=2, treatment of (XCVIII) with a trialkylsilyl triflate in the presence of a base such as triethylamine in a solvent such as ether furnishes the corresponding silyl enol ether (XCIX). Reaction of this intermediate with a nitro-olefin ($R^6R^7C=CR^6NO_2$) in the presence of a Lewis acid such as $TiCl_4/(TiOiPr)_4$ or $SnCl_4$ in a solvent such as dichloromethane at a temperature between –78° C. and room temperature provides the nitro-alkyl substituted cyclic ketone (C) (*Journal of the American Chemical Society*, 106(7), 2149-56; 1984; *Helvetica Chimica Acta*, 82(11), 1829-1842; 1999; *Canadian Journal of Chemistry*, 65(4), 836-50; 1987). Hydride reduction of this intermediate using a reagent such as lithium aluminum hydride in a solvent such as THF at a temperature between –20° C. and reflux provides amino alcohol (CI). The amino group of (CI) is selectively derivitized as described above to give (CII). Installation of the second amino group is effected by derivitization of the carbocyclic alcohol (CII) using methods described above to provide (CIII). Removal of the benzyl ether protecting group and oxidation of the resulting primary alcohol is effected as described previously to yield the requisite carboxylic acid (IV).

SCHEME 28

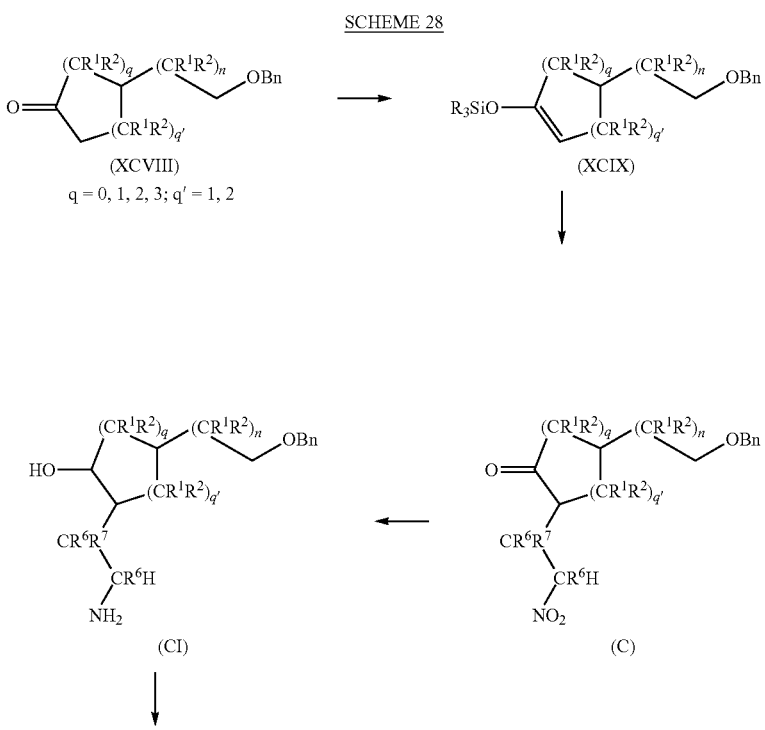

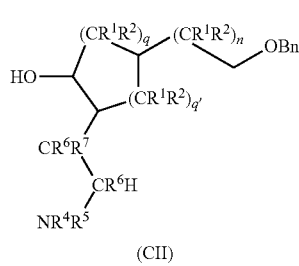

(CII)

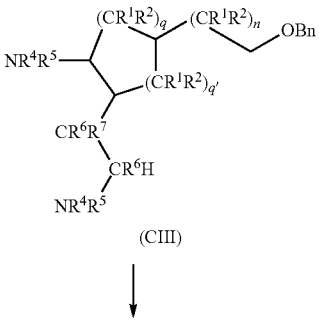

(CIII)

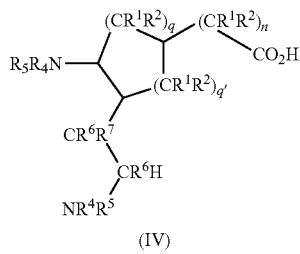

(IV)

For the case where t=1 (SCHEME 29), installation of the appropriate side chain functionality is achieved by reaction of silyl-enol ether (XCIX) with an iminium salt (where appropriate generated in situ from the N,O-acetal and trimethylsilyltriflate) in a solvent such as dichloromethane at a temperature between −78° C. and room temperature to provide amino ketone (CIV). Processing of the ketone in (CIV), as previously described, provides the diamino-functionalized scaffold (CV). Thereafter, removal of the benzyl ether and oxidation of the resulting primary alcohol in the usual manner yields the desired acid (IV).

of silyl-enol ether (XCIX) with methyl lithium, in a solvent such as THF, at a temperature between −20° C. and 0° C. to generate the corresponding Lithium enolate regioselectively. This is followed by treatment of the enolate with an electrophile such as an acrylamide (or acrylonitrile) to give (CIV). Processing of the ketone as already described provides the amine functionalized amide (CVII). Reduction of the amide with a reducing agent such as Lithium aluminum hydride in a solvent such as THF at a temperature between −10° C. and reflux yields the diamine (CVIII). This inter-

SCHEME 29

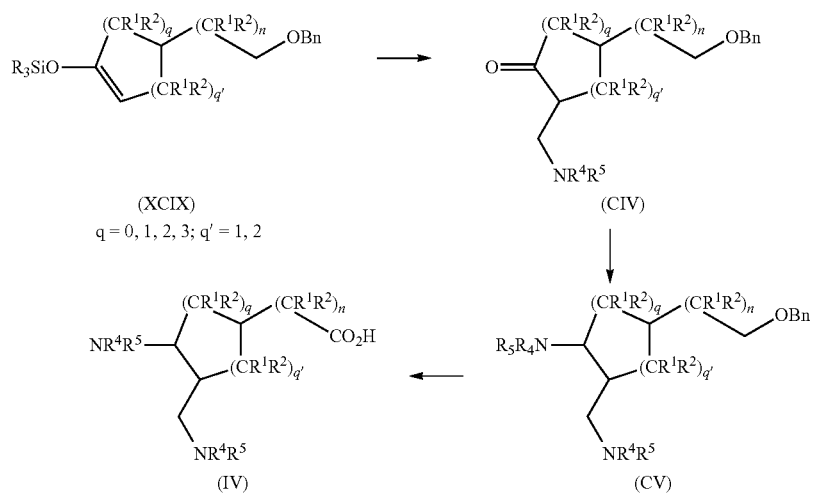

For the case where t=3 (SCHEME 30), installation of the appropriate side chain functionality is achieved by reaction mediate is then processed, as described above (debenzylation then oxidation), to provide the requisite acid (IV).

SCHEME 30

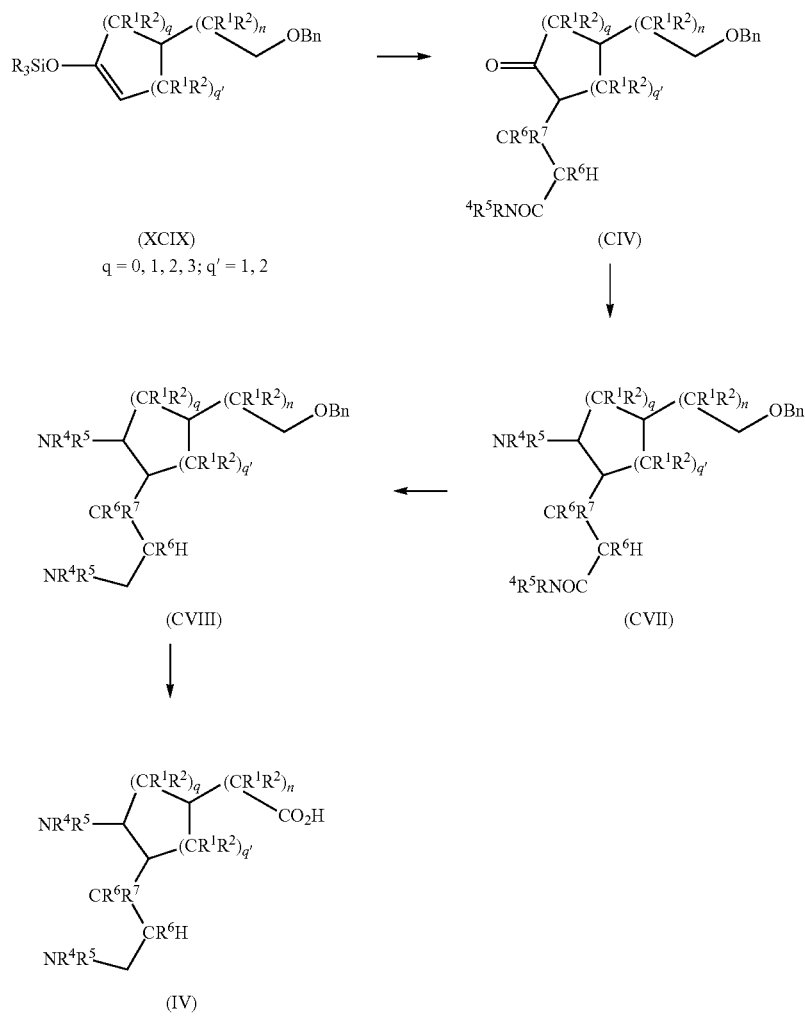

In the case where A is an optionally substituted 4-7 membered carbocycle, $Y_1$ is an optionally substituted r-amino-alkyl group (t=2, 3, 4), $Y_2$ is an optionally substituted amino-methylene, and both $Y_1$ and $Y_2$ are attached to the same ring carbon of A, the requisite acids (IV) (SCHEME 31) are prepared from the carbocyclic ketone (CIX). For example, conversion of (CIX) to the corresponding exocyclic nitrile (CX) is accomplished by treatment with TOSMIC and base as previously described. Treatment of (CX) with a base such as LDA, LHMDS or NaHMDS in a solvent such as THF and an imine, such as a t-butylsulphin-imine (*Chemical Reviews*, (2010), 110(6), 3600-3740) provides the t-butylsulphinamino-methyl substituted nitrile (CXI). Removal of the sulphinyl group by treatment with an acid such as trifluoroacetic acid in dichloromethane followed by derivatization of the primary amine as described above provides the amino nitrile (CXII). Reduction of the nitrile (CXII) with lithium aluminum hydride, as described above, yields the primary amine (CXIII). This amine is further derivatized, where appropriate, as described above (this may also include temporary derivatization using an easily removable protecting group) to give (CXIV). Subsequent processing of the exocyclic benzyl ether in (CXIV), using the usual procedures provides the requisite acid (IV).

SCHEME 31

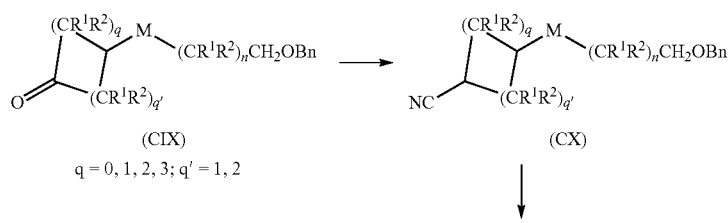

-continued

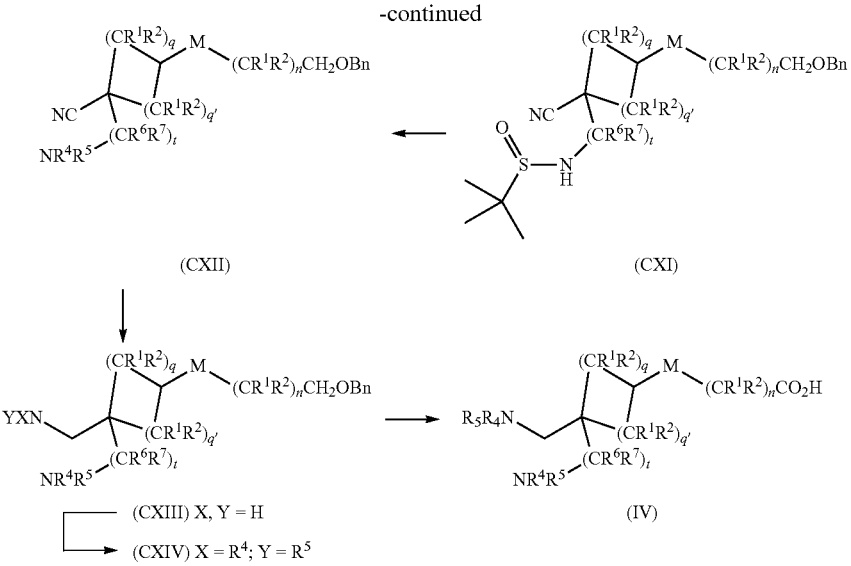

In the case where CycA is a 6 or 7 membered carbocycle, $Y_1$ is an optionally substituted r-amino-alkyl group (t=1, 2, 3), $Y_2$ is an optionally substituted amine and the ring carbon on CycA attached to $Y_1$ and the ring carbon on CycA attached to $Y_2$ are separated by a methylene, the requisite acids (IV) (SCHEME 32) are prepared from an appropriately substituted carbocyclic enone such as (CXV). For example, in the case where t=1, an appropriately functionalized one carbon unit is installed by treatment of the carbocyclic enone (CXV) with a cyanating reagent system such as trimethylsilyl cyanide or hydrogen cyanide in the presence of a base such as KF, $Cs_2CO_3$, $Bu_4NF$ or tetramethylguanidine in a suitable solvent, such as methanol, THF, DMA or acetonitrile to give (CXVI). Introduction of the nitrile can also be accomplished by treatment of the enone (CXV) with diethylaluminum cyanide in a solvent such as benzene, toluene or dichloromethane, at a temperature between about −20° C. and room temperature. Subsequent derivitization of the carbocyclic ketone (CXVI), (via reductive amination, conversion to the azide; azide reduction and further derivitization of the resulting primary amine), as described previously, affords the 1-amino-3-cyano substituted-carbocycle (CXVII). This intermediate is converted to the required aminomethyl derivative by reduction of the nitrile and functionalization of the resulting primary amine (CXVIII) as already described to provide (CXIX). Side chain processing in the usual manner provides (IV).

SCHEME 32

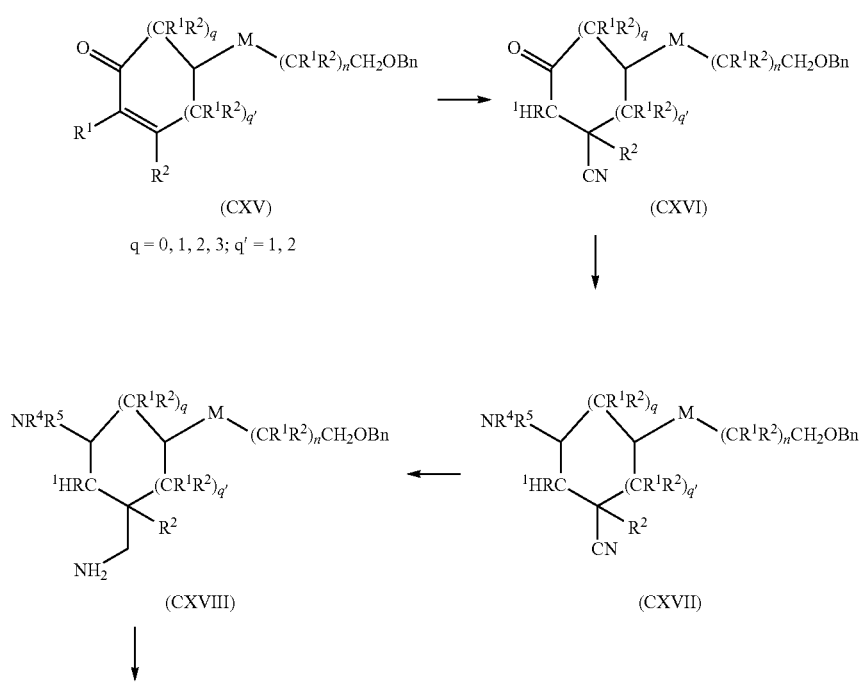

-continued

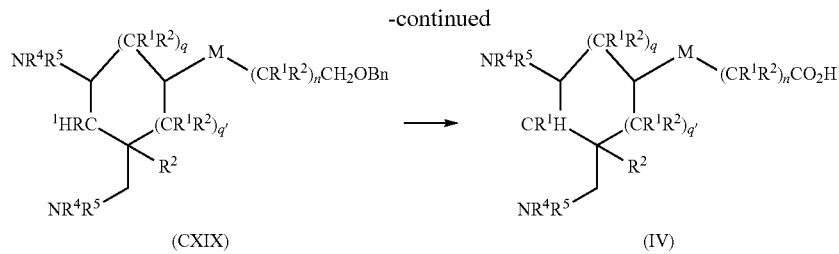

In the case where t=2, or 3 (SCHEME 33), the appropriately functionalized carbon scaffold is prepared by treatment of the carbocyclic enone (CXV) with an allyl-silane in a non-coordinating solvent such as dichloromethane in the presence of a Lewis acid such as $TiCl_4$, $SnCl_4$, or $BF_3$ etherate, at a temperature between $-78°$ C. and room temperature to yield the olefin functionalized carbocyclic ketone (CXX). Processing of the ketone functionality in (CXX), as already described, yields (CXXI). Oxidative cleavage of the olefin in (CXXI) and processing of the resulting aldehyde to the corresponding amine, as already outlined, provides (CXXII). This intermediate is then converted to the requisite acid (IV, t=2) by side chain processing in the usual manner. Alternatively, hydroboration of the olefin (CXXI) by treatment with a borane, such as 9-BBN in a solvent such as THF at around 0° C. followed by oxidative workup (NaOH/ $H_2O_2$) provides (CXXIII). Subsequent processing of (CXXIII) as already described, installs the amine functionality to give (CXXIV). Side chain processing of this intermediate yields acid (IV, t=3).

SCHEME 33

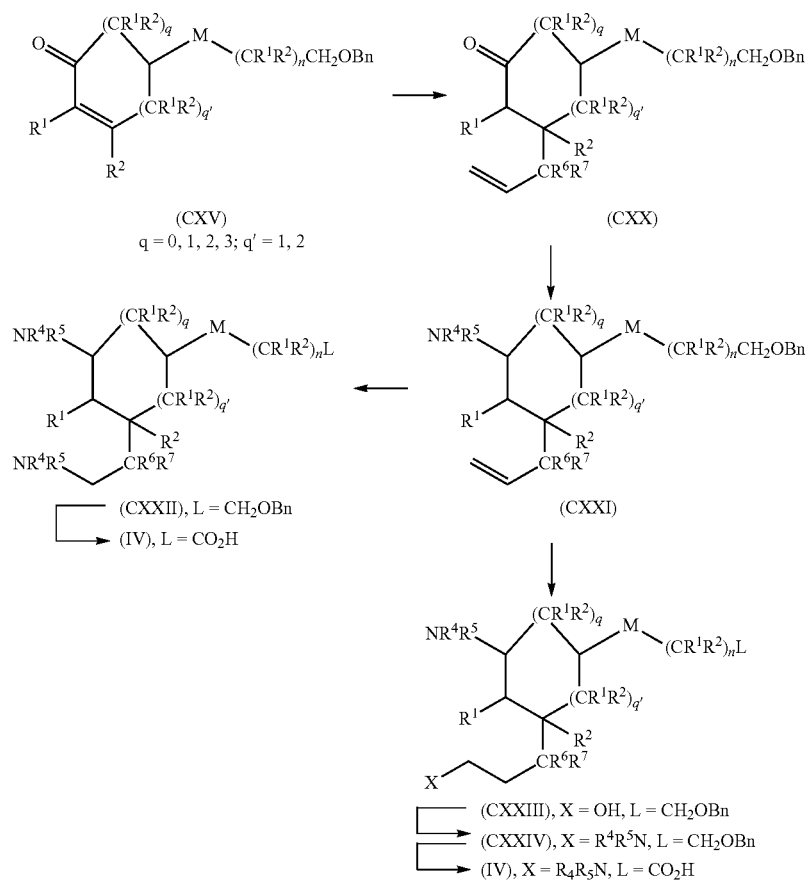

In the case where A is an optionally substituted 6 or 7 membered carbocycle, $Y_1$ is an optionally substituted-amine, $Y_2$ is an optionally substituted amine and the ring carbon on CycA attached to $Y_1$ and the ring carbon on CycA attached to $Y_2$ are separated by a methylene, the requisite acids (IV) (SCHEME 34) are prepared from an appropriately substituted carbocyclic enone such as (CII) by treatment with a suitable amine in the presence of a catalyst such as $RuCl_3$, $Cu(acac)_2$, $FeCl_3$, $Ce(NH_4)NO_3$ $Pd(acac)_2$ $NH_4PF_6$ in a solvent such as water or poly-ethylene-glycol (*Green Chemistry*, (2006), 8(4), 356-358; *Synthesis*, (2005), (13), 2129-2136; *Helvetica Chimica Acta*, (2004), 87(6), 1522-1526; *Advanced Synthesis & Catalysis*, (2005), 347 (6), 763-766; *Synthetic letters*, (2006), (10), 1549-1553) at a temperature between room temperature and 80° C. to give the β-amino-ketone (CXXV). Subsequent processing of the ketone functionality as described above yields the diamine (CXXVI). Conversion of (CXXVI) to acid (IV) is achieved by side chain processing as previously described.

a solvent such as DMF, DMA, DMSO, at a temperature between 5° C. and 80° C. (a catalyst such as tetrabutylammonium iodide may also be used) to give the corresponding latent amino substituted alkoxy-carbocycles (CXXVIII and CXXIX) respectively. Unmasking of the latent amine by treatment of (CXXVIII) with hydrazine in ethanol, or treat-

SCHEME 34

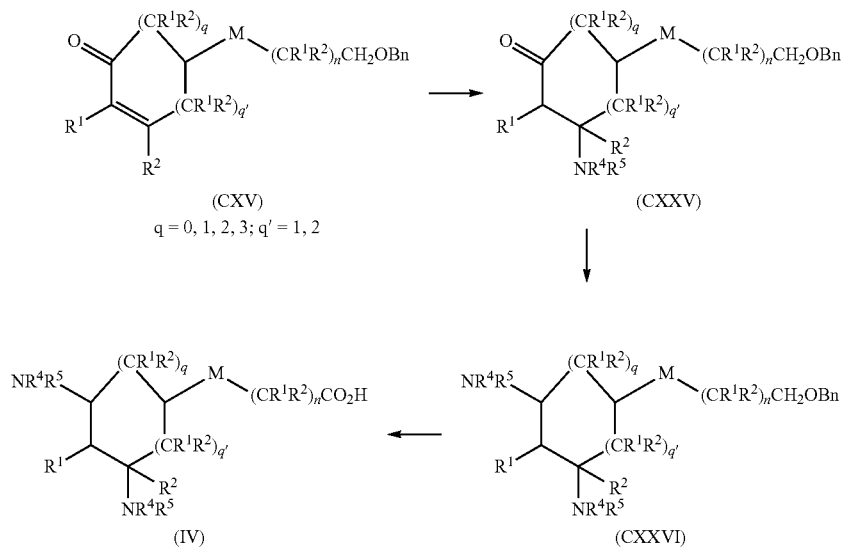

In the case where $Y_1$ is an optionally substituted aminoalkyl-oxy, the requisite acids (IV) (SCHEME 35) are prepared by treatment of an appropriate carbocyclic alcohol (CXXVII) with a pthalimido or azido substituted alkyl-halide in the presence of a base, such as sodium hydride, in ment of (CXXIX) with triphenylphosphine and water in THF provides the corresponding primary amine (CXXX). Amine derivitization as previously described yields (CXXXI). Processing of (CXXXI) by the standard method furnishes the requisite acid (IV).

SCHEME 35

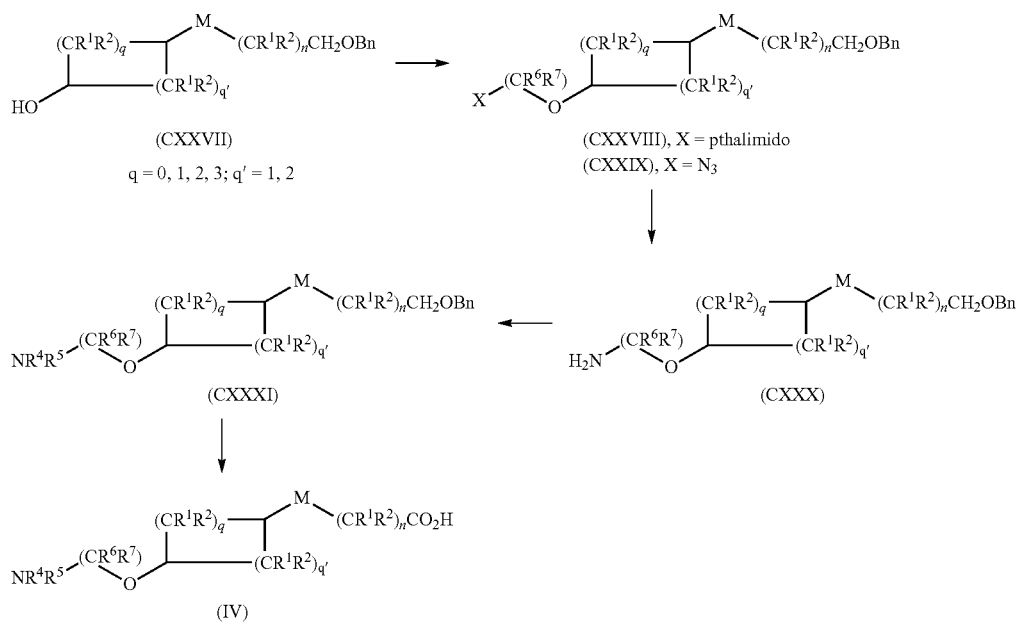

Alternatively (SCHEME 36), treatment of alcohol (CXVII) with a reagent system such as iodine/imidazole/Ph₃P or NBS/Ph₃P or with an appropriate sulphonyl chloride (or anhydride) in the presence of a base such as pyridine or triethylamine in a solvent such as THF or dichloromethane provides the corresponding iodide, bromide or sulphonate (CXXXII). Reaction of (CXXXII) with an appropriate alcohol in the presence of a base such as sodium hydride, in a solvent such as THF, DMF, DMA, or TBTU, or a mixture thereof, provides the alkoxy substituted carbocycles (CXXVIII) and (CXXIX). Conversion of these intermediates to (IV) is carried out as already described.

from an appropriate piperidinone such as (CXXXIII). For example, treatment of (CXXXIII) with α-methyl benzylamine (*Bioorganic and medicinal Chemistry Letters*, (2008), 18(4), 1312-1317) and an appropriate methyl-vinyl ketone derivative in toluene followed by cyclization with sodium methoxide in methanol affords the bicyclic ketone (CXXXIV). Hydrogenation of (CXXXIV) using a catalyst such as palladium on carbon in a solvent such as methanol and installation of the guanidinyl group as already described, yields ketone (CXXXV). Processing of ketone (CXXXV) as already outlined, provides the requisite acids

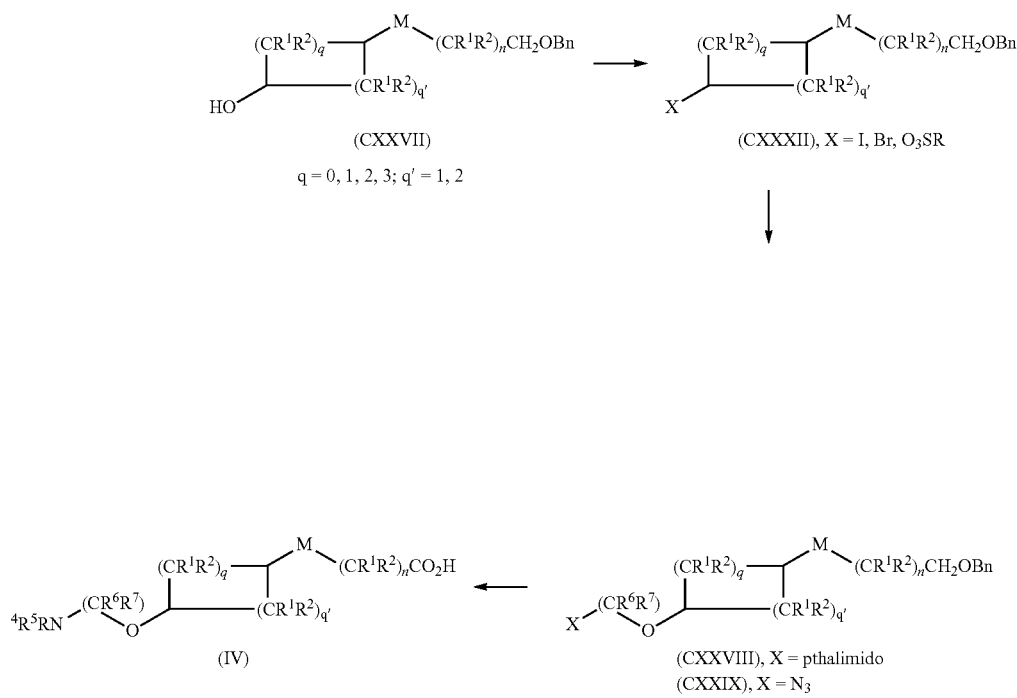

SCHEME 36

Formula (I) provides for the case where $Y_1$ and $Y_2$, taken together with the carbon atom or carbon atoms to which they are attached, form an optionally substituted carbocycle or optionally substituted heterocycle. A specific instance of this provision (SCHEME 37) is where CycA is a cyclohexane, $Y_1$ is an (N-methyl-guanidinyl)-methyl group. $Y_2$ is a methyl group. $Y_1$ and $Y_2$ are positioned vicinally to each other on CycA and $Y_1$ and $Y_2$ are linked to each other by formal fusion of two methyl groups to form a substituted piperidine. In this particular case, the requisite acids (IV) are prepared (IV, M=bond; n=1,2). Alternatively, reduction of (CXXXV) with a hydride reducing agent such as sodium borohydride in methanol at a temperature between −78° C. and 0° C. provides the corresponding alcohol which is treated with ethyl diazoacetate and a catalytic amount of Rh(acac)₂ dimer in a solvent such as dichloromethane to afford the ester (CXXXVI). Saponifacation of (CXXXVI) by brief treatment with lithium hydroxide in THF/methanol/water provides the acid (IV, M=O, n=1).

SCHEME 37

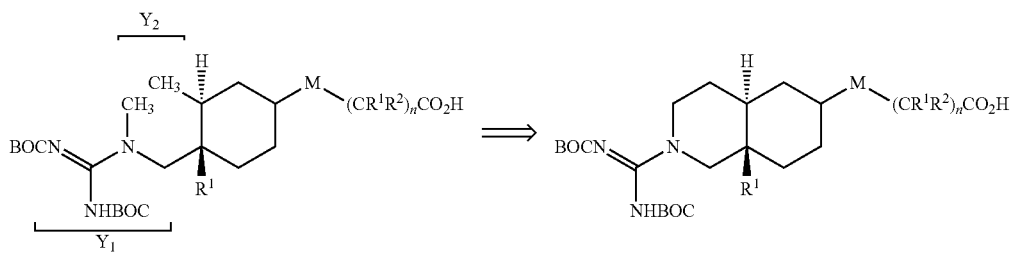

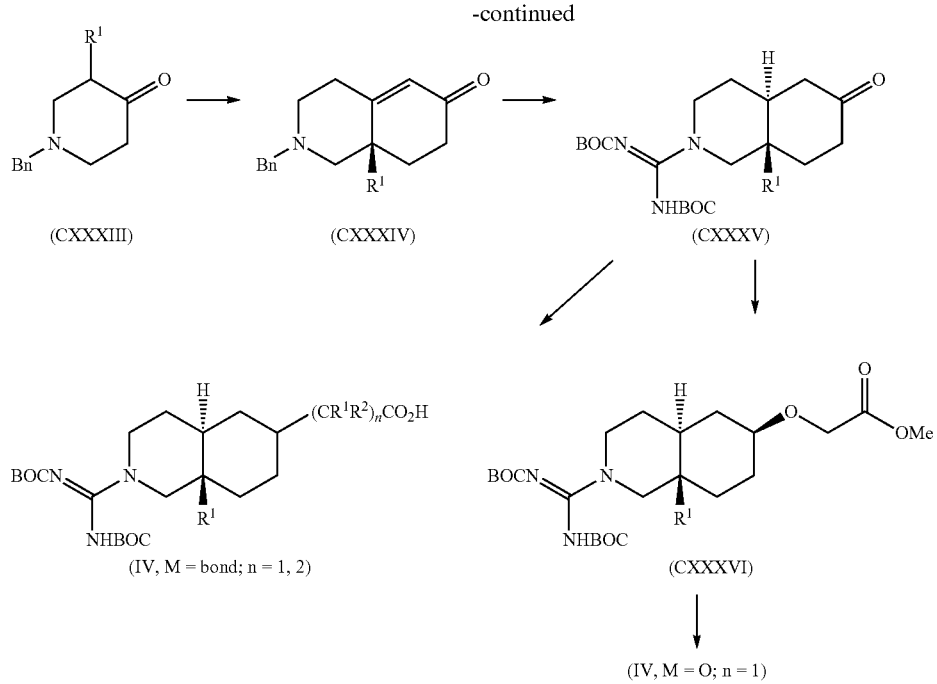

In the case where Z is a sulphonyl group (SCHEME 38), the requisite sulphonic acid is prepared from the corresponding activated carboxylic acid (V) by treatment with sodium hydroxythiopyridone in a solvent such as dichloromethane, at around room temperature to yield the Barton ester intermediate (CXXXVII). (CXXXVII) is treated with iodoform in $CCl_4$ under a tungsten UV lamp at around reflux temperature to provide the de-carboxylative-iodination product (CXXXVIII) (*Journal of Organic Chemistry*, 75(19), 6489-6501; 2010). Alternatively, treatment of acid (IV) with iodoso-benzene-diacetate and iodine in $CCl_4$, under a tungsten UV lamp, at around reflux temperature (*Journal of Organic Chemistry*, (1986), 51, 402) provides (CXXXVIII) directly. Treatment of (CXXXVIII) with sodium sulphite in aqueous ethanol, isopropanol or acetone, at a temperature between 60 and 90° C., followed by acidification yields the sulphonic acid (IV). Alternatively, treatment of (CXXXVIII) with thiourea in acetone, at around 60° C., provides the isothiouronium salt derivative (CXXXIX) (*Synthetic Letters*, (2010), 7, 1037). Cleavage of (CXXXVIII) with aq. sodium thiosulphate gives thiol (CXL). Treatment of (CXL) with performic acid (formic acid and aqueous $H_2O_2$ at around 0° C. to room temperature) provides (IV).

SCHEME 38

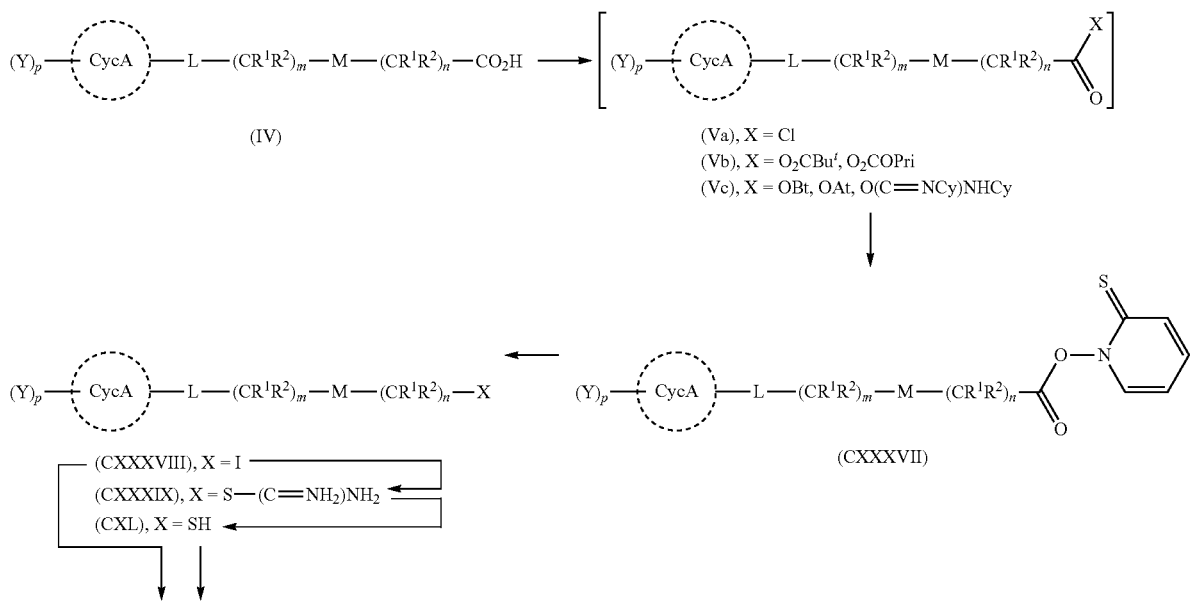

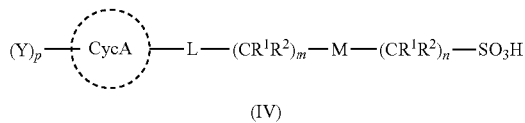

(IV)

SYNTHETIC EXAMPLES

The following preparations of compounds of Formula I or Formula Ia and intermediates are given to enable those of skill in the art to more clearly understand and to practice the present invention. They should not be considered as limiting the scope of the invention, but merely as illustrative and representative thereof.

Example 1

(R)-3-(trans-4-(aminomethyl)cyclohexanecarboxamido)-2-hydroxy-3,4-dihydro-2H-benzo[e][1,2]oxaborinine-8-carboxylic acid

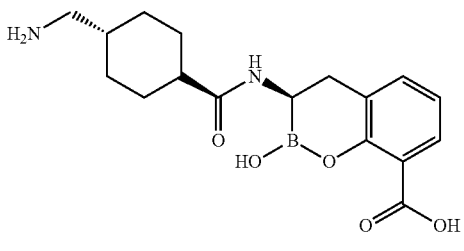

Step 1: Synthesis of tert-butyl 3-((2R)-2-(trans-4-((tert-butoxycarbonylamino)methyl)cyclohexanecarboxamido)-2-(2,9,9-trimethyl-3,5-dioxa-4-bora-tricyclo[6.1.1.0$^{2,6}$]dec-4-yl)ethyl)-2-methoxybenzoate To anhydrous CH$_2$Cl$_2$ (0.61 mL, 9.4 mmol) in THF (20 mL) under Argon at –100° C. (MeOH/Liq. N$_2$) was added n-BuLi (2.7 mL, 2.5 M in hexane) dropwise and the reaction mixture was stirred at same temperature for 30 min. A THF (5 mL) solution of 2-methoxy-3-(2,9,9-trimethyl-3,5-dioxa-4-bora-tricyclo[6.1.1.0$^{2,6}$]dec-4-ylmethyl)-benzoic acid tert-butyl ester (2.37 g, 5.92 mmol) was added over a period of 10 min. After 20 min, the cooling bath was removed and the reaction mixture was slowly warmed up to 0° C. and stirred at same temperature for 1 hr. The reaction mixture was then cooled to –78° C., LHMDS (8.0 mL, 1M in THF) was added slowly and the resultant reaction mixture was stirred while warming up to room temperature gradually overnight. Anhydrous MeOH (0.29 mL, 7.1 mmol) was added at –10° C., the reaction was stirred at same temperature for 1 hr and then at room temperature for 1 hr.

In a separate flask containing 0.386 g of 4-((tert-butoxycarbonylamino)methyl)cyclohexanecarboxylic acid (1.5 mmol), anhydrous CH$_2$Cl$_2$ (12 mL) was added. To this reaction mixture was added NMM (0.22 mL, 2 mmol), followed by HATU (0.570 g, 1.5 mmol). DMF (1 mL) was added and the resultant solution was stirred at room temperature (RT) for 1 hr, at which time a portion of the solution from above reaction (1.5 mmol) was added to the flask and the reaction was stirred for 2 hr. The reaction was quenched by addition of water (30 mL) and the aqueous phase extracted with EtOAc (3×50 mL). The organic phase was washed with brine, dried over Na$_2$SO$_4$, and concentrated in vacuo to afford the crude product, which was purified by flash chromatography on silica gel (hexane/EtOAc, 2:1 to 1:2) to afford the product (200 mg, 20%). ESI-MS m/z 669.1 (MH)$^+$.

Step 2: Synthesis of (R)-3-(trans-4-(aminomethyl)cyclohexanecarboxamido)-2-hydroxy-3,4-dihydro-2H-benzo[e][1,2]oxaborinine-8-carboxylic acid To a solution of tert-butyl 3-((2R)-2-(trans-4-((tert-butoxycarbonylamino)methyl)cyclohexanecarboxamido)-2-(2,9,9-trimethyl-3,5-dioxa-4-bora-tricyclo[6.1.1.0$^{2,6}$]dec-4-yl)ethyl)-2-methoxybenzoate from step 1 (200 mg, 0.30 mmol) in anhydrous CH$_2$Cl$_2$(5 mL) at –78° C. was added BCl$_3$ (2.1 mL, 1M in DCM, 2.1 mmol), and the reaction mixture was stirred at same temperature for 1 hr, at which time the reaction mixture was warmed up to 0° C. and stirred at same temperature for additional 1 hr. The reaction was quenched by addition of water (5 mL) at 0° C. The crude product was purified by reverse phase preparative HPLC and dried using lyophilization to afford the product (30 mg) as white solid. ESI-MS m/z 347 (MH)$^+$.

Example 2

(R)-3-(trans-4-aminocyclohexanecarboxamido)-2-hydroxy-3,4-dihydro-2H-benzo[e][1,2]oxaborinine-8-carboxylic acid

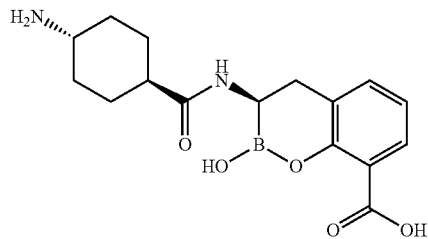 [SMILES: N[C@H]1CC[C@H](C(=O)N[C@H]2Cc3cccc(C(=O)O)c3OB2O)CC1]

Step 1: Synthesis of tert-butyl 3-((2R)-2-(trans-4-(tert-butoxycarbonylamino)cyclohexanecarboxamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and tran-4-(tert-butoxycarbonylamino)cyclohexanecarboxylic acid following procedure described in step 1 of Example 1. The crude product was purified by flash chromatography on silica gel (hexane/EtOAc, 2:1 to 1:2). ESI-MS m/z 655.1 (MH)$^+$.

Step 2: Synthesis of (R)-3-(trans-4-aminocyclohexanecarboxamido)-2-hydroxy-3,4-dihydro-2H-benzo[e][1,2]oxaborinine-8-carboxylic acid Prepared from tert-butyl 3-((2R)-2-(trans-4-(tert-butoxycarbonylamino)cyclohexanecarboxamido)-2-(2,9,9-trimethyl-3,5-dioxa-4-bora-tricyclo[6.1.1.0²,⁶]dec-4-yl)ethyl)-2-methoxybenzoate and BCl₃ following the procedure described in Step 2 of Example 1. The crude product was purified by reverse phase preparative HPLC and dried using lyophilization. ESI-MS m/z 333 (MH)⁺.

Example 3

(R)-3-(2-trans-4-(aminomethyl)cyclohexyl)acetamido)-2-hydroxy-3,4-dihydro-2H-benzo[e][1,2]oxaborinine-8-carboxylic acid

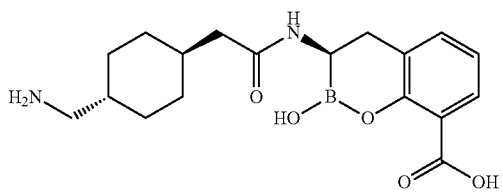 [SMILES: NC[C@H]1CC[C@H](CC(=O)N[C@H]2Cc3cccc(C(=O)O)c3OB2O)CC1]

Step 1: Synthesis of tert-butyl 34(2R)-2-(2-trans-4-((tert-butoxycarbonylamino)methyl)cyclohexyl)acetamido)-2-(2,9,9-trimethyl-3,5-dioxa-4-bora-tricyclo [6.1.1.0²,⁶]dec-4-yl)ethyl)-2-methoxybenzoate Prepared from 2-methoxy-3-(2,9,9-trimethyl-3,5-dioxa-4-bora-tricyclo[6.1.1.0²,⁶]dec-4-ylmethyl)-benzoic acid tert-butyl ester and 2-(trans-4-((tert-butoxycarbonylamino)methyl)cyclohexyl)acetic acid following procedure described in step 1 of Example 1. The crude product was purified by flash chromatography on silica gel (hexane/EtOAc, 2:1 to 1:2). ESI-MS m/z 683.1 (MH)⁺.

Step 2: Synthesis of (R)-3-(2-trans-4-(aminomethyl) cyclohexyl)acetamido)-2-hydroxy-3,4-dihydro-2H-benzo[e][1,2]oxaborinine-8-carboxylic acid Prepared from tert-butyl 3-((2R)-2-(2-trans-4-((tert-butoxycarbonylamino)methyl)cyclohexyl)acetamido)-2-(2,9,9-trimethyl-3,5-dioxa-4-bora-tricyclo[6.1.1.0²,⁶]dec-4-yl) ethyl)-2-methoxybenzoate and BCl₃ following the procedure described in Step 2 of Example 1. The crude product was purified by reverse phase preparative HPLC and dried using lyophilization. ESI-MS m/z 361 (MH)⁺.

Example 4

(R)-3-(2-(trans-4-(guanidinomethyl)cyclohexyl)acetamido)-2-hydroxy-3,4-dihydro-2H-benzo[e][1,2] oxaborinine-8-carboxylic acid

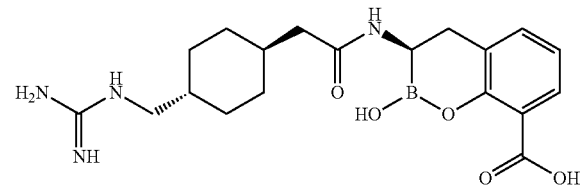

Synthesis of (R)-3-(2-(trans-4-(guanidinomethyl) cyclohexyl)acetamido)-2-hydroxy-3,4-dihydro-2H-benzo[e][1,2]oxaborinine-8-carboxylic acid To (R)-3-(2-trans-4-(aminomethyl)cyclohexyl)acetamido)-2-hydroxy-3,4-dihydro-2H-benzo[e][1,2]oxaborinine-8-carboxylic acid from Example 3 (12 mg) in MeOH (2 mL) was added tert-butyl (1H-pyrazol-1-yl)methanediylidenedicarbamate (12 mg) and stirred for 4 hr. The solvent was removed in vacuo. The residue was dissolved in 4N HCl in dioxane (2 mL) and stirred for 2 hr. The solvent was removed in vacuo and the crude product was purified by reverse phase preparative HPLC and dried using lyophilization. ESI-MS m/z 403 (MH)⁺.

Example 5

(R)-3-(2-(trans-4-((2-(dimethylamino)acetamido) methyl)cyclohexyl)acetamido)-2-hydroxy-3,4-dihydro-2H-benzo[e][1,2]oxaborinine-8-carboxylic acid

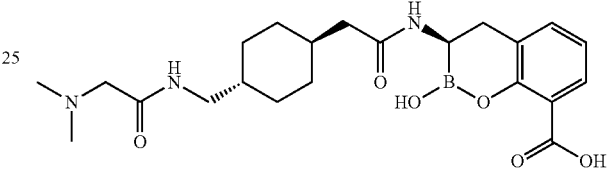

Step 1: Synthesis of 3-((2R)-2-(2-(trans-4-(aminomethyl)cyclohexyl)acetamido)-2-(2,9,9-trimethyl-3,5-dioxa-4-bora-tricyclo[6.1.1.0²,⁶]dec-4-yl)ethyl)-2-methoxybenzoic acid To tert-butyl 3-((2R)-2-(2-(trans-4-((tert-butoxycarbonylamino)methyl)cyclohexyl)acetamido)-2-(2,9,9-trimethyl-3,5-dioxa-4-bora-tricyclo[6.1.1.0²,⁶]dec-4-yl)ethyl)-2-methoxybenzoate (422 mg, 0.75 mmol from Example 3, Step 1) in a flask was added 4N HCl in dioxane (3 mL) and the reaction mixture stirred at RT for 1 hr. Removal of the solvents afforded the product as yellow foam.

Step 2: Synthesis of 3-((2R)-2-(2-(trans-4-((2-(dimethylamino)acetamido)methyl)cyclohexyl)acetamido)-2-(2,9,9-trimethyl-3,5-dioxa-4-bora-tricyclo [6.1.1.0²,⁶]dec-4-yl)ethyl)-2-methoxybenzoic acid To 3-((2R)-2-(2-(trans-4-(aminomethyl)cyclohexyl)acetamido)-2-(2,9,9-trimethyl-3,5-dioxa-4-bora-tricyclo [6.1.1.0²,⁶]dec-4-yl)ethyl)-2-methoxybenzoic acid from step 1 in THF (5 mL), was added TEA (0.35 mL), followed by 2-bromoacetyl bromide (0.07 mL, 0.8 mmol). The reaction mixture was stirred at RT for 1 hr. Water was added and aqueous phase extracted with EtOAc. The organic phase was dried and concentrated to provide the crude product, which was dissolved in THF (5 mL) and dimethyl amine (1 mL, 2N in THF) was added. After stirring at RT for 8 hr, the volatile components were removed in vacuo and the residue was carried on to the next step without further purification. ESI-MS m/z 612.1 (MH)⁺.

Step 3: Synthesis of (R)-3-(2-(trans-4-((2-(dimethylamino)acetamido)methyl)cyclohexyl)acetamido)-2-hydroxy-3,4-dihydro-2H-benzo[e][1,2]oxaborinine-8-carboxylic acid Prepared from 3-((2R)-2-(2-(trans-4-((2-(dimethylamino)acetamido)methyl)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid and BCl$_3$ following the procedure described in Step 2 of Example 1. The crude product was purified by reverse phase preparative HPLC and dried using lyophilization. ESI-MS m/z 446 (MH)$^+$.

Example 6

(R)-3-(2-(trans-4-aminocyclohexyl)acetamido)-2-hydroxy-3,4-dihydro-2H-benzo[e][1,2]oxaborinine-8-carboxylic acid

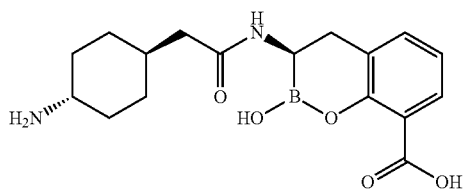 [SMILES: N[C@H]1CC[C@H](CC(=O)N[C@H]2Cc3cccc(C(=O)O)c3OB2O)CC1]

Step 1: Synthesis of 3-((2R)-2-(2-(trans-4-(tert-butoxycarbonylamino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(trans-4-(tert-butoxycarbonylamino)cyclohexyl)acetic acid following procedure described in step 1 of Example 1. The crude product was purified by flash chromatography on silica gel (hexane/EtOAc, 2:1 to 1:2). ESI-MS m/z 613.1 (MH)$^+$.

Step 2: Synthesis of (R)-3-(2-(trans-4-aminocyclohexyl)acetamido)-2-hydroxy-3,4-dihydro-2H-benzo[e][1,2]oxaborinine-8-carboxylic acid Prepared from 3-((2R)-2-(2-(trans-4-(tert-butoxycarbonylamino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid and BCl$_3$ following the procedure described in Step 2 of Example 1. The crude product was purified by reverse phase preparative HPLC and dried using lyophilization. ESI-MS m/z 347 (MH)$^+$.

Example 7

(R)-3-(2-(cis-4-aminocyclohexyl)acetamido)-2-hydroxy-3,4-dihydro-2H-benzo[e][1,2]oxaborinine-8-carboxylic acid

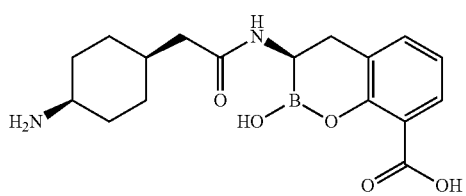 [SMILES: N[C@H]1CC[C@@H](CC(=O)N[C@H]2Cc3cccc(C(=O)O)c3OB2O)CC1]

Step 1: Synthesis of 3-((2R)-2-(2-(cis-4-(tert-butoxycarbonylamino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(cis-4-(tert-butoxycarbonylamino)cyclohexyl)acetic acid following procedure described in step 1 of Example 1. The crude product was purified by flash chromatography on silica gel (Hexane/EtOAc, 2:1 to 1:2). ESI-MS m/z 613.1 (MH)$^+$.

Step 2: Synthesis of (R)-3-(2-(cis-4-aminocyclohexyl)acetamido)-2-hydroxy-3,4-dihydro-2H-benzo[e][1,2]oxaborinine-8-carboxylic acid Prepared from 3-((2R)-2-(2-(cis-4-(tert-butoxycarbonylamino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid and BCl$_3$ following the procedure described in Step 2 of Example 1. The crude product was purified by reverse phase preparative HPLC and dried using lyophilization. ESI-MS m/z 347 (MH)$^+$.

Example 8

(R)-3-(2-(trans-4-((dimethylamino)methyl)cyclohexyl)-N-methylacetamido)-2-hydroxy-3,4-dihydro-2H-benzo[e][1,2]oxaborinine-8-carboxylic acid

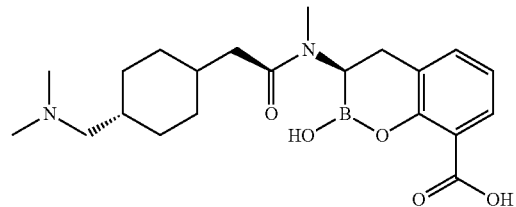

Step 1: [4-(Benzyloxycarbonylamino-methyl)-cyclohexyl]-acetic acid

Benzyl chloroformate (1.5 mL, 10.5 mmol) and sodium hydroxide (12.5 mL, 1N, 12.5 mmol) were added to a solution of trans-(4-aminomethylcyclohexyl)acetic acid (2.08 g, 10.0 mmol) in THF (32 mL) and H$_2$O (16 mL). The reaction was stirred at RT for 17 hr. The reaction was quenched with 1N HCl and extracted with EtOAc (2×). The combined organic layers were washed with brine, dried over Na$_2$SO$_4$, filtered, and concentrated to yield 1.91 g (62%) of product which was carried to the next step without purification. ESI-MS m/z 306 (MH)$^+$.

Step 2: 3-[2-{2-[4-(Benzyloxycarbonylamino-methyl)-cyclohexyl]-acetylamino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and [4-(Benzyloxycarbonylamino-methyl)-cyclohexyl]-acetic acid following procedure described in step 1 of Example 1. The crude product was purified by flash chromatography on silica gel (10-100% EtOAc/hexane) ESI-MS m/z 717 (MH)+.

Step 3: 3-[2-[2-(4-Aminomethyl-cyclohexyl)-acetylamino]-2-(2,9,9-trimethyl-3,5-dioxa-4-bora-tricyclo[6.1.1.0$^{2,6}$]dec-4-yl)-ethyl]-2-methoxy-benzoic acid tert-butyl ester A solution of 3-[2-{2-[4-(Benzyloxycarbonylaminomethyl)-cyclohexyl]-acetylamino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester (1.56 g, 2.18 mmol) in MeOH (22 mL) was purged with Argon for 5 minutes. Palladium on carbon (10%, 0.153 g) was added, flask evacuated, and the reaction stirred under hydrogen atmosphere for 6.5 hr. The reaction was filtered through a Celite-plugged filter frit, washed with MeOH and DCM, and concentrated to provide 1.29 g of crude product that was carried to the next step without purification. ESI-MS m/z 583 (MH)+.

Step 4: 3-[2-{[2-(4-Dimethylaminomethyl-cyclohexyl)-acetyl]-methyl-amino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester To a solution of 3-[2-[2-(4-Aminomethyl-cyclohexyl)-acetylamino]-2-(2,9,9-trimethyl-3,5-dioxa-4-bora-tricyclo[6.1.1.0$^{2,6}$]dec-4-yl)-ethyl]-2-methoxy-benzoic acid tert-butyl ester (0.208 g, 0.357 mmol) in DCM (3.8 mL) under Argon was added DIEA (0.18 mL, 1.03 mmol) and iodomethane (0.068 mL, 1.09 mmol). The reaction was stirred at RT for 4 hr. The reaction was quenched with MeOH, concentrated, and carried to the next step without purification. ESI-MS m/z 611 (MH)+.

Step 5: (R)-3-(2-(trans-4-((dimethylamino)methyl)cyclohexyl)-N-methylacetamido)-2-hydroxy-3,4-dihydro-2H-benzo[e][1,2]oxaborinine-8-carboxylic acid Prepared from 3-[2-{[2-(4-Dimethylaminomethyl-cyclohexyl)-acetyl]-methyl-amino}-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in step 2 of Example 1. The crude product was purified by reverse phase preparative HPLC and dried using lyophilization. ESI-MS m/z 403 (MH)+.

Example 9

(R)-3-(2-(trans-4-guanidinocyclohexyl)acetamido)-2-hydroxy-3,4-dihydro-2H-benzo[e][1,2]oxaborinine-8-carboxylic acid

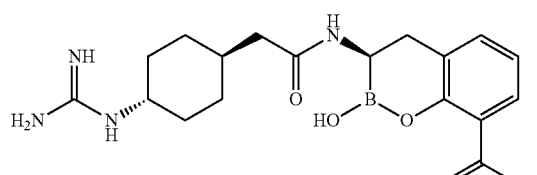

Synthesis of (R)-3-(2-(trans-4-guanidinocyclohexyl)acetamido)-2-hydroxy-3,4-dihydro-2H-benzo[e][1,2]oxaborinine-8-carboxylic acid Prepared from 3-((R)-2-(2-(trans-4-aminocyclohexyl)acetamido)-2-boronoethyl)-2-hydroxybenzoic acid (Example 6) following procedure described in Example 4. ESI-MS m/z 389 (MH)+.

Example 10

(R)-3-(2-(trans-4-((2-aminoethylamino)methyl)cyclohexyl)acetamido)-2-hydroxy-3,4-dihydro-2H-benzo[e][1,2]oxaborinine-8-carboxylic acid

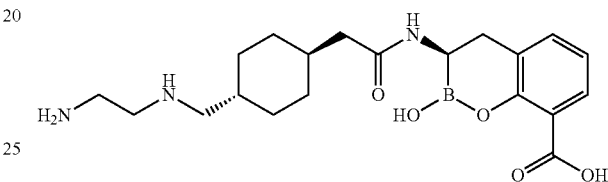

Step 1: 3-[2-(2-{4-[(2-tert-Butoxycarbonylaminoethylamino)-methyl]-cyclohexyl}-acetylamino)-2-(2,9,9-trimethyl-3,5-diox α-4-bora-tricyclo[6.1.1.0$^{2,6}$]dec-4-yl)-ethyl]-2-methoxy-benzoic acid tert-butyl ester A sealable reaction tube was charged with 3-[2-[2-(4-Aminomethyl-cyclohexyl)-acetylamino]-2-(2,9,9-trimethyl-3,5-dioxa-4-bora-tricyclo[6.1.1.0$^{2,6}$]dec-4-yl)-ethyl]-2-methoxy-benzoic acid tert-butyl ester (0.205 g, 0.352 mmol), potassium carbonate (0.057 g, 0.412 mmol), 2-(Boc-amino)ethyl bromide (0.095 g, 0.424 mmol), and DMF (3.0 mL). The tube was sealed and the reaction heated at 65° C. for 24 hr. The reaction was cooled to RT. The reaction was diluted with EtOAc and washed with 5% aqueous LiCl (2×) and brine. The organic layer was dried over Na$_2$SO$_4$, filtered, and concentrated to afford 0.120 g of crude product which was carried to the next step without purification. ESI-MS m/z 726 (MH)+.

Step 2: (R)-3-(2-(trans-4-((2-aminoethylamino)methyl)cyclohexyl)acetamido)-2-hydroxy-3,4-dihydro-2H-benzo[e][1,2]oxaborinine-8-carboxylic acid Prepared from 3-[2-(2-{4-[(2-tert-Butoxycarbonylaminoethylamino)-methyl]-cyclohexyl}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 2 of Example 1. The crude product was purified by reverse phase preparative HPLC and dried using lyophilization. ESI-MS m/z 404 (MH)+.

Example 11

(3R)-3-(2-(4-(aminomethyl)cyclohexylidene)acetamido)-2-hydroxy-3,4-dihydro-2H-benzo[e][1,2]oxaborinine-8-carboxylic acid

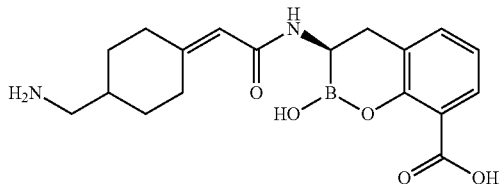

Step 1: [4-(tert-Butoxycarbonylamino-methyl)-cyclohexylidene]-acetic acid ethyl ester Potassium tert-butoxide (0.479 g, 4.27 mmol) was added to a solution of triethylphosphonoacetate (0.85 mL, 4.28 mmol) in DMF (6.5 mL) under Argon and the reaction stirred at RT for 10 min. (4-Oxo-cyclohexylmethyl)-carbamic acid tert-butyl ester (0.643 g, 2.83 mmol) in DMF (6.5 mL) was added drop wise over 8 min. After 20 min of stirring, a precipitate was observed and additional DMF (6.5 mL) was added and the reaction stirred for an additional 17 hr. The reaction was poured into ice cold $H_2O$ and extracted with $Et_2O$ (3×). The combined organic layers were washed with $H_2O$ and brine, dried over $Na_2SO_4$, filtered, and concentrated. Flash chromatography (0-30% EtOAc/hexane) afforded 0.784 g (93%) of product. ESI-MS m/z 298 (MH)+.

Step 2: [4-(tert-Butoxycarbonylamino-methyl)-cyclohexylidene]-acetic acid

To a solution of [4-(tert-Butoxycarbonylamino-methyl)-cyclohexylidene]-acetic acid ethyl ester (0.518 g, 1.74 mmol) in MeOH (16 mL) and THF (4 mL) was added sodium hydroxide (9.0 mL, 1N, 9.0 mmol) and the reaction stirred at RT for 23 hr. The reaction was quenched with $H_2O$ and extracted with EtOAc (2×). The aqueous layer was acidified to pH 1 with 1N HCl and extracted with EtOAc (3×). The combined organic layers were dried over $Na_2SO_4$, filtered, and concentrated in vacuo to provide 0.300 g (64%) of product. ESI-MS m/z 270 (MH)+.

Step 3: 3-[2-{2-[4-(tert-Butoxycarbonylamino-methyl)-cyclohexylidene]-acetylamino}-2-(2,9,9-trimethyl-3,5-dioxa-4-bora-tricyclo[6.1.1.0$^{2,6}$]dec-4-yl)-ethyl]-2-methoxy-benzoic acid tert-butyl ester Prepared from 2-Methoxy-3-[2-(2,9,9-trimethyl-3,5-dioxa-4-bora-tricyclo[6.1.1.02,6]dec-4-yl)-2-(trimethylsilanyl-amino)-ethyl]-benzoic acid tert-butyl ester and [4-(tert-Butoxycarbonylamino-methyl)-cyclohexylidene]-acetic acid following the procedure described in Step 1 of Example 1. The crude product was purified by flash chromatography on silica gel (0-100% EtOAc/hexane). ESI-MS m/z 681 (MH)+.

Step 4: (3R)-3-(2-(4-(aminomethyl)cyclohexylidene)acetamido)-2-hydroxy-3,4-dihydro-2H-benzo[e][1,2]oxaborinine-8-carboxylic acid Prepared from 3-[2-{2-[4-(tert-Butoxycarbonylamino-methyl)-cyclohexylidene]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 2 of Example 1. The crude product was purified by reverse phase preparative HPLC and dried using lyophilization. ESI-MS m/z 359 (MH)+.

Example 12

(R)-3-(2-(4-(aminomethyl)-1-(nitromethyl)cyclohexyl)acetamido)-2-hydroxy-3,4-dihydro-2H-benzo[e][1,2]oxaborinine-8-carboxylic acid

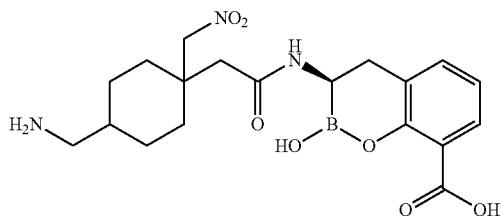 [SMILES: NCC1CCC(CC(=O)N[C@H]2Cc3cccc(C(=O)O)c3OB2O)(C[N+](=O)[O-])CC1]

Step 1: [4-(tert-Butoxycarbonylamino-methyl)-1-nitromethyl-cyclohexyl]-acetic acid ethyl ester A sealable reaction tube was charged with 2,8,9-Triisobutyl-2,5,8,9-tetraaza-1-phosphabicyclo[3.3.3]undecane (0.16 mL, 0.450 mmol) and THF (1.0 mL) under Argon. Nitromethane (0.23 mL, 4.24 mmol) was added and the reaction stirred at room temperature for 5 min then cooled to 0° C. for 15 min. [4-(tert-Butoxycarbonylamino-methyl)-cyclohexylidene]-acetic acid ethyl ester (0.261 g, 0.878 mmol) in THF (1.5 mL) was added slowly and the reaction stirred at RT for 15 min. The tube was sealed and the reaction heated at 70° C. for 17 hr. The reaction was cooled to room temperature, quenched with 0.5M HCl, and extracted with EtOAc (2×). The combined organic layers were washed with saturated $NaHCO_3$ and brine, dried over $Na_2SO_4$, filtered, and concentrated to provide 0.304 g of crude product which was carried to the next step without purification. ESI-MS m/z 359 (MH)+.

Step 2: [4-(tert-Butoxycarbonylamino-methyl)-1-nitromethyl-cyclohexyl]-acetic acid To a solution of [4-(tert-Butoxycarbonylamino-methyl)-1-nitromethyl-cyclohexyl]-acetic acid ethyl ester (0.304 g, 0.848 mmol) in MeOH (5.0 mL) and THF (1.5 mL) was added sodium hydroxide (4.2 mL, 1N, 4.2 mmol) and the reaction stirred at RT for 5 hr. The reaction was acidified to pH ~2 with 1N HCl and extracted with EtOAc (3×). The combined organic layers were dried over $Na_2SO_4$, filtered, and concentrated to provide 0.308 g of crude product that was carried to the next step without purification. ESI-MS m/z 331 (MH)+.

Step 3: 3-[2-{2-[4-(tert-Butoxycarbonylamino-methyl)-1-nitromethyl-cyclohexyl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-Methoxy-3-[2-(2,9,9-trimethyl-3,5-dioxa-4-bora-tricyclo[6.1.1.02,6]dec-4-yl)-2-(trimethylsilanyl-amino)-ethyl]-benzoic acid tert-butyl ester and [4-(tert- Butoxycarbonylamino-methyl)-1-nitromethyl-cyclohexyl]-acetic acid following the procedure described in Step 1 of Example 1. The crude product was purified by flash chromatography on silica gel (0-100% EtOAc/hexane). ESI-MS m/z 742 (MH)+.

Step 4: (R)-3-(2-(4-(aminomethyl)-1-(nitromethyl) cyclohexyl)acetamido)-2-hydroxy-3,4-dihydro-2H-benzo[e][1,2]oxaborinine-8-carboxylic acid Prepared from 3-[2-{2-[4-(tert-Butoxycarbonylamino-methyl)-1-nitromethyl-cyclohexyl]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and BCl₃ following the procedure described in Step 2 of Example 1. The crude product was purified by reverse phase preparative HPLC and dried using lyophilization. ESI-MS m/z 420 (MH)+.

Example 13

(R)-3-(2-(trans-4-((S)-2,3-diaminopropanamido) cyclohexyl)acetamido)-2-hydroxy-3,4-dihydro-2H-benzo[e][1,2]oxaborinine-8-carboxylic acid

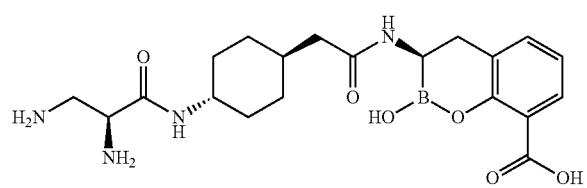 [SMILES: NC[C@H](N)C(=O)N[C@H]1CC[C@H](CC(=O)N[C@H]2Cc3cccc(C(=O)O)c3OB2O)CC1]

Synthesis of 3-((R)-2-borono-2-(2-trans-4-((S)-2,3-diaminopropanamido)cyclohexyl)acetamido)ethyl)-2-hydroxybenzoic acid To (S)-2-(benzyloxycarbonylamino)-3-(tert-butoxycarbonylamino)propanoic acid (85 mg, 0.25 mol) in DCM/DMF (4 mL, 1/1) was added NMM (1.2 eq) followed by HATU (95 mg, 0.26 mol). The reaction mixture was stirred at RT for 1 hr. In a separate vial, 3-((2R)-2-(2-(trans-4-(tert-butoxycarbonylamino)cyclohexyl)acetamido)-2-(2,9,9-trimethyl-3,5-dioxa-4-bora-tricyclo[6.1.1.02,6]dec-4-yl)ethyl)-2-methoxybenzoic acid tert-butyl ester (133 mg, 0.2 mmol Example 6) was treated with 4N HCl in dioxane (2 mL) and the resultant solution was stirred at RT for 2 hr. Solvent was then removed under reduced pressure. To this residue was added the active ester prepared above and the reaction mixture was stirred overnight at RT. Water was added and the aqueous phase extracted with EtOAc. The organic phase was washed with 1N HCl, sat. NaHCO₃, brine, dried and concentrated in vacuo to afford the product (0.100 g) as brown oil without further purification. ESI-MS m/z 833.1 (MH)+. The residue was then dissolved in MeOH and cat. Pd on carbon (20 mg) was added and stirred under hydrogen atmosphere overnight. After filtration and removal of the solvent, the residue was treated with BCl₃ following the procedure described in step 2 of Example 1 to afford the title compound. ESI-MS m/z 433 (MH)+.

Example 14

(R)-3-(2-(trans-4-(dimethylamino)cyclohexyl)acetamido)-2-hydroxy-3,4-dihydro-2H-benzo[e][1,2] oxaborinine-8-carboxylic acid

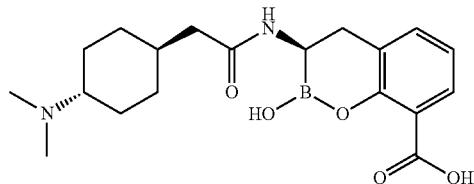 [SMILES: CN(C)[C@H]1CC[C@H](CC(=O)N[C@H]2Cc3cccc(C(=O)O)c3OB2O)CC1]

Synthesis of (R)-3-(2-(trans-4-(dimethylamino)cyclohexyl)acetamido)-2-hydroxy-3,4-dihydro-2H-benzo[e][1,2]oxaborinine-8-carboxylic acid To (R)-3-(2-(trans-4-aminocyclohexyl)acetamido)-2-hydroxy-3,4-dihydro-2H-benzo[e][1,2]oxaborinine-8-carboxylic acid (10.0 mg from Example 6) in MeOH (5 mL) was added formaldehyde (1.0 mL, 37% solution), followed by 10% Pd/C (20 mg). The reaction mixture was hydrogenated under H₂ balloon for 3 hr. The reaction mixture was filtrated and the solvent was removed under vacuum. The final product was purified by reverse phase preparative HPLC and dried using lyophilization. ESI-MS m/z 433 (MH)+.

Example 15

(R)-3-(2-(trans-4-(2-aminoethylamino)cyclohexyl) acetamido)-2-hydroxy-3,4-dihydro-2H-benzo[e][1,2] oxaborinine-8-carboxylic acid

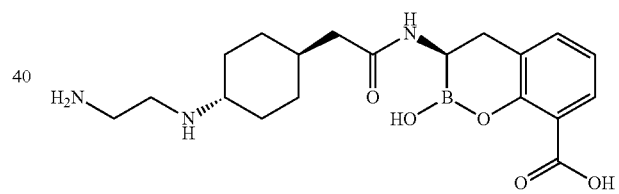

Step 1: Synthesis of (R)-3-(2-(trans-4-(2-(tert-butoxycarbonylamino)ethylamino)cyclohexyl)acetamido)-2-hydroxy-3,4-dihydro-2H-benzo[e][1,2] oxaborinine-8-carboxylic acid To (R)-3-(2-(trans-4-aminocyclohexyl)acetamido)-2-hydroxy-3,4-dihydro-2H-benzo[e][1,2]oxaborinine-8-carboxylic acid (Example 6, 15 mg) in MeOH (2 mL) was added tert-butyl 2-oxoethylcarbamate (20 mg). Pd/C (10% by weight, 10 mg) was added and the reaction mixture was stirred under H₂ balloon overnight. The reaction mixture was filtrated and the solvent was then removed under reduced pressure and the residue was carried on to the next step without further purification. ESI-MS m/z 490.1 (MH)+.

Step 2: Synthesis of (R)-3-(2-(trans-4-(2-aminoethylamino)cyclohexyl)acetamido)-2-hydroxy-3,4-dihydro-2H-benzo[e][1,2]oxaborinine-8-carboxylic acid To (R)-3-(2-(trans-4-(2-(tert-butoxycarbonylamino)ethylamino)cyclohexyl)acetamido)-2-hydroxy-3,4-dihydro-2H- benzo[e][1,2]oxaborinine-8-carboxylic acid (20 mg) in a flask was added 1 mL 4N HCl in dioxane. The resulting reaction mixture was stirred at RT for 2 hr. The solvent was removed in vacuo and the residue was purified by reverse phase preparative HPLC and dried using lyophilization. ESI-MS m/z 390 (MH)+.

Example 16

(R)-2-hydroxy-3-(2-(trans-4-(piperazin-1-yl)cyclohexyl)acetamido)-3,4-dihydro-2H-benzo[e][1,2]oxaborinine-8-carboxylic acid

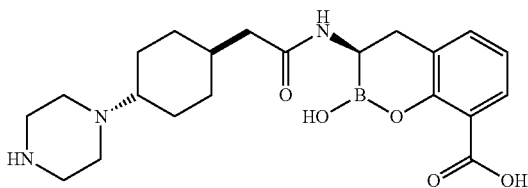

Step 1: Synthesis of 2-(4-(4-(tert-butoxycarbonyl)piperazin-1-yl)cyclohexyl)acetic acid To 2-(4-oxocyclohexyl)acetic acid (0.576 g, 3.7 mmol) and tert-butyl piperazine-1-carboxylate (0.700 g, 3.7 mmol) in MeOH, was added Pd on carbon (80 mg), and the resultant reaction mixture was stirred under hydrogen atmosphere overnight. The catalyst was removed via filtration and the solvent was removed under reduced pressure to afford the acid as white solid (1.2 g. 99%).

Step 2: Synthesis of 4-(4-{3-tert-butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-cyclohexyl)-piperazine-carboxylic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(4-(4-(tert-butoxycarbonyl)piperazin-1-yl)cyclohexyl)acetic acid following procedure described in step 1 of Example 1. The crude product was purified by flash chromatography on silica gel (hexane/EtOAc, 2:1 to 1:2). ESI-MS m/z 638.1 (MH)+.

Step 3: Synthesis of (R)-2-hydroxy-3-(2-(trans-4-(piperazin-1-yl)cyclohexyl)acetamido)-3,4-dihydro-2H-benzo[e][1,2]oxaborinine-8-carboxylic acid Prepared from 4-(4-{3-tert-butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-cyclohexyl)-piperazine-carboxylic acid tert-butyl ester and BCl$_3$ following the procedure described in Step 2 of Example 1. The crude product was purified by reverse phase preparative HPLC to obtain trans isomer as the major product, which was dried using lyophilization. ESI-MS m/z 416 (MH)+.

Example 17

(R)-2-hydroxy-3-(2-(cis-4-(piperazin-1-yl)cyclohexyl)acetamido)-3,4-dihydro-2H-benzo[e][1,2]oxaborinine-8-carboxylic acid

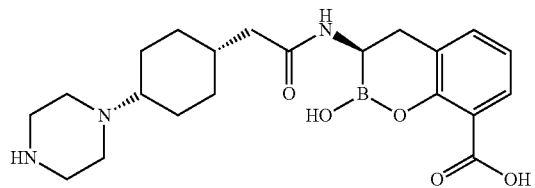

Synthesis of (R)-2-hydroxy-3-(2-(cis-4-(piperazin-1-yl)cyclohexyl)acetamido)-3,4-dihydro-2H-benzo[e][1,2]oxaborinine-8-carboxylic acid Prepared from 4-(4-{3-tert-butoxycarbonyl-2-methoxy-phenyl)-1-(2,9,9-trimethyl-3,5-dioxa-4-bora-tricyclo[6.1.1.0$^{2,6}$]dec-4-yl)-ethylcarbamoyl]-methyl}-cyclohexyl)-piperazine-carboxylic acid tert-butyl ester (from Example 16, step 2) and BCl$_3$ following the procedure described in Step 2 of Example 1. The crude product was purified by reverse phase preparative HPLC to obtain cis isomer as the minor product, which was dried using lyophilization. ESI-MS m/z 416 (MH)+.

Example 18

(3R)-3-[[2-[(1S,3S,4S)-3,4-bis(aminomethyl)cyclohexyl]acetyl]amino]-2-hydroxy-3,4-dihydro-1,2-benzoxaborinine-8-carboxylic acid and (3R)-3-[[2-[(1R,3R,4R)-3,4-bis(aminomethyl)cyclohexyl]acetyl]amino]-2-hydroxy-3,4-dihydro-1,2-benzoxaborinine-8-carboxylic acid

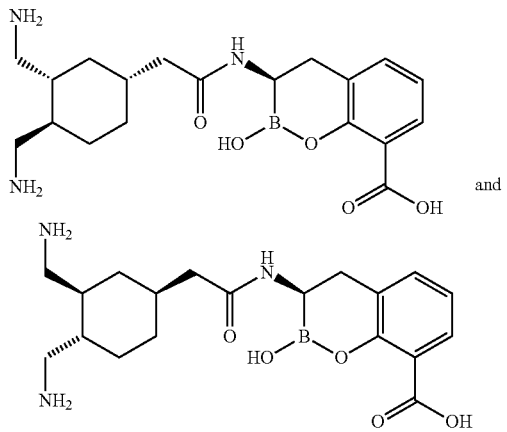

Step 1: Synthesis of (E)-N,N,N',N'-tetrabenzylbut-2-enediamide

To a cooled (−5° C.) solution of N,N-dibenzylamine (19.3 mL, 100 mmol) in DCM (200 mL) is added TEA (13.8 mL, 100 mmol). To this solution is added, drop wise over 5 minutes, fumaroyl chloride (4.2 mL, 40 mmol). On complete addition, the cold bath is removed and stirring continued for 1 hr. This solution is diluted with DCM, washed with HCl (approx. 100 mL of 1M aq.) then water (2×), dried over $MgSO_4$ and concentrated. The solid residue is crystallized from hot (109° C.) toluene to give the title compound (17.9 g) as a white solid. ESI-MS (m/z) 475 $(MH)^+$.

Step 2: Synthesis of (trans)-N,N,N',N'-tetrabenzyl-4-oxo-cyclohexane-1,2-dicarboxamide To a suspension of (E)-N,N,N',N'-tetrabenzylbut-2-enediamide (10.6 g, 22 mmol) in o-xylene (106 mL) is added hydroquinone (180 mg, 1.63 mmol) followed by 2-trimethylsilyloxy-1,3-butadiene (9.48 g, 66 mmol). The resulting mixture is flushed with Argon then sealed. The mixture is then heated to 135° C. and stirred at this temperature for 87 hr. The resulting solution is cooled then concentrated under reduced pressure. The residue is purified by silica chromatography (240 g silica eluting with 10% ethyl acetate in hexane) to give 12.81 g of product as an oil. This crude product is taken up in THF (10 mL) and MeOH (40 mL). To this solution is added potassium carbonate (2.76 g, 20 mmol). The resulting mixture is stirred for 10 min then diluted with $Et_2O$, washed with water and brine, dried over $MgSO_4$ and concentrated. The residue is purified by silica chromatography (160 g silica eluting with 20% ethyl acetate/20% dichloromethane in hexane) to give the title compound (10.11 g) as an oil. ESI-MS (m/z) 545 $(MH)^+$.

Step 3: Synthesis of Ethyl 2-[(trans)-3,4-bis(dibenzylcarbamoyl)cyclohexylidene]acetate To a cooled (−5° C.) suspension of sodium hydride (846 mg, 60% dispersion in mineral oil, 21.2 mmol) in THF (60 mL) is added, drop wise, triethylphosphonoacetate (4.2 mL, 21.2 mmol). On complete addition, the cold bath is removed and stirring continued for 20 min. The resulting solution is cooled to −5° C. To this solution is added a solution of (trans)-N,N,N',N'-tetrabenzyl-4-oxo-cyclohexane-1,2-dicarboxamide (10.11 g, 18.4 mmol) in THF (10 mL). On complete addition, the cold bath is removed and stirring continued for 30 min. To this solution is added HCl (30 mL, 1M aqueous). The resulting mixture is diluted with $Et_2O$, washed with brine, dried over $MgSO_4$ and concentrated. The residue is purified by silica chromatography (160 g silica eluting with 20% ethyl acetate/10% dichloromethane in hexane) to give the title compound (9.89 g) as an oil (4:1 mixture of and Z isomers). ESI-MS (m/z) 615 $(MH)^+$.

Step 4: Synthesis of (racemic)-Methyl 2-[(1R,3R,4R)-3,4-bis(dibenzylcarbamoyl)cyclohexyl]acetate To a solution of Ethyl 2-[(trans)-3,4-bis(dibenzylcarbamoyl)cyclohexylidene]acetate (9.27 g, 15 mmol) in dry MeOH (75 mL) is added Magnesium ribbon (1.08 g, 45 mmol). The suspension was stirred for 5 hr. To this homogeneous solution is added a further batch of Magnesium ribbon (200 mg, 8.2 mmol). This mixture is stirred for 17 hr. The resulting solution is extracted with EtOAc, washed with brine, dried over $MgSO_4$ and concentrated. The residue is purified by silica chromatography (eluting with 20% ethyl acetate/10% dichloromethane in hexane) to give the title compound (8.27 g) as a foam. ESI-MS (m/z) 617 $(MH)^+$.

Step 5: Synthesis of (racemic)-2-[(1R,3R,4R)-3,4-bis[(dibenzylamino)methyl]cyclohexyl]ethanol To a cooled (−10° C.) solution of (racemic)-Methyl 2-[(1R,3R,4R)-3,4-bis(dibenzylcarbamoyl)cyclohexyl]acetate (8.18 g, 13.5 mmol) in THF (40 mL) is added, drop wise, lithium aluminum hydride (50 mL, 1M in THF). On complete addition, the cold bath is removed and stirring continued for 15 min. The resulting solution is heated to 55° C. and stirred at this temperature for 2.5 hr. This solution is cooled to 0° C. To the resulting solution is added, drop wise, water (1.9 mL) then NaOH (1.9 mL, 5M aqueous) then water (0.95 mL). The resulting mixture is diluted with $Et_2O$ (100 mL), filtered through Celite and the filtrate concentrated under vacuum to give the title compound as an oil (8.1 g). ESI-MS (m/z) 547 $(MH)^+$.

Step 6: Synthesis of (racemic)-tert-butyl N-[[(1S,2S,4S)-2-[(tert-butoxycarbonylamino)methyl]-4-(2-hydroxyethyl)cyclohexyl]methyl]carbamate To a mixture of (racemic)-2-[(1R,3R,4R)-3,4-bis[(dibenzylamino)methyl]cyclohexyl]ethanol (8.1 g, 13 mmol) and palladium hydroxide on carbon (1.0 g, 20% palladium by weight) is added MeOH (70 mL). The resulting mixture is flushed with hydrogen gas (1 atm) and stirred for 17 hr. The system is then flushed with Argon, diluted with DCM and filtered through Celite. The filtrate is concentrated under vacuum. The residue is taken up in DCM (30 mL) and THF (20 mL). To this solution is added DIEA (4.6 mL, 26 mmol) followed by di-tert-butyl-dicarbonate (5.66 g, 26 mmol). The resulting solution is stirred for 2 hr then diluted with EtOAc, washed with water and brine, dried over $MgSO_4$ and concentrated. The residue is purified by silica chromatography (160 g silica, eluting with 80% ethyl acetate in hexane) to give the title compound (3.1 g) as a viscous oil. 1H NMR ($CDCl_3$) δ 0.7-1.0 (m, 1H), 1.05-1.35 (m, 4H), 1.4-1.75 (m, 4H), 1.46 (s, 18H), 1.75-1.96 (m, 2H), 2.9-3.05 (m, 2H), 3.05-3.75 (bm, 5H), 4.6-4.8 (bd, 1H), 4.95 (bs, 1H).

Step 7: Synthesis of (racemic)-2-[(1S,3S,4S)-3,4-bis[(tert-butoxycarbonylamino)methyl]cyclohexyl]acetic acid To a solution of (racemic)-tert-butyl N-[[(1S,2S,4S)-2-[(tert-butoxycarbonylamino)methyl]-4-(2-hydroxyethyl)cyclohexyl]methyl]carbamate (772 mg, 2 mmol) in acetonitrile (3 mL), carbon tetrachloride (3 mL) and water (4.5 mL) is added sodium periodate (1.28 g, 6 mmol) followed by $RuCl_3 \cdot H_2O$ (21 mg, 0.1 mmol). The resulting mixture is stirred for 2 hr then diluted with EtOAc, washed with brine, dried over $MgSO_4$ and concentrated. The residue is taken up in saturated sodium carbonate solution and extracted with EtOAc. The aqueous phase is acidified with HCl (2M aqueous) and extracted with EtOAc. The organic extract is washed with brine, dried over $MgSO_4$ and concentrated. This residue is purified by silica chromatography (eluting with ethyl acetate) to give the title compound (394 mg) as a viscous oil. 1H NMR (DMSO-$d_6$) δ 0.7-1.0 (m, 1H), 1.0-1.9 (m, 9H), 1.39 (s, 18H), 2.0-2.3 (m, 2H), 2.6-3.18 (m, 4H), 6.6-6.8 (bm, 2H).

Step 8: Synthesis of tert-Butyl 3-((2R)-2-(-[(1S,3S,4S)-3,4-bis[(tert-butoxycarbonylamino)methyl]cyclohexyl]acetamido)-2-(2,9,9-trimethyl-3,5-dioxa-4-bora-tricyclo[6.1.1.0$^{2,6}$]dec-4-yl)ethyl)-2-methoxybenzoate and tert-butyl 3-((2R)-2-(-[(1R,3R,4R)-3,4-bis[(tert-butoxycarbonylamino)methyl]cyclohexyl]acetamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and (racemic)-2-[(1S,3S,4S)-3,4-bis[(tert-butoxycarbonylamino)methyl]cyclohexyl]acetic acid following the procedure described in Step 1 of Example 1. Except the crude product is purified by silica chromatography (eluting with 30% ethyl acetate in hexane then 60% ethyl acetate in hexane) to provide the title compound ESI-MS (m/z) 834 (MNa)+.

Step 9: Synthesis of (3R)-3-[[2-[(1S,3S,4S)-3,4-bis(aminomethyl)cyclohexyl]acetyl]amino]-2-hydroxy-3,4-dihydro-1,2-benzoxaborinine-8-carboxylic acid and (3R)-3-[[2-[(1R,3R,4R)-3,4-bis(aminomethyl)cyclohexyl]acetyl]amino]-2-hydroxy-3,4-dihydro-1,2-benzoxaborinine-8-carboxylic acid Prepared from tert-Butyl 3-((2R)-2-(-[(1S,3S,4S)-3,4-bis[(tert-butoxycarbonylamino)methyl]cyclohexyl]acetamido)-2-(2,9,9-trimethyl-3,5-dioxa-4-bora-tricyclo[6.1.1.0$^{2,6}$]dec-4-yl)ethyl)-2-methoxybenzoate and tert-butyl 3-((2R)-2-(-[(1R,3R,4R)-3,4-bis[(tert-butoxycarbonylamino)methyl]cyclohexyl]acetamido)-2-(2,9,9-trimethyl-3,5-dioxa-4-bora-tricyclo[6.1.1.0$^{2,6}$]dec-4-yl)ethyl)-2-methoxybenzoate following the procedure described in Step 2 of Example 1. ESI-MS (m/z) 390 (MH)+.

Example 19

(3R)-3-[[(3S,4S)-3,4-diaminocyclopentanecarbonyl]amino]-2-hydroxy-3,4-dihydro-1,2-benzoxaborinine-8-carboxylic acid and (3R)-3-[[(3R,4R)-3,4-diaminocyclopentanecarbonyl]amino]-2-hydroxy-3,4-dihydro-1,2-benzoxaborinine-8-carboxylic acid

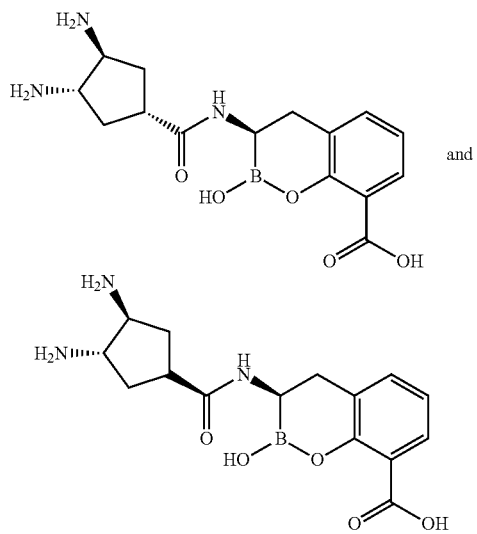

and

Step 1: Synthesis of (racemic)-Ethyl (3S,4S)-3,4-diazidocyclopentanecarboxylate

To a cooled (−20° C.) suspension of manganese triacetate (8.02 g, 30 mmol) in acetonitrile (120 mL) is added sodium azide (3.4 g, 50 mmol). To this mixture is added, drop wise, a solution of ethyl cyclopent-3-ene-1-carboxylate (1.4 g, 10 mmol) in TFA (14 mL) over approximately 10 min. The resulting mixture is stirred at a temperature between −25° C. and −19° C. for 3 hr, then allowed to warm to RT and stirred for 17 hr. To this mixture is added sodium thiosulphate (30 mL, 10% aqueous). This mixture is stirred for 5 min then extracted with hexane. The hexane extract is washed with saturated sodium bicarbonate solution (3×), then brine, dried over MgSO$_4$ and concentrated. This residue is purified by silica chromatography (90 g silica, eluting with 10% ethyl acetate in hexane) to give the title compound (1.278 g) as an oil. 1H NMR (DMSO-d$_6$) δ 1.15 (t, J=7 Hz, 3H), 1.68-1.91 (m, 2H), 2.13-2.35 (m, 2H), 3.01 (m, 1H), 3.97 (m, 2H), 4.05 (q, J=7 Hz, 2H).

Step 2: Synthesis of (racemic) Ethyl (3S,4S)-3,4-bis(tert-butoxycarbonylamino)cyclopentanecarboxylate To a solution of (racemic)-Ethyl (3S,4S)-3,4-diazidocyclopentanecarboxylate (3.8 g, 16.9 mmol) in THF (85 mL) is added triphenylphosphine (9.7 g, 37.18 mmol). The resulting solution is stirred for 17 hr. To this solution is added water (4.2 mL). The resulting solution is stirred for 6 hr. To this solution is added DIEA (8.9 mL, 51 mmol) followed by di-tert-butyl-dicarbonate (11.05 g, 51 mmol). This mixture is stirred for 2 hr then concentrated under vacuum. The residue is purified by silica chromatography (230 g silica, eluting with 20% ethyl acetate in hexane) to give the title compound (3.79 g) as a white solid. 1H NMR (DMSO-d$_6$) δ 1.15 (t, J=7 Hz, 3H), 1.36 (s, 18H), 1.5-1.66 (m, 2H), 1.91-2.11 (m, 2H), 2.81 (m, 1H), 3.61 (bm, 2H), 4.01 (q, J=7 Hz, 2), 6.8 (bs, 2H).

Step 3: Synthesis of (racemic)-(3S,4S)-3,4-bis(tert-butoxycarbonylamino)cyclopentanecarboxylate To a solution of (racemic) Ethyl (3S,4S)-3,4-bis(tert-butoxycarbonylamino)cyclopentanecarboxylate (790 mg, 2.12 mmol) in MeOH (3 mL), THF (6 mL) is added sodium hydroxide (3 mL, 1M aqueous). The resulting solution is stirred for 20 min then acidified with HCl (1M, aqueous). This mixture is diluted with EtOAc, washed with brine, dried over MgSO$_4$ and concentrated to give the title compound (671 mg) as a solid. 1H NMR (DMSO-d$_6$) δ 1.38 (s, 18H), 1.46-1.62 (m, 2H), 1.87-2.11 (m, 2H), 2.77 (m, 1H), 3.6 (bm, 2H), 6.75 (bs, 2H), 12.15 (bs, 1H).

Step 4: Synthesis of tert-Butyl 3-((2R)-24(3S,4S)-3,4-bis(tert-butoxycarbonylamino)cyclopentanecarboxamido)-2-(2,9,9-trimethyl-3,5-dioxa-4-bora-tricyclo[6.1.1.0$^{2,6}$]dec-4-yl)ethyl)-2-methoxybenzoate and tert-butyl 3-((2R)-2-(3R,4R)-3,4-bis(tert-butoxycarbonylamino)cyclopentanecarboxamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and (racemic)-(3S,4S)-3,4-bis(tert-butoxycarbonylamino)cyclopentanecarboxylate following the procedure described in Step 1 of Example 1. Except the crude product is purified by silica chromatography (eluting with 30% ethyl acetate in hexane then 60% ethyl acetate in hexane) to provide the title compound ESI-MS (m/z) 778 (MNa)+.

Step 5: Synthesis of (3R)-3-[[(3S,4S)-3,4-diaminocyclopentanecarbonyl]amino]-2-hydroxy-3,4-dihydro-1,2-benzoxaborinine-8-carboxylic acid and (3R)-3-[[(3R,4R)-3,4-diaminocyclopentanecarbonyl]amino]-2-hydroxy-3,4-dihydro-1,2-benzoxaborinine-8-carboxylic acid Prepared from tert-Butyl 3-((2R)-24(3S,4S)-3,4-bis(tert-butoxycarbonylamino)cyclopentanecarboxamido)-2-(2,9,9- trimethyl-3,5-dioxa-4-bora-tricyclo[6.1.1.0$^{2,6}$]dec-4-yl) ethyl)-2-methoxybenzoate and tert-butyl 3-((2R)-2-(3R, 4R)-3,4-bis(tert-butoxycarbonylamino) cyclopentanecarboxamido)-2-(2,9,9-trimethyl-3,5-dioxa-4-bora-tricyclo[6.1.1.0$^{2,6}$]dec-4-yl)ethyl)-2-methoxybenzoate following the procedure described in Step 2 of Example 1. ESI-MS (m/z) 334 (MH)$^+$.

Example 20

(3R)-3-[[(1S,3S,4S)-3,4-diaminocyclohexanecarbonyl]amino]-2-hydroxy-3,4-dihydro-1,2-benzoxaborinine-8-carboxylic acid and (3R)-3-[[(1R,3R,4R)-3,4-diaminocyclohexanecarbonyl]amino]-2-hydroxy-3,4-dihydro-1,2-benzoxaborinine-8-carboxylic acid

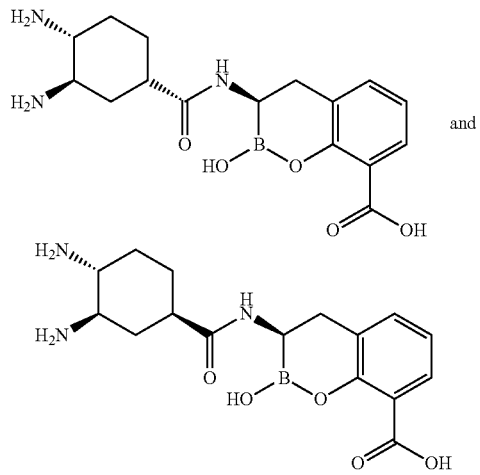

Step 1: Synthesis of (racemic)-methyl (1S,3R,4R)-3,4-diazidocyclohexanecarboxylate Prepared from methyl cyclohex-3-ene-1-carboxylate, using essentially the same procedure described in Step 1 of Example 19. This material was used without purification.

Step 2: Synthesis of (racemic)-methyl (1S,3R,4R)-3,4-bis(tert-butoxycarbonylamino)cyclohexanecarboxylate Prepared from (racemic)-methyl (3R,4R)-3,4-diazidocyclohexanecarboxylate using essentially the same procedure described in Step 2 of Example 19. 1H NMR (CDCl$_3$) δ 1.3-1.45 (m, 3H), 1.40 (s, 18H), 1.91 (m, 1H), 2.10 (m, 1H), 2.41 (m, 1H) m, 2.72 (m, 1H), 3.28 (m, 1H), 3.52 (m, 1H), 3.68 (s, 3H), 4.79 (bs, 1H), 4.93 (bs, 1H).

Step 3: Synthesis of (racemic)-(1S,3R,4R)-3,4-bis(tert-butoxycarbonylamino)cyclohexanecarboxylic acid Prepared from (racemic)-methyl (1S,3R,4R)-3,4-bis(tert-butoxycarbonylamino)cyclohexanecarboxylate using essentially the same procedure described in Step 3 of Example 19. 1H NMR (CDCl$_3$) δ 1.28-1.62 (m, 3H), 1.42 (s, 18H), 1.86 (m, 1H), 2.20 (m, 1H), 2.47 (m, 1H), 2.75 (m, 1H), 3.32 (m, 1H), 3.53 (m, 1H), 4.91 (bd, 1H), 5.55 (bd, 1H).

Step 4: Synthesis of tert-Butyl 3-((2R)-24(1S,3R,4R)-3,4-bis(tert-butoxycarbonylamino)cyclohexanecarboxamido)-2-(2,9,9-trimethyl-3,5-dioxa-4-bora-tricyclo[6.1.1.0$^{2,6}$]dec-4-yl)ethyl)-2-methoxybenzoate and tert-butyl 3-((2R)-2-((1R,3S,4S)-3,4-bis(tert-butoxycarbonylamino) cyclohexanecarboxamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and (racemic)-(1S,3R,4R)-3,4-bis(tert-butoxycarbonylamino)cyclohexanecarboxylic acid following the procedure described in Step 1 of Example 1. Except the crude product is purified by silica chromatography (eluting with 30% ethyl acetate in hexane then 60% ethyl acetate in hexane) to provide the title compound ESI-MS (m/z) 792 (MNa)$^+$.

Step 5: Synthesis of (3R)-3-[[(1S,3S,4S)-3,4-diaminocyclohexanecarbonyl]amino]-2-hydroxy-3,4-dihydro-1,2-benzoxaborinine-8-carboxylic acid and (3R)-3-[[(1R,3R,4R)-3,4-diaminocyclohexanecarbonyl]amino]-2-hydroxy-3,4-dihydro-1,2-benzoxaborinine-8-carboxylic acid Prepared from tert-Butyl 3-((2R)-24(1 S,3R,4R)-3,4-bis(tert-butoxycarbonylamino)cyclohexanecarboxamido)-2-(2,9,9-trimethyl-3,5-dioxa-4-bora-tricyclo[6.1.1.0$^{2,6}$]dec-4-yl)ethyl)-2-methoxybenzoate and tert-butyl 3-((2R)-2-((1R,3S,4S)-3,4-bis(tert-butoxycarbonyl amino) cyclohexanecarboxamido)-2-(2,9,9-trimethyl-3,5-diox α-4-bora-tricyclo[6.1.1.0$^{2,6}$]dec-4-yl)ethyl)-2-methoxybenzoate following the procedure described in Step 2 of Example 1. ESI-MS (m/z) 348 (MH)$^+$.

Example 21

(R)-3-(3-(trans-4-aminocyclohexyl)propanamido)-2-hydroxy-3,4-dihydro-2H-benzo[e][1,2]oxaborinine-8-carboxylic acid

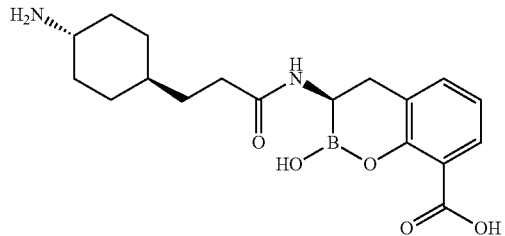 [SMILES: N[C@H]1CC[C@H](CCC(=O)N[C@H]2Cc3cccc(C(=O)O)c3OB2O)CC1]

Step 1: Synthesis of 3-((2R)-2-(3-(trans-4-(tert-butoxycarbonylamino)cyclohexyl)propanamido)-2-(2,9,9-trimethyl-3,5-dioxa-4-bora-tricyclo[6.1.1.0$^{2,6}$]dec-4-yl)ethyl)-2-methoxybenzoic acid tert butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 3-(trans-4-(tert-butoxycarbonylamino)cyclohexyl)propanoic acid following procedure described in step 1 of Example 1. The crude product was purified by flash chromatography on silica gel (hexane/EtOAc, 2:1 to 1:2). ESI-MS m/z 683.1 (MH)+.

Step 2: Synthesis of (R)-3-(3-(trans-4-aminocyclohexyl)propanamido)-2-hydroxy-3,4-dihydro-2H-benzo[e][1,2]oxaborinine-8-carboxylic acid Prepared from 3-((2R)-2-(3-(trans-4-(tert-butoxycarbonylamino)cyclohexyl)propanamido)-2-(2,9,9-trimethyl-3,5-dioxa-4-bora-tricyclo[6.1.1.0$^{2,6}$]dec-4-yl)ethyl)-2-methoxybenzoic acid tert-butyl ester and BCl$_3$ following the procedure described in Step 2 of Example 1. The crude product was purified by reverse phase preparative HPLC and dried using lyophilization. ESI-MS m/z 361 (MH)+.

Example 22

(R)-3-(3-(trans-4-guanidinocyclohexyl)propanamido)-2-hydroxy-3,4-dihydro-2H-benzo[e][1,2]oxaborinine-8-carboxylic acid

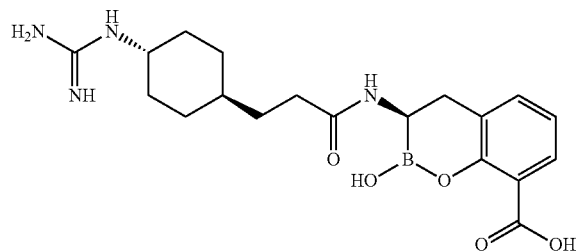

Synthesis of (R)-3-(3-(trans-4-guanidinocyclohexyl)propanamido)-2-hydroxy-3,4-dihydro-2H-benzo[e][1,2]oxaborinine-8-carboxylic acid Prepared from (R)-3-(3-(trans-4-aminocyclohexyl)propanamido)-2-hydroxy-3,4-dihydro-2H-benzo[e][1,2]oxaborinine-8-carboxylic acid (Example 21) following procedure described in Example 4. ESI-MS m/z 403 (MH)+.

Example 23

(R)-3-(2-(trans-4-((2-(dimethylamino)ethyl)(methyl)amino)cyclohexyl)acetamido)-2-hydroxy-3,4-dihydro-2H-benzo[e][1,2]oxaborinine-8-carboxylic acid

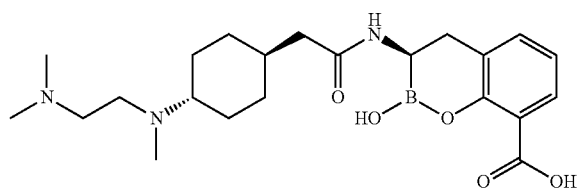 [SMILES: CN(C)CCN(C)[C@H]1CC[C@H](CC(=O)N[C@H]2Cc3cccc(C(=O)O)c3OB2O)CC1]

Synthesis of (R)-3-(2-(trans-4-((2-(dimethylamino)ethyl)(methyl)amino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e][1,2]oxaborinine-8-carboxylic acid (Example 15) following procedure described in Example 14. ESI-MS m/z 432 (MH)+.

Example 24

(R)-3-(2-(trans-4-(4-carbamimidoylpiperazin-1-yl)cyclohexyl)acetamido)-2-hydroxy-3,4-dihydro-2H-benzo[e][1,2]oxaborinine-8-carboxylic acid

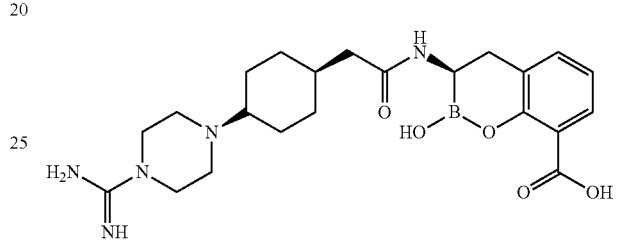

Synthesis of (R)-3-(2-(trans-4-(4-carbamimidoylpiperazin-1-yl)cyclohexyl)acetamido)-2-hydroxy-3,4-dihydro-2H-benzo[e][1,2]oxaborinine-8-carboxylic acid Prepared from (R)-2-hydroxy-3-(2-(cis-4-(piperazin-1-yl)cyclohexyl)acetamido)-3,4-dihydro-2H-benzo[e][1,2]oxaborinine-8-carboxylic acid (Example 17) following procedure described in Example 4. ESI-MS m/z 458 (MH)+.

Example 25

(R)-3-(2-(trans-4-(2-guanidinoethylamino)cyclohexyl)acetamido)-2-hydroxy-3,4-dihydro-2H-benzo[e][1,2]oxaborinine-8-carboxylic acid

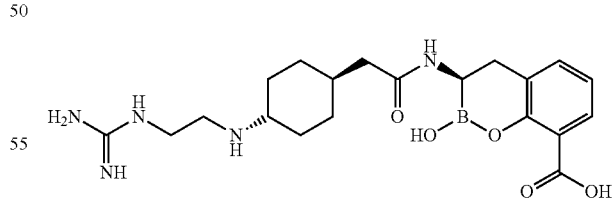

Synthesis of (R)-3-(2-(trans-4-(2-guanidinoethylamino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e]

[1,2]oxaborinine-8-carboxylic acid (Example 15) following procedure described in Example 4. ESI-MS m/z 432 (MH)+.

Example 26

(R)-2-hydroxy-3-(2-(trans-4-(2-hydroxyethylamino) cyclohexyl)acetamido)-3,4-dihydro-2H-benzo[e][1,2]oxaborinine-8-carboxylic acid

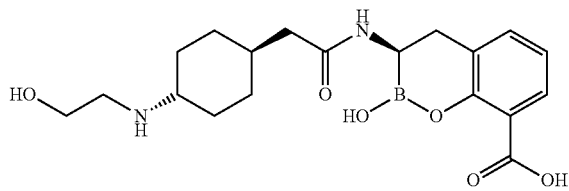

Step 1: Synthesis of (R)-3-(2-(trans-4-(2-(tert-butyldimethylsilyloxy)ethylamino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e][1,2]oxaborinine-8-carboxylic acid (Example 15) and 2-(tert-butyldimethylsilyloxy)acetaldehyde following procedure described in Step 1 of Example 15. ESI-MS m/z 505 (MH)+.

Step 2: Synthesis of (R)-2-hydroxy-3-(2-(trans-4-(2-hydroxyethylamino)cyclohexyl)acetamido)-3,4-dihydro-2H-benzo[e][1,2]oxaborinine-8-carboxylic acid To (R)-3-(2-(trans-4-(2-(tert-butyldimethylsilyloxy)ethylamino)cyclohexyl)acetamido)-2-hydroxy-3,4-dihydro-2H-benzo[e][1,2]oxaborinine-8-carboxylic acid from step 1 (100 mg) in a flask was added 4 mL 4N HCl in dioxane. The resulting reaction mixture was stirred at RT for 2 hr. The solvent was removed in vacuo and the residue was purified by reverse phase preparative HPLC and dried using lyophilization. ESI-MS m/z 391 (MH)+.

Example 27

(R)-2-hydroxy-3-(2-(trans-4-(pyridin-3-ylmethylamino)cyclohexyl)acetamido)-3,4-dihydro-2H-benzo[e][1,2]oxaborinine-8-carboxylic acid

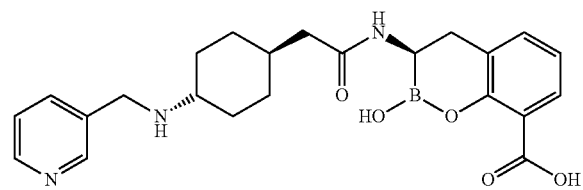

Synthesis of (R)-3-(2-(trans-4-(2-guanidinoethylamino)cyclohexyl)acetamido)-2-hydroxy-3,4-dihydro-2H-benzo[e][1,2]oxaborinine-8-carboxylic acid To 40 mg of (R)-3-(2-(trans-4-aminocyclohexyl)acetamido)-2-hydroxy-3,4-dihydro-2H-benzo[e][1,2]oxaborinine-8-carboxylic acid (Example 6) in MeOH (5 mL) was added TEA (0.03 mL), followed by nicotinaldehyde (20 mg), AcOH (0.01 mL) and sodium triacetoxyborohydride (25 mg). The reaction mixture was stirred at RT overnight. Solvent was then removed in vacuo and the residue purified by reverse phase HPLC to afford the title compound. ESI-MS m/z 438 (MH)+.

Example 28

(R)-3-(2-(trans-4-(carboxymethylamino)cyclohexyl) acetamido)-2-hydroxy-3,4-dihydro-2H-benzo[e][1,2] oxaborinine-8-carboxylic acid

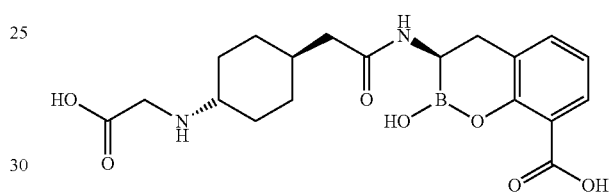

To (R)-3-(2-(trans-4-aminocyclohexyl)acetamido)-2-hydroxy-3,4-dihydro-2H-benzo[e][1,2]oxaborinine-8-carboxylic acid (Example 6) in MeOH was added TEA (2.5 eq), followed by ethyl bromoacetate (1.2 eq). The reaction mixture was stirred at RT overnight. To this reaction mixture was then added 1N NaOH and stirred for 6 hr. After concentration in vacuo, 1N HCl was added to adjust pH to 1. The reaction mixture was purified using reverse phase HPLC to afford the title compound. ESI-MS m/z 405 (MH)+.

Example 29

(R)-3-(2-(trans-4-(4,5-dihydro-1H-imidazol-1-yl) cyclohexyl)acetamido)-2-hydroxy-3,4-dihydro-2H-benzo[e][1,2]oxaborinine-8-carboxylic acid

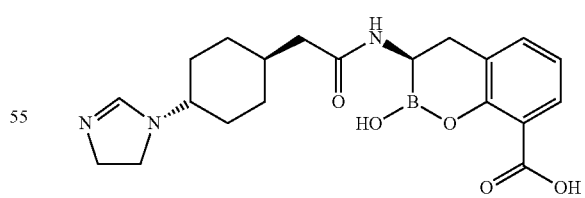

To (R)-3-(2-(trans-4-(2-amino ethylamino)cyclohexyl)acetamido)-2-hydroxy-3,4-dihydro-2H-benzo[e][1,2]oxaborinine-8-carboxylic acid (Example 15) in MeOH was added DIEA (2.5 eq), followed by isopropyl formimidate hydrochloride (1.2 eq). The reaction mixture was stirred at RT overnight. The mixture was then concentrated in vacuo and the crude product was purified using reverse phase HPLC to afford the title compound. ESI-MS m/z 400 (MH)+.

Example 30

(R)-3-(2-(trans-4-formimidamidocyclohexyl)acetamido)-2-hydroxy-3,4-dihydro-2H-benzo[e][1,2]oxaborinine-8-carboxylic acid

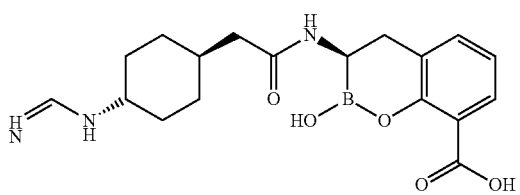

To (R)-3-(2-(trans-4-aminocyclohexyl)acetamido)-2-hydroxy-3,4-dihydro-2H-benzo[e][1,2]oxaborinine-8-carboxylic acid (Example 6) in MeOH was added DIEA (2.5 eq), followed by isopropyl formimidate hydrochloride (1.2 eq). The reaction mixture was stirred at RT overnight. The mixture was then concentrated in vacuo and the crude product was purified using reverse phase HPLC to afford the title compound. ESI-MS m/z 374 (MH)$^+$.

Example 31

(R)-3-(2-cyclohexylacetamido)-2-hydroxy-3,4-dihydro-2H-benzo[e][1,2]oxaborinine-8-carboxylic acid

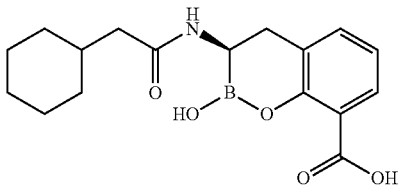 [SMILES: O=C(CC1CCCCC1)N[C@H]1Cc2cccc(C(=O)O)c2OB1O]

Step 1: Synthesis of tert-butyl 3-((2R)-2-(2-cyclohexylacetamido)-2-(2,9,9-trimethyl-3,5-dioxa-4-bora-tricyclo[6.1.1.02,6]dec-4-yl)ethyl)-2-methoxybenzoate Prepared from 2-methoxy-3-(2,9,9-trimethyl-3,5-dioxa-4-bora-tricyclo[6.1.1.0 2,6]dec-4-ylmethyl)-benzoic acid tert-butyl ester and 2-cyclohexylacetic acid following procedure described in step 1 of Example 1. The crude product was purified by flash chromatography on silica gel (Haxane/EtOAc).

Step 2: Synthesis of (R)-3-(3-(trans-4-aminocyclohexyl)propanamido)-2-hydroxy-3,4-dihydro-2H-benzo[e][1,2]oxaborinine-8-carboxylic acid Prepared from tert-butyl 3-((2R)-2-(2-cyclohexylacetamido)-2-(2,9,9-trimethyl-3,5-dioxa-4-bora-tricyclo[6.1.1.02,6]dec-4-yl)ethyl)-2-methoxybenzoate and BCl3 following the procedure described in Step 2 of Example 1. The crude product was purified by reverse phase preparative HPLC and dried using lyophilization. ESI-MS m/z 332 (MH)+.

Example 32

(R)-2-hydroxy-3-(2-(trans-4-(pyridin-2-ylmethylamino)cyclohexyl)acetamido)-3,4-dihydro-2H-benzo[e][1,2]oxaborinine-8-carboxylic acid

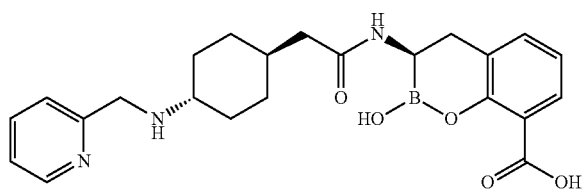 [SMILES: O=C(C[C@H]1CC[C@H](NCc2ccccn2)CC1)N[C@H]1Cc2cccc(C(=O)O)c2OB1O]

Synthesis of (R)-2-hydroxy-3-(2-(trans-4-(pyridin-2-ylmethylamino)cyclohexyl)acetamido)-3,4-dihydro-2H-benzo[e][1,2]oxaborinine-8-carboxylic acid Prepared from (R)-3-(2-(trans-4-aminocyclohexyl)acetamido)-2-hydroxy-3,4-dihydro-2H-benzo[e][1,2]oxaborinine-8-carboxylic acid (Example 6) and picolinaldehyde following the procedure in Example 27. The product was purified using reverse phase HPLC to afford the titled compound. ESI-MS m/z 438 (MH)$^+$.

Example 33

(R)-2-hydroxy-3-(2-(trans-4-(piperidin-4-ylmethylamino)cyclohexyl)acetamido)-3,4-dihydro-2H-benzo[e][1,2]oxaborinine-8-carboxylic acid

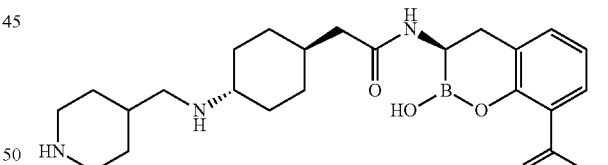

Synthesis (R)-2-hydroxy-3-(2-(trans-4-(piperidin-4-ylmethylamino)cyclohexyl)acetamido)-3,4-dihydro-2H-benzo[e][1,2]oxaborinine-8-carboxylic acid Prepared from (R)-3-(2-(trans-4-aminocyclohexyl)acetamido)-2-hydroxy-3,4-dihydro-2H-benzo[e][1,2]oxaborinine-8-carboxylic acid (Example 6) and tert-butyl 4-formylpiperidine-1-carboxylate following the procedure in Example 27. Boc group was removed by treatment with 4N HCl in dioxane. The product was purified using reverse phase HPLC to afford the titled compound. ESI-MS m/z 444 (MH)$^+$.

Example 34

(R)-3-(2-(trans-4-((1-carbamimidoylpiperidin-4-yl)methylamino)cyclohexyl)acetamido)-2-hydroxy-3,4-dihydro-2H-benzo[e][1,2]oxaborinine-8-carboxylic acid

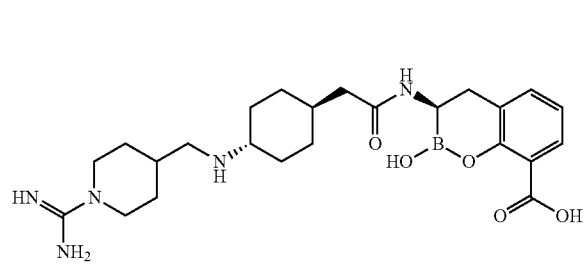 [SMILES: N=C(N)N1CCC(CN[C@H]2CC[C@H](CC(=O)N[C@H]3Cc4cccc(C(=O)O)c4OB3O)CC2)CC1]

Synthesis (R)-3-(2-(trans-4-((1-carbamimidoylpiperidin-4-yl)methylamino)cyclohexyl)acetamido)-2-hydroxy-3,4-dihydro-2H-benzo[e][1,2]oxaborinine-8-carboxylic acid Prepared from (R)-2-hydroxy-3-(2-(trans-4-(piperidin-4-ylmethylamino)cyclohexyl)acetamido)-3,4-dihydro-2H-benzo[e][1,2]oxaborinine-8-carboxylic acid (Example 33) and tert-butyl (1H-pyrazol-1-yl)methanediylidenedicarbamate following the procedure in Example 4. The product was purified using reverse phase HPLC to afford the titled compound. ESI-MS m/z 486 (MH)$^+$.

Example 35

(3R)-3-(2-(4-(3-aminoazetidin-1-yl)cyclohexyl)acetamido)-2-hydroxy-3,4-dihydro-2H-benzo[e][1,2]oxaborinine-8-carboxylic acid

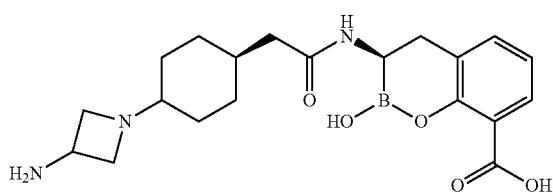

Synthesis of (3R)-3-(2-(4-(3-aminoazetidin-1-yl)cyclohexyl)acetamido)-2-hydroxy-3,4-dihydro-2H-benzo[e][1,2]oxaborinine-8-carboxylic acid Prepared from tert-butyl azetidin-3-ylcarbamate following the procedure described in Example 16. The product was purified using reverse phase HPLC to afford the titled compound. ESI-MS m/z 402 (MH)$^+$.

Example 36

(3R)-3-(2-(4-(azetidin-3-ylamino)cyclohexyl)acetamido)-2-hydroxy-3,4-dihydro-2H-benzo[e][1,2]oxaborinine-8-carboxylic acid

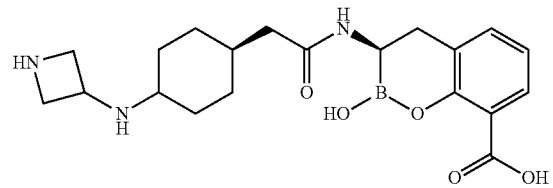

Synthesis of (3R)-3-(2-(4-(azetidin-3-ylamino)cyclohexyl)acetamido)-2-hydroxy-3,4-dihydro-2H-benzo[e][1,2]oxaborinine-8-carboxylic acid Prepared from tert-butyl 3-aminoazetidine-1-carboxylate following the procedure described in Example 16. The product was purified using reverse phase HPLC to afford the titled compound. ESI-MS m/z 402 (MH)$^+$.

Example 40

(R)-2-hydroxy-3-(2-(4-morpholinocyclohexyl)acetamido)-3,4-dihydro-2H-benzo[e][1,2]oxaborinine-8-carboxylic acid

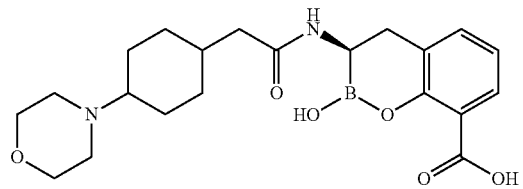 [SMILES: O=C(CC1CCC(N2CCOCC2)CC1)N[C@H]1Cc2cccc(C(=O)O)c2OB1O]

Synthesis of (R)-2-hydroxy-3-(2-(4-morpholinocyclohexyl)acetamido)-3,4-dihydro-2H-benzo[e][1,2]oxaborinine-8-carboxylic acid Prepared from morpholine and 2-(4-oxocyclohexyl)acetic acid following the procedure described in Example 16. The product was purified using reverse phase HPLC to afford the titled compound. ESI-MS m/z 417 (MH)$^+$.

Example 41

(3R)-3-(2-(4-(3-guanidinoazetidin-1-yl)cyclohexyl)acetamido)-2-hydroxy-3,4-dihydro-2H-benzo[e][1,2]oxaborinine-8-carboxylic acid

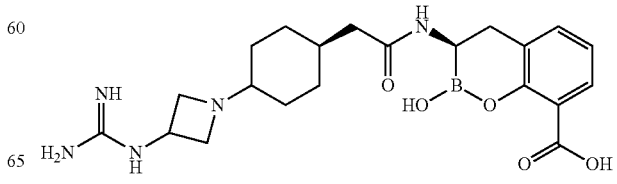

Synthesis of (3R)-3-(2-(4-(3-guanidinoazetidin-1-yl)cyclohexyl)acetamido)-2-hydroxy-3,4-dihydro-2H-benzo[e][1,2]oxaborinine-8-carboxylic acid Prepared from (3R)-3-(2-(4-(3-aminoazetidin-1-yl)cyclohexyl)acetamido)-2-hydroxy-3,4-dihydro-2H-benzo[e][1,2]oxaborinine-8-carboxylic acid (Example 35) and tert-butyl (1H-pyrazol-1-yl)methanediylidenedicarbamate following the procedure in Example 4. The product was purified using reverse phase HPLC to afford the titled compound. ESI-MS m/z 444 (MH)+.

Example 42

(R)-3-((R)-2-amino-2-cyclohexylacetamido)-2-hydroxy-3,4-dihydro-2H-benzo[e][1,2]oxaborinine-8-carboxylic acid

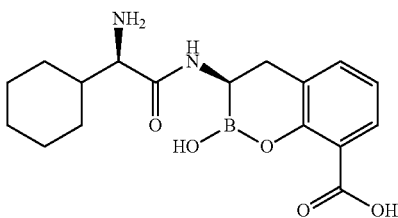

Synthesis of (R)-3-((R)-2-amino-2-cyclohexylacetamido)-2-hydroxy-3,4-dihydro-2H-benzo[e][1,2]oxaborinine-8-carboxylic acid Prepared from (R)-2-(tert-butoxycarbonylamino)-2-cyclohexylacetic acid using the procedure described in step 1 and step 2, Example 1. The product was purified using reverse phase HPLC to afford the titled compound. ESI-MS m/z 347 (MH)+.

Example 43

3-{2-[4-(2-Amino-ethylamino)-1-hydroxy-cyclohexyl]-acetylamino}-2-hydroxy-3,4-dihydro-2H-benzo[e][1,2]oxaborinine-8-carboxylic acid

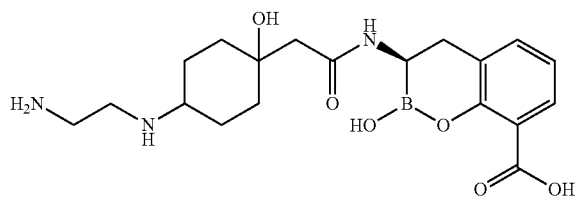 [SMILES: NCCNC1CCC(O)(CC(=O)N[C@H]2Cc3cccc(C(=O)O)c3OB2O)CC1]

Step 1: Synthesis of (1-Hydroxy-4-oxo-cyclohexyl)-acetic acid benzyl ester

To a suspension of zinc dust (2.06 g, 31.5 mmol) in diethyl ether (50 mL) under argon was added trimethylsilyl chloride (3.0 mL, 23.6 mmol) and the reaction stirred for 15 min at RT. The reaction was then heated at reflux for 25 min. Benzyl bromoacetate (3.9 mL, 24.6 mmol) and 1,4-cyclohexanedione monoethylene acetal (3.05 g, 19.6 mmol) were added and the reaction was kept at reflux for 1.3 hr. The reaction was then cooled to RT, quenched with 1N HCl (125 mL) and stirred overnight. The aqueous layer was extracted with Et2O (3×). The combined organic layers were washed with sat. NaHCO3, dried over MgSO4, filtered, and concentrated. The crude product was purified by flash chromatography on silica gel (0-60% EtOAc:Hexane) to provide 2.79 g (54%) of pure product. ESI-MS m/z 285 (M+Na)+.

Step 2: Synthesis of [4-(2-tert-Butoxycarbonylamino-ethylamino)-1-hydroxy-cyclohexyl]-acetic acid benzyl ester Titanium ethoxide (0.47 mL, 2.24 mmol) was added to a solution of (1-Hydroxy-4-oxo-cyclohexyl)-acetic acid benzyl ester (1.22 g, 4.65 mmol) and 2-(Boc-amino)ethylamine (0.97 g, 6.05 mmol) in DCM (5.0 mL) under argon. The reaction was stirred at RT for 5 hr. The reaction was concentrated in vacuo. The residue was diluted with methanol (23 mL) under argon and cooled to −78° C. Sodium triacetoxyborohydride (1.49 g, 7.03 mmol) was added in one portion and the reaction allowed to slowly warm to RT overnight. The reaction was quenched with 10% Na2CO3 and extracted with ethyl acetate (2×). The combined organic layers were washed with brine, dried over Na2SO4, filtered, and concentrated. The crude product was carried forward without purification. ESI-MS m/z 407 (MH)+.

Step 3: Synthesis of {4-[tert-Butoxycarbonyl-(2-tert-butoxycarbonylamino-ethyl)-amino]-1-hydroxy-cyclohexyl}-acetic acid benzyl ester Triethylamine (1.1 mL, 7.89 mmol) and di-tert-butyl dicarbonate (1.22 g, 5.59 mmol) were added to a solution of [4-(2-tert-Butoxycarbonylamino-ethylamino)-1-hydroxy-cyclohexyl]-acetic acid benzyl ester (1.89 g, 4.65 mmol) in DCM (46 mL) under argon. The reaction was stirred at RT for 17 hr. The reaction was quenched with brine and extracted with DCM (2×). The combined organic layers were dried over Na2SO4, filtered, and concentrated. The crude product was purified by flash chromatography on silica gel (0-75% EtOAc:Hexane). ESI-MS m/z 507 (MH)+.

Step 4: Synthesis of {4-[tert-Butoxycarbonyl-(2-tert-butoxycarbonylamino-ethyl)-amino]-1-hydroxy-cyclohexyl}-acetic acid A solution of {4-[tert-Butoxycarbonyl-(2-tert-butoxycarbonylamino-ethyl)-amino]-1-hydroxy-cyclohexyl}-acetic acid benzyl ester (0.540 g, 1.07 mmol) in methanol (15 mL) was purged with argon for 5 min. Palladium on carbon (10%, 0.127 g) was added, the flask evacuated, and the reaction stirred under a $H_2$ atmosphere for 19 hr. The reaction was filtered through a Celite-plugged filter frit, washed with methanol and DCM, and concentrated. The crude product was carried forward without purification. ESI-MS m/z 439 (M+Na)+.

Step 5: Synthesis of 3-[2-(2-{4-[tert-Butoxycarbonyl-(2-tert-butoxycarbonylamino-ethyl)-amino]-1-hydroxy-cyclohexyl}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.02,6]dec-4-ylmethyl)-benzoic acid tert-butyl ester and {4-[tert-Butoxycarbonyl-(2-tert-butoxycarbonylamino-ethyl)-amino]-1-hydroxy-cyclohexyl}-acetic acid following procedure described in step 1 of Example 1. The crude product was purified by flash chromatography on silica gel (5-100% EtOAc:Hexane). ESI-MS m/z 828 (MH)+.

Step 6: Synthesis of 3-{2-[4-(2-Amino-ethylamino)-1-hydroxy-cyclohexyl]-acetylamino}-2-hydroxy-3,4-dihydro-2H-benzo[e][1,2]oxaborinine-8-carboxylic acid Prepared from 3-[2-(2-{4-[tert-Butoxycarbonyl-(2-tert-butoxycarbonylamino-ethyl)-amino]-1-hydroxy-cyclohexyl}-acetylamino)-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 2 of Example 1. The crude product was purified by reverse phase preparative HPLC and dried using lyophilization. ESI-MS m/z 406 (MH)+.

Example 44

3-[2-(4-Amino-1-hydroxy-cyclohexyl)-acetylamino]-2-hydroxy-3,4-dihydro-2H-benzo[e][1,2]oxaborinine-8-carboxylic acid

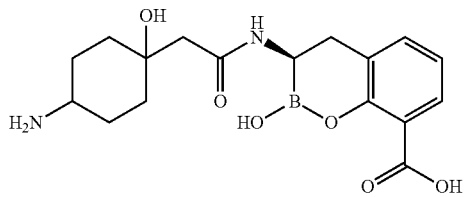 [SMILES: NC1CCC(O)(CC(=O)N[C@H]2Cc3cccc(C(=O)O)c3OB2O)CC1]

Step 1: Synthesis of (4-Benzylamino-1-hydroxy-cyclohexyl)-acetic acid benzyl ester Prepared from (1-Hydroxy-4-oxo-cyclohexyl)-acetic acid benzyl ester and benzylamine following the procedure described in Step 2 of Example 43. The crude product was purified by flash chromatography on silica gel (0-10% $CH_3OH:CH_2Cl_2$). ESI-MS m/z 354 (MH)+.

Step 2: Synthesis of (4-tert-Butoxycarbonylamino-1-hydroxy-cyclohexyl)-acetic acid A solution of (4-Benzylamino-1-hydroxy-cyclohexyl)-acetic acid benzyl ester (1.41 g, 3.99 mmol) and di-tert-butyl dicarbonate (0.952 g, 4.36 mmol) in ethanol (35 mL) was purged with argon for 5 min. Palladium hydroxide (20%, 0.608 g) was added, the flask evacuated, and the reaction stirred under a $H_2$ atmosphere at 65° C. for 43 hr. The reaction was cooled to RT, filtered through a Celite-plugged filter frit, washed with methanol and DCM, and concentrated. The crude product was carried forward without purification. ESI-MS m/z 296 (M+Na)+.

Step 3: Synthesis of 3-[2-[2-(4-tert-Butoxycarbonylamino-1-hydroxy-cyclohexyl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and (4-tert-Butoxycarbonylamino-1-hydroxy-cyclohexyl)-acetic acid following procedure described in step 1 of Example 1. The crude product was purified by flash chromatography on silica gel (5-100% EtOAc:Hexane). ESI-MS m/z 685 (MH)+.

Step 4: Synthesis of 3-[2-(4-Amino-1-hydroxy-cyclohexyl)-acetylamino]-2-hydroxy-3,4-dihydro-2H-benzo[e][1,2]oxaborinine-8-carboxylic acid Prepared from 3-[2-[2-(4-tert-Butoxycarbonylamino-1-hydroxy-cyclohexyl)-acetylamino]-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 2 of Example 1. The crude product was purified by reverse phase preparative HPLC and dried using lyophilization. ESI-MS m/z 363 (MH)+.

Example 45

3-[2-(4-Amino-cyclohexylamino)-acetylamino]-2-hydroxy-3,4-dihydro-2H-benzo[e][1,2]oxaborinine-8-carboxylic acid

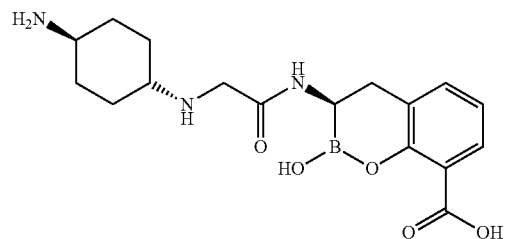

Step 1: Synthesis of (4-tert-Butoxycarbonylamino-cyclohexylamino)-acetic acid benzyl ester To a suspension of trans-N-Boc-1,4-diaminocyclohexane (0.256 g, 1.19 mmol) and potassium carbonate (0.663 g, 4.80 mmol) in acetonitrile (15 mL) and DMF (5 mL) was added benzyl bromoacetate (0.21 mL, 1.33 mmol) under argon and the reaction was stirred at RT for 19 hr. The reaction was diluted with ethyl acetate and washed with sat. $NaHCO_3$ and brine. The organic layer was dried over $Na_2SO_4$, filtered, and concentrated. The crude product was carried forward without purification. ESI-MS m/z 363 (MH)+.

Step 2: Synthesis of [tert-Butoxycarbonyl-(4-tert-butoxycarbonylamino-cyclohexyl)-amino]-acetic acid benzyl ester Prepared from (4-tert-Butoxycarbonylamino-cyclohexylamino)-acetic acid benzyl ester and di-tert-butyl dicarbonate following the procedure described in Step 3 of Example 43. The crude product was purified by flash chromatography on silica gel (0-50% EtOAc:Hexane). ESI-MS m/z 463 (MH)+.

Step 3: Synthesis of [tert-Butoxycarbonyl-(4-tert-butoxycarbonylamino-cyclohexyl)-amino]-acetic acid A solution of [tert-Butoxycarbonyl-(4-tert-butoxycarbonylamino-cyclohexyl)-amino]-acetic acid benzyl ester (0.277 g, 0.599 mmol) in methanol (6 mL) was purged with argon for 5 min. Palladium hydroxide (20%, 0.053 g) was added, the flask evacuated, and the reaction stirred under a $H_2$ atmosphere for 19 hr. The reaction was filtered through a Celite-plugged filter frit, washed with methanol and DCM, and concentrated. The crude product was carried forward without purification. ESI-MS m/z 395 (M+Na)+.

Step 4: Synthesis of 3-[2-{2-[tert-Butoxycarbonyl-(4-tert-butoxycarbonylamino-cyclohexyl)-amino]-acetylamino}-2-(2,9,9-trimethyl-3,5-dioxa-4-bora-tricyclo[6.1102,6]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and [tert-Butoxycarbonyl-(4-tert-butoxycarbonylamino-cyclohexyl)-amino]-acetic acid following procedure described in step 1 of Example 1. The crude product was purified by flash chromatography on silica gel (5-100% EtOAc:Hexane). ESI-MS m/z 784 (MH)+.

Step 5: Synthesis of 3-[2-(4-Amino-cyclohexylamino)-acetylamino]-2-hydroxy-3,4-dihydro-2H-benzo[e][1,2]oxaborinine-8-carboxylic acid Prepared from 3-[2-{2-[tert-Butoxycarbonyl-(4-tert-butoxycarbonylamino-cyclohexyl)-amino]-acetylamino}-2-(2,9,9-trimethyl-3,5-dioxa-4-bora-tricyclo[6.1.1.02,6]dec-4-yl)-ethyl]-2-methoxy-benzoic acid tert-butyl ester and $BCl_3$ following the procedure described in Step 2 of Example 1. The crude product was purified by reverse phase preparative HPLC and dried using lyophilization. ESI-MS m/z 362 (MH)+.

Example 46

(R)-3-(2-(cis-4-(2-aminoethylamino)cyclohexyl) acetamido)-2-hydroxy-3,4-dihydro-2H-benzo[e][1,2]oxaborinine-8-carboxylic acid

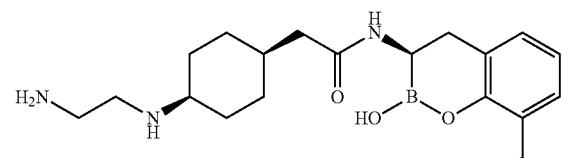

Synthesis of (R)-3-(2-(cis-4-(2-aminoethylamino) cyclohexyl)acetamido)-2-hydroxy-3,4-dihydro-2H-benzo[e][1,2]oxaborinine-8-carboxylic acid Prepared from (R)-3-(2-(cis-4-aminocyclohexyl)acetamido)-2-hydroxy-3,4-dihydro-2H-benzo[e][1,2]oxaborinine-8-carboxylic acid (Example 7) following the same procedure described in Example 10. The product was purified using reverse phase HPLC to afford the titled compound. ESI-MS m/z 390 (MH)+.

Example 47

(3R)-2-hydroxy-3-(2-(4-hydroxycyclohexyl)acetamido)-3,4-dihydro-2H-benzo[e][1,2]oxaborinine-8-carboxylic acid

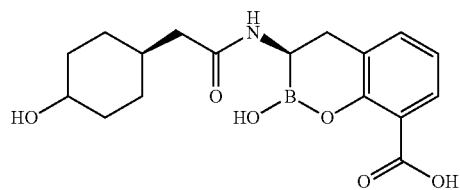

Step 1: Synthesis of tert-butyl 3-((2R)-2-(hexahydrobenzo[d][1,3,2]dioxaborol-2-yl)-2-(2,9,9-trimethyl-3,5-dioxa-4-bora-tricyclo[6.1.1.0$^{2,6}$]dec-4-yl) ethyl)-2-methoxybenzoate Prepared from 2-methoxy-3-(2,9,9-trimethyl-3,5-dioxa-4-bora-tricyclo[6.1.1.0$^6$]dec-4-ylmethyl)-benzoic acid tert-butyl ester and 2-(4-oxocyclohexyl)acetic acid following procedure described in step 1 of Example 1. The crude product was purified by flash chromatography on silica gel (Haxane/EtOAc). ESI-MS m/z 568.1 (MH)+.

Step 2: Synthesis of (3R)-2-hydroxy-3-(2-(4-hydroxycyclohexyl)acetamido)-3,4-dihydro-2H-benzo[e][1,2]oxaborinine-8-carboxylic acid (R)-2-hydroxy-3-(2-(4-oxocyclohexyl)acetamido)-3,4-dihydro-2H-benzo[e][1,2]oxaborinine-8-carboxylic acid was prepared from tert-butyl 3-((2R)-2-(hexahydrobenzo[d][1,3,2]dioxaborol-2-yl)-2-(2,9,9-trimethyl-3,5-dioxa-4-bora-tricyclo[6.1.1.0$^{2,6}$]dec-4-yl)ethyl)-2-methoxybenzoate as described in Step 2, Example 1. To the crude product in $H_2O$ and MeOH was added $NaBH_4$. The resulting reaction mixture was stirred at room temperature for 4 hr. After removal of MeOH, the product was purified by reverse phase preparative HPLC and dried using lyophilization. ESI-MS m/z 348 (MH)+.

Example 48

(R)-2-hydroxy-3-(2-(trans-4-(2-(pyridin-2-ylamino) ethylamino)cyclohexyl) acetamido)-3,4-dihydro-2H-benzo[e][1,2]oxaborinine-8-carboxylic acid

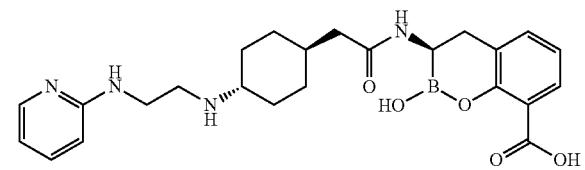 [SMILES: O=C(C[C@H]1CC[C@H](NCCNc2ccccn2)CC1)N[C@H]1Cc2cccc(C(=O)O)c2OB1O]

Step 1: Synthesis of [(1S)-2-(3-tert-butoxycarbonyl-2-methoxy-phenyl)-1-chloro-ethyl]boronic acid (+) pinanediolato diester

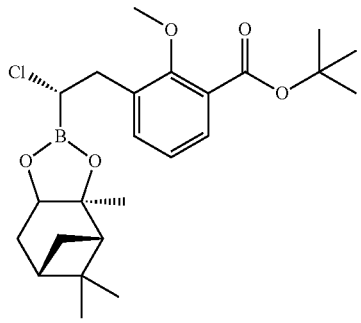 [SMILES: COc1c(C[C@@H](Cl)B2OC3C[C@@H]4C[C@@H](C4(C)C)[C@]3(C)O2)cccc1C(=O)OC(C)(C)C]

Step 1a: Synthesis of 3-carboxy-2-methoxy-phenyl boronic acid (+) pinandiolato diester To a mixture of 3-carboxy-2-methoxy-phenyl boronic acid (35.0 g, 178.5 mmol,) and (+) pinanediol (30.35 g, 178.5 mmol) was added toluene (400 mL). The resulting mixture was stirred for 3 hr then concentrated under vacuum (28 mmHg, bath temperature 40° C.). The resulting solid was dried by toluene azeotrope (2 times, approximately 100 mL). This residue was dried under high vacuum (approx. 1 mmHg) at room temperature for 17.5 hr to give the crude title compound which can be used without further purification. 48.06 g of this crude product was recrystallized from 150 mL of chloroform/hexane (1:5 v/v) to give the pure title compound. The mother liquor from the crystallization was concentrated and purified by silica chromatography (120 g silica eluted with 40-100% ethyl acetate in hexane) to give an additional batch of the title compound.

Step 1b: Synthesis of 3-tert-butyloxycarbonyl-2-methoxy-phenyl boronic acid (+) pinandiolato diester To recrystallized 3-carboxy-2-methoxy-phenyl boronic acid (+) pinandiolato diester (9.90 g, 30 mmol) was added thionyl chloride (20 ml, reagent grade) and the reaction flask vented through a CaCl$_2$ trap. The resulting solution was heated in an oil bath held at 95° C. and stirred for 1 hr. This solution was cooled to room temperature over about 10 min then concentrated under reduced pressure (20-30 mm Hg, 35° C.) until a constant weight of 10.57 g was achieved.

In a separate flask, to a cooled (−5° C.) solution of t-BuOH (3.7 mL, 39 mmol) in THF (100 mL) was added, dropwise, BuLi (14.4 mL, 2.5 M in hexane, 36 mmol) over about 5 min. On complete addition, the resulting solution was stirred for 20 min. To this solution was added the crude acid chloride (above) (10.57 g, 30 mmol) in THF (15 mL) over about 30 sec. On complete addition, the cold bath was removed and stirring continued for 4 hr. To this solution was added HCl (50 mL, 0.2 M aq). The mixture (pH=3) was extracted with ether and the ether extract washed with brine, dried over Magnesium sulfate and concentrated. The residue was purified by silica chromatography (120 g silica eluted with 2-20% ethyl acetate in hexane) to give the title compound as cream colored solid.

Step 1c: Synthesis of (3-tert-butoxycarbonyl-2-methoxy-phenyl)methylboronic acid (+)-pinanediolato diester To a cooled (−100° C. external temperature) solution of 3-tert-butyloxycarbonyl-2-methoxy-phenyl boronic acid (+) pinandiolato diester (34.6 g, 89.6 mmol) and chloro-iodomethane (10.3 mL, 140 mmol) in THF (250 mL) was added, dropwise down the side of the flask, BuLi (54 mL, 2.5 M in hexanes, 135 mmol) over 80 min. On complete addition, the reaction solution was stirred 15 min. To the resulting solution was added ZnCl$_2$ (90 mL, 1M in ether), dropwise down the side of the flask, over approximately 40 min. On complete addition, the cold bath was removed and stirring continued for 16.5 hr. The reaction mixture was diluted with NH$_4$Cl (300 mL, saturated aqueous) and ethyl acetate (700 mL). The separated organic extract was washed with a further portion of saturated NH$_4$Cl aq (100 mL) and brine (100 mL), dried over magnesium sulfate and concentrated. The residue was purified by silica chromatography (224 g silica eluted with hexane (1 L) then 10% ethyl acetate in hexane (2 L) to give the title compound as a colorless oil. This material slowly crystallized at −10° C.

Step 1d: Synthesis of [(1S)-2-(3-tert-butoxycarbonyl-2-methoxy-phenyl)-1-chloro-ethyl]boronic acid (+) pinanediolato diester Method 1:
To a cooled (−100° C. external temperature) solution of dichloromethane (2.27 mL, 35 mmol) in THF (44 mL) was added, dropwise down the side of the flask, BuLi (8.88 mL, 2.5 M in hexanes, 22 mmol) over 45 min. After approx. 80% of the BuLi was added, a white precipitate formed. On complete addition, the reaction mixture was stirred 30 min. To this mixture was added, dropwise down the side of the flask, (3-tert-butoxycarbonyl-2-methoxy-phenyl)methylboronic acid (+)-pinanediolato diester (8.0 g, 20 mmol) in THF (20 mL) over approximately 30 min. On complete addition, the resulting solution was stirred for 5 minutes. To this solution was added ZnCl$_2$ (22 mL, 1M in ether) dropwise down the side of the flask, over approximately 12 min. On complete addition, the cold bath was removed and replaced with a −10° C. bath. The reaction mixture was stirred for 1.25 hr. To this solution was added ice cold ether (300 mL) and ice cold saturated aqueous NH$_4$Cl (125 mL). The organic phase was washed with brine, dried over magnesium sulfate and concentrated under reduced pressure. The residue was purified by silica chromatography (120 g silica eluted with 2-20% ethyl acetate in hexane) to give the title compound as a colorless oil. This material slowly crystallized at −10° C.

Method 2:
(3-tert-butoxycarbonyl-2-methoxy-phenyl)methylboronic acid (+)-pinanediolato diester (2.0 g, 5 mmol) and dichloromethane (1.6 mL, 25 mmol) in THF (20 mL) was stirred at −60° C. for 30 min. To this solution was added LDA (6.5 mmol, 2 M solution from Aldrich) over a period of 10 min. The resultant reaction mixture was stirred at −60° C. for 20 min. ZnCl$_2$ (8.75 mmol, 1M solution in ether) was added at −60° C. slowly. The reaction mixture was stirred at −50 to −60° C. for 30 min. This resulting mixture was warmed up to 0° C. over a period of 1 hr, at which time, 10% H$_2$SO$_4$ solution (10 mL) was added and the reaction mixture stirred for 10 min. After phase separation, the organic phase was washed with water and brine. The organic phase was then dried and concentrated in vacuo. The residue was then purified by flash silica chromatography (EtOAc/Hexane:4/1) to give the title compound.

Step 2: Synthesis of ethyl 2-[4-[2-(2-pyridylamino) ethylamino]cyclohexyl]acetate To a mixture of 2-(N-[2-(amino)-ethyl]-amino)-pyridine (685 mg, 5 mmol) and ethyl 2-(4-oxocyclohexyl)acetate (786 mg, 4 mmol) was added dichloromethane (4 mL) followed by titanium ethoxide (420 µL, 2 mmol, technical grade). The resulting mixture was stirred for 4 hr then concentrated under reduced pressure. The residue was taken up in methanol (10 mL) and cooled to −78° C. To this solution was added sodium borohydride (228 mg, 6 mmol). On complete addition, the cold bath was removed and stirring continued for 1.25 hr. The mixture was diluted with dichloromethane and poured into saturated sodium carbonate solution (15 mL). The organic phase was separated, dried over magnesium sulfate and concentrated to give the crude title compound as a 6:1 mixture trans:cis isomers. This mixture was used without further purification.

Step 3: Synthesis of ethyl 2-[4-[tert-butoxycarbonyl-[2-[tert-butoxycarbonyl(2-pyridyl)amino]ethyl] amino]cyclohexyl]acetate To a solution of ethyl 2-[4-[2-(2-pyridylamino)ethylamino]cyclohexyl]acetate (1.31 g, 4 mmol) in dichloromethane (12 mL) was added di-tert-butyl-dicarbonate (2.18 g, 10 mmol) followed by diisopropylethylamine (1.76 mL, 10 mmol). The resulting solution was stirred for 4 hr, diluted with ethyl acetate, washed with and brine, dried over magnesium sulfate and concentrated. The residue was purified by silica chromatography (30 g silica; eluted with 20% ethyl acetate/10% dichloromethane in hexanes) to give the title compound as a 6:1 mixture of trans:cis isomers.

Step 4: Synthesis of 2-[4-[tert-butoxycarbonyl-[2-[tert-butoxycarbonyl(2-pyridyl)amino]ethyl]amino] cyclohexyl]acetic acid To a solution of ethyl 2-[4-[tert-butoxycarbonyl-[2-[tert-butoxycarbonyl(2-pyridyl)amino]ethyl]amino]cyclohexyl] acetate (968 mg, 1.91 mmol) in THF (3 mL); methanol (3 mL) and water (6 mL) was added lithium hydroxide monohydrate (397 mg, 9.7 mmol). The resulting solution was stirred for 2.25 hr, then acidified to pH 3 with 1 N HCl. The resulting mixture was extracted with dichloromethane (4 times). The combined organic extract was dried over magnesium sulfate and concentrated. The residue was purified by silica chromatography (10 g silica; eluted with 40-100% ethyl acetate in hexanes) to give the title compound as a 6:1 mixture of trans:cis isomers.

Step 5: Synthesis of tert-butyl 2-methoxy-3-((2R)-2-(2-(trans-4-(2-(pyridin-2-ylamino)ethylamino) cyclohexyl)acetamido)-2-(2,9,9-trimethyl-3,5-dioxa-4-bora-tricyclo[6.1.1.0$^{2,6}$]dec-4-yl)ethyl)benzoate To a cooled (−78° C.) solution of [(1S)-2-(3-tert-butoxycarbonyl-2-methoxy-phenyl)-1-chloro-ethyl]boronic acid (+) pinanediolato diester (from Step 1) (1.35 g, 3 mmol) in THF (9 mL) was added dropwise a solution of lithium bistrimethylsilylamide (3.0 mL, 1M in THF, 3 mmol). On complete addition, the cold bath was removed and stirring continued for 16.75 hours. The resulting solution, which was approximately 0.25M benzoic acid, 3-[(2R)-2-[bis(trimethylsilyl)amino]-2-[(3aS,4S,6S,7aR)-hexahydro-3a,5,5-trimethyl-4,6-methano-1,3,2-benzodioxaborol-2-yl]ethyl]-2-methoxy, 1,1-dimethylethyl ester in THF was used without further purification.

In a separate flask, to a mixture of 2-[4-[tert-butoxycarbonyl-[2-[tert-butoxycarbonyl(2-pyridyl)amino]ethyl] amino]cyclohexyl]acetic acid (477 mg, 1 mmol) and HATU (418 mg, 1.1 mmol) was added DMA (3 mL) followed by N-methyl-morpholine (120 µL, 1.1 mmol). The resulting solution was stirred for 90 minutes. To this solution was added a solution of Benzoic acid, 3-[(2R)-2-[bis(trimethylsilyl)amino]-2-[(3aS,4S,6S,7aR)-hexahydro-3a,5,5-trimethyl-4,6-methano-1,3,2-benzodioxaborol-2-yl]ethyl]-2-methoxy, 1,1-dimethylethyl ester (4 mL, 0.25M in THF 1 mmol). The resulting mixture was stirred for 2.5 hours, diluted with ethyl acetate washed with water and brine, dried over magnesium sulfate and concentrated. The residue was purified by silica chromatography (10 g silica; eluted with 20-100% ethyl acetate in hexanes) to give the title compound.

Step 6: Synthesis of (R)-2-hydroxy-3-(2-(trans-4-(2-(pyridin-2-ylamino)ethylamino)cyclohexyl) acetamido)-3,4-dihydro-2H-benzo[e][1,2]oxaborinine-8-carboxylic acid To a solution of tert-butyl 2-methoxy-3-((2R)-2-(2-(trans-4-(2-(pyridin-2-ylamino)ethylamino)cyclohexyl)acetamido)-2-(2,9,9-trimethyl-3,5-dioxa-4-bora-tricyclo[6.1.1.0$^{2,6}$]dec-4-yl)ethyl)benzoate (396 mg, 0.45 mmol) in 1,4-dioxane (6 mL) was added HCl (6 ml, 3M in water). The resulting solution was heated to reflux and stirred at this temperature for 3.5 hours. The resulting mixture was cooled to room temperature and extracted with ether (2×). The remaining aqueous solution was purified directly by reverse phase HPLC Phenomenex Luna C18 column 35×75 mm; Flow rate 40 mL/min; eluted with 5-70% CH$_3$CN in H$_2$O/ 0.1% TFA over 8 minutes. The title compound was isolated as the TFA salt by lyophilization.

Example 49

(R)-2-hydroxy-3-(2-(trans-4-(2-(methylsulfonamido) ethylamino)cyclohexyl)acetamido)-3,4-dihydro-2H-benzo[e][1,2]oxaborinine-8-carboxylic acid

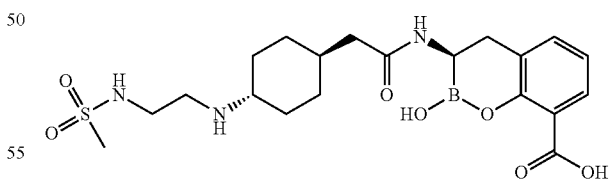

Step 1: Synthesis of tert-butyl N-[2-(methanesulfonamido)ethyl]carbamate

To a cooled (−10° C.) solution of 2-tert-butyl N-(2-aminoethyl)carbamate (1.60 g, 10 mmol) in dichloromethane (25 mL) was added triethylamine (1.38 mL, 10 mmol) followed by methanesulphonyl chloride (770 µL, 10 mmol). The resulting solution was stirred for 5 minutes then the cold bath was removed and stirring continued for 1 hr. The reaction mixture was then diluted with ethyl acetate washed with water and brine, dried over magnesium sulfate and concentrated to give the title compound as a solid. This material was used without further purification.

Step 2: Synthesis of N-(2-aminoethyl)methanesulfonamide; 2,2,2-trifluoroacetic acid salt To a solution of tert-butyl N-[2-(methanesulfonamido) ethyl]carbamate (2.23 g, 9.4 mmol) in dichloromethane (30 mL) was added trifluoroacetic acid (7.5 mL). The resulting solution was stirred for 1.5 hours then concentrated under vacuum to give the title compound as a white solid. This material was used without further purification.

Step 3: Synthesis of ethyl 2-[4-[2-(methanesulfonamido)ethylamino]cyclohexyl]acetate To a mixture of ethyl 2-(4-oxocyclohexyl)acetate (736 mg, 4 mmol) and N-(2-aminoethyl)methanesulfonamide; 2,2,2-trifluoroacetic acid salt (1.26 g, 5 mmol) in dichloromethane (6 mL) was added triethylamine (690 µL, 5 mmol) followed by Titanium (IV) ethoxide (420 µL, 2 mmol, technical grade). The resulting cloudy mixture was stirred for 4 hours then concentrated under reduced pressure. The residue was taken up in methanol (6 mL). This mixture was cooled to −78° C. To the resulting mixture was added sodium borohydride (187 mg, 4.8 mmol). On complete addition, the cold bath was allowed to expire and stirring continued for 15.5 hours. The resulting mixture was concentrated under reduced pressure to give a thick paste. This residue was taken up in dichloromethane (40 mL). To this mixture was added $Na_2CO_3$ (5.5 mL, saturated aqueous solution). The resulting mixture was stirred for 5 minutes. To this mixture was added celite (1.8 g). This mixture was stirred for 5 minutes then filtered through a pad of celite. The filtrate is washed with saturated aqueous $Na_2CO_3$, dried over magnesium sulfate and concentrated to give the title compound as a 6:1 mixture of trans: cis isomers. This material was used without further purification.

Step 4: Synthesis of ethyl 2-[4-[tert-butoxycarbonyl-[2-(methanesulfonamido)ethyl]amino]cyclohexyl]acetate To a solution of ethyl 2-[4-[2-(methanesulfonamido)ethylamino]cyclohexyl]acetate (1.1 g, 4 mmol) in dichloromethane (12 mL) was added di-tert-butyl-dicarbonate (1.74 g, 8 mmol) followed by diisopropylethylamine (1.4 mL, 8 mmol). The resulting solution was stirred for 4 hours then diluted with dichloromethane, washed with water, dried over magnesium sulfate and concentrated. The residue was purified by silica chromatography (25 g silica; eluted with 5-50% ethyl acetate in hexanes) to give the title compound as an oil 6:1 trans:cis isomers.

Step 5: Synthesis of trans 2-[4-[tert-butoxycarbonyl-[2-(methanesulfonamido)ethyl]amino]cyclohexyl]acetic acid To a solution of ethyl 2-[4-[tert-butoxycarbonyl-[2-(methanesulfonamido)ethyl]amino]cyclohexyl]acetate (0.842 g, 2.06 mmol) in methanol (4 mL); THF (4 mL) and water (4 mL) was added lithium hydroxide monohydrate (252 mg, 6 mmol). The resulting solution was stirred for 2 hours then acidified with HCl (7 mL, 1M aq.), diluted with ethyl acetate, washed with brine, dried over magnesium sulfate and concentrated. The residue was triturated with ether to give the title compound as a solid.

Step 6: Synthesis of [(1R)-1-[[2-[4-[tert-butoxycarbonyl-[2-(methanesulfonamido)ethyl]amino]cyclohexyl]acetyl]amino]-2-(3-tert-butoxycarbonyl-2-methoxy-phenyl)ethyl]boronic acid (+) pinanediolato di-ester The title compound was prepared using the same procedure as described in Example 48; Step 4 except using trans 2-[4-[tert-butoxycarbonyl-[2-(methanesulfonamido)ethyl] amino]cyclohexyl]acetic acid in place of 2-[4-[tert-butoxycarbonyl-[2-[tert-butoxycarbonyl(2-pyridyl)amino]ethyl] amino]cyclohexyl]acetic acid.

Step 7: Synthesis of (R)-2-hydroxy-3-(2-(trans-4-(2-(methylsulfonamido)ethylamino)cyclohexyl)acetamido)-3,4-dihydro-2H-benzo[e][1,2]oxaborinine-8-carboxylic acid To a solution of [(1R)-1-[[2-[4-[tert-butoxycarbonyl-[2-(methanesulfonamido)ethyl]amino]cyclohexyl]acetyl] amino]-2-(3-tert-butoxycarbonyl-2-methoxy-phenyl)ethyl] boronic acid (+) pinanediolato di-ester (460 mg, 0.55 mmol) in 1,4-dioxane (4 mL) was added HCl (4 ml, 3M in water). The resulting solution was heated to reflux and stirred at this temperature for 3.5 hours. The resulting mixture was cooled to room temperature and extracted with ether (2 times). The remaining aqueous solution was concentrated to 25% volume and the residue was purified directly by reverse phase HPLC Phenomenex Luna C18 column 35×75 mm; Flow rate 40 mL/min; eluted with 5-70% $CH_3CN$ in $H_2O$/0.1% TFA over 8 minutes. The title compound was isolated as the TFA salt by lyophilization.

Example 50

(S)-3-(2-(trans-4-(2-aminoethylamino)cyclohexyl) acetamido)-2-hydroxy-3,4-dihydro-2H-benzo[e][1,2] oxaborinine-8-carboxylic acid

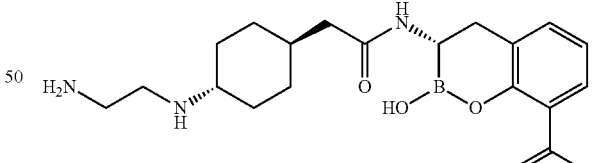

Step 1: Synthesis of 3-iodo-2-methoxy-benzaldehyde

To a solution of 3-iodo-2-hydroxy-benzaldehyde (4.0 g, 16.06 mmol) in DMA (32 mL) was added cesium carbonate (5.85 g, 18 mmol) followed by methyl iodide (1.12 mL, 18 mmol). The resulting mixture was stirred for 4.75 hours then diluted with ether, washed with water, dried over magnesium sulfate and concentrated. The residue was purified by silica chromatography (50 g silica; eluted with 0-20% ethyl acetate in hexanes) to give the title compound as an oil.

Step 2: Synthesis of 3-Iodo-2-methoxy-benzoic acid

To a solution of 3-iodo-2-methoxy-benzaldehyde (3.68 g, 14 mmol) in tert-butanol (70 mL) was added 2,3-dimethyl-but-2-ene (7 mL) followed by a solution comprising disodium hydrogen phosphate monohydrate (7.56 g 56 mmol) and sodium chlorite (7.56 g, approx. 66 mmol, technical grade) in water (70 mL). The resulting mixture was stirred for 20 minutes then diluted with ethyl acetate, washed with brine, dried over magnesium sulfate and concentrated. The residual solid was recrystallized from cyclohexane to give the title compound as a white solid.

Step 3: Synthesis of 3-Iodo-2-methoxy-benzoyl chloride

To 3-iodo-2-methoxy-benzoic acid (8.29 g, 29.8 mmol) was added thionyl chloride (15 mL). The resulting solution was stirred for 2 minutes then heated to 82° C. and stirred at this temperature for 30 minutes. The solution was then concentrated under reduced pressure to give the title compound. This material was used without further purification.

Step 4: Synthesis of tert-Butyl 3-iodo-2-methoxy-benzoate

To a cooled (−5° C.) solution of tert-butanol (12.87 mL, 30 mmol) in THF (30 mL) was added, dropwise, BuLi (12.0 mL, 2.5 M in hexanes, 30 mmol). On complete addition, the solution was stirred for 20 minutes. To this solution is added a solution of 3-Iodo-2-methoxy-benzoyl Chloride (8.8 g, 29.8 mmol) in THF (12 mL). On complete addition, the cold bath was removed and stirring continued for 1.5 hours. This solution was diluted with ethyl acetate, washed with water and brine, dried over magnesium sulfate and concentrated. The residue was purified by silica chromatography (50 g silica; eluted with 0-20% ethyl acetate in hexanes) to give the title compound as an oil.

Step 5: Synthesis of (3-tert-butoxycarbonyl-2-methoxy-phenyl)methylboronic acid (−)-pinanediolato diester To a cooled (−40° C.) solution of tert-Butyl 3-iodo-2-methoxy-benzoate (3.34 g, 10 mmol) in THF (25 mL) was added, dropwise, isopropylmagnesium chloride:lithium chloride complex (7.69 mL, 1.3 M in THF, 10 mmol). On complete addition, the solution was stirred for 20 minutes then cooled to −78° C. To this solution was added, dropwise down the side of the flask, chloro-methylboronic acid (−)-pinanediolato diester (2.28 g, 10 mmol) in THF (2 mL) (chloro-methylboronic acid (−)-pinanediolato diester was prepared according to Strynadka et al. *Biochemistry* 2000, 39, 5312; except using (−) pinanediol in place of (+) pinanediol). The resulting solution was stirred for 45 minutes. To this solution was added, dropwise, $ZnCl_2$ (10 mL, 1M in ether, 10 mmol). The resulting mixture was stirred for 5 minutes then the cold bath was removed and stirring continued for 2 hours. This mixture was diluted with ether, washed with 0.1 M HCl and brine, dried over magnesium sulfate and concentrated. The residue is purified by silica chromatography (50 g silica; eluted with 0-20% ethyl acetate in hexanes) to give the title compound as an oil. This material crystallizes on standing at −10° C.

Step 6: Synthesis of [(1R)-2-(3-tert-butoxycarbonyl-2-methoxy-phenyl)-1-chloro-ethyl]boronic acid (−) pinanediolato diester To a cooled (−100° C.) solution of dichloromethane (518 µL, 8 mmol) in THF (10 mL) was added, dropwise down the side of the flask, BuLi (2.0 mL, 2.5M in hexanes, 5 mmol) over about 20 minutes. A precipitate forms after about 75% of the BuLi was added. On complete addition, the resulting cloudy solution was stirred for 40 minutes. To this mixture was added, dropwise down the side of the flask, a solution of (3-tert-butoxycarbonyl-2-methoxy-phenyl)methylboronic acid (−)-pinanediolato diester (1.8 g, 4.5 mmol) in THF (4 mL). On complete addition, a solution of $ZnCl_2$ (5 mL, 1M in ether, 5 mmol) was added, dropwise, over about 8 minutes. The −100° C. bath was replaced with a −10° C. bath and the resulting mixture was allowed to stir for 1 hour. To this mixture was added a cold saturated solution of $NH_4Cl$ followed by cold ether (5° C.). The organic phase was separated, washed with brine, dried over magnesium sulfate and concentrated. The residue was purified by silica chromatography (25 g silica; eluted with 0-20% ethyl acetate in hexanes) to give the title compound as an oil. This material crystallizes on standing at −10° C.

Step 7: Synthesis of ethyl 2-[4-[tert-butoxycarbonyl-[3-(tert-butoxycarbonylamino)ethyl]amino]cyclohexyl]acetate The title compound (isolated as a 6.8:1 mixture of trans:cis wasomers) was prepared using essentially the same procedure used in Example 48, Step 2 except using tert-butyl Ethyl 2-[4-[3-(tert-butoxycarbonylamino)ethylamino]cyclohexyl]acetate in place of ethyl 2-[4-[2-(2-pyridylamino)ethylamino]cyclohexyl]acetate.

Step 8: Synthesis of trans-2-[4-[tert-butoxycarbonyl-[3-(tert-butoxycarbonylamino)ethyl]amino]cyclohexyl]acetic acid The title compound was prepared using essentially the same procedure used in Example 63, Step 3 except using Ethyl 2-[4-[tert-butoxycarbonyl-[3-(tert-butoxycarbonylamino)ethyl]amino]cyclohexyl]acetate in place of Ethyl 2-[4-[tert-butoxycarbonyl-[3-(tert-butoxycarbonylamino)propyl]amino]cyclohexyl]acetate.

Step 9: Synthesis of [(1S)-1-[[2-[trans-4-[tert-butoxycarbonyl-[2-(tert-butoxycarbonylamino)ethyl]amino]cyclohexyl]acetyl]amino]-2-(3-tert-butoxycarbonyl-2-methoxy-phenyl)ethyl]boronic acid (−) pinanediolato diester To a cooled (−20° C.) solution of [(1R)-2-(3-tert-butoxycarbonyl-2-methoxy-phenyl)-1-chloro-ethyl]boronic acid (−) pinanediolato diester (430 mg, 1 mmol) in THF (2 mL) was added, dropwise, a solution of lithium bistrimethylsilylamide (1.0 mL, 1M in THF, 1 mmol). On complete addition, the cold bath was removed and stirring continued for 1 hour. The resulting solution approximately 0.29M in [(1S)-1-[bis(trimethylsilyl)amino]-2-(3-tert-butoxycarbonyl-2-methoxy-phenyl)ethyl]boronic acid (−) pinandiolato diester was used without further action.

In a separate flask, to a mixture of 2-[4-trans-[tert-butoxycarbonyl-[2-(tert-butoxycarbonylamino)ethyl]amino]cyclohexyl]acetic acid (400 mg, 1 mmoml) and HATU (418 mg, 1.1 mmol) was added DMA (2 mL) followed by N-methyl-morpholine (120 μL, 1.1 mmol). The resulting solution was stirred for 90 minutes. To this solution was added the solution of approximately 0.29M in [(1S)-1-[bis(trimethylsilyl)amino]-2-(3-tert-butoxycarbonyl-2-methoxy-phenyl)ethyl]boronic acid (−) pinandiolato diester prepared above. The resulting mixture was stirred for 4 hours, diluted with ethyl acetate washed with water and brine, dried over magnesium sulfate and concentrated. The residue was purified by silica chromatography (10 g silica; eluted with 20-100% ethyl acetate in hexanes) to give the title compound as a foam.

Step 10: Synthesis of (S)-3-(2-(trans-4-(2-aminoethylamino)cyclohexyl)acetamido)-2-hydroxy-3,4-dihydro-2H-benzo[e][1,2]oxaborinine-8-carboxylic acid To a cooled (−78° C.) solution of [(1S)-1-[[2-[trans-4-[tert-butoxycarbonyl-[2-(tert-butoxycarbonylamino)ethyl]amino]cyclohexyl]acetyl]amino]-2-(3-tert-butoxycarbonyl-2-methoxy-phenyl)ethyl]boronic acid (−) pinanediolato diester (468 mg, 0.59 mmol) in dichloromethane (2 mL) was added, dropwise, a solution of $BCl_3$ (3 mL, 1M in $CH_2Cl_2$, 3 mmol). On complete addition, the resulting mixture was stirred for 30 minutes then warmed to 0° C. over 30 minutes. To was mixture was added water (6 mL). The resulting mixture was allowed to warm to room temperature over 20 minute. This mixture was extracted with ether and the remaining aqueous phase was purified by reverse phase HPLC (Phenomenex Luna C18 column 35×75 mm; Flow rate 40 mL/min; eluted with 5-45% $CH_3CN$ in $H_2O$/0.1% TFA over 8 minutes). The title compound was isolated as the TFA salt by lyophilization.

ESI-MS m/z 390 $(MH)^+$.

Example 51

(R)-2-hydroxy-3-(2-(trans-4-(2-(methylamino)ethylamino)cyclohexyl)acetamido)-3,4-dihydro-2H-benzo[e][1,2]oxaborinine-8-carboxylic acid

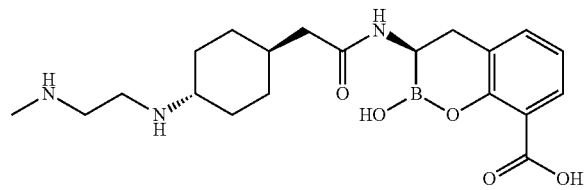 [SMILES: CNCCN[C@H]1CC[C@H](CC(=O)N[C@H]2Cc3cccc(C(=O)O)c3OB2O)CC1]

Prepared from 2-(trans-4-(tert-butoxycarbonyl(2-(tert-butoxycarbonyl(methyl)amino)ethyl)amino)cyclohexyl)acetic acid using the procedure described in step 1 and step 2, Example 1. The product was purified using reverse phase HPLC to afford the titled compound. ESI-MS m/z 404 $(MH)^+$.

Example 52

(R)-2-hydroxy-3-(2-(trans-4-(2-imino-3-methylimidazolidin-1-yl)cyclohexyl)acetamido)-3,4-dihydro-2H-benzo[e][1,2]oxaborinine-8-carboxylic acid

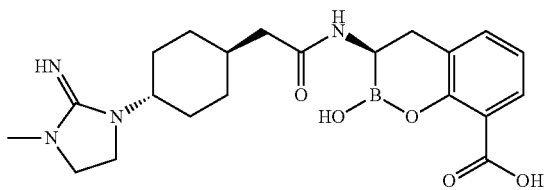 [SMILES: CN1CCN([C@H]2CC[C@H](CC(=O)N[C@H]3Cc4cccc(C(=O)O)c4OB3O)CC2)C1=N]

Synthesis of (R)-2-hydroxy-3-(2-(trans-4-(2-imino-3-methylimidazolidin-1-yl)cyclohexyl)acetamido)-3,4-dihydro-2H-benzo[e][1,2]oxaborinine-8-carboxylic acid To (R)-2-hydroxy-3-(2-(trans-4-(2-(methylamino)ethylamino)cyclohexyl)acetamido)-3,4-dihydro-2H-benzo[e][1,2]oxaborinine-8-carboxylic acid from Example 51 (10 mg) in MeOH (1 mL) was added tert-butyl (1H-pyrazol-1-yl)methanediylidenedicarbamate (12 mg) and TEA (0.1 mL). The reaction mixture was stirred at RT for 48 hr. The solvent was removed in vacuo. The residue was treated with a mixture of TFA (3 mL) and DCM (2 mL) and stirred for 1 hr. The solvent was then removed in vacuo and the crude product was purified by reverse phase preparative HPLC and dried using lyophilization. ESI-MS m/z 429 $(MH)^+$.

Example 53

(R)-3-(2-(trans-4-((S)-2-aminopropylamino)cyclohexyl)acetamido)-2-hydroxy-3,4-dihydro-2H-benzo[e][1,2]oxaborinine-8-carboxylic acid

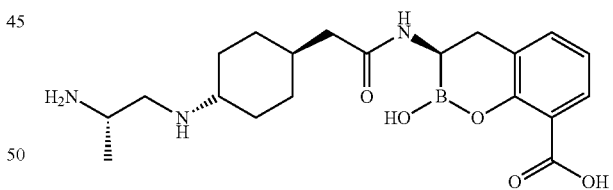

Step 1: Synthesis of 3-((2R)-2-(2-(trans-4-aminocyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid To tert-butyl 3-((2R)-2-(2-(tran-4-(tert-butoxycarbonylamino)cyclohexyl)acetamido)-2-(2,9,9-trimethyl-3,5-dioxa-4-bora-tricyclo[6.1.1.02,6]dec-4-yl)ethyl)-2-methoxybenzoate from Step 1 of Example 6 (640 mg) was added 4 N HCl in dioxane (4 mL). The resultant reaction mixture was stirred at RT for 1 hr. Diethyl ether was added to precipitate out the product as while solid (500 mg) which was used directly to the next step.

Step 2: Synthesis of 3-((2R)-2-(2-(trans-4-((S)-2-(tert-butoxycarbonylamino)propylamino) cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid Prepared from 3-((2R)-2-(2-(trans-4-amino)cyclohexyl) acetamido)-2-(2,9,9-trimethyl-3,5-dioxa-4-bora-tricyclo [6.1.1.0$^{2,6}$]dec-4-yl)ethyl)-2-methoxybenzoic acid and (S)-tert-butyl 1-oxopropan-2-ylcarbamate following the procedure described in Example 27.

Step 3: Synthesis of (R)-3-(2-(trans-4-((S)-2-aminopropylamino)cyclohexyl)acetamido)-2-hydroxy-3,4-dihydro-2H-benzo[e][1,2]oxaborinine-8-carboxylic acid To 3-((2R)-2-(2-(trans-4-((S)-2-(tert-butoxycarbonylamino)propylamino) cyclohexyl)acetamido)-2-(2,9,9-trimethyl-3,5-dioxa-4-bora-tricyclo[6.1.1.0$^{2,6}$]dec-4-yl) ethyl)-2-methoxybenzoic acid from Step 2 in a flask was added 3N aqueous HCl and the reaction mixture was stirred at refluxing for 1 hr. The product was purified using reverse phase HPLC and dried using lyophilization. ESI-MS m/z 409 (MH)$^+$.

Example 54

(R)-2-hydroxy-3-(2-(trans-4-(2-(methoxycarbonylamino)ethylamino) cyclohexyl)acetamido)-3,4-dihydro-2H-benzo[e][1,2]oxaborinine-8-carboxylic acid

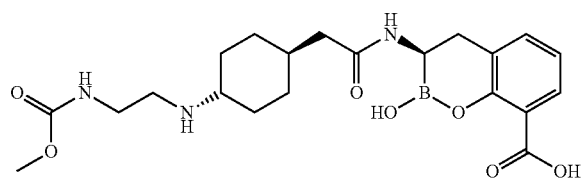

Synthesis of (R)-2-hydroxy-3-(2-(trans-4-(2-(methoxycarbonylamino)ethylamino) cyclohexyl)acetamido)-3,4-dihydro-2H-benzo[e][1,2]oxaborinine-8-carboxylic acid To (R)-2-hydroxy-3-(2-(trans-4-(2-(methylamino)ethylamino)cyclohexyl)acetamido)-3,4-dihydro-2H-benzo[e][1,2]oxaborinine-8-carboxylic acid from Example 51 (39 mg) in a mixture of H$_2$O (1 mL), THF (1 mL) and MeOH (1 mL) was added NaHCO$_3$ (200 mg), followed by methyl chloroformate (1.2 eq). The reaction mixture was stirred at RT overnight. The solvent was then removed in vacuo and the crude product was purified by reverse phase preparative HPLC and dried using lyophilization. ESI-MS m/z 448 (MH)$^+$.

Example 55

(R)-3-(2-(3-(2-aminoethylamino)cyclobutyl)acetamido)-2-hydroxy-3,4-dihydro-2H-benzo[e][1,2] oxaborinine-8-carboxylic acid

Step 1: Synthesis of methyl 2-(3-(2-(tert-butoxycarbonylamino)ethylamino)cyclobutyl)acetate To methyl 2-(3-oxocyclobutyl) acetate (284 mg) and tert-butyl 2-aminoethylcarbamate (336 mg) in a flask was added MeOH (10 mL) and Pd/C (10%, 50 mg). The reaction mixture was stirred under hydrogen atmosphere overnight. At the end of the reaction, catalyst was filtered through the Celite pad and the solvent was removed under reduced pressure. The crude product (577 mg) was carried on to the next step without further purification.

Step 2: Synthesis of methyl 2-(3-(tert-butoxycarbonyl(2-(tert-butoxycarbonylamino)ethyl)amino) cyclobutyl)acetate To the product from step 1 in DCM (15 mL) was added TEA (0.35 mL) and di-tert-butyl dicarbonate (480 mg). The reaction mixture was stirred at RT for overnight. The organic phase was washed with 1 N HCl, water and brine, dried over sodium sulfate. Removal of solvents under reduced pressure afforded the product (1.0 g) without further characterization.

Step 3: Synthesis of 2-(3-(tert-butoxycarbonyl(2-(tert-butoxycarbonylamino)ethyl)amino) cyclobutyl) acetic acid To methyl 2-(3-(tert-butoxycarbonyl(2-(tert-butoxycarbonylamino)ethyl)amino) cyclobutyl)acetate from step 2 in a mixture of MeOH and H$_2$O was added 1N NaOH (8 mL). The resultant reaction mixture was stirred at RT overnight. Half of the solvents were removed under reduced pressure and 1N HCl was added to adjust pH of the solution to 4. The aqueous phase was extracted with EtOAc for three times. The combined organic phase was then dried and concentrated in vacuo to afford the acid (0.9 g).

Step 4: Synthesis of tert-butyl 3-((R)-2-(2-(3-(tert-butoxycarbonyl(2-(tert-butoxycarbonylamino)ethyl) amino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(3-(tert-butoxycarbonyl(2-(tert-butoxycarbonylamino)ethyl)amino) cyclobutyl)acetic acid following procedure described in Step 1 of Example 1. The crude product was purified by flash chromatography on silica gel (hexane/EtOAc, 2:1 to 1:2). ESI-MS m/z 784.1 (MH)+.

Step 5: Synthesis of (R)-3-(2-(3-(2-aminoethyl-amino)cyclobutyl)acetamido)-2-hydroxy-3,4-dihydro-2H-benzo[e][1,2]oxaborinine-8-carboxylic acid Prepared from tert-butyl 3-((R)-2-(2-(3-(tert-butoxycarbonyl(2-(tert-butoxycarbonylamino)ethyl)amino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 1. The crude product was purified by reverse phase preparative HPLC and dried using lyophilization. ESI-MS m/z 362 (MH)+.

Example 56

(R)-3-(2-(3-aminocyclobutyl)acetamido)-2-hydroxy-3,4-dihydro-2H-benzo[e][1,2]oxaborinine-8-carboxylic acid

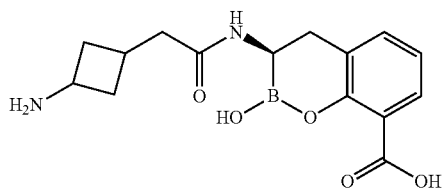 [SMILES: NC1CC(CC(=O)N[C@H]2Cc3cccc(C(=O)O)c3OB2O)C1]

Step 1: Synthesis of methyl 2-(3-(2,4-dimethoxybenzylamino)cyclobutyl)acetate

To methyl 2-(3-oxocyclobutyl)acetate (426 mg) and (2,4-dimethoxyphenyl)methanamine (501 mg) in a flask was added MeOH (20 mL) and Pd/C (10%, 100 mg). The reaction mixture was stirred under hydrogen atmosphere for overnight. Catalyst was removed by filtration through the Celite pad. Removal of the solvent afforded the crude product (850 mg) which was used directly to the next step without further purification.

Step 2: Synthesis of methyl 2-(3-(tert-butoxycarbonyl(2,4-dimethoxybenzyl)amino)cyclobutyl)acetate To the product from step 1 in DCM (20 mL) was added TEA (0.56 mL) and di-tert-butyl dicarbonate (900 mg). The reaction mixture was stirred at RT for overnight. The organic phase was washed with 1 N HCl, water and brine, dried over anhydrous sodium sulfate. Removal of solvents under reduced pressure to afford the product which was purified by flash chromatography (0.75 g).

Step 3: Synthesis of 2-(3-(tert-butoxycarbonyl(2,4-dimethoxybenzyl)amino)cyclobutyl)acetic acid To methyl 2-(3-(tert-butoxycarbonyl(2,4-dimethoxybenzyl)amino)cyclobutyl)acetate from step 2 in a mixture of MeOH, THF and H$_2$O was added 1N NaOH (10 mL). The resultant reaction mixture was stirred at RT for 2 hr. Half of the solvents were removed under reduce pressure and 1N HCl was added to adjust pH of the solution to 4. The aqueous phase was extracted with EtOAc for three times. The combined organic phase was then dried and concentrated in vacuo to afford the acid (0.67 g).

Step 4: Synthesis of tert-butyl 3-((2R)-2-(2-(3-(tert-butoxycarbonylamino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(3-(tert-butoxycarbonyl(2,4-dimethoxybenzyl)amino)cyclobutyl)acetic acid following procedure described in Step 1 of Example 1. The crude product was purified by flash chromatography on silica gel (hexane/EtOAc, 2:1 to 1:2). ESI-MS m/z 641.1 (MH)+.

Step 5. Synthesis of (R)-3-(2-(3-(2-aminoethyl-amino)cyclobutyl)acetamido)-2-hydroxy-3,4-dihydro-2H-benzo[e][1,2]oxaborinine-8-carboxylic acid Prepared from tert-butyl 34(2R)-2-(2-(3-(tert-butoxycarbonylamino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 1. The crude product was purified by reverse phase preparative HPLC and dried using lyophilization. ESI-MS m/z 319 (MH)+.

Example 57

(R)-3-(2-(3-(3-(2-aminoethyl)-1-(2-(3-(2-aminoethyl)ureido)ethyl)ureido)cyclobutyl)acetamido)-2-hydroxy-3,4-dihydro-2H-benzo[e][1,2]oxaborinine-8-carboxylic acid

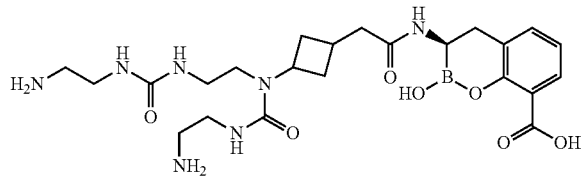 [SMILES: NCCNC(=O)NCCN(C(=O)NCCN)C1CC(CC(=O)N[C@H]2Cc3cccc(C(=O)O)c3OB2O)C1]

Step 1: Synthesis of 3-((2R)-2-(2-(3-(2-aminoethyl-amino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoic acid Prepared from of tert-butyl 3-((R)-2-(2-(3-(tert-butoxycarbonyl(2-(tert-butoxycarbonylamino)ethyl)amino)cyclobutyl)acetamido)-2(2,9,9-trimethyl-3,5-dioxa-4-bora-tricyclo[6.1.1.0$^{2,6}$]dec-4-yl)ethyl)-2-methoxybenzoate (Step 4 of Example 55) and 4 N HCl following the procedure described in Step 1 of Example 53.

Step 2: Synthesis of (R)-3-(2-(3-(3-(2-aminoethyl)-1-(2-(3-(2-aminoethyl)ureido)ethyl)ureido)cyclobutyl) acetamido)-2-hydroxy-3,4-dihydro-2H-benzo[e][1,2]oxaborinine-8-carboxylic acid To 1,1'-Carbonyldiimidazole (180 mg) in DCM (5 mL) was added tert-butyl 2-aminoethylcarbamate (160 mg). The resultant reaction mixture was stirred at RT for 1 hr. A portion of this solution (1 mL) was then added to 3-((2R)-2-(2-(3-(2-aminoethylamino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoic acid from step 1 (20 mg) in DMF and TEA (2 eq) in a different flask. The reaction mixture was stirred overnight. Water was added and extracted with EtOAc. The combine organic phases were dried and concentrated in vacuo to afford the product which was used directly to next step.

Step 3: Synthesis of (R)-3-(2-(3-(3-(2-aminoethyl)-1-(2-(3-(2-aminoethyl)ureido)ethyl)ureido)cyclobutyl) acetamido)-2-hydroxy-3,4-dihydro-2H-benzo[e][1,2]oxaborinine-8-carboxylic acid Prepared from (R)-3-(2-(3-(3-(2-aminoethyl)-1-(2-(3-(2-aminoethyl)ureido)ethyl)ureido)cyclobutyl) acetamido)-2-hydroxy-3,4-dihydro-2H-benzo[e][1,2]oxaborinine-8-carboxylic acid and BCl$_3$ following the procedure described in Step 2 of Example 1. The crude product was purified by reverse phase preparative HPLC and dried using lyophilization. ESI-MS m/z 534 (MH)$^+$.

Example 58

(R)-3-(2-(3-(3-(2-aminoethyl)ureido)cyclobutyl)acetamido)-2-hydroxy-3,4-dihydro-2H-benzo[e][1,2]oxaborinine-8-carboxylic acid

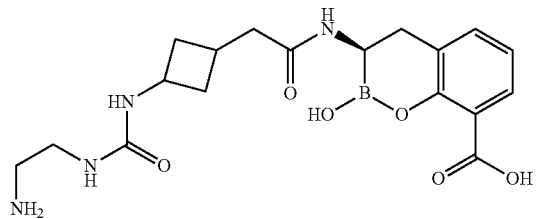 [SMILES: NCCNC(=O)NC1CC(CC(=O)N[C@H]2Cc3cccc(C(=O)O)c3OB2O)C1]

Synthesis of (R)-3-(2-(3-(3-(2-aminoethyl)ureido)cyclobutyl)acetamido)-2-hydroxy-3,4-dihydro-2H-benzo[e][1,2]oxaborinine-8-carboxylic acid Prepared from tert-butyl 3-((2R)-2-(2-(3-(tert-butoxycarbonylamino)cyclobutyl)acetamido)-2-(2,9,9-trimethyl-3,5-dioxa-4-bora-tricyclo[6.1.1.0$^{2,6}$]dec-4-yl)ethyl)-2-methoxybenzoate (Step 4 of Example 56) following the procedure described in Example 57. The crude product was purified by reverse phase preparative HPLC and dried using lyophilization. ESI-MS m/z 405 (MH)$^+$.

Example 59

(R)-3-(2-(trans-4-(3-(2-aminoethyl)ureido)cyclohexyl)acetamido)-2-hydroxy-3,4-dihydro-2H-benzo[e][1,2]oxaborinine-8-carboxylic acid

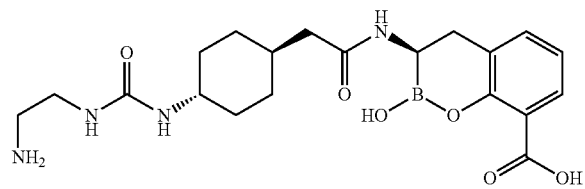 [SMILES: NCCNC(=O)N[C@H]1CC[C@H](CC(=O)N[C@H]2Cc3cccc(C(=O)O)c3OB2O)CC1]

Synthesis of (R)-3-(2-(trans-4-(3-(2-aminoethyl)ureido)cyclohexyl)acetamido)-2-hydroxy-3,4-dihydro-2H-benzo[e][1,2]oxaborinine-8-carboxylic acid Prepared from 3-((2R)-2-(2-(trans-4-aminocyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid (Step 1 of Example 53) following the procedure described in Example 57. The crude product was purified by reverse phase preparative HPLC and dried using lyophilization. ESI-MS m/z 433 (MH)$^+$.

Example 60

(R)-3-(2-(trans-4-(3-aminopropylamino)cyclohexyl)acetamido)-2-hydroxy-3,4-dihydro-2H-benzo[e][1,2]oxaborinine-8-carboxylic acid

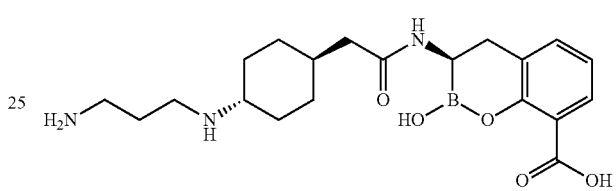

Step 1: Synthesis of ethyl 2-[4-[3-(tert-butoxycarbonylamino)propylamino]cyclohexyl]acetate The title compound (isolated as a 4:1 mixture of trans:cis isomers) was prepared using essentially the same procedure used in Example 48, Step 1 except using tert-butyl N-(3-aminopropyl)carbamate in place of 2-(N-[2-(amino)-ethyl]-amino)-pyridine.

Step 2: Synthesis of ethyl 2-[4-[tert-butoxycarbonyl-[3-(tert-butoxycarbonylamino)propyl]amino]cyclohexyl]acetate The title compound (isolated as a 4:1 mixture of trans:cis isomers) was prepared using essentially the same procedure used in Example 48, Step 2 except using tert-butyl Ethyl 2-[4-[3-(tert-butoxycarbonylamino)propylamino]cyclohexyl]acetate in place of ethyl 2-[4-[2-(2-pyridylamino)ethylamino]cyclohexyl]acetate.

Step 3. Synthesis of trans-2-[4-[tert-butoxycarbonyl-[3-(tert-butoxycarbonylamino)propyl]amino]cyclohexyl]acetic acid To a solution of ethyl 2-[4-[tert-butoxycarbonyl-[3-(tert-butoxycarbonylamino)propyl]amino]cyclohexyl]acetate (1.53 g, 3.47 mmol) in methanol (3 mL) and THF (3 mL) was added NaOH (7.5 mL, 1M aqueous). The resulting solution was stirred for 2.75 hours the acidified with HCl (8 mL, 1M aqueous). This mixture was extracted with ethyl acetate, washed with brine dried over magnesium sulfate and concentrated. The residue was taken up in ether (5 mL). To this solution was added (−) α-methyl-benzylamine (428 µL, 347 mmol) and the resulting solution allowed to stand overnight. The crystalline mass was filtered, washed with ether and the collected solid recrystallized from isopropanol/ether to give 1.1 g of solid. The material was suspended in ethyl acetate, washed with 1 M HCl aqueous, followed by brine, dried over magnesium sulfate and concentrated to give the title compound.

Step 4: Synthesis of [1-[[2-[4-[tert-butoxycarbonyl-[3-(tert-butoxycarbonylamino)propyl]amino]cyclohexyl]acetyl]amino]-2-(3-tert-butoxycarbonyl-2-methoxy-phenyl)ethyl]boronic acid (+) pinanediolato diester The title compound was prepared using essentially the same procedure described in Example 50; step 9, except using Trans-2-[4-[tert-butoxycarbonyl-[3-(tert-butoxycarbonylamino)propyl]amino]cyclohexyl]acetic acid in place of 2-[4-trans-[tert-butoxycarbonyl-[2-(tert-butoxycarbonylamino)ethyl]amino]cyclohexyl]acetic acid.

Step 5: Synthesis of (R)-3-(2-(trans-4-(3-aminopropylamino)cyclohexyl)acetamido)-2-hydroxy-3,4-dihydro-2H-benzo[e][1,2]oxaborinine-8-carboxylic acid The title compound was prepared using essentially the same procedure described in Example 49; step 7 except using [1-[[2-[4-[tert-butoxycarbonyl-[3-(tert-butoxycarbonylamino)propyl]amino]cyclohexyl]acetyl]amino]-2-(3-tert-butoxycarbonyl-2-methoxy-phenyl)ethyl]boronic acid (+) pinanediolato diester in place of [(1R)-1-[[2-[4-[tert-butoxycarbonyl-[2-(methanesulfonamido)ethyl]amino]cyclohexyl]acetyl]amino]-2-(3-tert-butoxycarbonyl-2-methoxy-phenyl)ethyl]boronic acid (+) pinanediolato di-ester.

Example 61

(R)-2-hydroxy-3-(2-(trans-4-(2-(2-hydroxyethylamino)ethylamino) cyclohexyl)acetamido)-3,4-dihydro-2H-benzo[e][1,2]oxaborinine-8-carboxylic acid

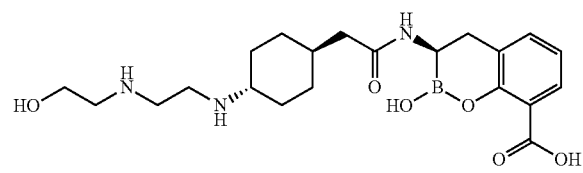 [SMILES: O=C(C[C@H]1CC[C@H](NCCNCCO)CC1)N[C@H]1Cc2cccc(C(=O)O)c2OB1O]

Step 1: Synthesis of (R)-3-(2-(trans-4-(2-(2-(tert-butyldimethylsilyloxy)ethylamino)ethylamino)cyclohexyl)acetamido)-2-hydroxy-3,4-dihydro-2H-benzo[e][1,2]oxaborinine-8-carboxylic acid To (R)-3-(2-(trans-4-(2-aminoethylamino)cyclohexyl)acetamido)-2-hydroxy-3,4-dihydro-2H-benzo[e][1,2]oxaborinine-8-carboxylic acid from Example 15 (92 mg) in MeOH (2 mL) was added TEA (70 μL), acetic acid (30 μL), 2-(tert-butyldimethylsilyloxy)acetaldehyde (35 mg) and sodium triacetoxyborohydride (212 mg). The reaction mixture was stirred overnight at RT. Solvent was removed under reduced pressure and the product was carried on to next step without further purification.

Step 2: Synthesis of (R)-2-hydroxy-3-(2-(trans-4-(2-(2-hydroxyethylamino)ethylamino)cyclohexyl)acetamido)-3,4-dihydro-2H-benzo[e][1,2]oxaborinine-8-carboxylic acid To the compound from step 1 was added a mixture of TFA (2 mL) and H₂O (0.2 mL). The resultant reaction mixture was stirred at RT for 2 hr. The solvents were then removed in vacuo and the residue purified by reverse phase preparative HPLC and dried using lyophilization. ESI-MS m/z 434 (MH)⁺.

Example 62

(R)-3-(2-(trans-4-(24(S)-2-aminopropylamino)ethylamino)cyclohexyl)acetamido)-2-hydroxy-3,4-dihydro-2H-benzo[e][1,2]oxaborinine-8-carboxylic acid

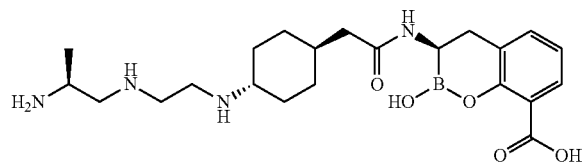 [SMILES: C[C@H](N)CNCCN[C@H]1CC[C@H](CC(=O)N[C@H]2Cc3cccc(C(=O)O)c3OB2O)CC1]

Step 1: Synthesis of (R)-3-(2-(trans-4-(2-((S)-2-(tert-butoxycarbonylamino)propylamino)ethylamino) cyclohexyl)acetamido)-2-hydroxy-3,4-dihydro-2H-benzo[e][1,2]oxaborinine-8-carboxylic acid To (R)-3-(2-(trans-4-(2-aminoethylamino)cyclohexyl)acetamido)-2-hydroxy-3,4-dihydro-2H-benzo[e][1,2]oxaborinine-8-carboxylic acid from Example 15 (92 mg) in MeOH (2 mL) was added TEA (70 μL), acetic acid (30 μL), (S)-tert-butyl 1-oxopropan-2-ylcarbamate (86 mg) and sodium triacetoxyborohydride (212 mg). The reaction mixture was stirred overnight at RT. Solvent was removed and the product was carried on to next step without further purification.

Step 2: Synthesis of (R)-3-(2-(trans-4-(24(S)-2-aminopropylamino)ethylamino)cyclohexyl)acetamido)-2-hydroxy-3,4-dihydro-2H-benzo[e][1,2]oxaborinine-8-carboxylic acid To the compound from step 1 was added 3N HCl (2 ml) and the resultant reaction mixture was heated at reflux for 1 hr. The solvents were then removed in vacuo and the residue purified by reverse phase preparative HPLC and dried using lyophilization. ESI-MS m/z 447 (MH)⁺.

Example 63

(R)-3-(2-(trans-4-((2-aminoethyl)(methyl)amino)cyclohexyl)acetamido)-2-hydroxy-3,4-dihydro-2H-benzo[e][1,2]oxaborinine-8-carboxylic acid

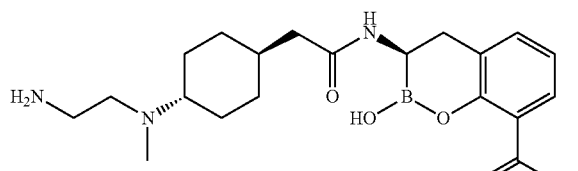

Step 1: Synthesis of ethyl 2-[4-[2-(tert-butoxycarbonylamino)ethylamino]cyclohexyl]acetate The title compound (isolated as a 6.5:1 mixture of trans:cis isomers) was prepared using essentially the same procedure used in Example 48, Step 1 except using tert-butyl N-(3-aminoethyl)carbamate in place of 2-(N-[2-(amino)-ethyl]-amino)-pyridine.

Step 2: Synthesis of Ethyl 2-[4-[2-(tert-butoxycarbonyl)ethyl-methyl-amino]cyclohexyl]acetate To a solution of ethyl 2-[4-[2-(tert-butoxycarbonylamino)ethylamino]cyclohexyl]acetate (326 mg, 1 mmol) in dichloromethane (4 mL) was added formalin (97 μL, 1.2 mmol) followed by acetic acid (60 μL, 1 mmol) and sodium triacetoxyborohydride (255 mg, 1.2 mmol). The resulting cloudy solution was stirred for 19 hours. To the mixture was added sodium carbonate (2 mL, saturated aqueous solution). The mixture was diluted with ethyl acetate and separated. The organic extract was washed with brine, dried over magnesium sulfate and concentrated. The residue was purified by silica chromatography (10 g silica; eluted with 2-20% methanol in dichloromethane) to give the title compound.

Step 3: Synthesis of 2-[4-[2-(tert-butoxycarbonylamino)ethyl-methyl-amino]cyclohexyl]acetic acid To a solution of ethyl 2-[4-[2-(tert-butoxycarbonylamino)ethyl-methyl-amino]cyclohexyl]acetate (231 mg, 0.67 mmol) in methanol (2 mL) and THF (2 mL) was added NaOH (1 mL, 2M aqueous solution). The resulting solution was stirred for 2.75 hours then concentrated under reduced pressure to approximately ¼ the original volume. The residue was acidified with HCl (3 mL, 1M aqueous solution). This solution was purified directly by reverse phase silica chromatography (30 g of $C_{18}$ silica; eluted with 5-100% acetonitrile/water/0.1% TFA) to give the title compound.

Step 4: Synthesis of [1-[[2-[4-[2-(tert-butoxycarbonylamino)ethyl-methyl-amino]cyclohexyl]acetyl]amino]-2-(3-tert-butoxycarbonyl-2-methoxy-phenyl)ethyl]boronic acid (+)-pinanedilato diester The title compound was prepared using essentially the same procedure described in Example 50; step 9, except using 2-[4-[2-(tert-butoxycarbonylamino)ethyl-methyl-amino]cyclohexyl]acetic acid in place of 2-[4-trans-[tert-butoxycarbonyl-[2-(tert-butoxycarbonylamino)ethyl]amino]cyclohexyl]acetic acid.

Step 6: Synthesis of (R)-3-(2-(trans-4-(2-aminoethyl)(methyl)amino)cyclohexyl)acetamido)-2-hydroxy-3,4-dihydro-2H-benzo[e][1,2]oxaborinine-8-carboxylic acid The title compound was prepared using essentially the same procedure described in Example 49; step 7 except using [1-[[2-[4-[2-(tert-butoxycarbonylamino)ethyl-methyl-amino]cyclohexyl]acetyl]amino]-2-(3-tert-butoxycarbonyl-2-methoxy-phenyl)ethyl]boronic acid (+)-pinanedilato diester in place of [(1R)-1-[[2-[4-[tert-butoxycarbonyl-[2-(methanesulfonamido)ethyl]amino]cyclohexyl]acetyl]amino]-2-(3-tert-butoxycarbonyl-2-methoxy-phenyl)ethyl]boronic acid (+) pinanediolato di-ester.

Example 64

(R)-2-hydroxy-3-(3-hydroxy-2-(trans-4-(2-(methylamino)ethylamino)cyclohexyl)propanamido)-3,4-dihydro-2H-benzo[e][1,2]oxaborinine-8-carboxylic acid

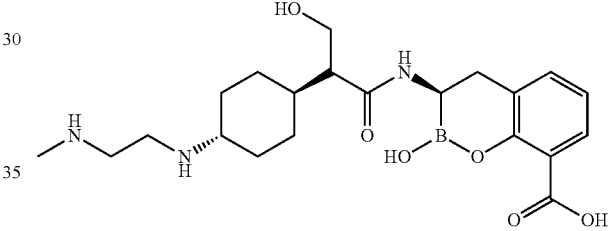

Step 1: Synthesis of tert-butyl 3-((2R)-2-(2-(trans-4-(tert-butoxycarbonyl(2-(tert-butoxycarbonyl(methyl)amino)ethyl)amino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(trans-4-(tert-butoxycarbonyl(2-(tert-butoxycarbonyl(methyl)amino) ethyl) amino)cyclohexyl) acetic acid following procedure described in step 1 of Example 1. The crude product was purified by flash chromatography on silica gel (hexane/EtOAc, 2:1 to 1:2).

Step 2. Synthesis of tert-butyl 3-((2R)-2-(2-(trans-4-(tert-butoxycarbonyl(2-(tert-butoxycarbonyl(methyl)amino)ethyl)amino)cyclohexyl)-3-hydroxypropanamido)-2-(2,9,9-trimethyl-3,5-dioxa-4-bora-tricyclo[6.1.1.0$^{2,6}$]dec-4-yl)ethyl)-2-methoxybenzoate To tert-butyl 3-((2R)-2-(2-(trans-4-(tert-butoxycarbonyl(2-(tert-butoxycarbonyl(methyl)amino)ethyl)amino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoate (110 mg) in THF (5 mL) was added LDA (2 M in benzene, 160 μL) at −76° C. The reaction mixture was stirred at same temperature for 30 min before formaldehyde (20 mg) was added. The reaction mixture was allowed to warm up to RT and stirred for 4 hr. Brine was added and extracted with EtOAc. The organic phase was dried and concentrated to afford the crude product which was used to next step without further purification.

Step 3: Synthesis of (R)-2-hydroxy-3-(3-hydroxy-2-(trans-4-(2-(methylamino)ethylamino)cyclohexyl)propanamido)-3,4-dihydro-2H-benzo[e][1,2]oxaborinine-8-carboxylic acid Prepared from tert-butyl 3-((2R)-2-(2-(trans-4-(tert-butoxycarbonyl(2-(tert-butoxycarbonyl(methyl)amino)ethyl)amino)cyclohexyl)-3-hydroxypropanamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 1. The crude product was purified by reverse phase preparative HPLC and dried using lyophilization. ESI-MS m/z 434 (MH)$^+$.

Example 65

(R)-3-(2-(trans-4-((R)-2-amino-3-hydroxypropylamino)cyclohexyl)acetamido)-2-hydroxy-3,4-dihydro-2H-benzo[e][1,2]oxaborinine-8-carboxylic acid

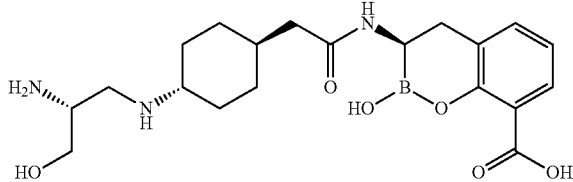

Step 1: Synthesis of benzyl 2-[trans-4-(amino)-cyclohexyl]acetate

To a solution of 2-[4-(tert-butoxycarbonylamino)cyclohexyl]acetic acid (1.0 g, 4 mmol) in DMF (10 mL) was added K$_2$CO$_3$ (600 mg, 4 mmol) followed by benzyl bromide (0.5 mL, 4.2 mmol). The resulting mixture was stirred for 16.75 hours, diluted with ether, washed with water (2×) followed by brine, dried over magnesium sulfate and concentrated. The residue was taken up in dichloromethane (12 mL). To this solution was added TFA (3 mL). The resulting solution was stirred for 2.5 hours then concentrated under reduced pressure. The residue was taken up in ethyl acetate, washed with saturated sodium bicarbonate solution followed by brine, dried over magnesium sulfate and concentrated under reduced pressure to give the title compound as a white solid.

Step 2: Synthesis of tert-Butyl (3R)-4-[[[4-(2-benzyloxy-2-oxo-ethyl)cyclohexyl]-tert-butoxycarbonyl-amino]methyl]-2,2-dimethyl-oxazolidine-3-carboxylate To a solution of tert-butyl (3R)-4-formyl-2,2-dimethyl-oxazolidine-3-carboxylate (460 mg, 2 mmol) in dichloromethane (6 mL) was added benzyl 2-[trans-4-(amino)-cyclohexyl]acetate (494 mg, 2 mmol) followed by sodium triacetoxyborohydride (636 mg, 3 mmol) and acetic acid (120 µL, 2 mmol). The resulting solution was stirred for 16.75 hours. To this solution was added sodium carbonate (saturated aqueous solution). The mixture was diluted with ethyl acetate, washed with brine, dried over magnesium sulfate and concentrated. The residue was taken up in dichloromethane (6 mL). To this solution was added di-tert-butyl dicarbonate (654 mg, 3 mmol) followed by triethylamine (460 µL, 3.3 mmol). This solution was stirred for 2 hours then diluted with ether, washed with brine, dried over magnesium sulfate and concentrated. The residue was purified by silica chromatography (25 g silica; eluted with 10-40% ethyl acetate in hexanes) to give the title compound as a white solid.

Step 3: Synthesis of 2-[4-[tert-butoxycarbonyl-[[(3R)-3-tert-butoxycarbonyl-2,2-dimethyl-oxazolidin-4-yl]methyl]amino]cyclohexyl]acetic acid To a solution of tert-Butyl (3R)-4-[[[4-(2-benzyloxy-2-oxo-ethyl)cyclohexyl]-tert-butoxycarbonyl-amino]methyl]-2,2-dimethyl-oxazolidine-3-carboxylate (520 mg, 0.928 mmol) in ethyl acetate (4 mL) was added palladium on carbon (56 mg, 10% palladium on dry carbon powder). The mixture was degassed, flushed with hydrogen gas and stirred under this atmosphere for 20 minutes. The system was again degassed then flushed with argon. This mixture was diluted with dichloromethane, filtered through celite and concentrated under reduced pressure. The residue was triturated with hexane to give the title compound as a white solid.

Step 4: Synthesis of [1-[[2-[4-[tert-butoxycarbonyl-[[(3R)-3-tert-butoxycarbonyl-2,2-dimethyl-oxazolidin-4-yl]methyl]amino]cyclohexyl]acetyl]amino]-2-(3-tert-butoxycarbonyl-2-methoxy-phenyl)ethyl] boronic acid (+) pinanediolato diester The title compound was prepared using essentially the same procedure described in Example 50; step 9, except using 2-[4-[tert-butoxycarbonyl-[[(3R)-3-tert-butoxycarbonyl-2,2-dimethyl-oxazolidin-4-yl]methyl]amino]cyclohexyl]acetic acid in place of 2-[4-trans-[tert-butoxycarbonyl-[2-(tert-butoxycarbonylamino)ethyl]amino]cyclohexyl] acetic acid.

Step 5: Synthesis of (R)-3-(2-(trans-4-((R)-2-amino-3-hydroxypropylamino)cyclohexyl)acetamido)-2-hydroxy-3,4-dihydro-2H-benzo[e][1,2]oxaborinine-8-carboxylic acid The title compound was prepared using essentially the same procedure described in Example 49; step 7 except using [1-[[2-[4-[tert-butoxycarbonyl-[[(3R)-3-tert-butoxycarbonyl-2,2-dimethyl-oxazolidin-4-yl]methyl]amino]cyclohexyl]acetyl]amino]-2-(3-tert-butoxycarbonyl-2-methoxy-phenyl)ethyl]boronic acid (+) pinanediolato diester in place of [(1R)-1-[[2-[4-[tert-butoxycarbonyl-[2-(methanesulfonamido)ethyl]amino]cyclohexyl]acetyl]amino]-2-(3-tert-butoxycarbonyl-2-methoxy-phenyl)ethyl] boronic acid (+) pinanediolato di-ester.

Example 66

(R)-2-hydroxy-3-(2-(trans-4-(2-(methylthio)ethyl-amino)cyclohexyl)acetamido)-3,4-dihydro-2H-benzo[e][1,2]oxaborinine-8-carboxylic acid

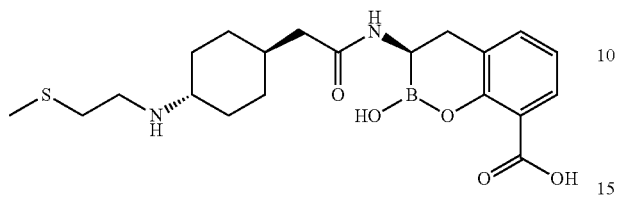

Step 1: Synthesis of ethyl 2-[4-(2-methylsulfanyl-ethylamino)cyclohexyl]acetate The title compound was prepared using essentially the same procedure used in Example 48, Step 1 except using 2-(methylthio)-ethylamine in place of 2-(N-[2-(amino)-ethyl]-amino)-pyridine.

Step 2: Synthesis of ethyl 2-[4-[tert-butoxycarbonyl(2-methylsulfanylethyl)amino]cyclohexyl]acetate The title compound (isolated as a 6.8:1 mixture of trans:cis wasomers) was prepared using essentially the same procedure used in Example 48, Step 2 except using Ethyl 2-[4-(2-methylsulfanylethylamino)cyclohexyl]acetate in place of ethyl 2-[4-[2-(2-pyridylamino)ethylamino]cyclohexyl]acetate.

Step 3: Synthesis of 2-[4-[tert-butoxycarbonyl(2-methylsulfanylethyl)amino]cyclohexyl]acetic acid To a solution of ethyl 2-[4-[tert-butoxycarbonyl(2-methylsulfanylethyl)amino]cyclohexyl]acetate (2.11 g, 5.89 mmol) in methanol (10 mL) and THF (10 mL) was added NaOH (10 mL, 1M aqueous). The resulting solution was stirred for 3.75 hours then acidified with HCl (2M, aqueous to pH 2). The mixture was extracted with ethyl acetate, washed with brine, dried over magnesium sulfate and concentrated. The residue was purified by silica chromatography (25 g silica; eluted with 20-60% ethyl acetate in hexanes) to give the title compound as a 6.9:1 mixture of trans to cis isomers.

Step 4: Synthesis of [2-(3-tert-butoxycarbonyl-2-methoxy-phenyl)-1-[[2-[4-[tert-butoxycarbonyl(methylsulfanylmethyl)amino]cyclohexyl]acetyl]amino]ethyl]boronic acid (+) pinanediolato diester The title compound was prepared using essentially the same procedure described in Example 50; step 9, except using 2-[4-[tert-butoxycarbonyl(2-methylsulfanylethyl)amino]cyclohexyl]acetic acid in place of 2-[4-trans-[tert-butoxycarbonyl-[2-(tert-butoxycarbonylamino)ethyl]amino]cyclohexyl]acetic acid.

Step 5: Synthesis of (R)-2-hydroxy-3-(2-(trans-4-(2-(methylthio)ethylamino)cyclohexyl)acetamido)-3,4-dihydro-2H-benzo[e][1,2]oxaborinine-8-carboxylic acid The title compound was prepared using essentially the same procedure described in Example 49; step 7 except using [2-(3-tert-butoxycarbonyl-2-methoxy-phenyl)-1-[[2-[4-[tert-butoxycarbonyl(methylsulfanylmethyl)amino]cyclohexyl]acetyl]amino]ethyl]boronic acid (+) pinanediolato diester in place of [(1R)-1-[[2-[4-[tert-butoxycarbonyl-[2-(methanesulfonamido)ethyl]amino]cyclohexyl]acetyl]amino]-2-(3-tert-butoxycarbonyl-2-methoxy-phenyl)ethyl]boronic acid (+) pinanediolato di-ester.

Example 67

(R)-3-(2-(trans-4-((S)-2-amino-3-hydroxypropylamino)cyclohexyl)acetamido)-2-hydroxy-3,4-dihydro-2H-benzo[e][1,2]oxaborinine-8-carboxylic acid

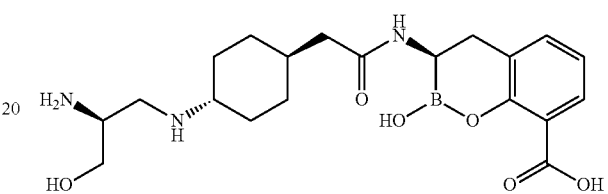

Step 1: Synthesis of tert-Butyl (3S)-4-[[[4-(2-benzyloxy-2-oxo-ethyl)cyclohexyl]-tert-butoxycarbonyl-amino]methyl]-2,2-dimethyl-oxazolidine-3-carboxylate The title compound was prepared using essentially the same procedure used in Example 65; step 2 except using tert-butyl (3S)-4-formyl-2,2-dimethyl-oxazolidine-3-carboxylate in place of tert-butyl (3R)-4-formyl-2,2-dimethyl-oxazolidine-3-carboxylate.

Step 2: Synthesis of 2-[4-[tert-butoxycarbonyl-[[(3S)-3-tert-butoxycarbonyl-2,2-dimethyl-oxazolidin-4-yl]methyl]amino]cyclohexyl]acetic acid The title compound was prepared using essentially the same procedure used in Example 65; step 3 except using tert-Butyl (3S)-4-[[[4-(2-benzyloxy-2-oxo-ethyl)cyclohexyl]-tert-butoxycarbonyl-amino]methyl]-2,2-dimethyl-oxazolidine-3-carboxylate in place of tert-Butyl (3R)-4-[[[4-(2-benzyloxy-2-oxo-ethyl)cyclohexyl]-tert-butoxycarbonyl-amino]methyl]-2,2-dimethyl-oxazolidine-3-carboxylate.

Step 3: Synthesis of [1-[[2-[4-[tert-butoxycarbonyl-[[(3S)-3-tert-butoxycarbonyl-2,2-dimethyl-oxazolidin-4-yl]methyl]amino]cyclohexyl]acetyl]amino]-2-(3-tert-butoxycarbonyl-2-methoxy-phenyl)ethyl]boronic acid (+) pinanediolato diester The title compound was prepared using essentially the same procedure described in Example 50; step 9, except using 2-[4-[tert-butoxycarbonyl-[[(3S)-3-tert-butoxycarbonyl-2,2-dimethyl-oxazolidin-4-yl]methyl]amino]cyclohexyl]acetic acid in place of 2-[4-trans-[tert-butoxycarbonyl-[2-(tert-butoxycarbonylamino)ethyl]amino]cyclohexyl]acetic acid.

Step 4: Synthesis of (R)-3-(2-(trans-4-((S)-2-amino-3-hydroxypropylamino)cyclohexyl)acetamido)-2-hydroxy-3,4-dihydro-2H-benzo[e][1,2]oxaborinine-8-carboxylic acid The title compound was prepared using essentially the same procedure described in Example 49; step 7 except using [1-[[2-[4-[tert-butoxycarbonyl-[[(3S)-3-tert-butoxy-carbonyl-2,2-dimethyl-oxazolidin-4-yl]methyl]amino]cyclohexyl]acetyl]amino]-2-(3-tert-butoxycarbonyl-2-methoxy-phenyl)ethyl]boronic acid (+) pinanediolato diester in place of [(1R)-1-[[2-[4-[tert-butoxycarbonyl-[2-(methanesulfonamido)ethyl]amino]cyclohexyl]acetyl]amino]-2-(3-tert-butoxycarbonyl-2-methoxy-phenyl)ethyl]boronic acid (+) pinanediolato diester.

Example 68

(R)-3-(2-(trans-4-(2-aminoacetamido)cyclohexyl)acetamido)-2-hydroxy-3,4-dihydro-2H-benzo[e][1,2]oxaborinine-8-carboxylic acid

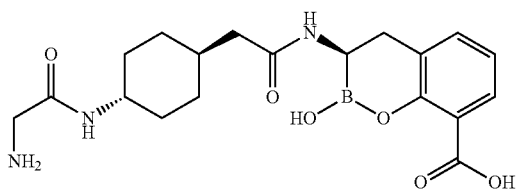 [SMILES: NCC(=O)N[C@H]1CC[C@H](CC(=O)N[C@H]2Cc3cccc(C(=O)O)c3OB2O)CC1]

Step 1: Synthesis of 3-((2R)-2-(2-(trans-4-(2-(tert-butoxycarbonylamino)acetamido)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid To 2-(tert-butoxycarbonylamino)acetic acid (175 mg) in a flask was added HATU (380 mg) and N-methyl morpholine (0.56 mL). After stirring at RT for 1 hr, this solution was added to 3-((2R)-2-(2-(trans-4-aminocyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid from Step 1 of Example 53 (110 mg) in DMF (3 mL). The resultant reaction mixture was stirred at RT overnight. Water was added to the reaction mixture and extracted with EtOAc. The organic phase was dried and concentrated in vacuo to afford the crude product which was used in next step without further purification.

Step 2: Synthesis of (R)-3-(2-(trans-4-(2-aminoacetamido)cyclohexyl)acetamido)-2-hydroxy-3,4-dihydro-2H-benzo[e][1,2]oxaborinine-8-carboxylic acid Prepared from 3-((2R)-2-(2-(trans-4-(2-(tert-butoxycarbonylamino)acetamido)cyclohexyl)acetamido)-2-(2,9,9-trimethyl-3,5-dioxa-4-bora-tricyclo[6.1.1.0$^{2,6}$]dec-4-yl)ethyl)-2-methoxybenzoic acid following procedure described in Step 2 of Example 62. The product was purified by reverse phase preparative HPLC and dried using lyophilization. ESI-MS m/z 404 (MH)$^+$.

Example 69

(R)-3-(2-(trans-4-(bis((1H-imidazol-2-yl)methyl)amino)cyclohexyl)acetamido)-2-hydroxy-3,4-dihydro-2H-benzo[e][1,2]oxaborinine-8-carboxylic acid

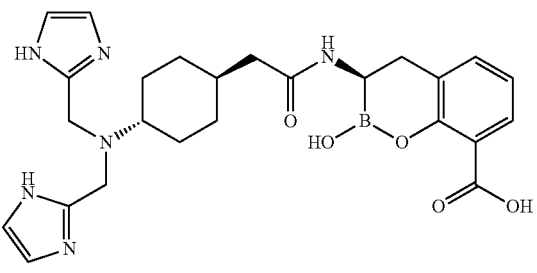 [SMILES: O=C(C[C@H]1CC[C@H](N(Cc2ncc[nH]2)Cc2ncc[nH]2)CC1)N[C@H]1Cc2cccc(C(=O)O)c2OB1O]

Synthesis of (R)-3-(2-(trans-4-(bis((1H-imidazol-2-yl)methyl)amino)cyclohexyl)acetamido)-2-hydroxy-3,4-dihydro-2H-benzo[e][1,2]oxaborinine-8-carboxylic acid Prepared from Prepared from (R)-3-(2-(trans-4-aminocyclohexyl)acetamido)-2-hydroxy-3,4-dihydro-2H-benzo[e][1,2]oxaborinine-8-carboxylic acid (Example 6) and 1H-imidazole-2-carbaldehyde following the procedure in Example 27. The product was purified using reverse phase HPLC to afford the titled compound. ESI-MS m/z 507 (MH)$^+$.

Example 70

(R)-3-(2-(trans-4-((1H-imidazol-5-yl)methylamino)cyclohexyl)acetamido)-2-hydroxy-3,4-dihydro-2H-benzo[e][1,2]oxaborinine-8-carboxylic acid

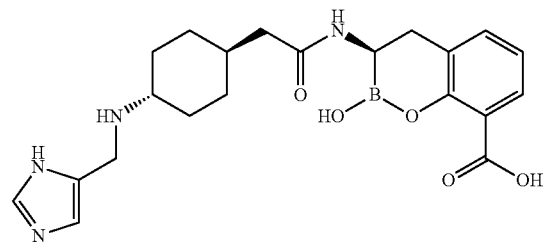 [SMILES: O=C(C[C@H]1CC[C@H](NCc2cnc[nH]2)CC1)N[C@H]1Cc2cccc(C(=O)O)c2OB1O]

Synthesis of (R)-3-(2-(trans-4-((1H-imidazol-5-yl)methylamino)cyclohexyl)acetamido)-2-hydroxy-3,4-dihydro-2H-benzo[e][1,2]oxaborinine-8-carboxylic acid Prepared from (R)-3-(2-(trans-4-aminocyclohexyl)acetamido)-2-hydroxy-3,4-dihydro-2H-benzo[e][1,2]oxaborinine-8-carboxylic acid (Example 6) and 1H-imidazole-5-carbaldehyde following the procedure in Example 27. The product was purified using reverse phase HPLC to afford the titled compound. ESI-MS m/z 427 (MH)$^+$.

Example 71

(R)-2-hydroxy-3-(2-(trans-4-(2-(isopropylamino)ethylamino)cyclohexyl)acetamido)-3,4-dihydro-2H-benzo[e][1,2]oxaborinine-8-carboxylic acid

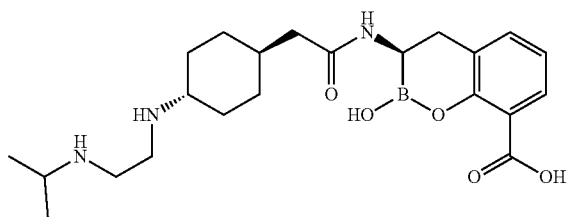 [SMILES: CC(C)NCCN[C@H]1CC[C@H](CC(=O)N[C@H]2Cc3cccc(C(=O)O)c3OB2O)CC1]

Synthesis of (R)-2-hydroxy-3-(2-(trans-4-(2-(isopropylamino)ethylamino)cyclohexyl)acetamido)-3,4-dihydro-2H-benzo[e][1,2]oxaborinine-8-carboxylic acid To (R)-3-(2-(trans-4-(2-aminoethylamino)cyclohexyl)acetamido)-2-hydroxy-3,4-dihydro-2H-benzo[e][1,2]oxaborinine-8-carboxylic acid from Example 15 (92 mg) in MeOH (2 mL) was added TEA (70 µL), acetic acid (30 µL), acetone (0.1 mL) and sodium triacetoxyborohydride (212 mg). The reaction mixture was stirred overnight at RT. Solvent was removed and the product was purified using reverse phase HPLC to afford the titled compound. ESI-MS m/z 432 (MH)$^+$.

Example 72

(R)-2-hydroxy-3-(2-trans-4-(2-(pyrimidin-2-ylamino)ethylamino)cyclohexyl)acetamido)-3,4-dihydro-2H-benzo[e][1,2]oxaborinine-8-carboxylic acid

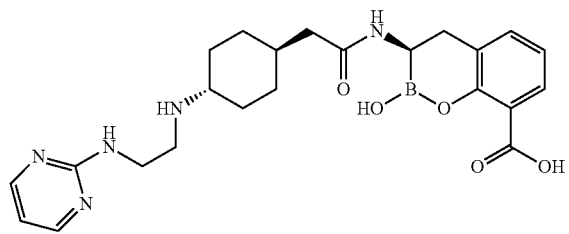 [SMILES: O=C(C[C@H]1CC[C@H](NCCNc2ncccn2)CC1)N[C@H]1Cc2cccc(C(=O)O)c2OB1O]

Synthesis of (R)-2-hydroxy-3-(2-trans-4-(2-(pyrimidin-2-ylamino)ethylamino)cyclohexyl)acetamido)-3,4-dihydro-2H-benzo[e][1,2]oxaborinine-8-carboxylic acid To (R)-3-(2-(trans-4-(2-aminoethylamino)cyclohexyl)acetamido)-2-hydroxy-3,4-dihydro-2H-benzo[e][1,2]oxaborinine-8-carboxylic acid from Example 15 (46 mg) in MeOH (2 mL) was added TEA (70 µL) and 2-chloropyrimidine (25 mg). The reaction mixture was stirred at 70° C. overnight. Solvent was removed and the product was purified using reverse phase HPLC to afford the titled compound. ESI-MS m/z 468 (MH)$^+$.

Example 73

(R)-3-(2-(trans-4-(2-(cyclopentylamino)ethylamino)cyclohexyl)acetamido)-2-hydroxy-3,4-dihydro-2H-benzo[e][1,2]oxaborinine-8-carboxylic acid

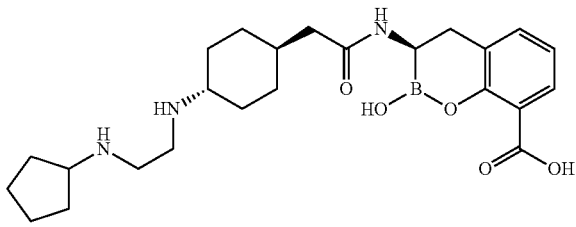 [SMILES: O=C(C[C@H]1CC[C@H](NCCNC2CCCC2)CC1)N[C@H]1Cc2cccc(C(=O)O)c2OB1O]

Synthesis of (R)-3-(2-(trans-4-(2-(cyclopentylamino)ethylamino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e][1,2]oxaborinine-8-carboxylic acid and cyclopentanone following the procedure described in Example 71. The product was purified using reverse phase HPLC to afford the titled compound. ESI-MS m/z 458 (MH)$^+$.

Example 74

(R)-3-(2-(trans-4-(2-(cyclopropylmethylamino)ethylamino)cyclohexyl)acetamido)-2-hydroxy-3,4-dihydro-2H-benzo[e][1,2]oxaborinine-8-carboxylic acid

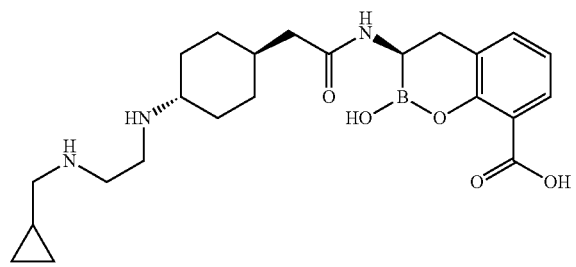 [SMILES: O=C(C[C@H]1CC[C@H](NCCNCC2CC2)CC1)N[C@H]1Cc2cccc(C(=O)O)c2OB1O]

Synthesis of (R)-3-(2-(trans-4-(2-(cyclopropylmethylamino)ethylamino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e][1,2]oxaborinine-8-carboxylic acid and cyclopropanecarbaldehyde following the procedure described in Example 71. The product was purified using reverse phase HPLC to afford the titled compound. ESI-MS m/z 444 (MH)$^+$.

Example 75

(R)-3-(2-(trans-4-(2-(bis(cyclopropylmethyl)amino)ethylamino)cyclohexyl) acetamido)-2-hydroxy-3,4-dihydro-2H-benzo[e][1,2]oxaborinine-8-carboxylic acid

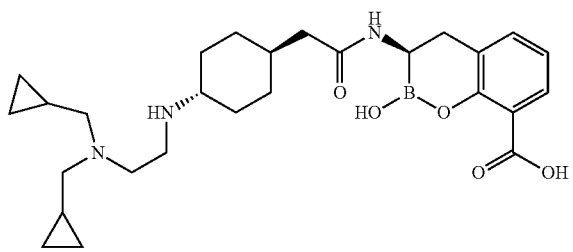 [SMILES: O=C(C[C@H]1CC[C@H](NCCN(CC2CC2)CC2CC2)CC1)N[C@H]1Cc2cccc(C(=O)O)c2OB1O]

Synthesis of (R)-3-(2-(trans-4-(2-(bis(cyclopropylmethyl)amino)ethylamino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e][1,2]oxaborinine-8-carboxylic acid and cyclopropanecarbaldehyde following the procedure described in Example 71. The product was purified using reverse phase HPLC to afford the titled compound. ESI-MS m/z 498 (MH)$^+$.

Example 76

(R)-3-(2-(trans-4-(1,3-diaminopropyl)cyclohexyl)acetamido)-2-hydroxy-3,4-dihydro-2H-benzo[e][1,2]oxaborinine-8-carboxylic acid

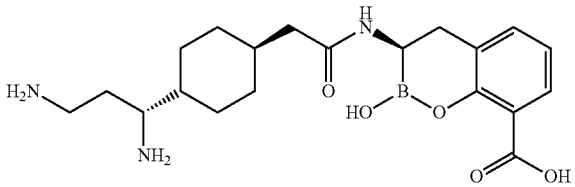

Synthesis of 2-(trans-4-(2,2,12,12-tetramethyl-4,10-dioxo-3,11-dioxa-5,9-diazatridecan-6-yl)cyclohexyl) acetic acid

Step 1: Synthesis of ethyl 2-(1,4-dioxaspiro[4.5]decan-8-yl)acetate

To a cooled (0° C.) suspension of NaH (60%, 4.4 g, 110 mmol) in THF (200 mL) was added triethyl phosphonoacetate (25.16 g, 110 mmol) at a rate so as to produce gentle gas evolution. After complete addition, the homogeneous solution was stirred for 30 min. The this solution was added 1,4-cyclohexanedione monoethylene ketal (15.62 g, 100 mmol) in THF (40 mL) over 10 min. After complete addition, the ice bath was removed and stirring continued for 3 h. The reaction was quenched by addition of saturated aqueous NH$_4$Cl, extracted with EtOAc, washed with brine, dried over Na$_2$SO$_4$. Filtration and evaporation to dryness gave the crude product which was used in the next step without further purification.

The above crude product (25.3 g, 100 mmol) was dissolved in MeOH (80 mL) and added 10% Pd/C (1 g). The resulting mixture was hydrogenated at 35 psi for 3 h. After filtration and evaporation, the residue was purified by flash column chromatography (eluent: 20% EtOAc in hexanes to 30%) gave the product colorless oil (20 g, 87%).

Step 2: Synthesis of 2-(1,4-dioxaspiro[4.5]decan-8-yl)ethanol

To a solution of ethyl 2-(1,4-dioxaspiro[4.5]decan-8-yl)acetate from Step 1 (3.31 g, 14.5 mmol) in Et$_2$O (80 mL) at 0° C. under N$_2$ was added LiAlH$_4$ (1M in THF, 13.66 mL, 13.66 mmol) in 15 min. The resulting mixture was stirred at 0° C. for another 20 min and quenched by addition of saturated aqueous NH$_4$Cl solution, extracted with EtOAc, dried over Na$_2$SO$_4$. Filtration and evaporation to dryness gave the alcohol as white solid (2.76 g, 100%). LC/MC: 187.1 (MH)$^+$.

Step 3: Synthesis of 8-(2-(benzyloxy)ethyl)-1,4-dioxaspiro[4.5]decane

To a precooled (0° C.) suspension of NaH (60% in mineral, 0.44 g, 11 mmol) in THF (20 mL) was added 2-(1,4-dioxaspiro[4.5]decan-8-yl)ethanol (1.86 g, 10 mmol) in THF (10 mL). The resulting solution was stirred at 0° C. for 10 min, and allowed to warm to RT, and stirred for 1 h. To the above mixture was added benzyl bromide (1.78 g, 15 mmol) and the resulting mixture was stirred at rt overnight. The reaction was quenched by addition of saturated aqueous NH$_4$Cl solution, extracted with EtOAc, washed with brine, dried over Na$_2$SO$_4$. Purification by flash column chromatography (eluent: 20% EtOAc in hexanes to 30%) gave the product (2.3 g, 83%). LC/MC: 277.1 (MH)$^+$.

Step 4: Synthesis of 4-(2-(benzyloxy)ethyl)cyclohexanone

A solution of 8-(2-(benzyloxy)ethyl)-1,4-dioxaspiro[4.5]decane (2.30 g, 8.32 mmol) in acetonitrile (18 mL) was added 6N HCl solution and the resulting solution was stirred at rt for 2 h. After removal of acetonitrile by evaporation, the residue was neutralized by solid NaHCO$_3$, extracted with EtOAc, dried over Na$_2$SO$_4$. Filtration and evaporation to dryness gave the ketone as white solid (1.84 g, 95.5%).

Step 5: Synthesis of ((2-(4-methylenecyclohexyl)ethoxy)methyl)benzene

To a cooled (−78° C.) mixture of Ph$_3$PCH$_2$Br (5.42 g, 14.88 mmol) in THF (25 mL) was added KO$^t$Bu (1M in THF, 17.05 mL, 17.05 mmol) dropwise under N$_2$. The resulting mixture was stirred at 0° C. for 1 h and warmed to rt for another 1.5 h. The reaction mixture was then cooled to −40° C., added a solution of 4-(2-(benzyloxy)ethyl)cyclohexanone (1.8 g, 7.75 mmol) in THF (15 mL) dropwise. The mixture was then stirred at rt overnight and quenched by brine, extracted with EtOAc, dried over Na$_2$SO$_4$. Purification by flash column chromatography (eluent: 20% EtOAc in hexanes to 30%) gave the titled product (1.77 g, 99%). LC/MC: 231.1 (MH)$^+$.

Step 6: Synthesis of (trans-4-(2-(benzyloxy)ethyl)cyclohexyl)methanol

To a cooled (0 C) solution of ((2-(4-methylenecyclohexyl)ethoxy)methyl)benzene (9.68 g, 41.66 mmol) in THF (200 mL) was added $B_2H_6 \cdot Me_2S$ complex (2M in THF, 41.66 mL, 83.32 mmol) under $N_2$. After being stirred at 0° C. for 2 h and at rt for another 2 h, the solution was cooled to 0° C. and added a mixture of 3M aqueous NaOH solution (34 ml) and 30% hydrogen peroxide solution (34 mL) dropwise. The resulting mixture was stirred at 0° C. for 1 h and at rt for 1.5 h. Aqueous workup and purification by flash column chromatography (eluent: 40% EtOAc in hexanes) gave the product as yellow oil (7.04 g, 68%). LC/MC: 249.1 $(MH)^+$.

Step 7: Synthesis of (trans-4-(2-(benzyloxy)ethyl)cyclohexanecarbaldehyde

A solution of DMSO (2.20 mL, 31 mmol) in DCM (45 mL) was added dropwise to a precooled (−78° C.) solution of oxalyl chloride (2.9 mL, 33.8 mmol) in DCM (45 mL) under $N_2$. After stirring at −78° C. for 10 min, a solution of (trans-4-(2-(benzyloxy)ethyl)cyclohexyl)methanol (7.0 g, 28.18 mmol) in DCM (45 mL) was added dropwise. The resulting solution was stirred at −78° C. for 15 min, and TEA (23.6 mL, 169.1 mmol) was added. The solution was stirred at −78° C. for 15 min and at rt for 20 min. The reaction was diluted with DCM, washed with 1M HCl solution and brine, dried over $Na_2SO_4$. Purification by flash column chromatography (eluent: 20% EtOAc in hexanes) gave the product aldehyde as yellow oil (6.86 g, 98.8%).

Step 8: Synthesis of (R,E)-N-((trans-4-(2-(benzyloxy)ethyl)cyclohexyl)methylene)-2-methylpropane-2-sulfinamide To a solution of (trans-4-(2-(benzyloxy)ethyl)cyclohexanecarbaldehyde (6.45 g, 26.18 mmol) and (R)-(+)-tert-butylsulfinamide (3.49 g, 28.8 mmol) in THF (66 mL) was added titanium(IV) ethoxide (8.78 mL, 41.89 mmol) under $N_2$. The resulting solution was stirred at rt for 20 h and quenched by addition of saturated $NaHCO_3$ solution dropwise. The mixture was vigorously stirred for 30 min and filtered through a pad of Celite, concentration. Purification by flash column chromatography (eluent: 20% EtOAc in hexanes to 30%) gave the titled product (8.38 g, 92%). LC/MC: 350.1 $(MH)^+$.

Step 9: Synthesis of (R)—N-(1-(trans-4-(2-(benzyloxy)ethyl)cyclohexyl)but-3-enyl)-2-methylpropane-2-sulfinamide To a cooled (0° C.) solution of (R,E)-N-((trans-4-(2-(benzyloxy)ethyl)cyclohexyl)methylene)-2-methylpropane-2-sulfinamide in DCM (65 mL) was added allylmagnesium chloride (2M in THF, 5.87 mL, 11.74 mmol) dropwise under $N_2$. The resulting mixture was stirred at 0° C. for 1 h and quenched by addition of saturated $NH_4Cl$ solution, separated. The aqueous phase was extracted with EtOAc and combined organic phase were washed with brine, dried over $Na_2SO_4$. Purification by flash column chromatography (eluent: 20% EtOAc in hexanes) gave the product (2.57 g, 100%). LC/MC: 392.1 $(MH)^+$.

Step 10: Synthesis of tert-butyl-1-((trans-4-(2-(benzyloxy)ethyl)cyclohexyl)but-3-enylcarbamate To a stirred solution of (R)—N-(1-(trans-4-(2-(benzyloxy)ethyl)cyclohexyl)but-3-enyl)-2-methylpropane-2-sulfinamide (2.56 g, 6.5 mmol) in MeOH (3.5 mL) was added 4M HCl solution in 1,4-dioxane (3.25 mL, 13 mmol). The resulting solution was stirred at rt for 30 min and then concentrated. The residue was dissolved in EtOAc, washed with brine, dried over $Na_2SO_4$. Filtration and evaporation to dryness gave the crude product.

To a cooled (0° C.) solution of the above crude product in DCM (40 mL) was added di-tert-butyl dicarbonate (1.75 g, 7.8 mmol) and TEA (3.62 mL, 26 mmol). The mixture was slowly warmed to rt and stirred at rt for 4 h. The reaction was quenched by addition of saturated $NH_4Cl$ solution, separated. The aqueous phase was extracted with DCM and the combined DCM extracts were washed with 20% citric acid, brine, dried over $Na_2SO_4$. Purification by flash column chromatography (eluent: 20% EtOAc in hexanes) gave the product as colorless gel (2.78 g, 40%). LC/MC: 388.1 $(MH)^+$.

Step 11: Synthesis of tert-butyl-1-(trans-4-(2-(benzyloxy)ethyl)cyclohexyl)-3-oxopropylcarbamate To a solution of tert-butyl-1-((trans-4-(2-(benzyloxy)ethyl)cyclohexyl)but-3-enylcarbamate (6.5 mmol) in 1,4-dioxane (118 mL) and water (38 mL) was added N-methylmorpholine-N-oxide (1.52 g, 13 mmol) and $OsO_4$ (4 wt % in water, 1.4 mL, 0.23 mmol). The resulting mixture was stirred at rt for 18 h and was added $NaIO_4$ (4.87 g, 22.75 mmol). The resulting mixture was stirred at rt for 4 h and quenched by addition of saturated aqueous $Na_2S_2O_3$ solution. After aqueous workup, the residue was purified by flash column chromatography (eluent: 10% EtOAc in hexanes to 30%) to give the aldehyde as colorless oil (2.36 g, 89.7%). LC/MC: 412.1 $(MNa)^+$.

Step 12: Synthesis of tert-butyl 1-(trans-4-(2-hydroxyethyl)cyclohexyl)-3-oxopropylcarbamate A solution of the aldehyde from above step (2.36 g, 6.06 mmol) in MeOH (20 mL) was added 10% Pd/C (0.2 g). The resulting mixture was hydrogenated via a $H_2$ balloon at rt overnight. Filtration and evaporation to dryness afforded the product as colorless gel (1.87 g, 100%). LC/MS: 322.1 $(MNa)^+$.

Step 13: Synthesis of 2-(trans-4-(1-(tert-butoxycarbonylamino)-3-oxopropyl)cyclohexyl)ethyl acetate To a solution of tert-butyl 1-(trans-4-(2-hydroxyethyl)cyclohexyl)-3-oxopropylcarbamate (1.88 g, 6.28 mmol) in DCM (60 mL) was added DMAP (cat. amount), followed by addition of TEA (2.63 mL, 18.84 mmol) and acetic anhydride (0.89 mL, 9.42 mmol) at 0° C. under $N_2$. The mixture was stirred at rt for 3 h, and diluted with DCM, quenched by addition of aqueous $NaHCO_3$ solution. The organic phase was separated and dried over $Na_2SO_4$. Purification by flash column chromatography (eluent: 40% EtOAc in hexanes) gave the product as colorless gel (1.90 g, 88.6%).

Step 14: Synthesis of 2-(trans-4-(1-(tert-butoxycarbonylamino)-3-hydroxypropyl)cyclohexyl)ethyl acetate To a cooled (ethylene glycol+dry ice) solution of 2-(trans-4-(1-(tert-butoxycarbonylamino)-3-oxopropyl)cyclohexyl) ethyl acetate (1.88 g, 5.5 mmol) in ethanol (90 mL) was added $NaBH_4$ (0.212 g, 5.5 mmol). The mixture was stirred at −10~15° C. for 10 min and 0° C. for 10 min, and then quenched by addition of saturated aqueous NH₄Cl solution (30 mL) and brine (30 mL). After removal of the volatile by evaporation, the aqueous residue was extracted with EtOAc, dried over Na₂SO₄. Purification by flash column chromatography (eluent: 30% EtOAc in hexanes to 40%) gave the alcohol product (1.0 g, 53%). LC/MC: 366.1 (MNa)⁺.

Step 15: Synthesis of 2-(trans-4-(3-azido-1-(tert-butoxycarbonylamino)propyl)cyclohexyl)ethyl acetate To a cooled (0° C.) solution of 2-(trans-4-(1-(tert-butoxycarbonylamino)-3-hydroxypropyl)cyclohexyl)ethyl acetate (1.0 g, 2.9 mmol) in DCM (15 mL) was added TEA (0.81 mL, 5.82 mmol) and methanesulfonyl chloride (0.34 mL, 4.35 mmol) dropwise under N₂. The mixture was stirred at rt for 3 h and diluted with DCM, washed with aqueous NH₄Cl solution, dried over Na₂SO₄. Purification by flash column chromatography (eluent: 40% EtOAc in hexanes) gave the mesylate as yellow oil (0.96 g, 79%). LC/MC: 444.1 (MNa)⁺. A mixture of the mesylate (0.95 g, 2.25 mmol) and NaN₃ (1.17 g, 18 mmol) in DMF (25 mL) was heated at 80° C. overnight. After aqueous workup, the crude product was purified by flash column chromatography (eluent: 30% EtOAc in hexanes) to give the azide as yellow oil (0.74 g, 89%). LC/MS: 391.1 (MNa)⁺.

Step 16: Synthesis of 2-(trans-4-(3-amino-1-(tert-butoxycarbonylamino)propyl)cyclohexyl)ethyl acetate A mixture of the azide from Step 15(0.72 g, 1.95 mmol) and 10% Pd/C (0.1 g) in MeOH (20 mL) was hydrogenated via a H₂ balloon at rt for 18 h. Filtration and evaporation to dryness afforded the amine in a quantitative yield. LC/MS: 343.1 (MH)⁺.

Step 17: Synthesis of 2-(trans-4-(2,2,12,12-tetramethyl-4,10-dioxo-3,11-dioxa-5,9-diazatridecan-6-yl)cyclohexyl)ethyl acetate To a cooled (0° C.) solution of 2-(trans-4-(3-amino-1-(tert-butoxycarbonylamino)propyl)cyclohexyl)ethyl acetate (1.95 mmol) in DCM (15 mL) was added di-tert-butyl dicarbonate (0.53 g, 2.34 mmol) and TEA (1.09 mL, 7.8 mmol). The mixture was slowly warmed to rt and stirred at rt overnight. After being quenched by aqueous NH₄Cl solution, the reaction was extracted with DCM, washed by 0.5N aqueous HCl solution, brine, and dried over Na₂SO₄. Filtration and evaporation to dryness afforded the crude product. LC/MS: 465.1 (MNa)⁺.

Step 18: Synthesis of tert-butyl-1-(4-(2-hydroxyethyl)cyclohexyl)propane-1,3-diyldicarbamate To a solution of 2-(trans-4-(2,2,12,12-tetramethyl-4,10-dioxo-3,11-dioxa-5,9-diazatridecan-6-yl)cyclohexyl)ethyl acetate (1.95 mmol) in MeOH (5 mL) was added K₂CO₃ (0.135 g, 0.975 mmol) and the resulting mixture was stirred at rt for 3 h. The reaction was quenched by addition of aqueous NH₄Cl solution. After removal of MeOH by evaporation, the residue was extracted with EtOAc, dried over Na₂SO₄. Filtration and evaporation to dryness afforded the product as white foam (0.71 g, 91%). LC/MS: 423.1 (MNa)⁺.

Step 19: Synthesis of 2-(trans-4-(2,2,12,12-tetramethyl-4,10-dioxo-3,11-dioxa-5,9-diazatridecan-6-yl)cyclohexyl)acetic acid A mixture of the tert-butyl-1-(4-(2-hydroxyethyl)cyclohexyl)propane-1,3-diyldicarbamate (1.95 mmol), ruthenium (III) chloride hydrate (0.008 g, 0.039 mmol), sodium periodate (1.67 g, 2.8 mmol) in carbon tetrachloride (10 mL), acetonitrile (10 ml) and water (10 mL) was stirred at rt for 2 h. The reaction mixture was cooled to 0° C. and added 0.5N HCl (10 mL), extracted with DCM, dried over Na₂SO₄. Purification by flash column chromatography (eluent: 40% EtOAc in hexanes) gave the titled acid as white foam (0.67 g, 83%). LC/MC: 437.1 (MNa)⁺.

Synthesis of (R)-3-(2-(trans-4-(1,3-diaminopropyl)cyclohexyl)acetamido)-2-hydroxy-3,4-dihydro-2H-benzo[e][1,2]oxaborinine-8-carboxylic acid To a cooled (−25° C.) solution of [(1S)-2-(3-tert-butoxycarbonyl-2-methoxy-phenyl)-1-chloro-ethyl]boronic acid (+) pinanediolato diester (Example 48, Step 1, 0.41 g, 0.92 mmol) in THF (2 mL) was added LHMDS (1 mL, 1M in THF) dropwise under N₂. After completion of addition, the reaction was stirred at RT for 1.5 h. Meanwhile, in a separate flask, to a mixture of 2-(trans-4-(2,2,12,12-tetramethyl-4,10-dioxo-3,11-diox α-5,9-diaz atridecan-6-yl)cyclohexyl)acetic acid (0.38 g, 0.92 mmol) and HATU (0.38 g, 1 mmol) was added DMA (2 mL) and 4-methylmorpholine (0.11 mL) and the resulting mixture was stirred at rt under N2 for 1.5 h. After 1.5 h, the two solutions were mixed and stirred at RT overnight. After aqueous workup, the residue was purified by FC chromatography (eluent: 30% EtOAc in hexanes to 40%, to 50%) to give the product (0.25 g, 33%). LC/MS: 848.2 (MNa)⁺.

To a solution of above product (0.22 g, 0.266 mmol) in 1,4-dioxane (0.6 mL) was added 3N aqueous HCl (3 mL). The resulting mixture was heated at 100° C. for 3 h. After cooling to RT, the residue was extracted with ether and the aqueous residue was concentrated. Reverse phase HPLC and lyophilization of the collection gave the title compound as white solid. LC/MS: 404.1 (MH)⁺.

Example 77

(R)-3-(2-(trans-4-(1,2-diaminoethyl)cyclohexyl)acetamido)-2-hydroxy-3,4-dihydro-2H-benzo[e][1,2]oxaborinine-8-carboxylic acid

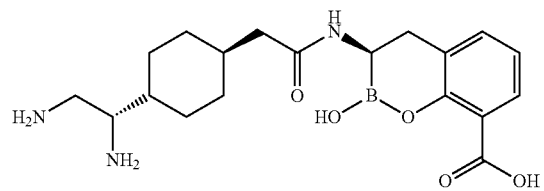

Synthesis of 2-(trans-4-(2,2,11,11-tetramethyl-4,9-dioxo-3,10-dioxa-5,8-diazadodecan-6-yl)cyclohexyl)acetic acid

Step 1: Synthesis of ethyl 2-(4-oxocyclohexyl)acetate

To a solution of ethyl 2-(1,4-dioxaspiro[4.5]decan-8-yl)acetate (from Step 1, Example 77, 4.71 g, 19.44 mmol) in acetonitrile (45 mL) was added 6N HCl aqueous solution (45 mL). The resulting mixtures was stirred at rt for 2 h and neutralized with solid NaHCO$_3$ to pH 8, extracted with EtOAc. The organic phase was washed with brine, dried over Na$_2$SO$_4$. Filtration and evaporation to dryness gave the ketone product as colorless oil (2.97 g, 78.1%).

Step 2: Synthesis of ethyl 2-(4-methylenecyclohexyl)acetate

To a cooled (0° C.) suspension of methyl triphenylphosphonium bromide (8.58 g, 23.5 mmol) in THF (60 mL) was added KOtBu (3.17 g, 28.3 mmol) in portions under N$_2$. The reaction was slowly warmed to rt and stirred for 1 h. The resulting mixture was cooled to 0° C. and added a solution of ethyl 2-(4-oxocyclohexyl)acetate (2.9 g, 15.7 mmol) in THF (15 mL). The resulting mixture was stirred at RT for 2 h and at 50° C. overnight. After cooling to RT, the reaction was quenched by addition of saturated NH$_4$Cl, extracted with EtOAc, washed with brine, dried over Na$_2$SO$_4$. Purification by flash column chromatography (eluent: 20% EtOAc in hexanes) gave the product as colorless oil (2.11 g, 73.7%).

Step 3: Synthesis of ethyl 2-(trans-4-(hydroxymethyl)cyclohexyl)acetate

9-BBN (0.5 N in THF, 57.5 mL, 28.75 mmol) was added to a solution of ethyl 2-(4-methylenecyclohexyl)acetate (2.10 g, 11.5 mmol) in THF (20 mL) at 0° C. under N$_2$. The mixture was warmed to RT and stirred at RT for 3 h. The reaction mixture was cooled to 0° C. and a mixture of 20% NaOAc solution (40 mL) and 30% H$_2$O$_2$ (30 mL) was added dropwise. The resulting mixture was warmed to RT and stirred for 40 min, quenched by saturated NH$_4$Cl solution, diluted with EtOAc, and separated. The organic phase was washed with saturated Na$_2$S$_2$O$_3$ solution, brine and dried over Na$_2$SO$_4$. Purification by flash column chromatography (eluent: 30% EtOAc in hexanes to 40%) gave the product alcohol as colorless oil (1.66 g, 72.1%). LC/MC: 201.1 (MH)$^+$.

Step 4: Synthesis of ethyl 2-(trans-4-formylcyclohexyl)acetate

A solution of DMSO (0.64 mL, 9.06 mmol) in DCM (2 mL) was added dropwise to a precooled (−78° C.) solution of oxalyl chloride (0.85 mL, 9.9 mmol) in DCM (2 mL) under N$_2$. After stirring at −78° C. for 10 min, a solution of ethyl 2-(trans-4-(hydroxymethyl)cyclohexyl)acetate (1.65 g, 8.23 mmol) in DCM (12 mL) was added dropwise. The resulting solution was stirred at −78° C. for 15 min, and TEA (6.89 mL) was added. The solution was stirred at −78° C. for 15 min and at rt for 20 min. The reaction was diluted with DCM, washed with 1M HCl solution and brine, dried over Na$_2$SO$_4$. Purification by flash column chromatography (eluent: 20% EtOAc in hexanes to 30%) gave the ketone product as yellow oil (0.76 g, 47%). LC/MC: 199.1 (MH)$^+$.

Step 5: Synthesis of ethyl 2-(trans-4-(amino(cyano)methyl)cyclohexyl)acetate A mixture of ethyl 2-(trans-4-formylcyclohexyl)acetate (0.75 g, 3.78 mmol), NaCN (0.21 g, 4.28 mmol), saturated aqueous NH$_4$OH solution (0.53 mL) and NH$_4$Cl (0.24 g) in EtOH (22 mL) and water (11 mL) was heated at 70° C. overnight. After removal of organic solvent, the residue was extracted with EtOAc, washed with saturated NaHCO$_3$ solution and brine, dried over Na2SO4. Filtration and evaporation to dryness gave the crude product. LC/MC: 225.1 (MH)$^+$.

Step 6: Synthesis of ethyl 2-(trans-4-(tert-butoxycarbonylamino)(cyano)methyl)cyclohexyl)acetate To a solution of ethyl 2-(trans-4-(amino(cyano)methyl)cyclohexyl)acetate (3.70 mmol) in THF (25 mL) was added di-tert-butyldicarbonate (1.25 g, 5.55 mmol) and NaHCO$_3$ (0.62 g, 7.4 mmol). The resulting mixture was stirred at RT overnight. Aqueous workup and purification by flash column chromatography (eluent: 30% EtOAc in hexanes) gave the product (0.54 g, 45%). LC/MC: 347.1 (MNa)$^+$.

Step 7: Synthesis of ethyl 2-(trans-4-(2-amino-1-(tert-butoxycarbonylamino)ethyl)cyclohexyl)acetate A solution of ethyl 2-(trans-4-(tert-butoxycarbonylamino)(cyano)methyl)cyclohexyl)acetate (1.63 mmol) in acetic acid (15 mL) was added Pd(OH)$_2$ (0.2 g). The resulting mixture was hydrogenated at RT under 55 psi for 3 days. Filtration and evaporation to dryness gave the crude product. LC/MC: 329.1 (MH)$^+$.

Step 8: Synthesis of ethyl 2-(trans-4-(2,2,11,11-tetramethyl-4,9-dioxo-3,10-dioxa-5,8-diazadodecan-6-yl)cyclohexyl)acetate A mixture of ethyl 2-(trans-4-(2-amino-1-(tert-butoxycarbonylamino)ethyl)cyclohexyl)acetate (1.63 mmol), di-tert-butyldicarbonate (0.44 g, 1.96 mmol) and TEA (2.27 mL, 16.3 mmol) in DCM (15 mL) was stirred at RT overnight. The reaction was quenched by addition of saturated NH$_4$Cl solution and separated. The organic phase was washed with 0.5N HCl, brine, and dried over Na$_2$SO$_4$. Purification by flash column chromatography (eluent: 20% EtOAc in hexanes to 30%) gave the product as colorless oil (0.58 g, 83%). LC/MC: 451.1 (MNa)$^+$.

Step 9: Synthesis of 2-(trans-4-(2,2,11,11-tetramethyl-4,9-dioxo-3,10-dioxa-5,8-diazadodecan-6-yl)cyclohexyl)acetic acid To a solution of ethyl 2-(trans-4-(2,2,11,11-tetramethyl-4,9-dioxo-3,10-dioxa-5,8-diazadodecan-6-yl)cyclohexyl)acetate (0.58 g, 1.35 mmol) in THF (5 mL) and MeOH (5 mL) was added 3N NaOH (2.25 mL, 6.75 mmol). The resulting mixture was stirred at RT for 3 h. After removal of volatiles by evaporation, the residue was acidified by 0.5N HCl solution to pH ~4.5 and extracted with EtOAc, dried over Na$_2$SO$_4$. Filtration and evaporation to dryness gave the acid in a quantitative yield. LC/MS: 423.1 (MNa)$^+$.

Synthesis of (R)-3-(2-(trans-4-(1,2-diaminoethyl)cyclohexyl)acetamido)-2-hydroxy-3,4-dihydro-2H-benzo[e][1,2]oxaborinine-8-carboxylic acid Prepared from 2-(trans-4-(2,2,11,11-tetramethyl-4,9-dioxo-3,10-dioxa-5,8-diazadodecan-6-yl)cyclohexyl)acetic acid following the coupling and deprotection procedure described in Example 76. The product was obtained as white solid. LC/MS: 390.1 (MH)$^+$.

Example 78

(R)-3-(2-(trans-4-(2-(ethylamino)ethylamino)cyclohexyl)acetamido)-2-hydroxy-3,4-dihydro-2H-benzo[e][1,2]oxaborinine-8-carboxylic acid

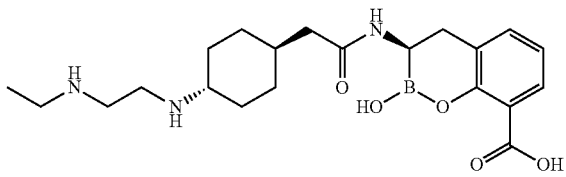 [SMILES: CCNCCN[C@H]1CC[C@H](CC(=O)N[C@H]2Cc3cccc(C(=O)O)c3OB2O)CC1]

Synthesis of (R)-3-(2-(trans-4-(2-(ethylamino)ethylamino)cyclohexyl)acetamido)-2-hydroxy-3,4-dihydro-2H-benzo[e][1,2]oxaborinine-8-carboxylic acid Prepared from (R)-3-(2-(trans-4-(2-aminoethylamino)cyclohexyl)acetamido)-2-hydroxy-3,4-dihydro-2H-benzo[e][1,2]oxaborinine-8-carboxylic acid and acetaldehyde following the procedure described in Example 71. The product was purified using reverse phase HPLC to afford the titled compound. ESI-MS m/z 418 (MH)+.

Example 79

(R)-3-(2-(trans-4-(2-(dimethylamino)ethylamino)cyclohexyl)acetamido)-2-hydroxy-3,4-dihydro-2H-benzo[e][1,2]oxaborinine-8-carboxylic acid

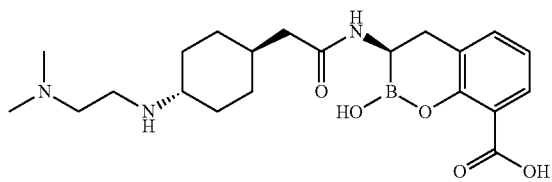 [SMILES: CN(C)CCN[C@H]1CC[C@H](CC(=O)N[C@H]2Cc3cccc(C(=O)O)c3OB2O)CC1]

Step 1: Synthesis of 2-(trans-4-(tert-butoxycarbonyl(2-(dimethylamino)ethyl)amino)cyclohexyl)acetic acid To 2-(trans-4-(tert-butoxycarbonylamino)cyclohexyl)acetic acid (1.47 g) in DMF (10 mL) was added Na$_2$CO$_3$ (0.907 g) and benzyl bromide (0.75 mL). The resultant reaction mixture was stirred at RT for overnight. Water was then added and extracted with EtOAc. The organic phase was dried and concentrated to afford the desired product as white solid (1.60 g). To this solid was added 4N HCl (10 mL) and the reaction mixture was stirred at RT for 1 hr. Diethyl ether was then added to the reaction mixture to precipitate out the benzyl 2-(trans-4-aminocyclohexyl)acetate HCl salt as white solid.

To benzyl 2-(trans-4-aminocyclohexyl)acetate HCl salt (860 mg) in DMF was added K$_2$CO$_3$ (414 mg) and 2-bromo-N,N-dimethylethanamine HBr salt (700 mg). The resultant reaction mixture was stirred at 60° C. for overnight. Water was then added and extracted with EtOAc. The organic phase was dried and concentrated to afford the crude product which was used directly in next step.

To above product in DCM (20 mL) was added TEA (1 mL) and di-tert-butyl dicarbonate (1.5 g). The reaction mixture was stirred at RT for overnight. Organic phase was washed with brine, dried and concentrated. The residue was purified by HPLC. To this product in MeOH (10 mL) was added Pd/C (10%, 50 mg) and the reaction mixture was stirred under hydrogen atmosphere for overnight. The catalyst was filtered through Celite pad and the solvent removed under reduced pressure to afford 2-(trans-4-(tert-butoxycarbonyl(2-(dimethylamino)ethyl)amino)cyclohexyl)acetic acid as yellow foam (250 mg).

Step 2: Synthesis of tert-butyl 3-((2R)-2-(2-(trans-4-(tert-butoxycarbonyl(2-(dimethylamino)ethyl)amino)cyclohexyl)acetamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(trans-4-(tert-butoxycarbonyl(2-(dimethylamino)ethyl)amino) cyclohexyl)acetic acid following procedure described in Step 1 of Example 1.

Step 3: Synthesis of (R)-3-(2-(trans-4-(2-(dimethylamino)ethylamino)cyclohexyl)acetamido)-2-hydroxy-3,4-dihydro-2H-benzo[e][1,2]oxaborinine-8-carboxylic acid To the compound from step 2 (40 mg) was added 3N HCl (2 ml) and the resultant reaction mixture was heated at reflux for 1 hr. The solvents were then removed in vacuo and the residue purified by reverse phase preparative HPLC and dried using lyophilization. ESI-MS m/z 418 (MH)+.

TABLE 1

Examples of compounds

| Example | Structure | MW | ESI-MS (m/z) for [MH]+ |
|---|---|---|---|
| 1 | 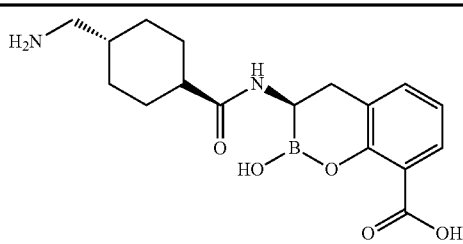 | 346 | 347 |

TABLE 1-continued

Examples of compounds

| Example | Structure | MW | ESI-MS (m/z) for [MH]+ |
|---|---|---|---|
| 2 | 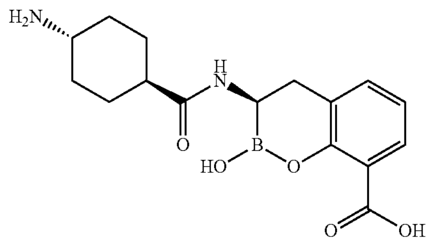 [SMILES: N[C@H]1CC[C@H](C(=O)N[C@H]2Cc3cccc(C(=O)O)c3OB2O)CC1] | 332 | 333 |
| 3 | 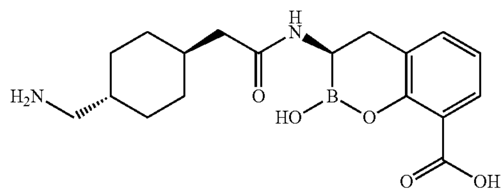 [SMILES: NC[C@H]1CC[C@H](CC(=O)N[C@H]2Cc3cccc(C(=O)O)c3OB2O)CC1] | 360 | 361 |
| 4 | 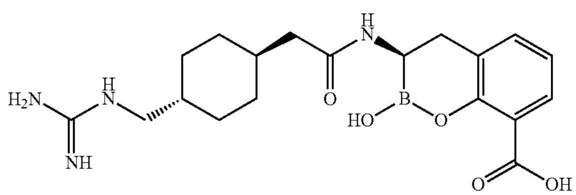 [SMILES: N=C(N)NC[C@H]1CC[C@H](CC(=O)N[C@H]2Cc3cccc(C(=O)O)c3OB2O)CC1] | 402 | 403 |
| 5 | 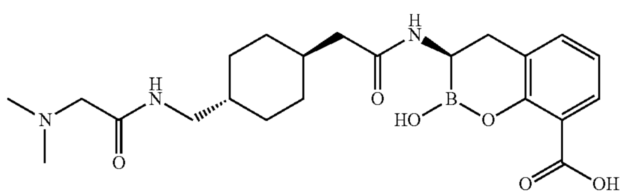 [SMILES: CN(C)CC(=O)NC[C@H]1CC[C@H](CC(=O)N[C@H]2Cc3cccc(C(=O)O)c3OB2O)CC1] | 445 | 446 |
| 6 | 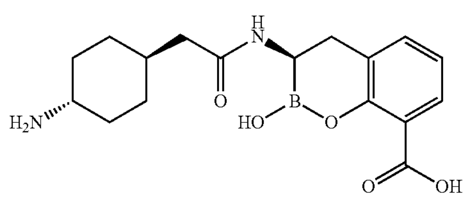 [SMILES: N[C@H]1CC[C@H](CC(=O)N[C@H]2Cc3cccc(C(=O)O)c3OB2O)CC1] | 346 | 347 |
| 7 | 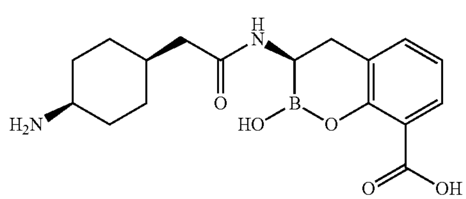 [SMILES: N[C@H]1CC[C@@H](CC(=O)N[C@H]2Cc3cccc(C(=O)O)c3OB2O)CC1] | 346 | 347 |
| 8 | 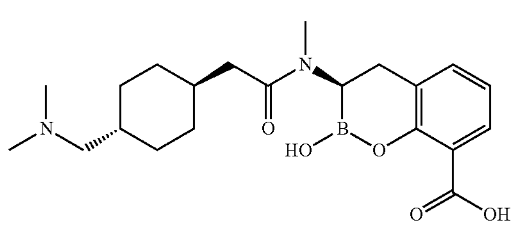 [SMILES: CN(C)C[C@H]1CC[C@H](CC(=O)N(C)[C@H]2Cc3cccc(C(=O)O)c3OB2O)CC1] | 402 | 403 |

TABLE 1-continued

Examples of compounds

| Example | Structure | MW | ESI-MS (m/z) for [MH]+ |
|---|---|---|---|
| 9 | 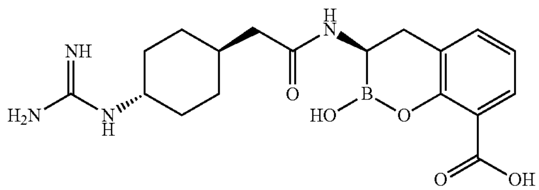 [SMILES: N=C(N)N[C@H]1CC[C@H](CC(=O)N[C@H]2Cc3cccc(C(=O)O)c3OB2O)CC1] | 388 | 389 |
| 10 | 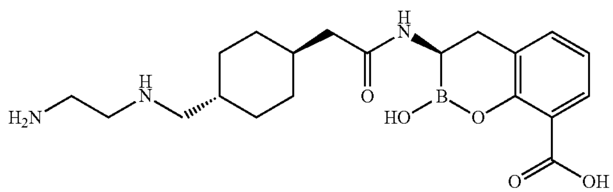 [SMILES: NCCNC[C@H]1CC[C@H](CC(=O)N[C@H]2Cc3cccc(C(=O)O)c3OB2O)CC1] | 403 | 404 |
| 11 | 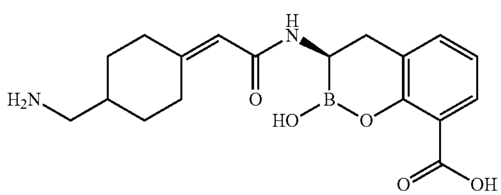 [SMILES: NCC1CCC(=CC(=O)N[C@H]2Cc3cccc(C(=O)O)c3OB2O)CC1] | 358 | 359 |
| 12 | 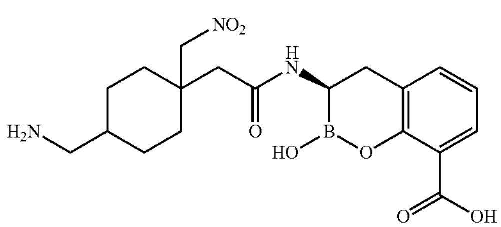 [SMILES: NCC1CCC(CC(=O)N[C@H]2Cc3cccc(C(=O)O)c3OB2O)(C[N+](=O)[O-])CC1] | 419 | 420 |
| 13 | 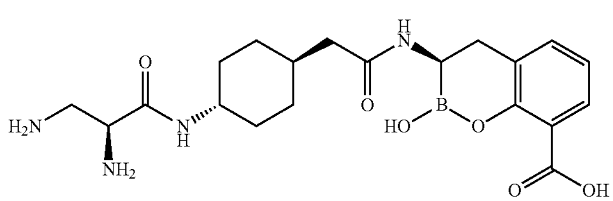 [SMILES: NC[C@H](N)C(=O)N[C@H]1CC[C@H](CC(=O)N[C@H]2Cc3cccc(C(=O)O)c3OB2O)CC1] | 432 | 433 |
| 14 | 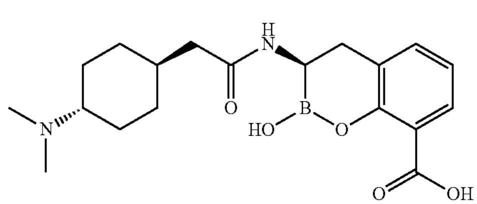 [SMILES: CN(C)[C@H]1CC[C@H](CC(=O)N[C@H]2Cc3cccc(C(=O)O)c3OB2O)CC1] | 374 | 375 |
| 15 | 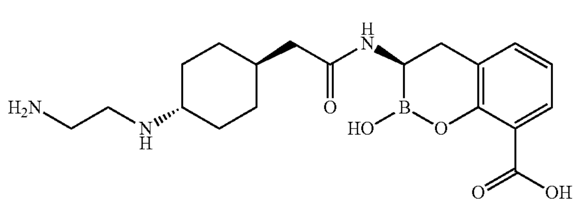 | 389 | 390 |

TABLE 1-continued

Examples of compounds

| Example | Structure | MW | ESI-MS (m/z) for [MH]+ |
|---|---|---|---|
| 16 | 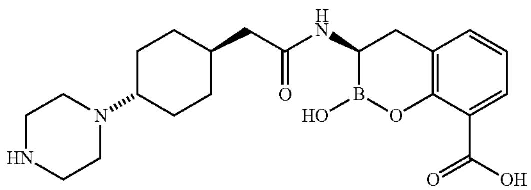 [SMILES: O=C(C[C@H]1CC[C@H](N2CCNCC2)CC1)N[C@H]1Cc2cccc(C(=O)O)c2OB1O] | 415 | 416 |
| 17 | 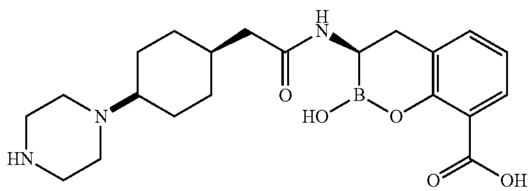 [SMILES: O=C(C[C@H]1CC[C@@H](N2CCNCC2)CC1)N[C@H]1Cc2cccc(C(=O)O)c2OB1O] | 415 | 416 |
| 18 | | 389 | 390 |
| 19 | | 333 | 334 |

TABLE 1-continued

Examples of compounds

| Example | Structure | MW | ESI-MS (m/z) for [MH]+ |
|---|---|---|---|
| 20 | 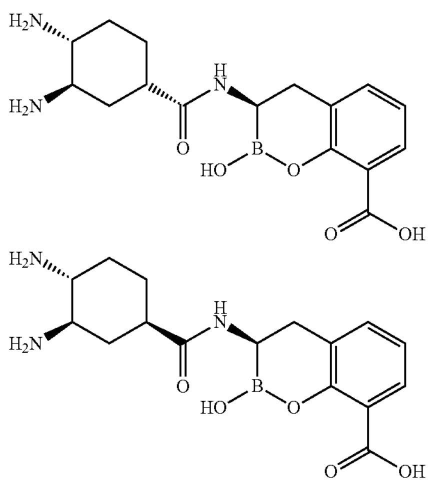 | 347 | 348 |
| 21 | 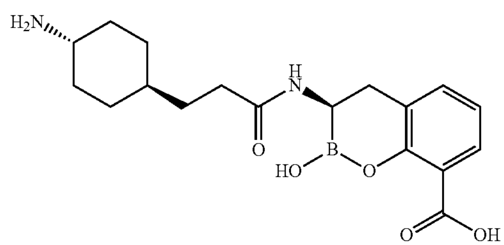 [SMILES: N[C@H]1CC[C@H](CCC(=O)N[C@H]2Cc3cccc(C(=O)O)c3OB2O)CC1] | 360 | 361 |
| 22 | 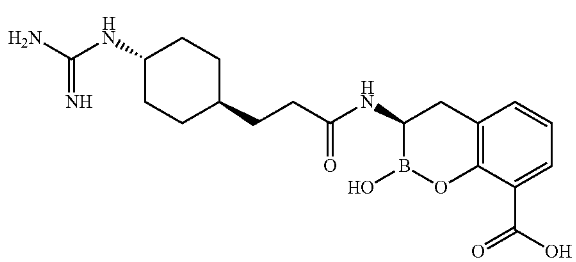 [SMILES: N=C(N)N[C@H]1CC[C@H](CCC(=O)N[C@H]2Cc3cccc(C(=O)O)c3OB2O)CC1] | 402 | 403 |
| 23 | 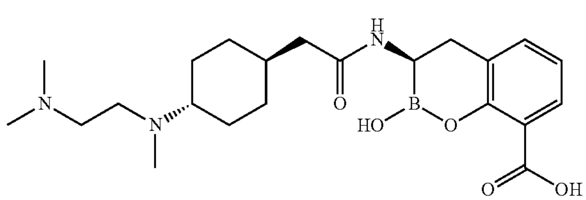 [SMILES: CN(C)CCN(C)[C@H]1CC[C@H](CC(=O)N[C@H]2Cc3cccc(C(=O)O)c3OB2O)CC1] | 431 | 432 |
| 24 | 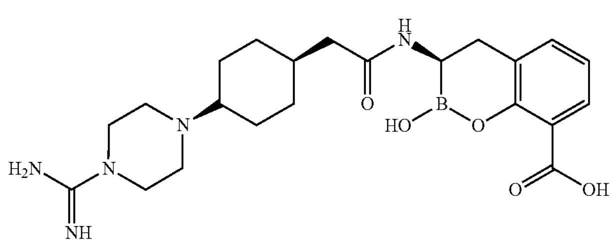 | 457 | 458 |

TABLE 1-continued

Examples of compounds

| Example | Structure | MW | ESI-MS (m/z) for [MH]+ |
|---|---|---|---|
| 25 | 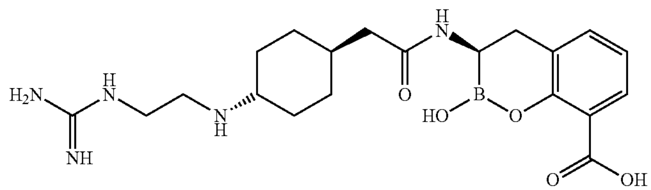 | 431 | 432 |
| 26 | 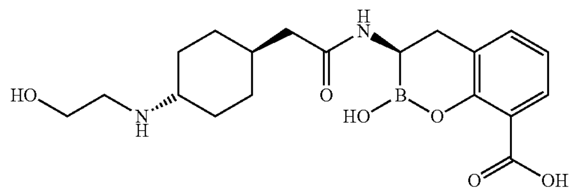 | 390 | 391 |
| 27 | 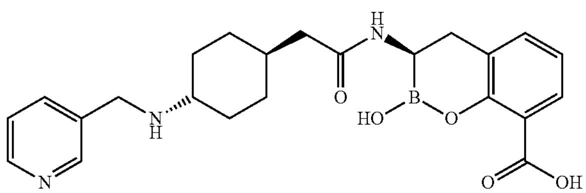 | 437 | 438 |
| 28 | 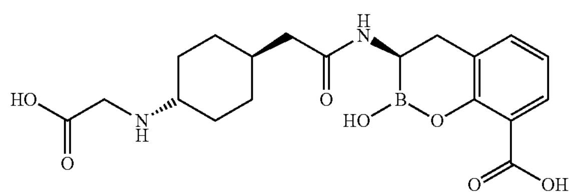 | 404 | 405 |
| 29 | 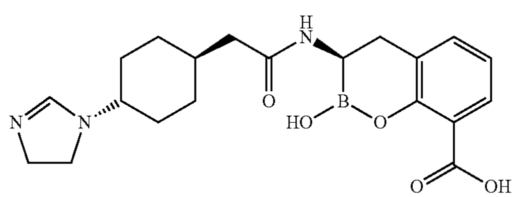 | 399 | 400 |
| 30 | 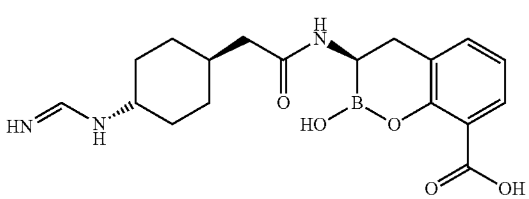 | 373 | 374 |
| 31 | 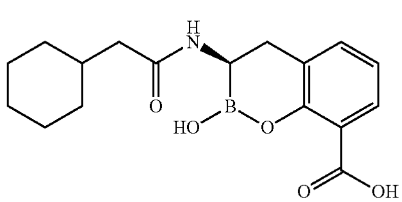 [SMILES: O=C(CC1CCCCC1)N[C@H]1Cc2cccc(C(=O)O)c2OB1O] | 331.2 | 332 |

TABLE 1-continued

Examples of compounds

| Example | Structure | MW | ESI-MS (m/z) for [MH]+ |
|---|---|---|---|
| 32 | 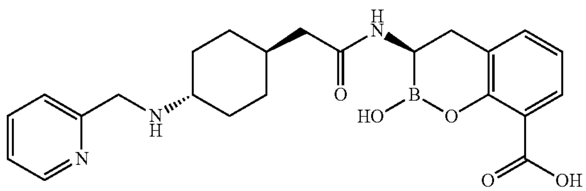 [SMILES: O=C(C[C@H]1CC[C@H](NCc2ccccn2)CC1)N[C@H]1Cc2cccc(C(=O)O)c2OB1O] | 437.3 | 438 |
| 33 | 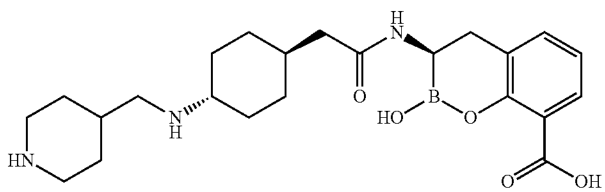 [SMILES: O=C(C[C@H]1CC[C@H](NCC2CCNCC2)CC1)N[C@H]1Cc2cccc(C(=O)O)c2OB1O] | 443.3 | 444 |
| 34 | 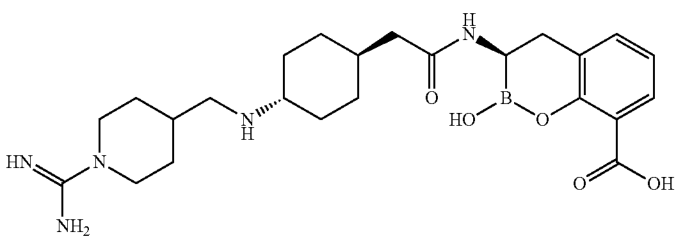 [SMILES: N=C(N)N1CCC(CN[C@H]2CC[C@H](CC(=O)N[C@H]3Cc4cccc(C(=O)O)c4OB3O)CC2)CC1] | 485.4 | 486 |
| 35 | 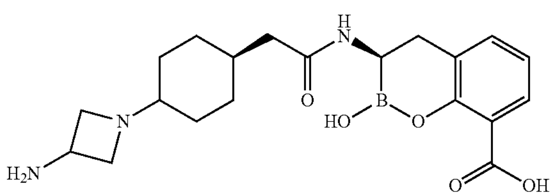 | 401.3 | 402 |
| 36 | 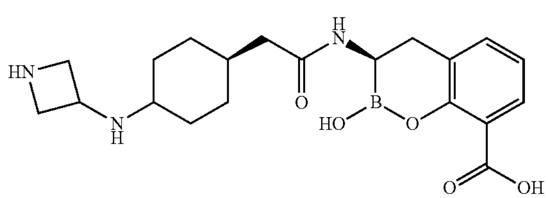 | 401.3 | 402 |
| 37 | 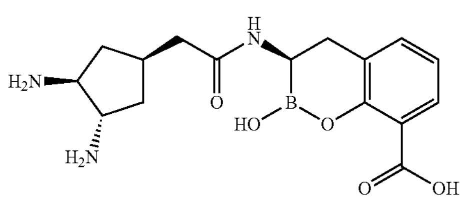 | 347.2 | 348 |
| 38 | 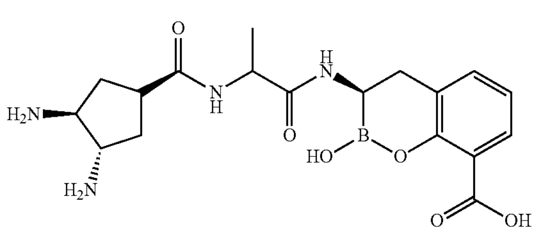 | 404.2 | 405 |

TABLE 1-continued

Examples of compounds

| Example | Structure | MW | ESI-MS (m/z) for [MH]+ |
|---|---|---|---|
| 39 | 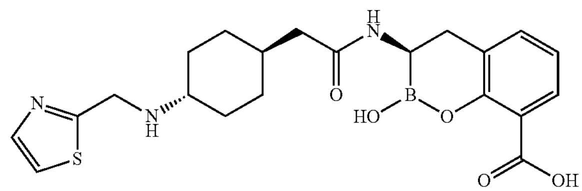 [SMILES: O=C(C[C@H]1CC[C@H](NCc2nccs2)CC1)N[C@H]1Cc2cccc(C(=O)O)c2OB1O] | 443.3 | 444 |
| 40 | 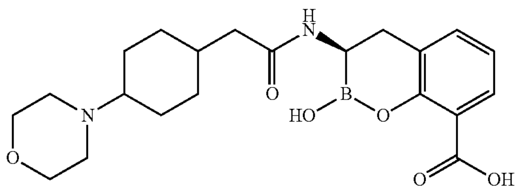 [SMILES: O=C(CC1CCC(N2CCOCC2)CC1)N[C@H]1Cc2cccc(C(=O)O)c2OB1O] | 416.3 | 417 |
| 41 | 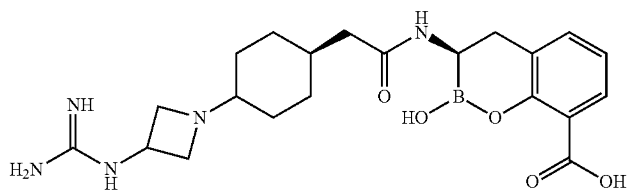 | 443.3 | 444 |
| 42 | 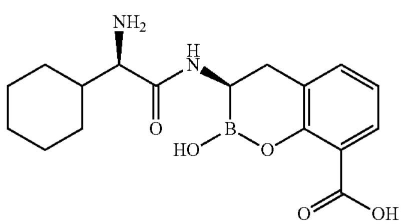 [SMILES: N[C@@H](C(=O)N[C@H]1Cc2cccc(C(=O)O)c2OB1O)C1CCCCC1] | 346.2 | 347 |
| 43 | 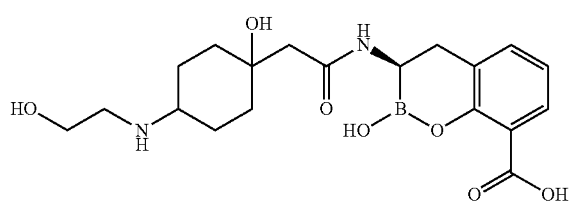 [SMILES: O=C(CC1(O)CCC(NCCO)CC1)N[C@H]1Cc2cccc(C(=O)O)c2OB1O] | 405.2 | 406 |
| 44 | 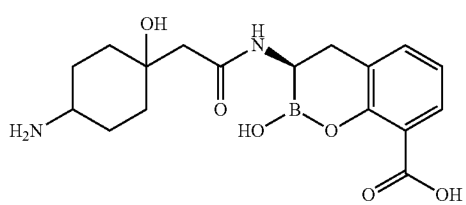 [SMILES: NC1CCC(O)(CC(=O)N[C@H]2Cc3cccc(C(=O)O)c3OB2O)CC1] | 362.2 | 363 |
| 45 | 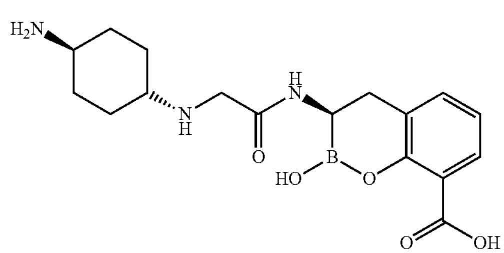 | 361.2 | 362 |

TABLE 1-continued

Examples of compounds

| Example | Structure | MW | ESI-MS (m/z) for [MH]+ |
|---|---|---|---|
| 46 | 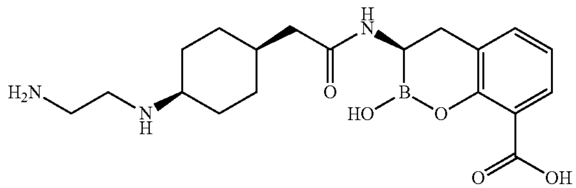 [SMILES: NCCN[C@H]1CC[C@@H](CC(=O)N[C@H]2Cc3cccc(C(=O)O)c3OB2O)CC1] | 389.2 | 390 |
| 47 | 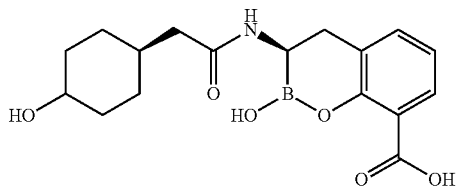 | 347.2 | 348 |
| 48 | 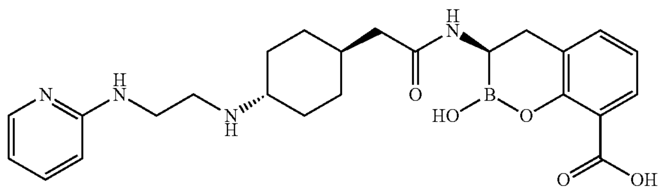 [SMILES: O=C(C[C@H]1CC[C@H](NCCNc2ccccn2)CC1)N[C@H]1Cc2cccc(C(=O)O)c2OB1O] | 466.3 | 467 |
| 49 | 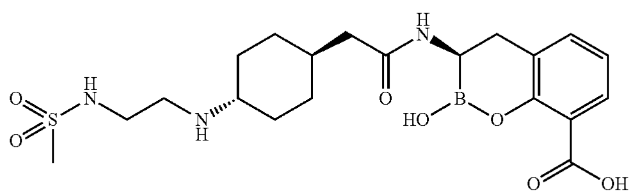 [SMILES: CS(=O)(=O)NCCN[C@H]1CC[C@H](CC(=O)N[C@H]2Cc3cccc(C(=O)O)c3OB2O)CC1] | 467.3 | 468 |
| 50 | 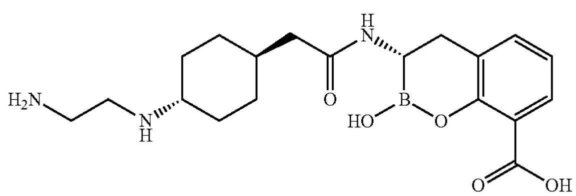 [SMILES: NCCN[C@H]1CC[C@H](CC(=O)N[C@@H]2Cc3cccc(C(=O)O)c3OB2O)CC1] | 389.2 | 390 |
| 51 | 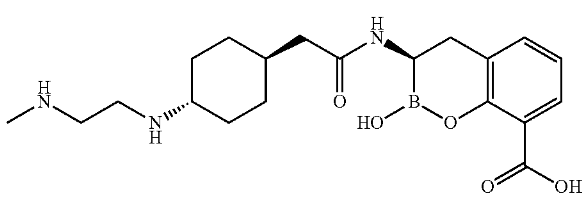 [SMILES: CNCCN[C@H]1CC[C@H](CC(=O)N[C@H]2Cc3cccc(C(=O)O)c3OB2O)CC1] | 403.2 | 404 |
| 52 | 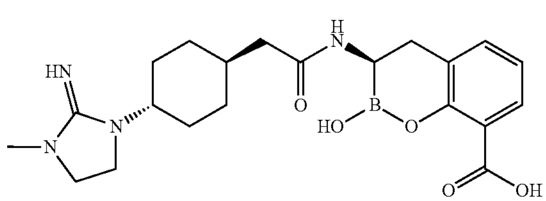 [SMILES: CN1CCN([C@H]2CC[C@H](CC(=O)N[C@H]3Cc4cccc(C(=O)O)c4OB3O)CC2)C1=N] | 428.3 | 429 |

TABLE 1-continued

Examples of compounds

| Example | Structure | MW | ESI-MS (m/z) for [MH]+ |
|---------|-----------|------|------------------------|
| 53 | 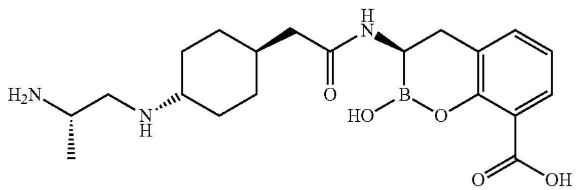 | 408.3 | 409 |
| 54 | 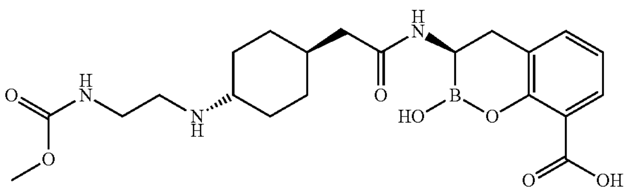 | 447.3 | 448 |
| 55 | 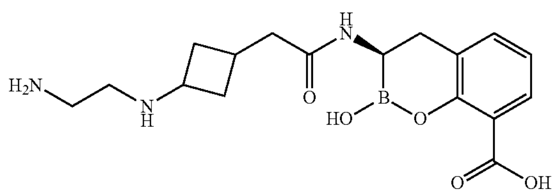 [SMILES: NCCNC1CC(CC(=O)N[C@H]2Cc3cccc(C(=O)O)c3OB2O)C1] | 361.2 | 362 |
| 56 | 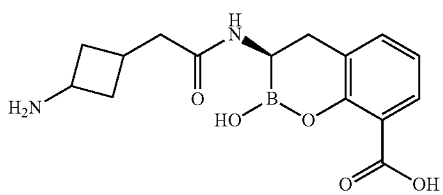 [SMILES: NC1CC(CC(=O)N[C@H]2Cc3cccc(C(=O)O)c3OB2O)C1] | 318.1 | 319 |
| 57 | 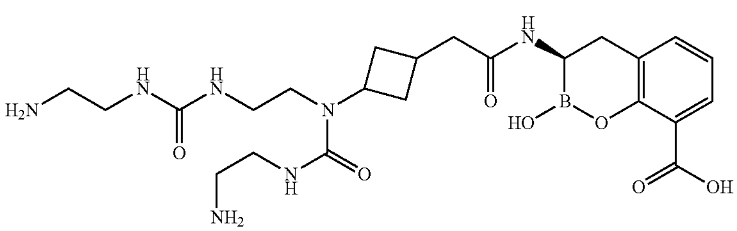 [SMILES: NCCNC(=O)NCCN(C(=O)NCCN)C1CC(CC(=O)N[C@H]2Cc3cccc(C(=O)O)c3OB2O)C1] | 533.4 | 534 |
| 58 | 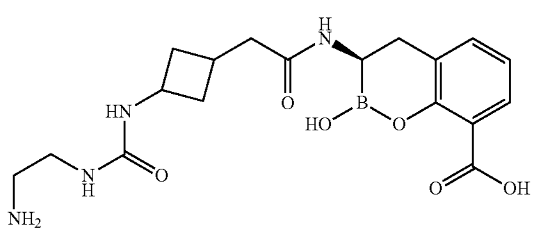 [SMILES: NCCNC(=O)NC1CC(CC(=O)N[C@H]2Cc3cccc(C(=O)O)c3OB2O)C1] | 404.2 | 405 |
| 59 | 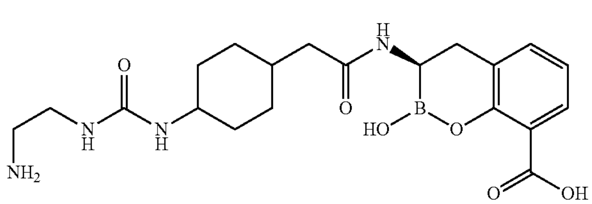 [SMILES: NCCNC(=O)NC1CCC(CC(=O)N[C@H]2Cc3cccc(C(=O)O)c3OB2O)CC1] | 432.3 | 433 |

TABLE 1-continued

Examples of compounds

| Example | Structure | MW | ESI-MS (m/z) for [MH]+ |
|---|---|---|---|
| 60 | 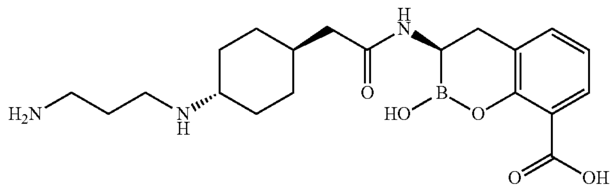 [SMILES: NCCCN[C@H]1CC[C@H](CC(=O)N[C@H]2Cc3cccc(C(=O)O)c3OB2O)CC1] | 403.3 | 404 |
| 61 | 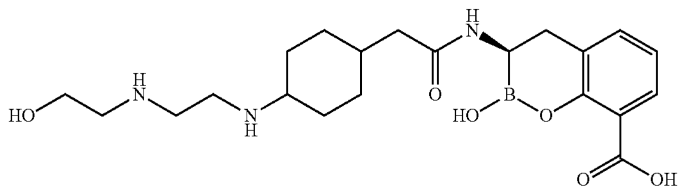 [SMILES: O=C(CC1CCC(NCCNCCO)CC1)N[C@H]1Cc2cccc(C(=O)O)c2OB1O] | 433.3 | 434 |
| 62 | 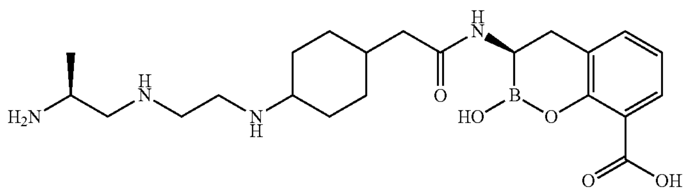 [SMILES: C[C@H](N)CNCCNC1CCC(CC(=O)N[C@H]2Cc3cccc(C(=O)O)c3OB2O)CC1] | 446.4 | 447 |
| 63 | 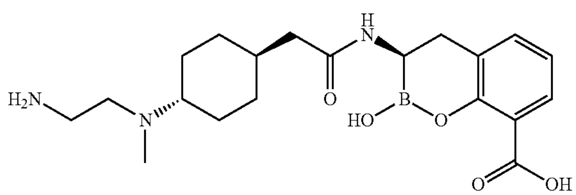 [SMILES: CN(CCN)[C@H]1CC[C@H](CC(=O)N[C@H]2Cc3cccc(C(=O)O)c3OB2O)CC1] | 403.3 | 404 |
| 64 | 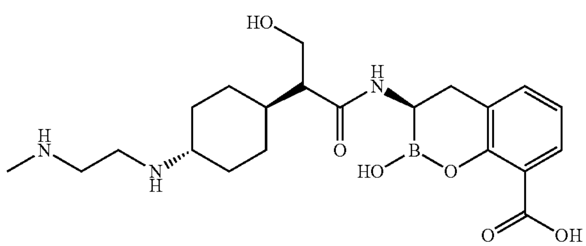 [SMILES: CNCCN[C@H]1CC[C@H](C(CO)C(=O)N[C@H]2Cc3cccc(C(=O)O)c3OB2O)CC1] | 433.2 | 434 |
| 65 | 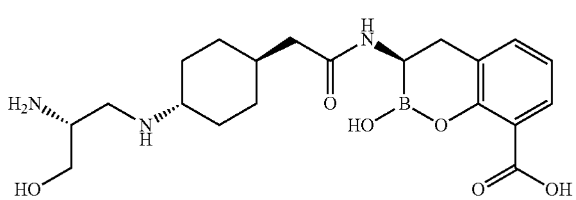 [SMILES: N[C@@H](CO)CN[C@H]1CC[C@H](CC(=O)N[C@H]2Cc3cccc(C(=O)O)c3OB2O)CC1] | 419.2 | 420 |
| 66 | 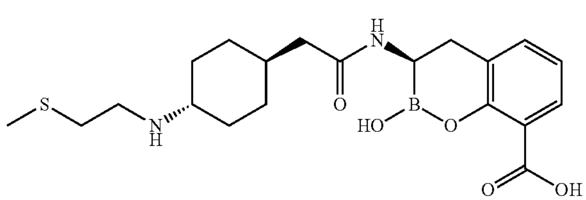 [SMILES: CSCCN[C@H]1CC[C@H](CC(=O)N[C@H]2Cc3cccc(C(=O)O)c3OB2O)CC1] | 420.2 | 421 |

TABLE 1-continued

Examples of compounds

| Example | Structure | MW | ESI-MS (m/z) for [MH]+ |
|---|---|---|---|
| 67 | 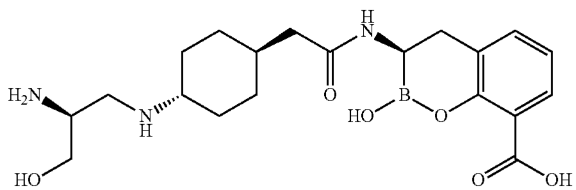 [SMILES: N[C@H](CO)CN[C@H]1CC[C@H](CC(=O)N[C@H]2Cc3cccc(C(=O)O)c3OB2O)CC1] | 419.2 | 420 |
| 68 | 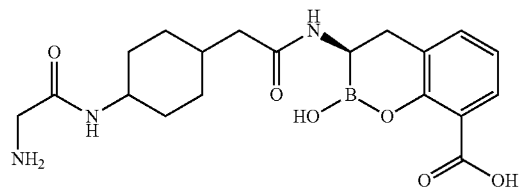 [SMILES: NCC(=O)NC1CCC(CC(=O)N[C@H]2Cc3cccc(C(=O)O)c3OB2O)CC1] | 403.2 | 404 |
| 69 | 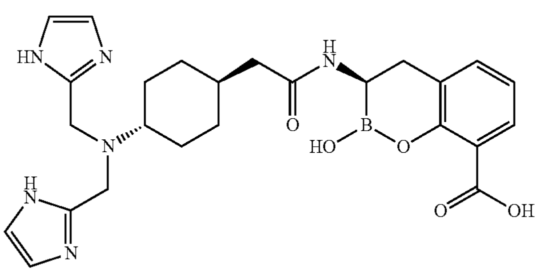 [SMILES: O=C(C[C@H]1CC[C@H](N(Cc2ncc[nH]2)Cc2ncc[nH]2)CC1)N[C@H]1Cc2cccc(C(=O)O)c2OB1O] | 506.3 | 507 |
| 70 | 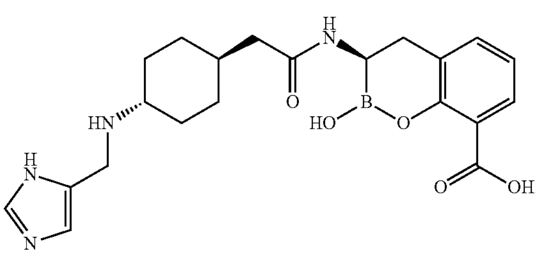 [SMILES: O=C(C[C@H]1CC[C@H](NCc2cnc[nH]2)CC1)N[C@H]1Cc2cccc(C(=O)O)c2OB1O] | 426.2 | 427 |
| 71 | 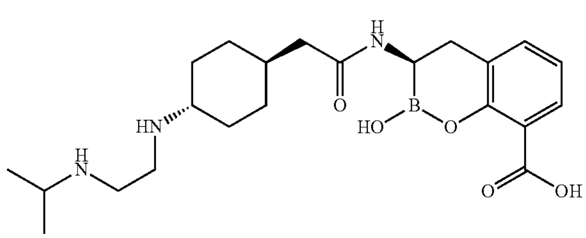 [SMILES: CC(C)NCCN[C@H]1CC[C@H](CC(=O)N[C@H]2Cc3cccc(C(=O)O)c3OB2O)CC1] | 431.3 | 432 |
| 72 | 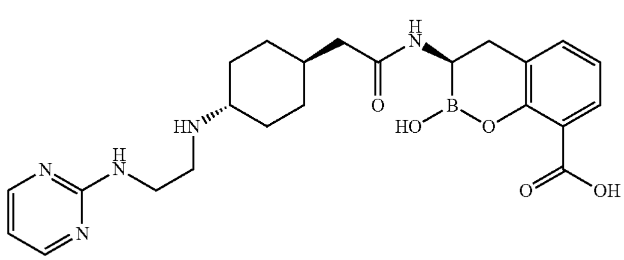 [SMILES: O=C(C[C@H]1CC[C@H](NCCNc2ncccn2)CC1)N[C@H]1Cc2cccc(C(=O)O)c2OB1O] | 467.3 | 468 |

TABLE 1-continued

Examples of compounds

| Example | Structure | MW | ESI-MS (m/z) for [MH]+ |
|---|---|---|---|
| 73 | 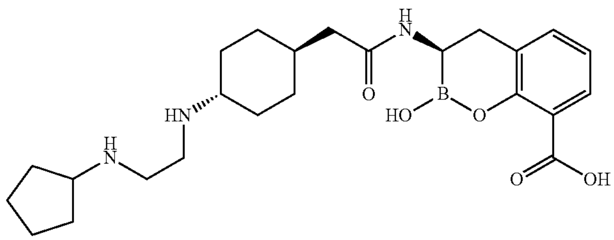 [SMILES: O=C(C[C@H]1CC[C@H](NCCNC2CCCC2)CC1)N[C@H]1Cc2cccc(C(=O)O)c2OB1O] | 457.3 | 458 |
| 74 | 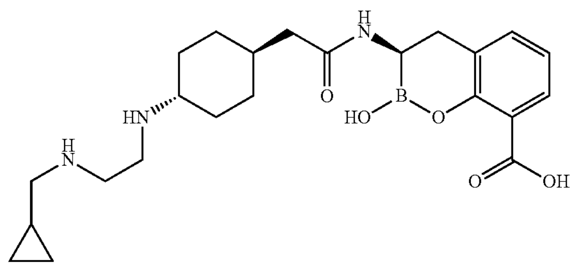 [SMILES: O=C(C[C@H]1CC[C@H](NCCNCC2CC2)CC1)N[C@H]1Cc2cccc(C(=O)O)c2OB1O] | 443.3 | 444 |
| 75 | 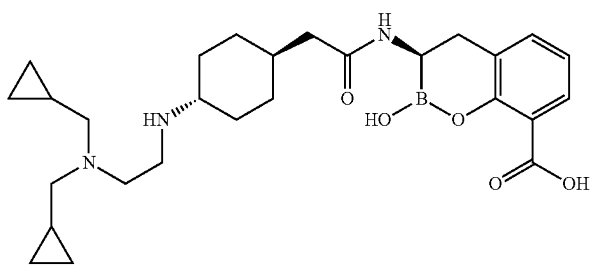 [SMILES: O=C(C[C@H]1CC[C@H](NCCN(CC2CC2)CC2CC2)CC1)N[C@H]1Cc2cccc(C(=O)O)c2OB1O] | 497.3 | 498 |
| 76 | 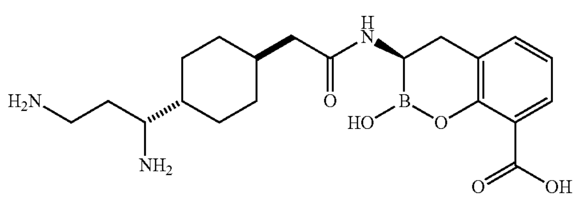 [SMILES: NCCC(N)[C@H]1CC[C@H](CC(=O)N[C@H]2Cc3cccc(C(=O)O)c3OB2O)CC1] | 403.2 | 404 |
| 77 | 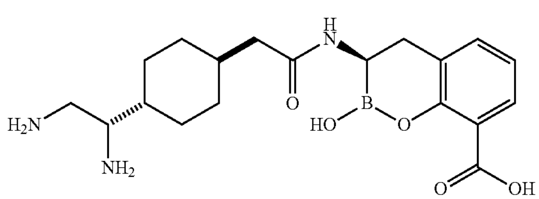 [SMILES: NCC(N)[C@H]1CC[C@H](CC(=O)N[C@H]2Cc3cccc(C(=O)O)c3OB2O)CC1] | 389.2 | 390 |
| 78 | 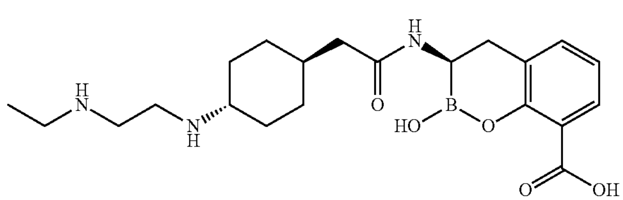 [SMILES: CCNCCN[C@H]1CC[C@H](CC(=O)N[C@H]2Cc3cccc(C(=O)O)c3OB2O)CC1] | 417.3 | 418 |

TABLE 1-continued

Examples of compounds

| Example | Structure | MW | ESI-MS (m/z) for [MH]+ |
|---|---|---|---|
| 79 | 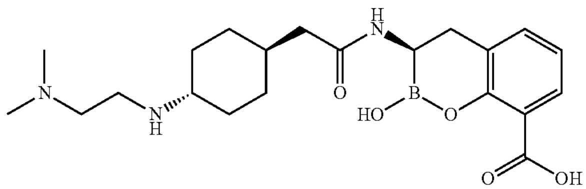 [SMILES: CN(C)CCN[C@H]1CC[C@H](CC(=O)N[C@H]2Cc3cccc(C(=O)O)c3OB2O)CC1] | 417.3 | 418 |
| 80 | 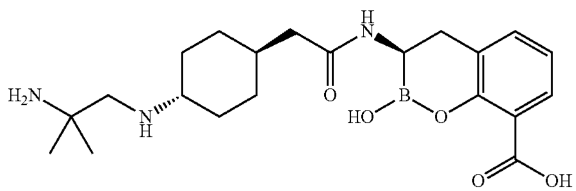 [SMILES: CC(C)(N)CN[C@H]1CC[C@H](CC(=O)N[C@H]2Cc3cccc(C(=O)O)c3OB2O)CC1] | | |
| 81 | 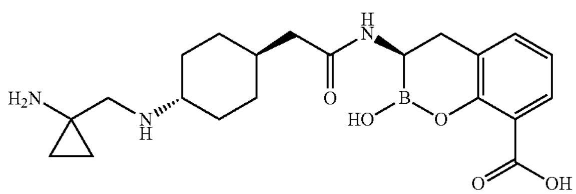 [SMILES: NC1(CN[C@H]2CC[C@H](CC(=O)N[C@H]3Cc4cccc(C(=O)O)c4OB3O)CC2)CC1] | | |
| 82 | 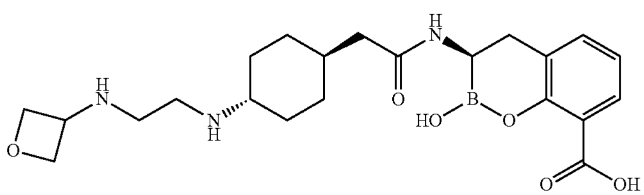 [SMILES: O=C(C[C@H]1CC[C@H](NCCNC2COC2)CC1)N[C@H]1Cc2cccc(C(=O)O)c2OB1O] | | |
| 83 | 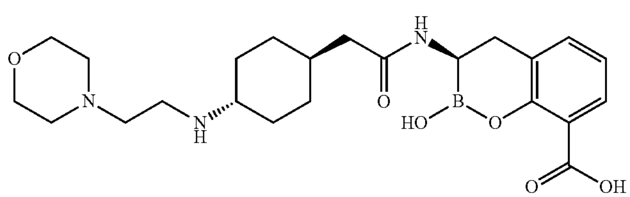 [SMILES: O=C(C[C@H]1CC[C@H](NCCN2CCOCC2)CC1)N[C@H]1Cc2cccc(C(=O)O)c2OB1O] | | |
| 84 | 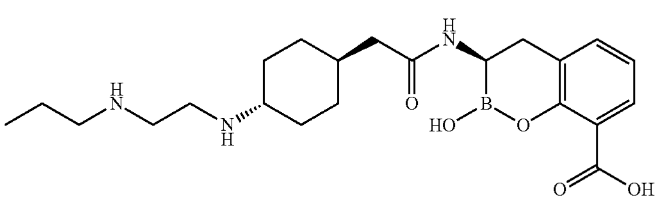 [SMILES: CCCNCCN[C@H]1CC[C@H](CC(=O)N[C@H]2Cc3cccc(C(=O)O)c3OB2O)CC1] | | |
| 85 | 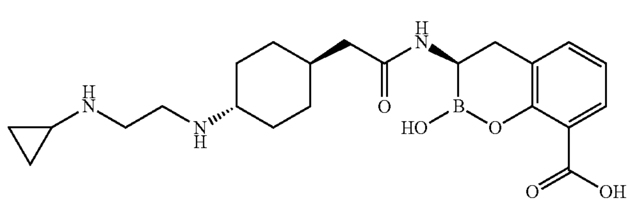 [SMILES: O=C(C[C@H]1CC[C@H](NCCNC2CC2)CC1)N[C@H]1Cc2cccc(C(=O)O)c2OB1O] | | |

TABLE 1-continued

Examples of compounds

| Example | Structure | ESI-MS MW (m/z) for [MH]+ |
|---|---|---|
| 86 | 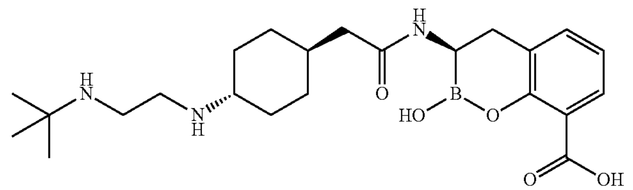 [SMILES: CC(C)(C)NCCN[C@H]1CC[C@H](CC(=O)N[C@H]2Cc3cccc(C(=O)O)c3OB2O)CC1] | |
| 87 | 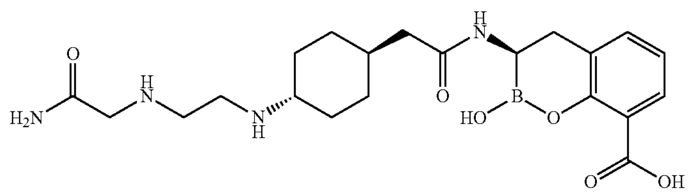 [SMILES: NC(=O)CNCCN[C@H]1CC[C@H](CC(=O)N[C@H]2Cc3cccc(C(=O)O)c3OB2O)CC1] | |
| 88 | 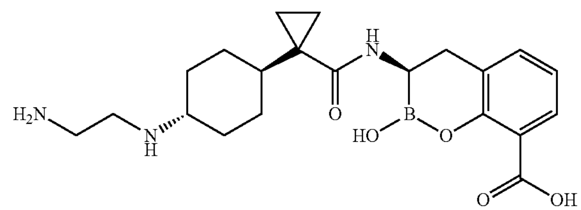 [SMILES: NCCN[C@H]1CC[C@H](C2(C(=O)N[C@H]3Cc4cccc(C(=O)O)c4OB3O)CC2)CC1] | |
| 89 | 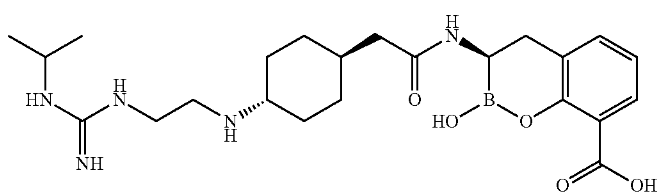 [SMILES: CC(C)NC(=N)NCCN[C@H]1CC[C@H](CC(=O)N[C@H]2Cc3cccc(C(=O)O)c3OB2O)CC1] | |
| 90 | 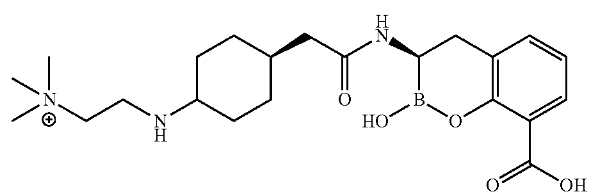 | |
| 91 | 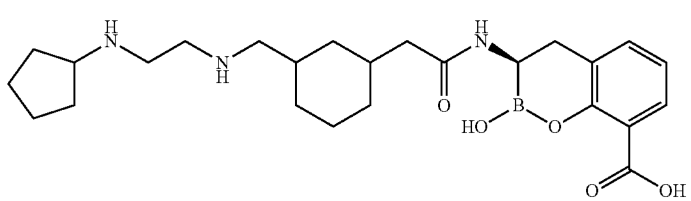 [SMILES: O=C(CC1CCCC(CNCCNC2CCCC2)C1)N[C@H]1Cc2cccc(C(=O)O)c2OB1O] | |
| 92 | 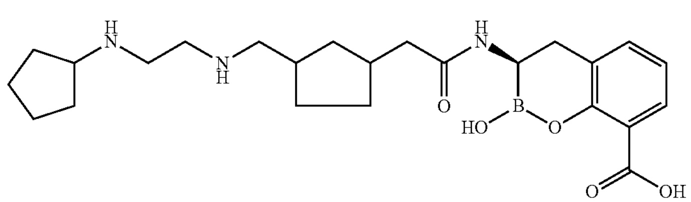 [SMILES: O=C(CC1CCC(CNCCNC2CCCC2)C1)N[C@H]1Cc2cccc(C(=O)O)c2OB1O] | |

TABLE 1-continued

Examples of compounds

| Example | Structure | MW | ESI-MS (m/z) for [MH]+ |
|---------|-----------|----|------------------------|
| 93 | 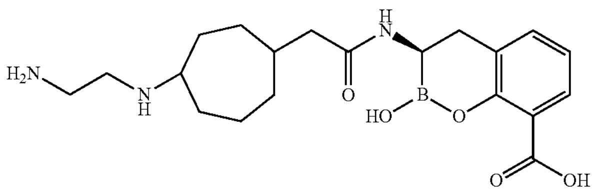 [SMILES: NCCNC1CCCC(CC(=O)N[C@H]2Cc3cccc(C(=O)O)c3OB2O)CC1] | | |
| 94 | 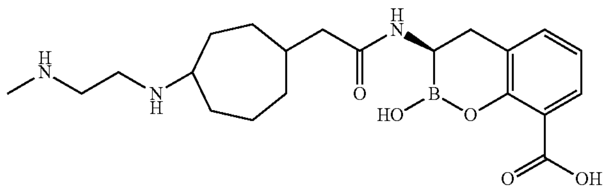 [SMILES: CNCCNC1CCCC(CC(=O)N[C@H]2Cc3cccc(C(=O)O)c3OB2O)CC1] | | |
| 95 | 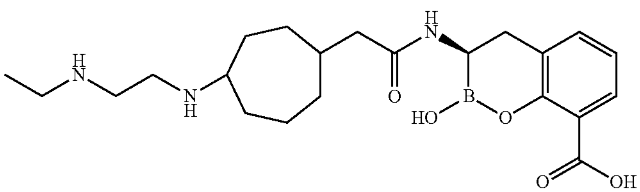 [SMILES: CCNCCNC1CCCC(CC(=O)N[C@H]2Cc3cccc(C(=O)O)c3OB2O)CC1] | | |
| 96 | 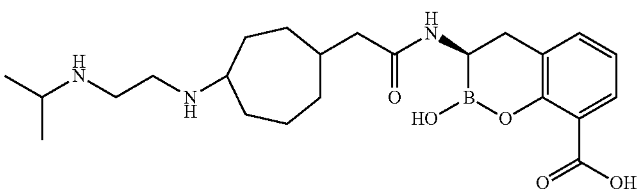 [SMILES: CC(C)NCCNC1CCCC(CC(=O)N[C@H]2Cc3cccc(C(=O)O)c3OB2O)CC1] | | |
| 97 | 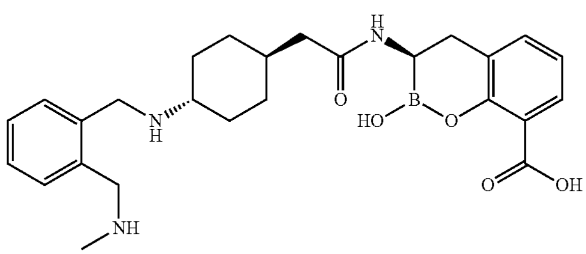 [SMILES: CNCc1ccccc1CN[C@H]1CC[C@H](CC(=O)N[C@H]2Cc3cccc(C(=O)O)c3OB2O)CC1] | | |
| 98 | 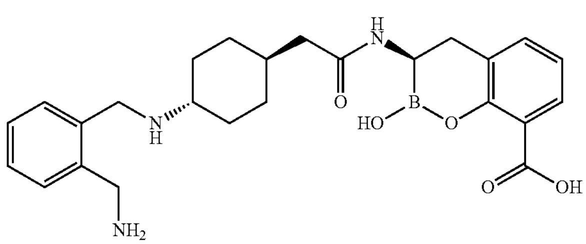 [SMILES: NCc1ccccc1CN[C@H]1CC[C@H](CC(=O)N[C@H]2Cc3cccc(C(=O)O)c3OB2O)CC1] | | |
| 99 | 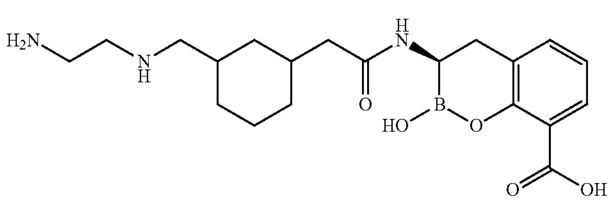 [SMILES: NCCNCC1CCCC(CC(=O)N[C@H]2Cc3cccc(C(=O)O)c3OB2O)C1] | | |

TABLE 1-continued
Examples of compounds
| Example | Structure | MW | ESI-MS (m/z) for [MH]+ |
|---|---|---|---|
| 100 | 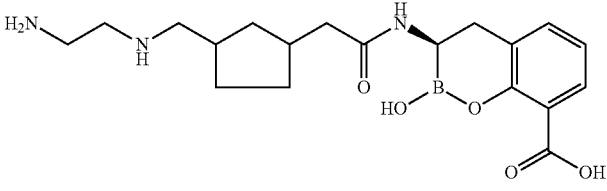 [SMILES: NCCNCC1CCC(CC(=O)N[C@H]2Cc3cccc(C(=O)O)c3OB2O)C1] | | |
| 101 | 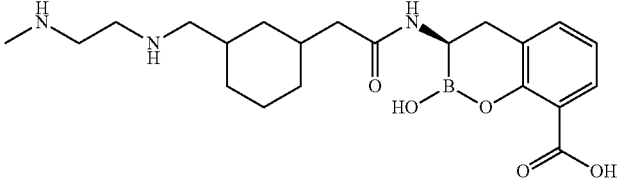 [SMILES: CNCCNCC1CCCC(CC(=O)N[C@H]2Cc3cccc(C(=O)O)c3OB2O)C1] | | |
| 102 | 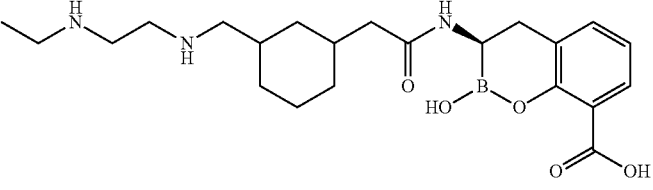 [SMILES: CCNCCNCC1CCCC(CC(=O)N[C@H]2Cc3cccc(C(=O)O)c3OB2O)C1] | | |
| 103 | 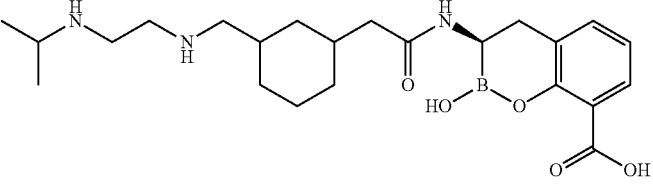 [SMILES: CC(C)NCCNCC1CCCC(CC(=O)N[C@H]2Cc3cccc(C(=O)O)c3OB2O)C1] | | |
| 104 | 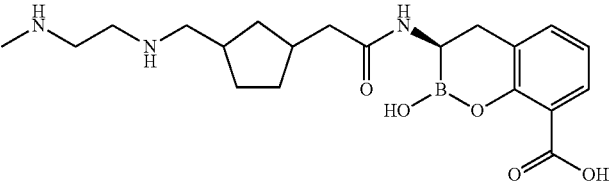 [SMILES: CNCCNCC1CCC(CC(=O)N[C@H]2Cc3cccc(C(=O)O)c3OB2O)C1] | | |
| 105 | 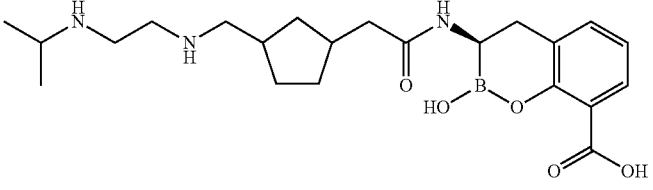 [SMILES: CC(C)NCCNCC1CCC(CC(=O)N[C@H]2Cc3cccc(C(=O)O)c3OB2O)C1] | | |
| 106 | 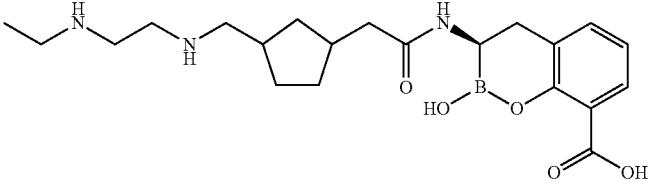 [SMILES: CCNCCNCC1CCC(CC(=O)N[C@H]2Cc3cccc(C(=O)O)c3OB2O)C1] | | |

Example 107

Parenteral Composition of a Compound of Formula I or Formula Ia

To prepare a parenteral pharmaceutical composition suitable for administration by injection, 100 mg of a compound of Formula I or Formula Ia, or a water soluble pharmaceutically acceptable salt thereof, is dissolved in DMSO and then mixed with 10 ml of 0.9% sterile saline solution. The mixture is incorporated into a dosage unit suitable for administration by injection.

Example 108

Oral Composition of a Compound of Formula I or Formula Ia

To prepare a pharmaceutical composition for oral delivery, 400 mg of a compound of Formula I or Formula Ia and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

BIOLOGICAL EXAMPLES

Example I

Experimental Method for β-Lactamase Enzyme Assays Isolation of β-Lactamases

For SHV-5, Kpc-2, p99AmpC and OXA-1 β-lactamases, *E. coli* BL21(DE3) bacterial cells carrying expression plasmids (expressed as native untagged proteins) for the individual β-lactamases were grown in 1 L of Superbroth (Teknova Inc. Hollister, Calif.) supplemented with 100 μg/ml kanamycin selection and 1×5052 (0.5% glycerol, 0.05% glucose and 0.2% α-lactose) at 35° C. for 18-20 hours. Cells were harvested by centrifugation (4,000×g, 4° C., 20 min), resuspended in 50 ml of 10 mM HEPES pH 7.5 (1/20 of the initial volume). The cells were lysed by sonication (5 pulses of 45 seconds) at 45 W on ice. The lysates were clarified by centrifugation at 10,000×g for 40 minutes at 4° C. Samples were diluted 5-fold in 50 mM sodium acetate pH 5.0, stored overnight at 4° C., after which they were centrifuged at 10,000×g for 30 minutes to clarify, and filtered through 0.45 μm filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre-equilibrated in 50 mM Hepes pH 7.5, 150 mM NaCl. Active fractions were pooled concentrated, quantitated by BCA protein determination (Thermo Scientific, Rockford, Ill.), dialyzed into PBS and frozen at −80° C. in 20% glycerol until use.

For Vim-2 metallo β-lactamase, the procedure was identical with the following exceptions, first the protein was not pH adjusted to pH 5 with 50 mM sodium acetate, second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run ($3^{rd}$ step) on the Q sepharose anion exchange column to achieve acceptable purity (>90%).

β-Lactamase Inhibition.

To determine the level of inhibition of β-lactamase enzymes, compounds were diluted in PBS at pH 7.4 to yield concentrations ranging from 100 to 0.00005 μM in 96-well microtiter plates. An equal volume of diluted enzyme stock was added, and the plates were incubated at 37° C. for 15 min. Nitrocefin was used as substrate for p99 AmpC, VIM-2 and OXA-1 and dispensed into each well at a final concentration of 100 μM. Absorbance at 486 nm was immediately monitored for 10 min using a Biotek Powerwave XS2 microplate spectrophotometer using the GENS softweare package (Biotek Instruments, Winooski Vt.). In an analogous fashion, imipenem was used as substrate for Kpc-2 and Cefotaxime was used for SHV-5, while changes in absorbance upon hydrolysis of the β-lactam ring were monitored at 300 nm and 260 nm respectively in UV-transparent 96-well microtiter assay plates. Maximum rates of hydrolysis were compared to those in control wells (without inhibitors), and percentages of enzyme inhibition were calculated for each concentration of inhibitor. The concentration of inhibitor needed to reduce the initial rate of hydrolysis of substrate by 50% ($IC_{50}$) was calculated as the residual activity of β-lactamase at 486 nm using GraFit version 7 kinetics software package (Erithacus Software, Surrey, UK).

Example II

Inhibition of Diverse β-Lactamases by Exemplary Compounds

Using the methodology described above, examples of the current invention were evaluated for their ability to inhibit β-lactamase enzymes from all four Ambler classifications (A through D). The results of these assays are summarized in Table 3 for representative enzymes across different subtypes (note SHV-5 represents an Ambler Class A Extended Spectrum β-Lactamases, KPC-2 exemplifies a Class A carbapenemase, P99 represents chromosomal Class C AmpC, OXA-1 represents a Class D oxacillinase and VIM-2 represents a class B zinc-dependent metallo-β-lactamase also possessing carbapenemase activity), where A represents an $IC_{50}$ of 10-100 μM, B represents an $IC_{50}$ of 1 to 10 μM, C represents an $IC_{50}$ of 0.1 to 1 μM, and D represents an $IC_{50}$ of <0.1 μM. NT=Not tested.

TABLE 3

Inhibition of Diverse β-Lactamases by Exemplary Compounds

| EXAMPLE | Class A SHV-5 | Class A KPC-2 | Class B VIM-2 | Class C AmpC | Class D OXA-1 |
|---|---|---|---|---|---|
| 1 | B | C | C | D | D |
| 2 | A | C | C | D | C |
| 3 | D | C | B | D | D |
| 4 | D | D | C | D | D |
| 5 | D | D | B | D | D |
| 6 | D | D | C | D | D |
| 7 | D | D | B | D | C |
| 8 | D | D | B | D | C |
| 9 | D | D | C | D | D |
| 10 | D | D | C | D | C |
| 11 | C | B | B | D | C |
| 12 | C | C | B | D | C |
| 13 | D | D | C | D | D |
| 14 | D | D | C | D | D |
| 15 | D | D | D | D | C |
| 16 | D | D | B | D | D |
| 17 | C | D | B | D | C |
| 18 | D | D | D | D | D |
| 19 | C | D | D | D | D |
| 20 | B | C | D | D | C |
| 21 | D | D | B | D | D |
| 22 | D | D | C | D | D |
| 23 | D | D | C | D | C |
| 24 | D | D | B | D | D |
| 25 | D | D | D | D | D |
| 26 | D | D | B | D | C |
| 27 | D | D | C | D | D |
| 28 | D | D | B | D | C |
| 29 | D | D | C | D | D |
| 30 | D | D | C | D | C |
| 31 | D | D | B | D | D |
| 32 | D | D | C | D | D |
| 33 | D | D | C | D | D |
| 34 | D | D | C | D | D |
| 35 | D | D | C | D | D |
| 36 | D | D | B | D | D |
| 37 | B | D | C | D | D |
| 38 | D | C | C | D | C |
| 39 | D | D | B | D | D |
| 40 | C | D | D | D | D |
| 41 | D | D | C | D | D |
| 42 | C | D | B | D | C |
| 43 | D | D | D | D | D |
| 44 | C | C | B | C | C |
| 45 | D | D | B | D | C |
| 46 | C | D | C | D | D |
| 47 | D | D | B | D | D |
| 48 | D | D | C | D | D |
| 49 | D | D | C | D | D |
| 50 | C | C | C | C | C |
| 51 | D | D | D | D | D |
| 52 | D | D | A | D | D |
| 53 | D | D | D | D | D |
| 54 | D | D | C | C | D |
| 55 | D | D | C | D | D |
| 56 | C | D | C | D | D |
| 57 | D | D | C | D | D |
| 58 | D | D | C | D | D |
| 59 | D | D | C | D | D |
| 60 | D | D | D | D | D |
| 61 | D | D | D | D | D |
| 62 | D | D | D | D | D |
| 63 | D | D | D | D | D |
| 64 | D | C | D | D | D |
| 65 | D | D | D | D | D |
| 66 | D | D | B | D | D |
| 67 | D | D | C | D | D |
| 68 | D | D | C | D | D |
| 69 | D | D | D | D | D |
| 70 | D | D | C | D | D |
| 71 | D | D | D | D | D |
| 72 | D | D | C | D | D |
| 73 | D | D | D | D | D |
| 74 | D | D | D | D | D |
| 75 | D | D | D | D | D |
| 76 | D | D | D | D | D |
| 77 | D | C | C | D | D |
| 78 | D | D | D | D | D |
| 79 | D | D | D | D | D |

Example III

In vitro Antibacterial Assays of β-Lactamase Inhibition

To determine the ability of test compounds to potentiate the inhibition of the growth of bacterial strains that produce beta-lactamase enzymes, classic cell based broth microdilution MIC assays were employed. Six bacteria strains producing beta-lactamase enzymes were used: *E. coli* expressing the Class A Extended Spectrum Beta-Lactamase (ESBL) CTX-M-15, *E. cloacae* expressing the Class C P99, *K. pneumoniae* expressing the Class A carbapenemase KPC-2, *P. aeruginosa* expressing the Class B carbapenemase VIM-2, *K. pneumoniae* expressing the class A carbapenemase KPC-2 and the class B carbapenemase VIM-4, and *S. aureus* producing the Class A penicillinase PC-1. The assay was conducted in Cation Adjusted Mueller Hinton Broth (CAMHB, BD #212322, BD Diagnostic Systems, Sparks, Md.). Bacteria strains were grown for 3-5 hours in CAMBH broth. Test compounds were added to a microtiter plate in 2-fold serial dilutions in CAMHB in a final concentration range of 32 μg/mL to 0.25 μg/ml. An overlay of CAMHB containing a Beta-lactam was added to the compounds at a final static concentration of 4 μg/ml. Ceftazidime (CAZ, Sigma #C3809-1G, Sigma-Aldrich, St. Louis, Mo.) was used as the partner antibiotic for *E. coli* expressing Ambler Class A ESBL CTX-M-15 (MIC alone >128 μg/ml), and *E. cloacae* expressing Class C P99 (MIC alone=128 μg/mL). Meropenem (Mero, USP #1392454, U.S. Pharmacopeia, Rockville, Md.) was used as the partner antibiotic for *K. pneumoniae* expressing Ambler Class A carbapenemase KPC-3 (MIC alone >128 μg/mL), *P. aeruginosa* expressing Class A carbapenemase VIM-2 (MIC alone=16 μg/mL), and *K. pneumoniae* expressing the Ambler Class A carbapenemase KPC-2 and Ambler Class B carbapenemase VIM-4 (MIC alone=64 μg/mL). Piperacillin (Pip, Fisher #ICN15626801, MP Biomidicals, Solon, Ohio) was used as the partner antibiotic for *S. aureus* producing the Class A penicillinase PC-1 (MIC alone=64 μg/ml). Titration of test compounds with MIC readout indicates the concentration of test article needed to sufficiently inhibit beta-lactamase enzyme activity and protect the intrinsic antibacterial activity of the beta-lactam. In addition to the titration of test compounds the MICs of a panel of control beta-lactams is also tested to ensure the strains are behaving consistently from test to test. Once the test compound and antibiotics are added the plates can be inoculated according to CLSI broth microdilution method. After inoculation the plates are incubated for 16-20 hours at 37° C. then the Minimal Inhibitory Concentration (MIC) of the test compound is determined visually.

Using the methodology described above, examples of the current invention were evaluated for their ability to inhibit the growth of β-lactamase-producing bacteria in the presence of a β-lactam antibiotic.

Representative results are shown in Table 3 where A represents an MIC>16 μg/mL, B represents an MIC between 1 and 16 μg/mL inclusive, and C represents an MIC of <1 μg/mL. NT=Not Tested.

Example IV

In Vitro Antibacterial Activity of Exemplary Compounds

Using the methodology described above in EXAMPLE III, exemplary compounds for Formula I or Formula Ia were evaluated for their ability to inhibit the growth of β-lactamase producing bacteria in the presence of a β-lactam antibiotic.

Representative results are shown in Table 4 where A represents an MIC of the fixed β-lactam antibiotic in the presence of >32 μg/mL of a β-lactamase inhibitor of exemplary compounds, B represents the MIC in the presence of between 8 and 32 μg/mL of a β-lactamase inhibitor of exemplary compounds, and C represents the MIC in the presence of ≤4 μg/mL of a β-lactamase inhibitor of exemplary compounds. NT=Not Tested.

TABLE 4

Broad spectrum inhibition of bacterial growth. MIC of example compounds of the invention in the presence of a fixed amount (4 μg/mL) of designated β-lactam antibiotics ceftazidime (CAZ), meropenem (Mero), Piperacillin (Pip).

| | MIC (μg/mL) of exemplary compounds in presence of fixed β-lactams | | | | | |
|---|---|---|---|---|---|---|
| | Fixed CAZ | | Fixed Mero | | | Fixed Pip |
| | ESBLs (Class A and C) | | Carbapenemases (Classes A and B) | | K.P. | Penicillinase |
| EXAMPLE | E. coli ESBL4 CTX-M-15 | E. cl. 144200 p99 AmpC | K.P. 156319 KPC-3 | P. aerug. Ps296 VIM-2 | A-1797 KPC-2 VIM-4 | S. aureus MSSA-7 PC-1 |
| 1 | C | C | C | C | C | B |
| 2 | C | C | C | C | C | B |
| 3 | C | C | C | C | B | C |
| 4 | C | C | C | C | B | C |
| 5 | C | C | B | C | A | C |
| 6 | C | C | C | C | C | C |
| 7 | C | C | C | A | A | B |
| 8 | C | C | B | B | A | C |
| 9 | C | C | C | B | B | C |
| 10 | C | C | C | B | C | C |
| 11 | C | C | C | B | B | NT |
| 12 | C | C | B | B | A | NT |
| 13 | C | C | B | C | B | C |
| 14 | C | C | C | A | B | C |
| 15 | C | C | C | C | C | C |
| 16 | C | C | C | B | A | C |
| 17 | C | C | C | A | A | C |
| 18 | C | C | C | C | B | NT |
| 19 | C | C | C | C | C | NT |
| 20 | C | C | C | C | B | NT |
| 21 | C | C | C | B | A | C |
| 22 | C | C | C | B | C | C |
| 23 | C | C | C | A | A | C |
| 24 | C | C | C | B | C | C |
| 25 | C | C | C | C | C | C |
| 26 | C | C | C | C | C | C |
| 27 | C | C | C | B | B | C |
| 28 | C | C | C | B | A | C |
| 29 | C | C | C | B | A | C |
| 30 | C | C | C | B | B | C |
| 31 | C | C | B | B | A | C |
| 32 | C | C | C | B | A | C |
| 33 | C | C | C | B | B | C |
| 34 | C | C | C | C | B | C |
| 35 | C | C | C | C | B | C |
| 36 | C | C | C | C | B | C |
| 37 | C | C | C | C | B | C |
| 38 | C | C | C | C | C | C |

TABLE 4-continued

Broad spectrum inhibition of bacterial growth. MIC of example compounds of the invention in the presence of a fixed amount (4 µg/mL) of designated β-lactam antibiotics ceftazidime (CAZ), meropenem (Mero), Piperacillin (Pip).

| | MIC (µg/mL) of exemplary compounds in presence of fixed β-lactams | | | | | |
|---|---|---|---|---|---|---|
| | Fixed CAZ | | Fixed Mero Carbapenemases (Classes A and B) | | | Fixed Pip |
| | ESBLs (Class A and C) | | | | K.P. | Penicillinase |
| EXAMPLE | E. coli ESBL4 CTX-M-15 | E. cl. 144200 p99 AmpC | K.P. 156319 KPC-3 | P. aerug. Ps296 VIM-2 | A-1797 KPC-2 VIM-4 | S. aureus MSSA-7 PC-1 |
| 39 | C | C | C | B | B | C |
| 40 | C | C | C | A | A | C |
| 41 | C | C | C | B | C | C |
| 42 | C | C | C | C | B | B |
| 43 | C | C | C | C | A | C |
| 44 | C | C | C | B | C | B |
| 45 | C | C | C | B | B | C |
| 46 | C | C | C | C | C | C |
| 47 | C | C | C | B | A | C |
| 48 | C | C | C | B | B | C |
| 49 | C | C | C | B | B | C |
| 50 | C | C | A | C | B | C |
| 51 | C | C | C | C | C | C |
| 52 | C | C | B | A | A | C |
| 53 | C | C | C | C | C | C |
| 54 | C | C | C | C | B | C |
| 55 | C | C | C | C | C | C |
| 56 | C | C | C | C | C | C |
| 57 | C | C | C | C | B | C |
| 58 | C | C | C | C | C | C |
| 59 | C | C | C | C | B | C |
| 60 | C | C | C | C | C | C |
| 61 | C | C | C | C | C | C |
| 62 | C | C | C | B | C | C |
| 63 | C | C | C | C | C | C |
| 64 | C | C | C | C | C | C |
| 65 | C | C | C | B | C | C |
| 66 | C | C | C | B | B | C |
| 67 | C | C | C | C | C | C |
| 68 | C | C | C | B | B | C |
| 69 | C | C | C | C | A | C |
| 70 | C | C | C | C | B | C |
| 71 | C | C | C | C | C | C |
| 72 | C | C | C | C | B | C |
| 73 | C | C | C | C | C | C |
| 74 | C | C | C | C | C | C |
| 75 | C | C | C | C | C | C |
| 76 | C | C | C | B | C | C |
| 77 | C | C | C | C | B | C |
| 78 | C | C | C | C | C | C |
| 79 | C | C | C | C | C | C |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I) or Formula (Ia), a pharmaceutically acceptable salt, solvate, polymorph, stereoisomer, tautomer, N-oxide, dimer or trimer thereof:

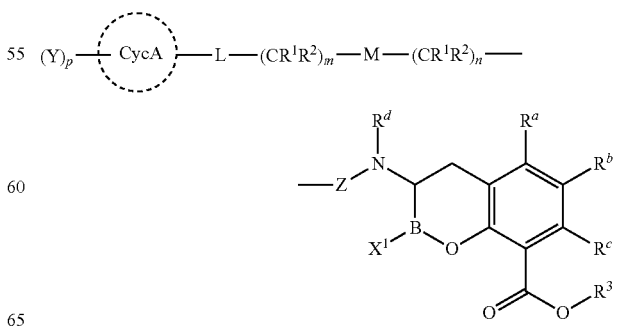

Formula (I)

-continued

Formula (Ia)

$(Y)_p$—⟨CycA⟩—L—$(CR^1R^2)_m$—M—$(CR^1R^2)_n$—

[Structure showing: —Z—N(R^d)—CH(—B(X^1)(X^2))—CH_2—Ar where Ar bears R^a, R^b, R^c, OH, and C(=O)O—R^3 substituents]

wherein:

L is a bond, —$CR^1R^2$—, >C=O, or =$CR^1$—;
M is a bond, —O—, —S—, —S(O)—, >$SO_2$, or —N($R^4$)—;
m is 0, 1, or 2;
n is 0, 1, 2, or 3;
 provided that
  when n is 0, then M is a bond;
p is 0, 1, 2, 3, or 4;
 provided that
  when p is 0, then L is —$CR^1R^2$— or =$CR^1$—;
$X^1$ and $X^2$ are independently selected from —OH, —$OR^8$, or F;
Z is >C=O, >C=S, or >$SO_2$;
CycA is an optionally substituted 3-10 membered non-aromatic carbocycle, wherein an optional olefin functionality of the non-aromatic carbocycle is not directly attached to an oxygen, sulfur, or nitrogen substituent;
$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —$OR^{10}$, —$NR^4R^5$, and —$SR^{10}$;
each $R^1$ and $R^2$ is independently selected from the group consisting of hydrogen, fluoro, chloro, bromo, optionally substituted $C_1$-$C_6$ alkyl, optionally substituted $C_3$-$C_6$ cycloalkyl, —OH, —$OR^{10}$, —$SR^{10}$, and —$NR^4R^5$,
 or $R^1$ and $R^2$ taken together form an oxo, oxime, or an optionally substituted carbocycle or optionally substituted heterocycle with the carbon to which they are attached;
$R^3$ is hydrogen, optionally substituted $C_1$-$C_6$ alkyl, or a pharmaceutically acceptable prodrug;
each $R^d$, $R^4$ and $R^5$ is independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
 or $R^4$ and $R^5$ taken together form an optionally substituted heterocycle with the nitrogen to which they are attached;

each $R^8$ is independently selected from the group consisting of optionally substituted $C_1$-$C_6$ alkyl, optionally substituted $C_3$-$C_6$ cycloalkyl, and a pharmaceutically acceptable boronate ester group;
each $R^{10}$ is independently selected from the group consisting of optionally substituted $C_1$-$C_6$ alkyl and optionally substituted $C_3$-$C_6$ cycloalkyl;
and each Y is independently a group comprising 1-50 non-hydrogen atoms.

2. The compound of claim 1, wherein $R^a$, $R^b$, and $R^c$ are hydrogen.

3. The compound of claim 1, wherein $R^3$ is hydrogen.

4. The compound of claim 1, wherein $X^1$ and $X^2$ are —OH.

5. The compound of claim 1, wherein $R^d$ is hydrogen or $C_1$-$C_4$-alkyl.

6. The compound of claim 1, wherein Z is >C=O.

7. The compound of claim 1, wherein:
L is a bond or >C=O;
M is a bond or —N($R^4$)—; and
m and n are 0.

8. The compound claim 1, wherein:
L is —$CR^1R^2$— or =$CR^1$—;
M is a bond; and
m and n are 0.

9. The compound of claim 1, wherein CycA is selected from the group consisting of cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent.

10. The compound of claim 9, wherein CycA is cyclohexane.

11. The compound of claim 1 wherein each Y is independently selected from the group consisting of
fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, =O, —OH, —$OR^{10}$, —$SR^{10}$, —$NR^4R^5$, —$(CR^6R^7)_vNR^4R^5$, —$NR^4(CR^6R^7)_vR_6$, —$NR^4(CR^6R^7)_vNR^4R^5$, —$NR^4(CR^6R^7)_vNR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$S(O)_{0,1,2}(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$S(O)_{0,1,2}(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$S(O)_{0,1,2}(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$NR^4(CR^6R^7)_vNR^4C(=NR^4)NR^4R^5$, —$O(CR^6R^7)_vC(=NR^4)NR^5C(=NR^5)NR^4R^5$, —$S(O)_{0,1,2}(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —C(O)NR⁴R⁵, —(CR⁶R⁷)ᵥC(O)NR⁴R⁵, —SO₂NR⁴R⁵, -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, —N(R⁴)-Heteroaryl-NR⁴R⁵, —N(R⁴)-Heterocyclyl-NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, —(CR⁶R⁷)ᵥHeterocyclyl-N(R⁴)C(=NR⁵)NR⁴R⁵, —NR⁴(CR⁶R⁷)ᵥHeterocyclyl-C(=NR⁵)NR⁴R⁵, —(CR⁶R⁷)ᵥHeteroaryl, —(CR⁶R⁷)ᵥHeterocyclyl, —O-Heteroaryl, —O-Heterocyclyl, —NR⁴(CR⁶R⁷)ᵥHeteroaryl, —NR⁴(CR⁶R⁷)ᵥHeterocyclyl, —O(CR⁶R⁷)ᵥHeteroaryl, —O(CR⁶R⁷)ᵥHeterocyclyl, —NR⁴(CR⁶R⁷)ᵥNR⁵-Heteroaryl, —NR⁴(CR⁶R⁷)ᵥNR⁵-Heterocyclyl, —O(CR⁶R⁷)ᵥNR⁵-Heteroaryl, —O(CR⁶R⁷)ᵥNR⁵-Heterocyclyl, —O(CR⁶R⁷)ᵥO-Heterocyclyl, —NR⁴R⁵R⁹⁺Q⁻, —(CR⁶R⁷)ᵥNR⁴R⁵R⁹⁺Q⁻, —NR⁴(CR⁶R⁷)ᵥNR⁴R⁵R⁹⁺Q⁻, —NR⁴R⁹⁺(CR⁶R⁷)ᵥNR⁴R⁵R⁹⁺Q⁻₂, —(CR⁶R⁷)ᵥ(T)⁺Q⁻, and —O(CR⁶R⁷)ᵥNR⁴R⁵R⁹⁺Q⁻;

wherein:
  each T is independently selected from the group consisting of pyridine-1-yl, pyrimidin-1-yl, and thiazol-3-yl;
  each Q is independently a pharmaceutically acceptable counterion; and
  each v is independently 1, 2, 3, or 4;
or Y taken together with the carbon atom to which it is attached forms an optionally substituted spiro-carbocycle or optionally substituted spiro-heterocycle;
or two Ys taken together with the carbon atoms to which they are attached form an optionally substituted carbocycle or an optionally substituted heterocycle;

each R⁶ and R⁷ is independently selected from the group consisting of hydrogen, fluoro, chloro, bromo, optionally substituted C₁-C₆ alkyl, optionally substituted alkoxyalkyl, optionally substituted hydroxyalkyl, optionally substituted C₃-C₆ cycloalkyl, —OH, —OR¹⁰, —SR¹⁰, —NR⁴R⁵, —NR⁴C(O)R⁵, —NR⁴C(O)OR⁵, —NR⁴C(O)NR⁵, —C(O)OR⁵, —C(O)NR⁴R⁵, —C(N=R⁵)NR⁴R⁵, —NR⁴SO₂R⁵, optionally substituted heterocyclyl, optionally substituted aryl, and optionally substituted heteroaryl;
  or R⁶ and R⁷ taken together form an oxo, oxime, or an optionally substituted carbocycle or an optionally substituted heterocycle with the carbon to which they are attached;
each R⁹ is independently optionally substituted C₁-C₆ alkyl.

12. The compound of claim 1, wherein at least one Y is selected from the group consisting of fluoro, chloro, optionally substituted C₁-C₆ alkyl, =O, —OH, —OR¹⁰, —NR⁴R⁵, —(CR⁶R⁷)ᵥNR⁴R⁵, —NR⁴(CR⁶R⁷)ᵥNR⁴R⁵, —O(CR⁶R⁷)ᵥNR⁴R⁵, —N(R⁴)C(O)(CR⁶R⁷)ᵥNR⁴R⁵, —(CR⁶R⁷)ᵥN(R⁴)C(O)(CR⁶R⁷)ᵥNR⁴R⁵, —C(O)NR⁴(CR⁶R⁷)ᵥNR⁴R⁵, —S(O)₀,₁,₂NR⁴(CR⁶R⁷)ᵥNR⁴R⁵, —NR⁵C(O)NR⁴(CR⁶R⁷)ᵥNR⁴R⁵, —OC(O)NR⁴(CR⁶R⁷)ᵥNR⁴R⁵, —NR⁵C(=NR⁷)NR⁴(CR⁶R⁷)ᵥNR⁴R⁵, —N(R⁴)C(=NR⁵)R⁶, —(CR⁶R⁷)ᵥN(R⁴)C(=NR⁵)R⁶, —NR⁴(CR⁶R⁷)ᵥN(R⁴)C(=NR⁵)R⁶, —O(CR⁶R⁷)ᵥN(R⁴)C(=NR⁵)R⁶, —(CR⁶R⁷)ᵥC(=NR⁵)NR⁴R⁵, —NR⁴(CR⁶R⁷)ᵥC(=NR⁵)NR⁴R⁵, —O(CR⁶R⁷)ᵥC(=NR⁵)NR⁴R⁵, —(CR⁶R⁷)ᵥN(R⁴)C(=NR⁵)NR⁴R⁵, —NR⁴(CR⁶R⁷)ᵥN(R⁴)C(=NR⁵)NR⁴R⁵, —O(CR⁶R⁷)ᵥN(R⁴)C(=NR⁵)NR⁴R⁵, —NR⁴C(=NR⁵)NR⁴C(=NR⁵)NR⁴R⁵, —(CR⁶R⁷)ᵥC(=NR⁴)NR⁵C(=NR⁴)NR⁴R⁵, —NR⁴(CR⁶R⁷)ᵥC(=NR⁴)NR⁵C(=NR⁴)NR⁴R⁵, —O(CR⁶R⁷)ᵥC(=NR⁴)NR⁵C(=NR⁴)NR⁴R⁵, —NR⁴C(=NR⁵)NR⁴R⁵, —C(=NR⁴)NR⁴R⁵, —C(=NR⁴)NR⁴C(O)R⁶, —NR⁴SO₂R⁶, —NR⁴C(O)R⁶, —NR⁴C(=O)OR⁶, —C(O)NR⁴R⁵, —(CR⁶R⁷)ᵥC(O)NR⁴R⁵, —(CR⁶R⁷)ᵥNR⁴R⁵(CR⁶R⁷)ᵥNR⁴R⁵, —NR⁴R⁵(CR⁶R⁷)ᵥR₆, —NR⁴R⁵(CR⁶R⁷)ᵥHeterocyclyl-C(=NR⁵)NR⁴R⁵, —NR⁴(CR⁶R⁷)ᵥNR⁴C(=NR⁴)NR⁴R⁵, —NR⁴(CR⁶R⁷)ᵥNR⁴R⁵(CR⁶R⁷)ᵥNR⁴R⁵, -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, —N(R⁴)-Heteroaryl-NR⁴R⁵, —N(R⁴)-Heterocycyl-NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, —(CR⁶R⁷)ᵥHeterocyclyl-N(R⁴)C(=NR⁵)NR⁴R⁵, —(CR⁶R⁷)ᵥHeteroaryl, —(CR⁶R⁷)ᵥHeterocyclyl, —O-Heteroaryl, —O-Heterocyclyl, —NR⁴(CR⁶R⁷)ᵥHeteroaryl, —NR⁴(CR⁶R⁷)ᵥHeterocyclyl, —O(CR⁶R⁷)ᵥHeteroaryl, —O(CR⁶R⁷)ᵥHeterocyclyl, and —O(CR⁶R⁷)ᵥO-Heterocyclyl.

13. The compound of claim 1, wherein at least one Y is selected from the group consisting of —NR⁴R⁵, —NR⁴C(=NR⁵)NR⁴R⁵, —C(=NR⁴)NR⁴R⁵, —N(R⁴)C(=NR⁵)R⁶, —(CR⁶R⁷)ᵥNR⁴R⁵, —(CR⁶R⁷)ᵥN(R⁴)C(=NR⁵)NR⁴R⁵, —NR⁴(CR⁶R⁷)ᵥNR⁴R⁵, —NR⁴(CR⁶R⁷)ᵥOR¹⁰, —(CR⁶R⁷)ᵥNR⁴(CR⁶R⁷)ᵥNR⁴R⁵, NR⁵C(=NR⁵)NR⁴(CR⁶R⁷)ᵥNR⁴R⁵, —NR⁴(CR⁶R⁷)ᵥN(R⁴)C(=NR⁵)NR⁴R⁵, —NR⁵C(O)CR⁶(NR⁴R⁵)(CR⁶R⁷)ᵥNR⁴R⁵, —(CR⁶R⁷)ᵥC(=NR⁵)NR⁴R⁵, —(CR⁶R⁷)ᵥN(R⁴)C(O)(CR⁶R⁷)ᵥNR⁴R⁵, —C(=NR⁴)NR⁴C(O)R⁶, —NR⁴(CR⁶R⁷)ᵥHeteroaryl, and —O(CR⁶R⁷)ᵥNR⁴R⁵.

14. The compound of claim 1, wherein p is 1 or 2.

15. The compound of claim 1, wherein R⁴ and R⁵ are independently hydrogen or optionally substituted C₁-C₆ alkyl.

16. The compound of claim 11, wherein R⁶ and R⁷ are independently hydrogen, fluoro, or optionally substituted C₁-C₆ alkyl.

17. The compound of claim 1, wherein the compound is selected from the group represented by the following structures:

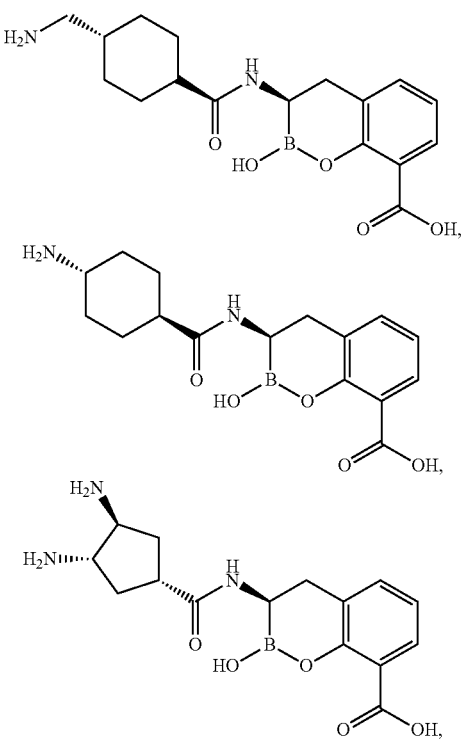

217
-continued
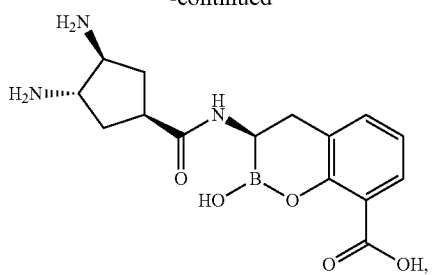
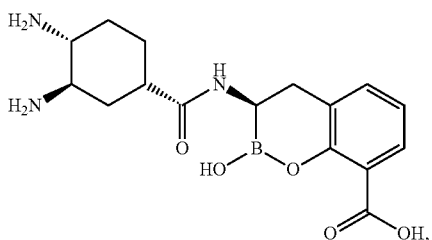
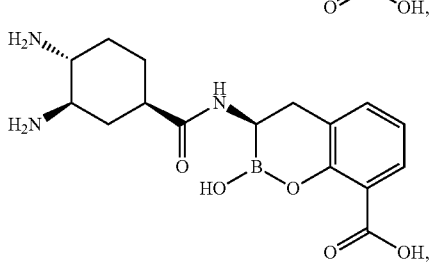
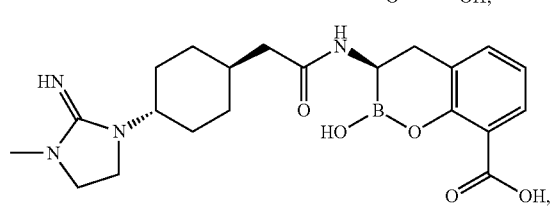
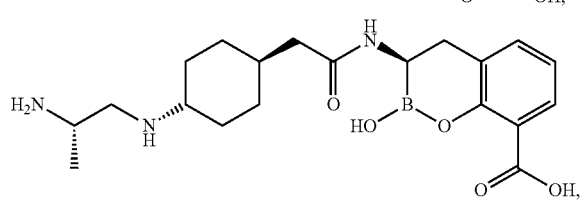
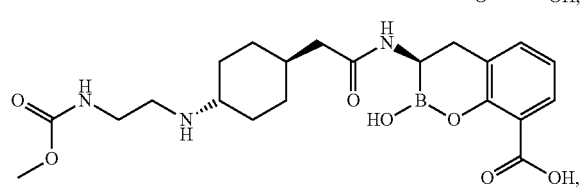
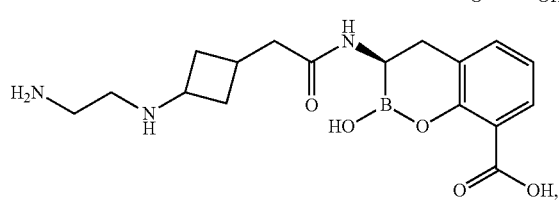
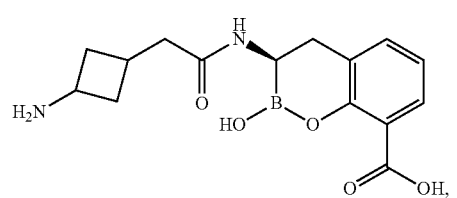
218
-continued
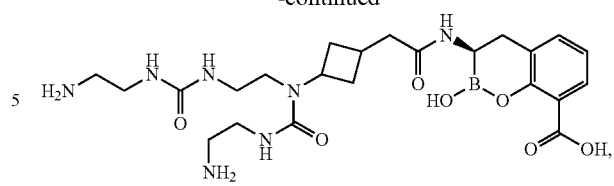
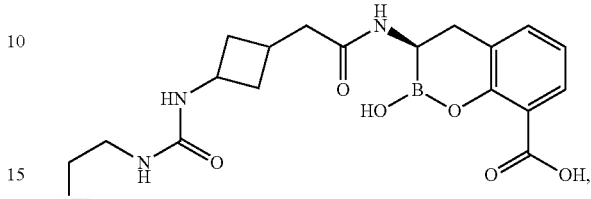
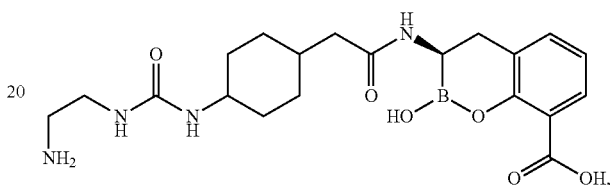
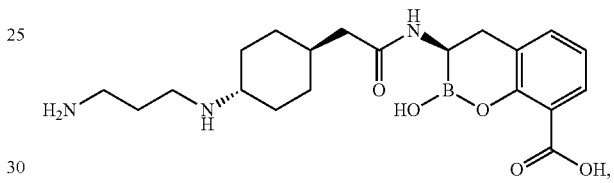
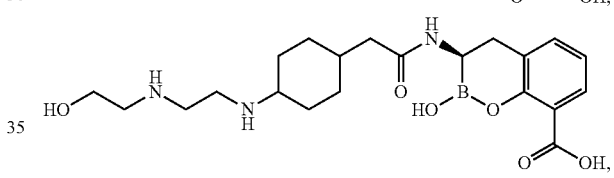
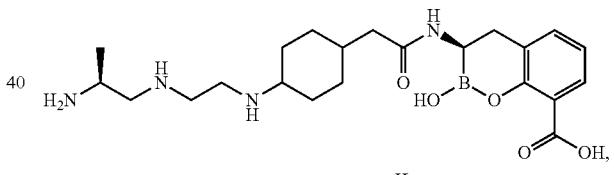
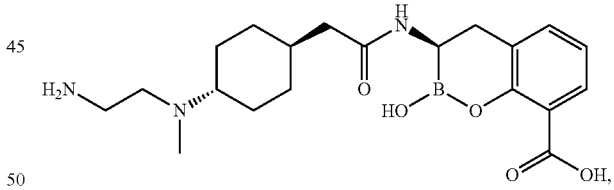
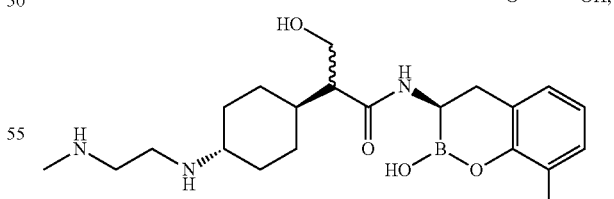
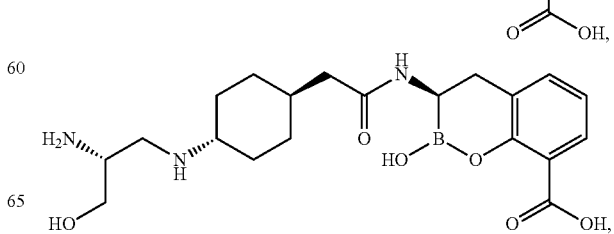

219
-continued
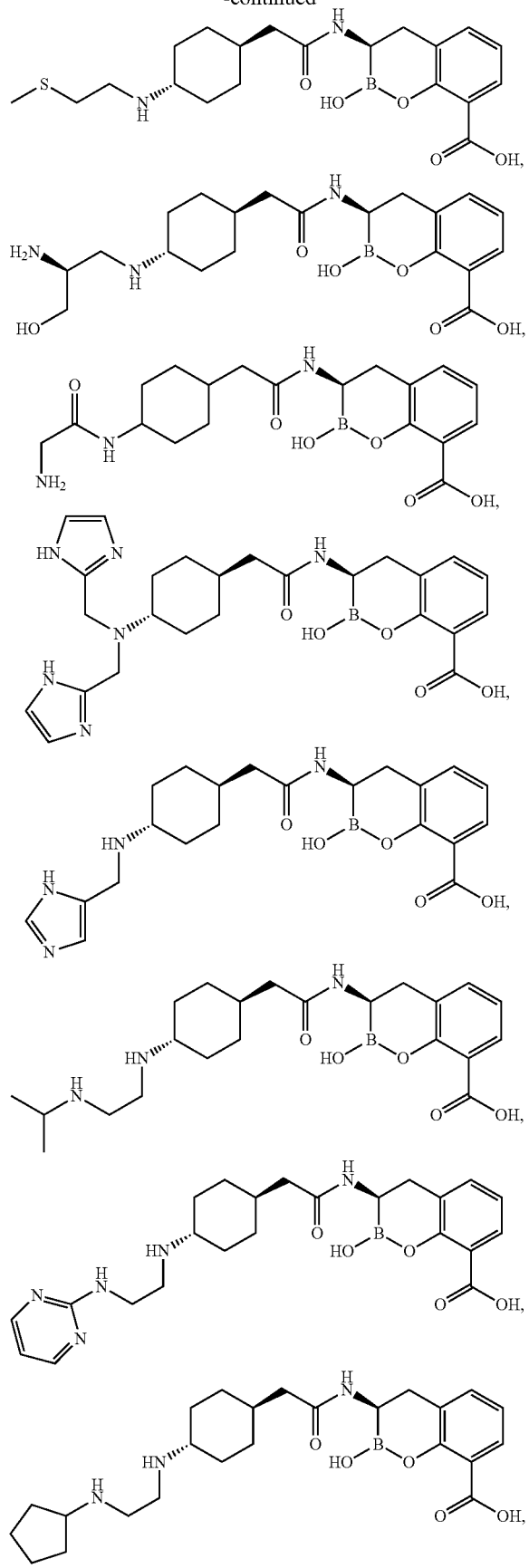
220
-continued
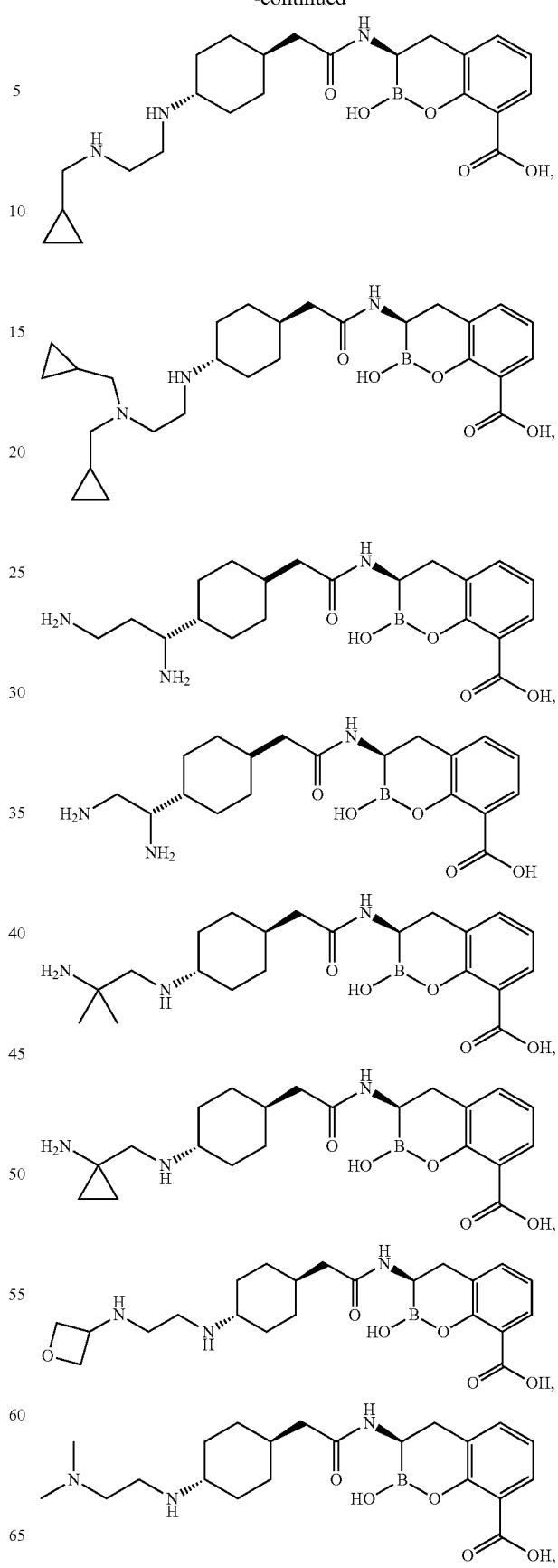

221
-continued
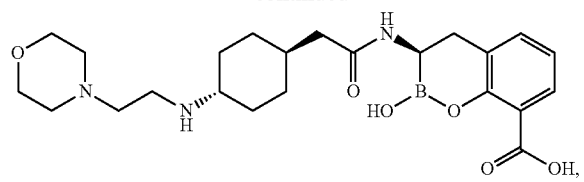
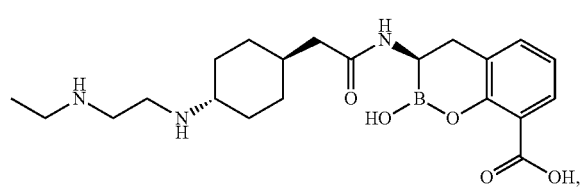
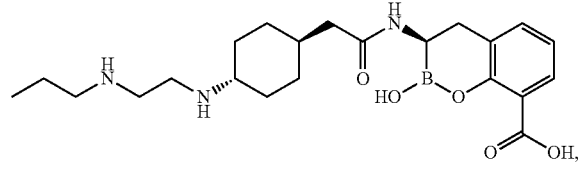
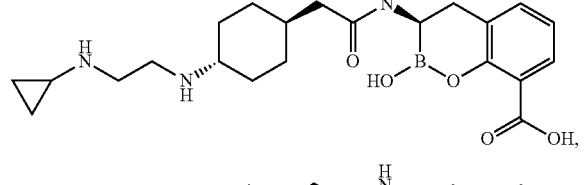
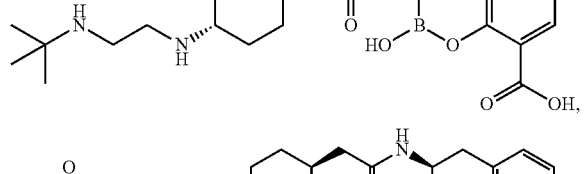
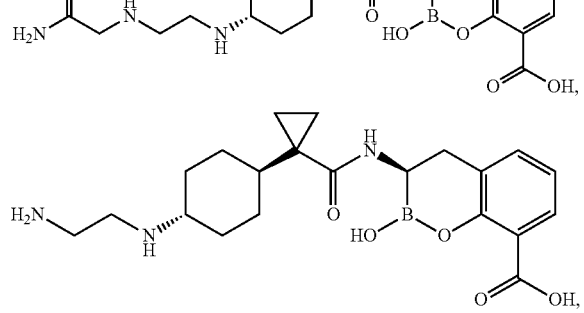
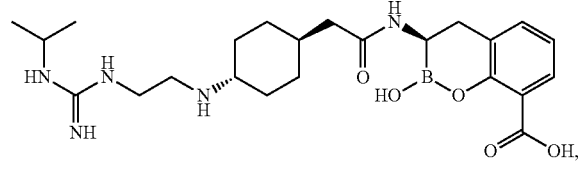
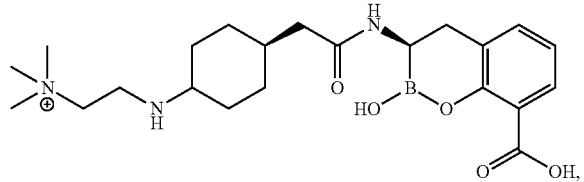
222
-continued
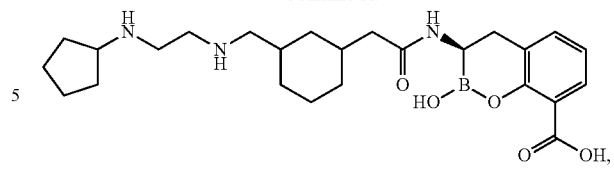
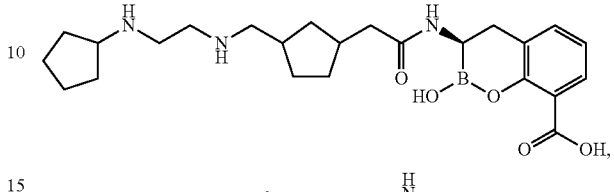
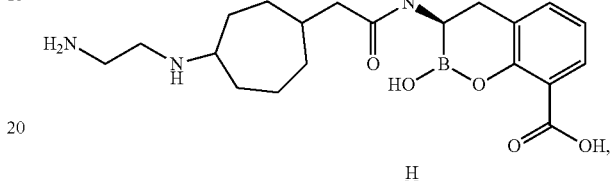
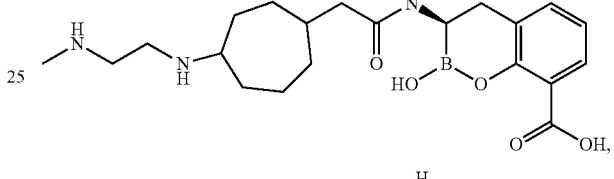
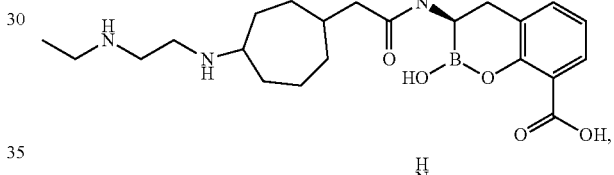
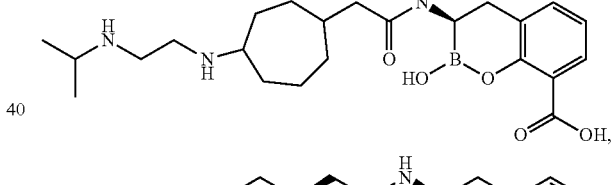
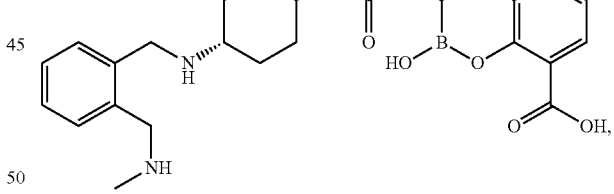
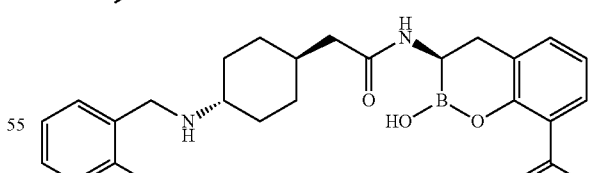
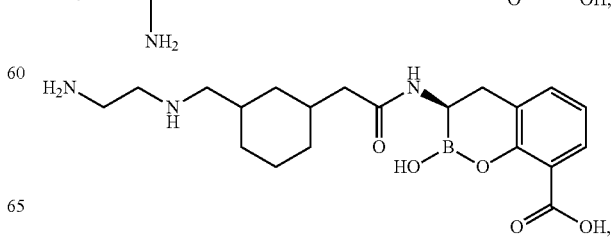

223
-continued

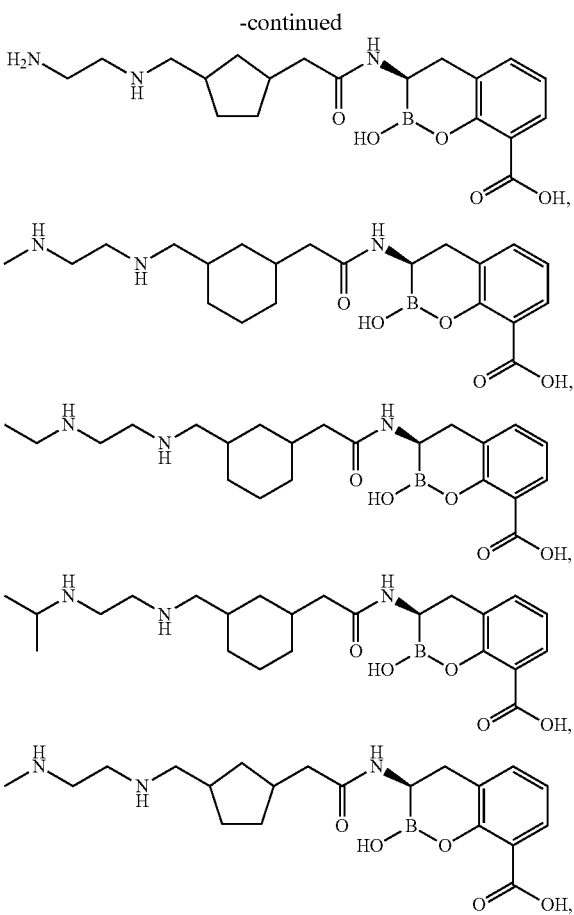

224
-continued

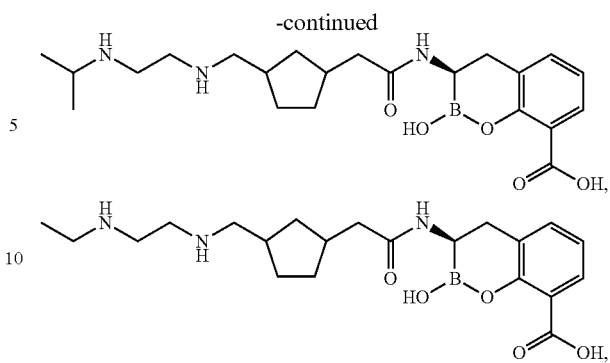

or a pharmaceutically acceptable salt, solvate, polymorph, stereoisomer, tautomer, metabolite, N-oxide, dimer or trimer thereof, wherein the compound is present in a closed, cyclic form according to Formula I and as shown in the structures above, an open, acyclic form according to Formula Ia, or mixtures thereof.

18. A pharmaceutical composition comprising a compound of claim 1 or a pharmaceutically acceptable salt, solvate, polymorph, stereoisomer, tautomer, metabolite, N-oxide, or isomer thereof, and a pharmaceutically acceptable excipient.

19. The pharmaceutical composition of claim 18, further comprising a beta-lactam antibiotic.

20. A method of treating a bacterial infection in a subject, comprising administering to the subject a pharmaceutical composition of claim 18, optionally in combination with a beta-lactam antibiotic.

21. The compound of claim 1, wherein each Y is independently a group comprising 1-50 non-hydrogen atoms selected from the group consisting of C, N, O, S, and P.

* * * * *